US012797423B2

(12) United States Patent
Holm et al.

(10) Patent No.: US 12,797,423 B2
(45) Date of Patent: Nov. 17, 2026

(54) TREATMENT OF TUMORS BY A COMBINATION OF AN ONCOLYTIC ADENOVIRUS, A CDK4/6 INHIBITOR AND A FURTHER THERAPEUTICALLY ACTIVE AGENT

(71) Applicant: KLINIKUM RECHTS DER ISAR DER TECHNISCHEN UNIVERSITÄT MÜNCHEN, Munich (DE)

(72) Inventors: Per Sonne Holm, Fürstenfeldbruck (DE); Roman Nawroth, Alling (DE)

(73) Assignee: KLINIKUM RECHTS DER ISAR DER TECHNISCHEN UNIVERSITÄT MÜNCHEN, Munich (DE)

( * ) Notice: Subject to any disclaimer, the term of this patent is extended or adjusted under 35 U.S.C. 154(b) by 849 days.

(21) Appl. No.: 17/640,720

(22) PCT Filed: Sep. 7, 2020

(86) PCT No.: PCT/EP2020/074980

§ 371 (c)(1),
(2) Date: Mar. 4, 2022

(87) PCT Pub. No.: WO2021/044061

PCT Pub. Date: Mar. 11, 2021

(65) Prior Publication Data

US 2022/0354911 A1 Nov. 10, 2022

(30) Foreign Application Priority Data

Sep. 5, 2019 (EP) .................................... 19000396
Sep. 12, 2019 (EP) .................................... 19000406

(51) Int. Cl.

| | |
|---|---|
| ***A61K 35/761*** | (2015.01) |
| ***A61K 31/496*** | (2006.01) |
| ***A61K 31/506*** | (2006.01) |
| ***A61K 31/519*** | (2006.01) |
| ***A61K 45/06*** | (2006.01) |
| ***A61P 35/00*** | (2006.01) |

(52) U.S. Cl.

CPC .......... *A61K 35/761* (2013.01); *A61K 31/496* (2013.01); *A61K 31/506* (2013.01); *A61K 31/519* (2013.01); *A61K 45/06* (2013.01); *A61P 35/00* (2018.01)

(58) Field of Classification Search

None

See application file for complete search history.

(56) References Cited

U.S. PATENT DOCUMENTS

2018/0008688 A1 1/2018 Munn

FOREIGN PATENT DOCUMENTS

| | | | | |
|---|---|---|---|---|
| JP | 2017501187 A | 1/2017 | | |
| JP | 2017516862 A | 6/2017 | | |
| WO | WO-2012022496 A2 * | 2/2012 | ........... | A61K 35/761 |
| WO | WO-2018195202 A1 * | 10/2018 | | |
| WO | WO-2018237158 A1 * | 12/2018 | ........... | A61K 31/167 |
| WO | 2019170283 A1 | 9/2019 | | |

OTHER PUBLICATIONS

Czolk et al., "Irradiation enhances the therapeutic effect of the oncolytic adenovirus XVir-N-31 in brain tumor initiating cells", International Journal of Molecular Medicine, vol. 44, pp. 1484-1494 (Year: 2019).*

Rognoni et al., "Adenovirus-based virotherapy enabled by cellular YB-1 expression in vitro and in vivo", Cancer Gene Therapy, vol. 16, pp. 753-763 (Year: 2009).*

Ashish P. Shah et al., "A Review on DNA Repair Inhibition by PARP Inhibitors in Cancer Therapy", Folia Medica, vol. 60, No. 1, Mar. 1, 2018 (Mar. 1, 2018), p. 39-47, XP055755544.

Anonymous, "Oncolytic Viral Therapy", Apr. 10, 2019 (Apr. 10, 2019), Retrieved from the Internet: URL:https://www.pegsummit.com/Oncolytic-Viral-Therapy, XP055594785.

Nadiia Lypova et al, "Targeting Palbociclib-Resistant Estrogen Receptor-Positive Breast Cancer Cells via Oncolytic Virotherapy", Cancers, vol. 11, No. 5, May 16, 2019 (May 16, 2019), p. 684, XP055594787.

"Abstracts des 71. Kongresses der Deutschen Gesellschaft für Urologie e.V", Aug. 20, 2019 (Aug. 20, 2019), vol. 58, No. 1, p. 2-128, XP036872317.

Montserrat Pérez-Salvia et al, "Bromodomain inhibitors and cancer therapy: From structures to applications", Epigenetics, vol. 12, No. 5, Dec. 2, 2016 (Dec. 2, 2016), p. 323-339, XP055452716.

Sanjeev Shangary et al, "Small-Molecule Inhibitors of the MDM2-p53 Protein-Protein Interaction to Reactivate 053 Function: A Novel Approach for Cancer Therapy", Annual Review of Pharmacology and Toxicology, vol. 49, No. 1, Feb. 1, 2009 (Feb. 1, 2009), p. 223-241, XP055075317.

(Continued)

*Primary Examiner* — Michelle F. Paguio Frising

(74) *Attorney, Agent, or Firm* — Lisa Mueller; Casimir Jones SC

(57) ABSTRACT

The present invention is related to a combination of an adenovirus, a CDK4/inhibitor and at least one further agent selected from the group comprising a PARP inhibitor, a bromodomain inhibitor, nutlin or a derivative of nutlin.

10 Claims, 70 Drawing Sheets

Specification includes a Sequence Listing.

(56) References Cited

OTHER PUBLICATIONS

Eva Lichtenegger et al, "The Oncolytic Adenovirus XVir-N-31 as a Novel Therapy in Muscle-Invasive Bladder Cancer", Human Gene Therapy, vol. 30, No. 1, Jan. 1, 2019 (Jan. 1, 2019), p. 44-56, XP055754949.
Husna, S.M.N., et al., Inhibitors targeting CDK4/6, PARP and PI3K in breast cancer: a review. Therapeutic Advances in Medical Oncology, Nov. 9, 2018, vol. 10, pp. 1-21.
Koll, Florestan, et al. (2015). 32 Treatment of bladder cancer with YB-1 dependent oncolytic adenovirus: Preliminary in vitro studies. European Urology Supplements. 14. 10.1016/S1569-9056(15)60035-5.
Ingemarsdotter CK, et al., Paclitaxel resistance increases oncolytic adenovirus efficacy via upregulated CAR expression and dysfunctional cell cycle control. Mol Oncol. Apr. 2015;9(4):791-805. doi: 10.1016/j.molonc.2014.12.007. Epub Dec. 29, 2014.
Ma J, et al., E2F promoter-regulated oncolytic adenovirus with p16 gene induces cell apoptosis and exerts antitumor effect on gastric cancer. Dig Dis Sci. Jul. 2009;54(7):1425-31. doi: 10.1007/s10620-008-0543-0. Epub Nov. 26, 2008.
PEGS Boston, Oncolytic Viral Therapy brochure, Apr. 19, 2019, https://www.pegsummit.com/Oncolytic-Viral-Therapy, pp. 1-11.

* cited by examiner

*Asterisks (*) indicate artefacts from cell fixing*

Fig. 21
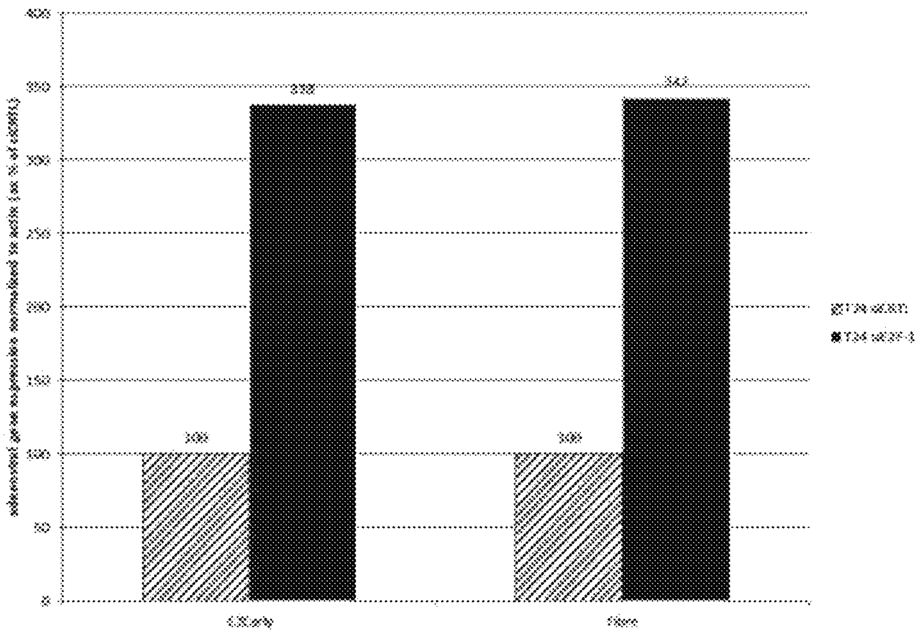
Fig. 22
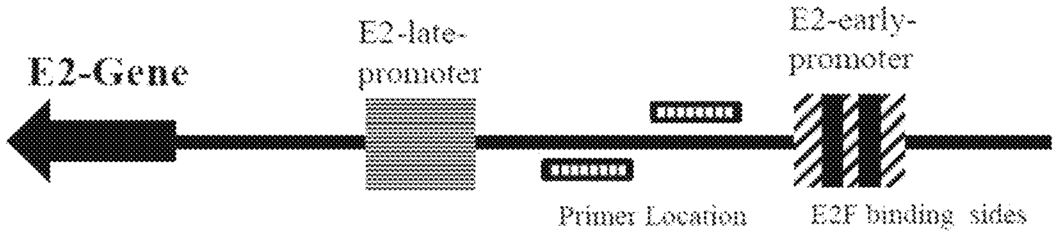
Fig. 23
Wild-type E2-early-promoter
5-AGTTTTCGCGCTTAAATTTGAGAAAGGGCGCGAAACTAGTCCTT
3-TCAAAAGCGCGAATTTAAACTCTTTCCCGCGCTTTGATCAGGAA
5-AGGAGTCGGATTTAAATTTGAGAAAGTAATAGGTACTAGTCCTT
3-TCCTCAGCCTAAATTTAAACTCTTTCATTATCCATGATCAGGAA
Mutated E2-early-promoter Abemaciclib Palbociclib Ribociclib

Dinaciclib

Olaparib

Veliparib

Rucaparib

Talazoparib (Taken from Montserrat Perez-Savia and Manel Esteller: Bromodomain inhibitors and cancer therapy: From structure to applications. EPIGENTCS 2017, 12, 323-339)

JQ1

OTX-015

I-BET151

CPI-0610

BET inhibitors (+)-JQ1

I-BET762

OTX-015

I-BET151

CPI-203

PFI-1

MS436

CPI-0610

Ad-Delta 24 and Ad-Delta 24-RGD

Nutlin 3

NVP-HDM201 (HDM-201)

Idasanutlin (RG-7388)

AM-8553

SAR405838 (MI-773)

Nutlin-3a

AMG232

| | |
|---|---|
| AdWt 20MOI + 200nm JQ1 | 2.20 |
| dl1119 20MOI + 200nm JQ1 | 6.13 |
| Addelta24 20MOI + 200nm JQ1 | 0.73 |
| XVir-N-31 20MOI + 200nm JQ1 | 31.40 |
| AdWt/E2Fm 20MOI + 200nm JQ1 | 4.56 |

TREATMENT OF TUMORS BY A COMBINATION OF AN ONCOLYTIC ADENOVIRUS, A CDK4/6 INHIBITOR AND A FURTHER THERAPEUTICALLY ACTIVE AGENT

SEQUENCE LISTING STATEMENT

The contents of the electronic sequence listing titled Sequence-listing-as-originally-filed.xml (Size: 10,268 bytes; and Date of Creation: Mar. 4, 2022) is herein incorporated by reference in its entirety.

The present invention is related to combination of an oncolytic virus and a CDK4/inhibitor; the use of such combination in the treatment of a disease such as tumor; an oncolytic virus, preferably an oncolytic adenovirus for use in the treatment of a disease such as tumor together with a CDK4/6 inhibitor; and a CDK4/6 inhibitor for use in the treatment of a disease such as tumor together with an oncolytic virus, preferably an oncolytic adenovirus.

A number of therapeutic concepts are currently used in the treatment of tumors. Apart from using surgery, chemotherapy and radiotherapy are predominant. All these techniques are, however, associated with considerable side effects. The use of replication selective oncolytic viruses provides for a new platform for the treatment of tumors. In connection therewith a selective intratumor replication of a viral agent is initiated which results in virus replication, lysis of the infected tumor cell and spreading of the virus to adjacent tumor cells. As the replication capabilities of the virus is limited to tumor cells, normal tissue is spared from replication and thus from lysis by the virus.

The problem underlying the present invention is the provision of means so as to increase the efficacy of tumor therapy based on oncolytic viruses and adenovirus in particular.

These and other problems are solved by the subject matter of the attached independent claims; preferred embodiments may be taken from the attached dependent claims.

The problem underling present invention is also solved in a first aspect, which is also a first embodiment of such first aspect by a combination comprising an adenovirus and a CDK4/6 inhibitor and at least one further agent selected from the group comprising a PARP inhibitor, a bromodomain inhibitor and nutlin or a nutlin derivative.

In the following, further embodiments of such first aspect are disclosed.

Embodiment 2: The combination of Embodiment 1, wherein the adenovirus is an oncolytic adenovirus.

Embodiment 3: The combination of any one of Embodiments 1 and 2, wherein the adenovirus is replicating in a YB-1 dependent manner.

Embodiment 4: The combination of Embodiment 3, wherein the adenovirus is replication deficient in cells which lack YB-1 in the nucleus, but is replicating in cells which have YB-1 in the nucleus.

Embodiment 5: The combination of any one of Embodiments 2 to 4, wherein the adenovirus encodes an oncogene protein, wherein the oncogene protein transactivates at least one adenoviral gene, whereby the adenoviral gene is selected from the group comprising E1B55 kDa, E4orf6, E4orf3 and E3ADP.

Embodiment 6: The combination of Embodiment 5, wherein the oncogene protein is E1A protein.

Embodiment 7: The combination of Embodiment 6, wherein the E1A protein is capable of binding a functional Rb tumor suppressor gene product.

Embodiment 8: The combination of Embodiment 6, wherein the E1A protein is incapable of binding a functional Rb tumor suppressor gene product.

Embodiment 9: The combination of any one of Embodiments 6 to 8, wherein the E1A protein does not induce the localization of YB-1 into the nucleus.

Embodiment 10: The combination of any one of Embodiments 5 to 9, wherein the oncogene protein exhibits one or several mutations or deletions compared to the wildtype oncogene protein E1A.

Embodiment 11: The combination of Embodiment 10, wherein the deletion is one selected from the group comprising deletions of the CR3 stretches and deletions of the N-terminus and deletions of the C-terminus.

Embodiment 12: The combination of any one of Embodiments 6 to 11, wherein the E1A protein is capable of binding to Rb.

Embodiment 13: The combination of any one of Embodiments 6 to 12, wherein the E1A protein comprises one or several mutations or deletions compared to the wildtype oncogene protein, whereby the deletion is preferably a deletion in the CR1 region and/or CR2 region.

Embodiment 14: The combination of Embodiment 13, wherein the E1A protein is incapable of binding to Rb.

Embodiment 15: The combination of any one of Embodiments 1 to 14, wherein the virus is an adenovirus expressing E1A12 S protein.

Embodiment 16: The combination of any one of Embodiments 1 to 15, wherein the virus is an adenovirus lacking expression of E1A13S protein.

Embodiment 17: The combination of any one of Embodiments 1 to 16, wherein the virus is an adenovirus lacking a functionally active adenoviral E3 region.

Embodiment 18: The combination of any one of Embodiments 1 to 17, wherein the virus is an adenovirus lacking expression of E1B 19 kDa protein.

Embodiment 19: The combination of any one of Embodiments 1 to 18, wherein the virus is an adenovirus expressing an RGD motif at a fibre.

Embodiment 20: The combination of any one of Embodiments 1 to 19, wherein the virus is an adenovirus serotype 5.

Embodiment 21: The combination of any one of Embodiment 1 to 20, wherein the adenovirus is selected from the group comprising XVir-N-31, dl520, AdΔ24, AdΔ24-RGD, dl922-947, E1Ad/01/07, dl1119/1131, CB 016, VCN-01, E1Adl1107, E1Adl1101, ORCA-010, Enadenotucirev and viruses lacking an expressed viral oncogene which is capable of binding a functional Rb tumor suppressor gene product.

Embodiment 22: The combination of Embodiment 21, wherein the adenovirus is XVir-N-31.

Embodiment 23: The combination of Embodiment 21, wherein the adenovirus is dl520, wherein the adenoviral E3 region is functionally inactive.

Embodiment 24: The combination of any one of Embodiment 21 to 23, wherein the adenovirus is dl520, wherein dl520 is lacking expression of E1B 19 kDa protein.

Embodiment 25: The combination of any one of Embodiments 21 to 24, wherein the adenovirus is dl520 expressing an RGD motif at a fibre.

Embodiment 26: The combination of any one of Embodiments 1 to 25, wherein the virus encodes YB-1.

Embodiment 27: The combination of Embodiment 26, wherein the gene coding for YB-1 is under the control of a tissue-specific promoter, tumor-specific promoter and/or a YB-1 dependent promoter.

Embodiment 28: The combination of Embodiment 27, wherein the YB-1 dependent promoter is the adenoviral E2 late promoter.

Embodiment 29: The combination of any one of Embodiments 1 to 28, wherein the CDK4/6 inhibitor is a compound which reduces Rb phosphorylation in a cell, preferably a tumor cell.

Embodiment 30: The combination of any one of Embodiments 1 to 29, wherein the CDK4/6 inhibitor is a compound which reduces Rb expression in a cell, preferably a tumor cell.

Embodiment 31: The combination of any one of Embodiments 1 to 30, wherein the CDK4/6 inhibitor is selected from the group comprising palbociclib which is also referred to as PD 0332991, abemaciclib which is also referred to as LY-2835219, ribociclib which is also referred to as LEE011, Trilaciclib which is also referred to as G1T28, and Dinaciclib.

Embodiment 32: The combination of any one of Embodiments 1 to 31, wherein the CDK4/6 inhibitor causes G1 arrest in a cell and inhibits E2F1.

Embodiment 33: The combination of any one of Embodiments 1 to 32, wherein the composition further comprises a PARP inhibitor.

Embodiment 34: The combination of Embodiment 33, wherein the PARP inhibitor is selected from the group comprising olaparib, veliparib, rucaparib and BMN673.

Embodiment 35: The combination of any one of Embodiments 1 to 32, wherein the composition further comprises a bromodomain inhibitor.

Embodiment 36: The combination of Embodiment 35, wherein the bromodomain inhibitor is selected from the group comprising JQ-1, OTX-015, I-BET151, CPI-0610, I-BET762, CPI203, PFI-1 and MS 436.

Embodiment 37: The combination of any one of Embodiments 1 to 36, wherein the composition further comprises a nutlin or a derivative thereof.

Embodiment 38: The composition of Embodiment 37, wherein the nutlin is nutlin-3.

Embodiment 39: The composition of any one of Embodiments 37 and 38, wherein the derivative of nutlin is selected from the group comprising NVP-HDM201, Idasanutlin, AM-8553, SAR405838, Nutlin-3a, AMG232.

Embodiment 40: The combination of any one of embodiments 1 to 39, wherein the constituents of the combination are for separate administration.

Embodiment 41: The combination of any one of embodiments 1 to 39, wherein the constituents of the combination are for combined administration.

The problem underling present invention is also solved in a second aspect, which is also a first embodiment of such second aspect by the combination according to the first aspect, including any embodiments thereof, for use in the treatment of a diseases, more preferably a tumor or cancer. comprising an adenovirus and a CDK4/6 inhibitor.

In the following, further embodiments of such second aspect are disclosed.

Embodiment 1: A combination comprising an adenovirus and a CDK4/6 inhibitor for use in a method for the treatment and/or prevention of a disease, preferably a tumor or cancer.

Embodiment 2: The combination for use of Embodiment 1, wherein the adenovirus is an oncolytic adenovirus.

Embodiment 3: The combination of for use any one of Embodiments 1 and 2, wherein the adenovirus is replicating in a YB-1 dependent manner.

Embodiment 4: The combination for use of Embodiment 3, wherein the adenovirus is replication deficient in cells which lack YB-1 in the nucleus, but is replicating in cells which have YB-1 in the nucleus.

Embodiment 5: The combination for use of any one of Embodiments 2 to 4, wherein the adenovirus encodes an oncogene protein, wherein the oncogene protein transactivates at least one adenoviral gene, whereby the adenoviral gene is selected from the group comprising E1B55 kDa, E4orf6, E4orf3 and E3ADP.

Embodiment 6: The combination for use of Embodiment 5, wherein the oncogene protein is E1A protein.

Embodiment 7: The combination for use of Embodiment 6, wherein the E1A protein is capable of binding a functional Rb tumor suppressor gene product.

Embodiment 8: The combination for use of Embodiment 6, wherein the E1A protein is incapable of binding a functional Rb tumor suppressor gene product.

Embodiment 9: The combination for use of any one of Embodiments 6 to 8, wherein the E1A protein does not induce the localization of YB-1 into the nucleus.

Embodiment 10: The combination for use of any one of Embodiments 5 to 9, wherein the oncogene protein exhibits one or several mutations or deletions compared to the wildtype oncogene protein E1A.

Embodiment 11: The combination for use of Embodiment 10, wherein the deletion is one selected from the group comprising deletions of the CR3 stretches and deletions of the N-terminus and deletions of the C-terminus.

Embodiment 12: The combination for use of any one of Embodiments 6 to 11, wherein the E1A protein is capable of binding to Rb.

Embodiment 13: The combination for use of any one of Embodiments 6 to 12, wherein the E1A protein comprises one or several mutations or deletions compared to the wildtype oncogene protein, whereby the deletion is preferably a deletion in the CR1 region and/or CR2 region.

Embodiment 14: The combination for use of Embodiment 13, wherein the E1A protein is incapable of binding to Rb.

Embodiment 15: The combination for use of any one of Embodiments 1 to 14, wherein the virus is an adenovirus expressing E1A12 S protein.

Embodiment 16: The combination for use of any one of Embodiments 1 to 15, wherein the virus is an adenovirus lacking expression of E1A13S protein.

Embodiment 17: The combination for use of any one of Embodiments 1 to 16, wherein the virus is an adenovirus lacking a functionally active adenoviral E3 region.

Embodiment 18: The combination for use of any one of Embodiments 1 to 17, wherein the virus is an adenovirus lacking expression of E1B 19 kDa protein.

Embodiment 19: The combination for use of any one of Embodiments 1 to 18, wherein the virus is an adenovirus expressing an RGD motif at a fibre.

Embodiment 20: The combination for use of any one of Embodiments 1 to 19, wherein the virus is an adenovirus serotype 5.

Embodiment 21: The combination for use of any one of Embodiment 1 to 20, wherein the adenovirus is selected from the group comprising XVir-N-31, dl520, AdΔ24, AdΔ24-RGD, dl922-947, E1Ad/01/07, dl1119/1131, CB 016, VCN-01, E1Adl1107, E1Adl1101, ORCA-010, Enadenotucirev and viruses lacking an expressed viral oncogene which is capable of binding a functional Rb tumor suppressor gene product.

Embodiment 22: The combination for use of Embodiment 21, wherein the adenovirus is XVir-N-31.

Embodiment 23: The combination for use of Embodiment 21, wherein the adenovirus is dl520, wherein the adenoviral E3 region is functionally inactive.

Embodiment 24: The combination for use of any one of Embodiment 21 to 23, wherein the adenovirus is dl520, wherein dl520 is lacking expression of E1B 19 kDa protein.

Embodiment 25: The combination for use of any one of Embodiments 21 to 24, wherein the adenovirus is dl520 expressing an RGD motif at a fibre.

Embodiment 26: The combination for use of any one of Embodiments 1 to 25, wherein the virus encodes YB-1.

Embodiment 27: The combination for use of Embodiment 26, wherein the gene coding for YB-1 is under the control of a tissue-specific promoter, tumor-specific promoter and/or a YB-1 dependent promoter.

Embodiment 28: The combination for use of Embodiment 27, wherein the YB-1 dependent promoter is the adenoviral E2 late promoter.

Embodiment 29: The combination for use of any one of Embodiments 1 to 28, wherein the CDK4/6 inhibitor is a compound which reduces Rb phosphorylation in a cell, preferably a tumor cell.

Embodiment 30: The combination for use of any one of Embodiments 1 to 29, wherein the CDK4/6 inhibitor is a compound which reduces Rb expression in a cell, preferably a tumor cell.

Embodiment 31: The combination for use of any one of Embodiments 1 to 30, wherein the CDK4/6 inhibitor is selected from the group comprising palbociclib which is also referred to as PD 0332991, abemaciclib which is also referred to as LY-2835219, ribociclib which is also referred to as LEE011, Trilaciclib which is also referred to as G1T28, and Dinaciclib.

Embodiment 32: The combination for use of any one of Embodiments 1 to 31, wherein the CDK4/6 inhibitor causes G1 arrest in a cell and inhibits E2F1.

Embodiment 33: The combination for use of any one of Embodiments 1 to 32, wherein the composition further comprises a PARP inhibitor.

Embodiment 34: The combination for use of Embodiment 33, wherein the PARP inhibitor is selected from the group comprising olaparib, veliparib, rucaparib and BMN673.

Embodiment 35: The combination for use of any one of Embodiments 1 to 32, wherein the composition further comprises a bromodomain inhibitor.

Embodiment 36: The combination for use of Embodiment 35, wherein the bromodomain inhibitor is selected from the group comprising JQ-1, OTX-015, I-BET151, CPI-0610, I-BET762, CPI203, PFI-1 and MS 436.

Embodiment 37: The combination for use of any one of embodiments 1 to 36, wherein the constituents of the combination are for separate administration.

Embodiment 38: The combination for use of any one of Embodiments 1 to 37, wherein cells of the tumor have a disruption of the CDK4/6 signaling pathway.

Embodiment 39: The combination for use of any one of Embodiments 1 to 38, wherein cells of the tumor have an uncontrolled G1-S transition of the cell cycle.

Embodiment 40: The combination for use of any one of Embodiments 1 to 38, wherein cells of the tumor have a loss of function mutation or a deletion in a gene selected from the group comprising RB1 gene, CDKN2A gene and CDKN2B gene.

Embodiment 41: The combination for use of any one of Embodiments 1 to 38, wherein cells of the tumor have an amplification of a gene and/or an activating mutation in a gene.

Embodiment 42: The combination for use of Embodiment 41, wherein the gene is selected from the group comprising CCND1, E2F1, E2F2, E2F3, CDK4 and CDK6.

Embodiment 43: The combination for use of Embodiment 41, wherein the gene is one coding for a component of a mitogenic signaling pathway.

Embodiment 44. The combination for use of Embodiment 43, wherein the mitogenic signaling pathway is selected from the group comprising the PI3K pathway and the MAPK pathway.

Embodiment 45. The combination for use of any one of Embodiment 1 to 44, wherein the cells of the tumor cells have a resistance to or are insensitive to one or several pharmaceutically active agents and/or radiation.

Embodiment 46: The combination for use of Embodiment 45, wherein the pharmaceutically active agent is a cytostatic.

Embodiment 47: The combination for use of claim 46, wherein the resistance is mediated by an ABC transporter.

Embodiment 48: The combination for use of claim 47, wherein the ABC transporter is selected from the group comprising MRP and MDR, in particular MDR-1.

Embodiment 49: The combination for use of any one of embodiments 45 to 48, wherein the resistance is a multiple resistance or polyresistance, particular a multiple or polyresistance against a cytostatic and/or radiation.

Embodiment 50: The combination for use of any one of Embodiments 1 to 49, wherein the cells of the tumor are Rb-positive.

Embodiment 51: The combination for use of any one of Embodiments 1 to 50, wherein the cells of the tumor have YB-1 in the nucleus.

Embodiment 52: The combination for use of any one of Embodiments 1 to 51, wherein the cells of the tumor have YB-1 in the nucleus after induction.

Embodiment 53: The combination for use of Embodiment 52, wherein the transport of YB-1 into the nucleus is triggered by at least one measure selected from the group comprising irradiation, administration of cytostatics and hyperthermia.

Embodiment 54: The combination for use of Embodiment 53, wherein the measure is applied to a cell, an organ or an organism, preferably an organism in need thereof, more preferably an organism suffering from the tumor.

Embodiment 55: The combination for use of any one of claims 1 to 54, wherein the tumor is selected from the group comprising bladder cancer, breast cancer, metastatic breast cancer (mBC), melanoma, glioma, pancreatic cancer, hepatocellular carcinoma, lung adenocarcinoma, sarcoma, ovarian cancer, renal cancer, prostate cancer, and leukemia.

The problem underling present invention is also solved in a third aspect, which is also a first embodiment of such third aspect by an adenovirus for use in the treatment and/or prevention of a diseases in a subject, more preferably a tumor or cancer, wherein the method comprises administering to the subject an adenovirus and a CDK4/6 inhibitor.

In the following, further embodiments of such third aspect are disclosed.

Embodiment 2: The adenovirus for use of Embodiment 1, wherein the adenovirus is an oncolytic adenovirus.

Embodiment 3: The adenovirus of for use any one of Embodiments 1 and 2, wherein the adenovirus is replicating in a YB-1 dependent manner.

Embodiment 4: The adenovirus for use of Embodiment 3, wherein the adenovirus is replication deficient in cells which lack YB-1 in the nucleus, but is replicating in cells which have YB-1 in the nucleus.

Embodiment 5: The adenovirus for use of any one of Embodiments 2 to 4, wherein the adenovirus encodes an oncogene protein, wherein the oncogene protein transactivates at least one adenoviral gene, whereby the adenoviral gene is selected from the group comprising E1B55 kDa, E4orf6, E4orf3 and E3ADP.

Embodiment 6: The adenovirus for use of Embodiment 5, wherein the oncogene protein is E1A protein.

Embodiment 7: The adenovirus for use of Embodiment 6, wherein the E1A protein is capable of binding a functional Rb tumor suppressor gene product.

Embodiment 8: The adenovirus for use of Embodiment 6, wherein the E1A protein is incapable of binding a functional Rb tumor suppressor gene product.

Embodiment 9: The adenovirus for use of any one of Embodiments 6 to 8, wherein the E1A protein does not induce the localization of YB-1 into the nucleus.

Embodiment 10: The adenovirus for use of any one of Embodiments 5 to 9, wherein the oncogene protein exhibits one or several mutations or deletions compared to the wildtype oncogene protein E1A.

Embodiment 11: The adenovirus for use of Embodiment 10, wherein the deletion is one selected from the group comprising deletions of the CR3 stretches and deletions of the N-terminus and deletions of the C-terminus.

Embodiment 12: The adenovirus for use of any one of Embodiments 6 to 11, wherein the E1A protein is capable of binding to Rb.

Embodiment 13: The adenovirus for use of any one of Embodiments 6 to 12, wherein the E1A protein comprises one or several mutations or deletions compared to the wildtype oncogene protein, whereby the deletion is preferably a deletion in the CR1 region and/or CR2 region.

Embodiment 14: The adenovirus for use of Embodiment 13, wherein the E1A protein is incapable of binding to Rb.

Embodiment 15: The adenovirus for use of any one of Embodiments 1 to 14, wherein the virus is an adenovirus expressing E1A12 S protein.

Embodiment 16: The adenovirus for use of any one of Embodiments 1 to 15, wherein the virus is an adenovirus lacking expression of E1A13S protein.

Embodiment 17: The adenovirus for use of any one of Embodiments 1 to 16, wherein the virus is an adenovirus lacking a functionally active adenoviral E3 region.

Embodiment 18: The adenovirus for use of any one of Embodiments 1 to 17, wherein the virus is an adenovirus lacking expression of E1B 19 kDa protein.

Embodiment 19: The adenovirus for use of any one of Embodiments 1 to 18, wherein the virus is an adenovirus expressing an RGD motif at a fibre.

Embodiment 20: The adenovirus for use of any one of Embodiments 1 to 19, wherein the virus is an adenovirus serotype 5.

Embodiment 21: The adenovirus for use of any one of Embodiment 1 to 20, wherein the adenovirus is selected from the group comprising XVir-N-31, dl520, AdΔ24, AdΔ24-RGD, dl922-947, E1Ad/01/07, dl1119/1131, CB 016, VCN-01, E1Adl1107, E1Adl1101, ORCA-010, Enadenotucirev and viruses lacking an expressed viral oncogene which is capable of binding a functional Rb tumor suppressor gene product.

Embodiment 22: The adenovirus for use of Embodiment 21, wherein the adenovirus is XVir-N-31.

Embodiment 23: The adenovirus for use of Embodiment 21, wherein the adenovirus is dl520, wherein the adenoviral E3 region is functionally inactive.

Embodiment 24: The adenovirus for use of any one of Embodiment 21 to 23, wherein the adenovirus is dl520, wherein dl520 is lacking expression of E1B 19 kDa protein.

Embodiment 25: The adenovirus for use of any one of Embodiments 21 to 24, wherein the adenovirus is dl520 expressing an RGD motif at a fibre.

Embodiment 26: The adenovirus for use of any one of Embodiments 1 to 25, wherein the virus encodes YB-1.

Embodiment 27: The adenovirus for use of Embodiment 26, wherein the gene coding for YB-1 is under the control of a tissue-specific promoter, tumor-specific promoter and/or a YB-1 dependent promoter.

Embodiment 28: The adenovirus for use of Embodiment 27, wherein the YB-1 dependent promoter is the adenoviral E2 late promoter.

Embodiment 29: The adenovirus for use of any one of Embodiments 1 to 28, wherein the CDK4/6 inhibitor is a compound which reduces Rb phosphorylation in a cell, preferably a tumor cell.

Embodiment 30: The adenovirus for use of any one of Embodiments 1 to 29, wherein the CDK4/6 inhibitor is a compound which reduces Rb expression in a cell, preferably a tumor cell.

Embodiment 31: The adenovirus for use of any one of Embodiments 1 to 30, wherein the CDK4/6 inhibitor is selected from the group comprising palbociclib which is also referred to as PD 0332991, abemaciclib which is also referred to as LY-2835219, ribociclib which is also referred to as LEE011, Trilaciclib which is also referred to as G1T28, and Dinaciclib.

Embodiment 32: The adenovirus for use of any one of Embodiments 1 to 31, wherein the CDK4/6 inhibitor causes G1 arrest in a cell and inhibits E2F1.

Embodiment 33: The adenovirus for use of any one of Embodiments 1 to 32, wherein the method further comprises administering a PARP inhibitor to the subject.

Embodiment 34: The adenovirus for use of Embodiment 33, wherein the PARP inhibitor is selected from the group comprising olaparib, veliparib, rucaparib and BMN673.

Embodiment 35: The adenovirus for use of any one of Embodiments 1 to 32, wherein the method further comprises administering a bromodomain inhibitor to the subject.

Embodiment 36: The adenovirus for use of Embodiment 35, wherein the bromodomain inhibitor is selected from the group comprising JQ-1, OTX-015, I-BET151, CPI-0610, I-BET762, CPI203, PFI-1 and MS 436.

Embodiment 37: The adenovirus for use of any one of embodiments 1 to 36, wherein the adenovirus, the CDK4/6 inhibitor, the PARP inhibitor and/or the bromodomain inhibitor are administered to the subject separately or as any combination.

Embodiment 38: The adenovirus for use of any one of Embodiments 1 to 37, wherein cells of the tumor have a disruption of the CDK4/6 signaling pathway.

Embodiment 39: The adenovirus for use of any one of Embodiments 1 to 38, wherein cells of the tumor have an uncontrolled G1-S transition of the cell cycle.

Embodiment 40: The adenovirus for use of any one of Embodiments 1 to 38, wherein cells of the tumor have a loss of function mutation or a deletion in a gene selected from the group comprising RB1 gene, CDKN2A gene and CDKN2B gene.

Embodiment 41: The adenovirus for use of any one of Embodiments 1 to 38, wherein cells of the tumor have an amplification of a gene and/or an activating mutation in a gene.

Embodiment 42: The adenovirus for use of Embodiment 41, wherein the gene is selected from the group comprising CCND1, E2F1, E2F2, E2F3, CDK4 and CDK6.

Embodiment 43: The adenovirus for use of Embodiment 41, wherein the gene is one coding for a component of a mitogenic signaling pathway.

Embodiment 44. The adenovirus for use of Embodiment 43, wherein the mitogenic signaling pathway is selected from the group comprising the PI3K pathway and the MAPK pathway.

Embodiment 45. The adenovirus for use of any one of Embodiment 1 to 44, wherein the cells of the tumor cells have a resistance to or are insensitive to one or several pharmaceutically active agents and/or radiation.

Embodiment 46: The adenovirus for use of Embodiment 45, wherein the pharmaceutically active agent is a cytostatic.

Embodiment 47: The adenovirus for use of claim 46, wherein the resistance is mediated by an ABC transporter.

Embodiment 48: The adenovirus for use of claim 47, wherein the ABC transporter is selected from the group comprising MRP and MDR, in particular MDR-1.

Embodiment 49: The adenovirus for use of any one of embodiments 45 to 48, wherein the resistance is a multiple resistance or polyresistance, particular a multiple or polyresistance against a cytostatic and/or radiation.

Embodiment 50: The adenovirus for use of any one of Embodiments 1 to 49, wherein the cells of the tumor are Rb-positive.

Embodiment 51: The adenovirus for use of any one of Embodiments 1 to 50, wherein the cells of the tumor have YB-1 in the nucleus.

Embodiment 52: The adenovirus for use of any one of Embodiments 1 to 51, wherein the cells of the tumor have YB-1 in the nucleus after induction.

Embodiment 53: The adenovirus for use of Embodiment 52, wherein the transport of YB-1 into the nucleus is triggered by at least one measure selected from the group comprising irradiation, administration of cytostatics and hyperthermia.

Embodiment 54: The adenovirus for use of Embodiment 53, wherein the measure is applied to a cell, an organ or an organism, preferably an organism in need thereof, more preferably an organism suffering from the tumor.

Embodiment 55: The adenovirus for use of any one of claims 1 to 54, wherein the tumor is selected from the group comprising bladder cancer, breast cancer, metastatic breast cancer (mBC), melanoma, glioma, pancreatic cancer, hepatocellular carcinoma, lung adenocarcinoma, sarcoma, ovarian cancer, renal cancer, prostate cancer, and leukemia.

The problem underling present invention is also solved in a fourth aspect, which is also a first embodiment of such fourth aspect by a CDK4/6 inhibitor for use in the treatment and/or prevention of a diseases in a subject, more preferably a tumor or cancer, wherein the method comprises administering to the subject an adenovirus and a CDK4/6 inhibitor.

In the following, further embodiments of such fourth aspect are disclosed.

Embodiment 2: The CDK4/6 inhibitor for use of Embodiment 1, wherein the adenovirus is an oncolytic adenovirus.

Embodiment 3: The CDK4/6 inhibitor of for use any one of Embodiments 1 and 2, wherein the adenovirus is replicating in a YB-1 dependent manner.

Embodiment 4: The CDK4/6 inhibitor for use of Embodiment 3, wherein the adenovirus is replication deficient in cells which lack YB-1 in the nucleus, but is replicating in cells which have YB-1 in the nucleus.

Embodiment 5: The CDK4/6 inhibitor for use of any one of Embodiments 2 to 4, wherein the adenovirus encodes an oncogene protein, wherein the oncogene protein transactivates at least one adenoviral gene, whereby the adenoviral gene is selected from the group comprising E1B55 kDa, E4orf6, E4orf3 and E3ADP.

Embodiment 6: The CDK4/6 inhibitor for use of Embodiment 5, wherein the oncogene protein is E1A protein.

Embodiment 7: The CDK4/6 inhibitor for use of Embodiment 6, wherein the E1A protein is capable of binding a functional Rb tumor suppressor gene product.

Embodiment 8: The CDK4/6 inhibitor for use of Embodiment 6, wherein the E1A protein is incapable of binding a functional Rb tumor suppressor gene product.

Embodiment 9: The CDK4/6 inhibitor for use of any one of Embodiments 6 to 8, wherein the E1A protein does not induce the localization of YB-1 into the nucleus.

Embodiment 10: The CDK4/6 inhibitor for use of any one of Embodiments 5 to 9, wherein the oncogene protein exhibits one or several mutations or deletions compared to the wildtype oncogene protein E1A.

Embodiment 11: The CDK4/6 inhibitor for use of Embodiment 10, wherein the deletion is one selected from the group comprising deletions of the CR3 stretches and deletions of the N-terminus and deletions of the C-terminus.

Embodiment 12: The CDK4/6 inhibitor for use of any one of Embodiments 6 to 11, wherein the E1A protein is capable of binding to Rb.

Embodiment 13: The CDK4/6 inhibitor for use of any one of Embodiments 6 to 12, wherein the E1A protein comprises one or several mutations or deletions compared to the wildtype oncogene protein, whereby the deletion is preferably a deletion in the CR1 region and/or CR2 region.

Embodiment 14: The CDK4/6 inhibitor for use of Embodiment 13, wherein the E1A protein is incapable of binding to Rb.

Embodiment 15: The CDK4/6 inhibitor for use of any one of Embodiments 1 to 14, wherein the virus is an adenovirus expressing E1A12 S protein.

Embodiment 16: The CDK4/6 inhibitor for use of any one of Embodiments 1 to 15, wherein the virus is an adenovirus lacking expression of E1A13S protein.

Embodiment 17: The CDK4/6 inhibitor for use of any one of Embodiments 1 to 16, wherein the virus is an adenovirus lacking a functionally active adenoviral E3 region.

Embodiment 18: The CDK4/6 inhibitor for use of any one of Embodiments 1 to 17, wherein the virus is an adenovirus lacking expression of E1B 19 kDa protein.

Embodiment 19: The CDK4/6 inhibitor for use of any one of Embodiments 1 to 18, wherein the virus is an adenovirus expressing an RGD motif at a fibre.

Embodiment 20: The CDK4/6 inhibitor for use of any one of Embodiments 1 to 19, wherein the virus is an adenovirus serotype 5.

Embodiment 21: The CDK4/6 inhibitor for use of any one of Embodiment 1 to 20, wherein the adenovirus is selected from the group comprising XVir-N-31, dl520, AdΔ24, AdΔ24-RGD, dl922-947, E1Ad/01/07, dl1119/1131, CB 016, VCN-01, E1Adl1107, E1Adl1101, ORCA-010, Enadenotucirev and viruses lacking an expressed viral oncogene which is capable of binding a functional Rb tumor suppressor gene product.

Embodiment 22: The CDK4/6 inhibitor for use of Embodiment 21, wherein the adenovirus is XVir-N-31.

Embodiment 23: The CDK4/6 inhibitor for use of Embodiment 21, wherein the adenovirus is dl520, wherein the adenoviral E3 region is functionally inactive.

Embodiment 24: The CDK4/6 inhibitor for use of any one of Embodiment 21 to 23, wherein the adenovirus is dl520, wherein dl520 is lacking expression of E1B 19 kDa protein.

Embodiment 25: The CDK4/6 inhibitor for use of any one of Embodiments 21 to 24, wherein the adenovirus is dl520 expressing an RGD motif at a fibre.

Embodiment 26: The CDK4/6 inhibitor for use of any one of Embodiments 1 to 25, wherein the virus encodes YB-1.

Embodiment 27: The CDK4/6 inhibitor for use of Embodiment 26, wherein the gene coding for YB-1 is under the control of a tissue-specific promoter, tumor-specific promoter and/or a YB-1 dependent promoter.

Embodiment 28: The CDK4/6 inhibitor for use of Embodiment 27, wherein the YB-1 dependent promoter is the adenoviral E2 late promoter.

Embodiment 29: The CDK4/6 inhibitor for use of any one of Embodiments 1 to 28, wherein the CDK4/6 inhibitor is a compound which reduces Rb phosphorylation in a cell, preferably a tumor cell.

Embodiment 30: The CDK4/6 inhibitor for use of any one of Embodiments 1 to 29, wherein the CDK4/6 inhibitor is a compound which reduces Rb expression in a cell, preferably a tumor cell.

Embodiment 31: The CDK4/6 inhibitor for use of any one of Embodiments 1 to 30, wherein the CDK4/6 inhibitor is selected from the group comprising palbociclib which is also referred to as PD 0332991, abemaciclib which is also referred to as LY-2835219, ribociclib which is also referred to as LEE011, Trilaciclib which is also referred to as G1T28, and Dinaciclib.

Embodiment 32: The CDK4/6 inhibitor for use of any one of Embodiments 1 to 31, wherein the CDK4/6 inhibitor causes G1 arrest in a cell and inhibits E2F1.

Embodiment 33: The CDK4/6 inhibitor for use of any one of Embodiments 1 to 32, wherein the method further comprises administering a PARP inhibitor to the subject.

Embodiment 34: The CDK4/6 inhibitor for use of Embodiment 33, wherein the PARP inhibitor is selected from the group comprising olaparib, veliparib, rucaparib and BMN673.

Embodiment 35: The CDK4/6 inhibitor for use of any one of Embodiments 1 to 32, wherein the method further comprises administering a bromodomain inhibitor to the subject.

Embodiment 36: The CDK4/6 inhibitor for use of Embodiment 35, wherein the bromodomain inhibitor is selected from the group comprising JQ-1, OTX-015, I-BET151, CPI-0610, I-BET762, CPI203, PFI-1 and MS 436.

Embodiment 37: The CDK4/6 inhibitor for use of any one of embodiments 1 to 36, wherein the adenovirus, the CDK4/6 inhibitor, the PARP inhibitor and/or the bromodomain inhibitor are administered to the subject separately or as any combination.

Embodiment 38: The CDK4/6 inhibitor for use of any one of Embodiments 1 to 37, wherein cells of the tumor have a disruption of the CDK4/6 signaling pathway.

Embodiment 39: The CDK4/6 inhibitor for use of any one of Embodiments 1 to 38, wherein cells of the tumor have an uncontrolled G1-S transition of the cell cycle.

Embodiment 40: The CDK4/6 inhibitor for use of any one of Embodiments 1 to 38, wherein cells of the tumor have a loss of function mutation or a deletion in a gene selected from the group comprising RB1 gene, CDKN2A gene and CDKN2B gene.

Embodiment 41: The CDK4/6 inhibitor for use of any one of Embodiments 1 to 38, wherein cells of the tumor have an amplification of a gene and/or an activating mutation in a gene.

Embodiment 42: The CDK4/6 inhibitor for use of Embodiment 41, wherein the gene is selected from the group comprising CCND1, E2F1, E2F2, E2F3, CDK4 and CDK6.

Embodiment 43: The CDK4/6 inhibitor for use of Embodiment 41, wherein the gene is one coding for a component of a mitogenic signaling pathway.

Embodiment 44. The CDK4/6 inhibitor for use of Embodiment 43, wherein the mitogenic signaling pathway is selected from the group comprising the PI3K pathway and the MAPK pathway.

Embodiment 45. The CDK4/6 inhibitor for use of any one of Embodiment 1 to 44, wherein the cells of the tumor cells have a resistance to or are insensitive to one or several pharmaceutically active agents and/or radiation.

Embodiment 46: The CDK4/6 inhibitor for use of Embodiment 45, wherein the pharmaceutically active agent is a cytostatic.

Embodiment 47: The CDK4/6 inhibitor for use of claim 46, wherein the resistance is mediated by an ABC transporter.

Embodiment 48: The CDK4/6 inhibitor for use of claim 47, wherein the ABC transporter is selected from the group comprising MRP and MDR, in particular MDR-1.

Embodiment 49: The CDK4/6 inhibitor for use of any one of embodiments 45 to 48, wherein the resistance is a multiple resistance or polyresistance, particular a multiple or polyresistance against a cytostatic and/or radiation.

Embodiment 50: The CDK4/6 inhibitor for use of any one of Embodiments 1 to 49, wherein the cells of the tumor are Rb-positive.

Embodiment 51: The CDK4/6 inhibitor for use of any one of Embodiments 1 to 50, wherein the cells of the tumor have YB-1 in the nucleus.

Embodiment 52: The CDK4/6 inhibitor for use of any one of Embodiments 1 to 51, wherein the cells of the tumor have YB-1 in the nucleus after induction.

Embodiment 53: The CDK4/6 inhibitor for use of Embodiment 52, wherein the transport of YB-1 into the nucleus is triggered by at least one measure selected from the group comprising irradiation, administration of cytostatics and hyperthermia.

Embodiment 54: The CDK4/6 inhibitor for use of Embodiment 53, wherein the measure is applied to a cell, an organ or an organism, preferably an organism in need thereof, more preferably an organism suffering from the tumor.

Embodiment 55: The CDK4/6 inhibitor for use of any one of claims 1 to 54, wherein the tumor is selected from the group comprising bladder cancer, breast cancer, metastatic breast cancer (mBC), melanoma, glioma, pancreatic cancer, hepatocellular carcinoma, lung adenocarcinoma, sarcoma, ovarian cancer, renal cancer, prostate cancer, and leukemia.

The problem underling present invention is also solved in a fifth aspect, which is also a first embodiment of such fifth aspect by a PARP inhibitor for use in the treatment and/or prevention of a diseases in a subject, more preferably a tumor or cancer, wherein the method comprises administering to the subject an adenovirus, a CDK4/6 inhibitor and a PARP inhibitor.

In the following, further embodiments of such fifth aspect are disclosed.

Embodiment 2: The PARP inhibitor for use of Embodiment 1, wherein the adenovirus is an oncolytic adenovirus.

Embodiment 3: The PARP inhibitor of for use any one of Embodiments 1 and 2, wherein the adenovirus is replicating in a YB-1 dependent manner.

Embodiment 4: The PARP inhibitor for use of Embodiment 3, wherein the adenovirus is replication deficient in cells which lack YB-1 in the nucleus, but is replicating in cells which have YB-1 in the nucleus.

Embodiment 5: The PARP inhibitor for use of any one of Embodiments 2 to 4, wherein the adenovirus encodes an oncogene protein, wherein the oncogene protein transactivates at least one adenoviral gene, whereby the adenoviral gene is selected from the group comprising E1B55 kDa, E4orf6, E4orf3 and E3ADP.

Embodiment 6: The PARP inhibitor for use of Embodiment 5, wherein the oncogene protein is E1A protein.

Embodiment 7: The PARP inhibitor for use of Embodiment 6, wherein the E1A protein is capable of binding a functional Rb tumor suppressor gene product.

Embodiment 8: The PARP inhibitor for use of Embodiment 6, wherein the E1A protein is incapable of binding a functional Rb tumor suppressor gene product.

Embodiment 9: The PARP inhibitor for use of any one of Embodiments 6 to 8, wherein the E1A protein does not induce the localization of YB-1 into the nucleus.

Embodiment 10: The PARP inhibitor for use of any one of Embodiments 5 to 9, wherein the oncogene protein exhibits one or several mutations or deletions compared to the wildtype oncogene protein E1A.

Embodiment 11: The PARP inhibitor for use of Embodiment 10, wherein the deletion is one selected from the group comprising deletions of the CR3 stretches and deletions of the N-terminus and deletions of the C-terminus.

Embodiment 12: The PARP inhibitor for use of any one of Embodiments 6 to 11, wherein the E1A protein is capable of binding to Rb.

Embodiment 13: The PARP inhibitor for use of any one of Embodiments 6 to 12, wherein the E1A protein comprises one or several mutations or deletions compared to the wildtype oncogene protein, whereby the deletion is preferably a deletion in the CR1 region and/or CR2 region.

Embodiment 14: The PARP inhibitor for use of Embodiment 13, wherein the E1A protein is incapable of binding to Rb.

Embodiment 15: The PARP inhibitor for use of any one of Embodiments 1 to 14, wherein the virus is an adenovirus expressing E1A12 S protein.

Embodiment 16: The PARP inhibitor for use of any one of Embodiments 1 to 15, wherein the virus is an adenovirus lacking expression of E1A13S protein.

Embodiment 17: The PARP inhibitor for use of any one of Embodiments 1 to 16, wherein the virus is an adenovirus lacking a functionally active adenoviral E3 region.

Embodiment 18: The PARP inhibitor for use of any one of Embodiments 1 to 17, wherein the virus is an adenovirus lacking expression of E1B 19 kDa protein.

Embodiment 19: The PARP inhibitor for use of any one of Embodiments 1 to 18, wherein the virus is an adenovirus expressing an RGD motif at a fibre.

Embodiment 20: The PARP inhibitor for use of any one of Embodiments 1 to 19, wherein the virus is an adenovirus serotype 5.

Embodiment 21: The PARP inhibitor for use of any one of Embodiment 1 to 20, wherein the adenovirus is selected from the group comprising XVir-N-31, dl520, AdΔ24, AdΔ24-RGD, dl922-947, E1Ad/01/07, dl1119/1131, CB 016, VCN-01, E1Adl1107, E1Adl1101, ORCA-010, Enadenotucirev and viruses lacking an expressed viral oncogene which is capable of binding a functional Rb tumor suppressor gene product.

Embodiment 22: The PARP inhibitor for use of Embodiment 21, wherein the adenovirus is XVir-N-31.

Embodiment 23: The PARP inhibitor for use of Embodiment 21, wherein the adenovirus is dl520, wherein the adenovirual E3 region is functionally inactive.

Embodiment 24: The PARP inhibitor for use of any one of Embodiment 21 to 23, wherein the adenovirus is dl520, wherein dl520 is lacking expression of E1B 19 kDa protein.

Embodiment 25: The PARP inhibitor for use of any one of Embodiments 21 to 24, wherein the adenovirus is dl520 expressing an RGD motif at a fibre.

Embodiment 26: The PARP inhibitor for use of any one of Embodiments 1 to 25, wherein the virus encodes YB-1.

Embodiment 27: The PARP inhibitor for use of Embodiment 26, wherein the gene coding for YB-1 is under the control of a tissue-specific promoter, tumor-specific promoter and/or a YB-1 dependent promoter.

Embodiment 28: The PARP inhibitor for use of Embodiment 27, wherein the YB-1 dependent promoter is the adenoviral E2 late promoter.

Embodiment 29: The PARP inhibitor for use of any one of Embodiments 1 to 28, wherein the CDK4/6 inhibitor is a compound which reduces Rb phosphorylation in a cell, preferably a tumor cell.

Embodiment 30: The PARP inhibitor for use of any one of Embodiments 1 to 29, wherein the CDK4/6 inhibitor is a compound which reduces Rb expression in a cell, preferably a tumor cell.

Embodiment 31: The PARP inhibitor for use of any one of Embodiments 1 to 30, wherein the CDK4/6 inhibitor is selected from the group comprising palbociclib which is also referred to as PD 0332991, abemaciclib which is also referred to as LY-2835219, ribociclib which is also referred to as LEE011, Trilaciclib which is also referred to as G1T28, and Dinaciclib.

Embodiment 32: The PARP inhibitor for use of any one of Embodiments 1 to 31, wherein the CDK4/6 inhibitor causes G1 arrest in a cell and inhibits E2F1.

Embodiment 33: The PARP inhibitor for use of any one of Embodiments 1 to 32, wherein the method further comprises administering a PARP inhibitor to the subject.

Embodiment 34: The PARP for use of Embodiment 33, wherein the PARP inhibitor is selected from the group comprising olaparib, veliparib, rucaparib and BMN673.

Embodiment 35: The PARP inhibitor for use of any one of Embodiments 1 to 32, wherein the method further comprises administering a bromodomain inhibitor to the subject.

Embodiment 36: The PARP inhibitor for use of Embodiment 35, wherein the bromodomain inhibitor is selected from the group comprising JQ-1, OTX-015, I-BET151, CPI-0610, I-BET762, CPI203, PFI-1 and MS 436.

Embodiment 37: The PARP inhibitor for use of any one of embodiments 1 to 36, wherein the adenovirus, the CDK4/6 inhibitor, the PARP inhibitor and/or the bromodomain inhibitor are administered to the subject separately or as any combination.

Embodiment 38: The PARP inhibitor for use of any one of Embodiments 1 to 37, wherein cells of the tumor have a disruption of the CDK4/6 signaling pathway.

Embodiment 39: The PARP inhibitor for use of any one of Embodiments 1 to 38, wherein cells of the tumor have an uncontrolled G1-S transition of the cell cycle.

Embodiment 40: The PARP inhibitor for use of any one of Embodiments 1 to 38, wherein cells of the tumor have a loss of function mutation or a deletion in a gene selected from the group comprising RB1 gene, CDKN2A gene and CDKN2B gene.

Embodiment 41: The PARP inhibitor for use of any one of Embodiments 1 to 38, wherein cells of the tumor have an amplification of a gene and/or an activating mutation in a gene.

Embodiment 42: The PARP inhibitor for use of Embodiment 41, wherein the gene is selected from the group comprising CCND1, E2F1, E2F2, E2F3, CDK4 and CDK6.

Embodiment 43: The PARP inhibitor for use of Embodiment 41, wherein the gene is one coding for a component of a mitogenic signaling pathway.

Embodiment 44. The PARP inhibitor for use of Embodiment 43, wherein the mitogenic signaling pathway is selected from the group comprising the PI3K pathway and the MAPK pathway.

Embodiment 45. The PARP inhibitor for use of any one of Embodiment 1 to 44, wherein the cells of the tumor cells have a resistance to or are insensitive to one or several pharmaceutically active agents and/or radiation.

Embodiment 46: The PARP inhibitor for use of Embodiment 45, wherein the pharmaceutically active agent is a cytostatic.

Embodiment 47: The PARP inhibitor for use of claim 46, wherein the resistance is mediated by an ABC transporter.

Embodiment 48: The PARP inhibitor for use of claim 47, wherein the ABC transporter is selected from the group comprising MRP and MDR, in particular MDR-1.

Embodiment 49: The PARP inhibitor for use of any one of embodiments 45 to 48, wherein the resistance is a multiple resistance or polyresistance, particular a multiple or polyresistance against a cytostatic and/or radiation.

Embodiment 50: The PARP inhibitor for use of any one of Embodiments 1 to 49, wherein the cells of the tumor are Rb-positive.

Embodiment 51: The PARP inhibitor for use of any one of Embodiments 1 to 50, wherein the cells of the tumor have YB-1 in the nucleus.

Embodiment 52: The PARP inhibitor for use of any one of Embodiments 1 to 51, wherein the cells of the tumor have YB-1 in the nucleus after induction.

Embodiment 53: The PARP inhibitor for use of Embodiment 52, wherein the transport of YB-1 into the nucleus is triggered by at least one measure selected from the group comprising irradiation, administration of cytostatics and hyperthermia.

Embodiment 54: The PARP inhibitor for use of Embodiment 53, wherein the measure is applied to a cell, an organ or an organism, preferably an organism in need thereof, more preferably an organism suffering from the tumor.

Embodiment 55: The PARP inhibitor for use of any one of claims 1 to 54, wherein the tumor is selected from the group comprising bladder cancer, breast cancer, metastatic breast cancer (mBC), melanoma, glioma, pancreatic cancer, hepatocellular carcinoma, lung adenocarcinoma, sarcoma, ovarian cancer, renal cancer, prostate cancer, and leukemia.

The problem underling present invention is solved in a sixth aspect, which is also a first embodiment of such sixth aspect by a bromodomain inhibitor for use in the treatment and/or prevention of a diseases in a subject, more preferably a tumor or cancer, wherein the method comprises administering to the subject an adenovirus, a CDK4/6 inhibitor and a bromodomain inhibitor.

In the following, further embodiments of such sixth aspect are disclosed.

Embodiment 2: The bromodomain inhibitor for use of Embodiment 1, wherein the adenovirus is an oncolytic adenovirus.

Embodiment 3: The bromodomain inhibitor of for use any one of Embodiments 1 and 2, wherein the adenovirus is replicating in a YB-1 dependent manner.

Embodiment 4: The bromodomain inhibitor for use of Embodiment 3, wherein the adenovirus is replication deficient in cells which lack YB-1 in the nucleus, but is replicating in cells which have YB-1 in the nucleus.

Embodiment 5: The bromodomain inhibitor for use of any one of Embodiments 2 to 4, wherein the adenovirus encodes an oncogene protein, wherein the oncogene protein transactivates at least one adenoviral gene, whereby the adenoviral gene is selected from the group comprising E1B55 kDa, E4orf6, E4orf3 and E3ADP.

Embodiment 6: The bromodomain inhibitor for use of Embodiment 5, wherein the oncogene protein is E1A protein.

Embodiment 7: The bromodomain inhibitor for use of Embodiment 6, wherein the E1A protein is capable of binding a functional Rb tumor suppressor gene product.

Embodiment 8: The bromodomain inhibitor for use of Embodiment 6, wherein the E1A protein is incapable of binding a functional Rb tumor suppressor gene product.

Embodiment 9: The bromodomain inhibitor for use of any one of Embodiments 6 to 8, wherein the E1A protein does not induce the localization of YB-1 into the nucleus.

Embodiment 10: The bromodomain inhibitor for use of any one of Embodiments 5 to 9, wherein the oncogene protein exhibits one or several mutations or deletions compared to the wildtype oncogene protein E1A.

Embodiment 11: The bromodomain inhibitor for use of Embodiment 10, wherein the deletion is one selected from the group comprising deletions of the CR3 stretches and deletions of the N-terminus and deletions of the C-terminus.

Embodiment 12: The bromodomain inhibitor for use of any one of Embodiments 6 to 11, wherein the E1A protein is capable of binding to Rb.

Embodiment 13: The bromodomain inhibitor for use of any one of Embodiments 6 to 12, wherein the E1A protein comprises one or several mutations or deletions compared to the wildtype oncogene protein, whereby the deletion is preferably a deletion in the CR1 region and/or CR2 region.

Embodiment 14: The bromodomain inhibitor for use of Embodiment 13, wherein the E1A protein is incapable of binding to Rb.

Embodiment 15: The bromodomain inhibitor for use of any one of Embodiments 1 to 14, wherein the virus is an adenovirus expressing E1A12 S protein.

Embodiment 16: The bromodomain inhibitor for use of any one of Embodiments 1 to 15, wherein the virus is an adenovirus lacking expression of E1A13S protein.

Embodiment 17: The bromodomain inhibitor for use of any one of Embodiments 1 to 16, wherein the virus is an adenovirus lacking a functionally active adenoviral E3 region.

Embodiment 18: The bromodomain inhibitor for use of any one of Embodiments 1 to 17, wherein the virus is an adenovirus lacking expression of E1B 19 kDa protein.

Embodiment 19: The bromodomain inhibitor for use of any one of Embodiments 1 to 18, wherein the virus is an adenovirus expressing an RGD motif at a fibre.

Embodiment 20: The bromodomain inhibitor for use of any one of Embodiments 1 to 19, wherein the virus is an adenovirus serotype 5.

Embodiment 21: The bromodomain inhibitor for use of any one of Embodiment 1 to 20, wherein the adenovirus is selected from the group comprising XVir-N-31, dl520, AdΔ24, AdΔ24-RGD, dl922-947, E1Ad/01/07, dl1119/1131, CB 016, VCN-01, E1Adl1107, E1Adl1101, ORCA-010, Enadenotucirev and viruses lacking an expressed viral oncogene which is capable of binding a functional Rb tumor suppressor gene product.

Embodiment 22: The bromodomain inhibitor for use of Embodiment 21, wherein the adenovirus is XVir-N-31.

Embodiment 23: The bromodomain inhibitor for use of Embodiment 21, wherein the adenovirus is dl520, wherein the adenovirual E3 region is functionally inactive.

Embodiment 24: The bromodomain inhibitor for use of any one of Embodiment 21 to 23, wherein the adenovirus is dl520, wherein dl520 is lacking expression of E1B 19 kDa protein.

Embodiment 25: The bromodomain inhibitor for use of any one of Embodiments 21 to 24, wherein the adenovirus is dl520 expressing an RGD motif at a fibre.

Embodiment 26: The bromodomain inhibitor for use of any one of Embodiments 1 to 25, wherein the virus encodes YB-1.

Embodiment 27: The bromodomain inhibitor for use of Embodiment 26, wherein the gene coding for YB-1 is under the control of a tissue-specific promoter, tumor-specific promoter and/or a YB-1 dependent promoter.

Embodiment 28: The bromodomain inhibitor for use of Embodiment 27, wherein the YB-1 dependent promoter is the adenoviral E2 late promoter.

Embodiment 29: The bromodomain inhibitor for use of any one of Embodiments 1 to 28, wherein the CDK4/6 inhibitor is a compound which reduces Rb phosphorylation in a cell, preferably a tumor cell.

Embodiment 30: The bromodomain inhibitor for use of any one of Embodiments 1 to 29, wherein the CDK4/6 inhibitor is a compound which reduces Rb expression in a cell, preferably a tumor cell.

Embodiment 31: The bromodomain inhibitor for use of any one of Embodiments 1 to 30, wherein the CDK4/6 inhibitor is selected from the group comprising palbociclib which is also referred to as PD 0332991, abemaciclib which is also referred to as LY-2835219, ribociclib which is also referred to as LEE011, Trilaciclib which is also referred to as G1T28, and Dinaciclib.

Embodiment 32: The bromodomain inhibitor for use of any one of Embodiments 1 to 31, wherein the CDK4/6 inhibitor causes G1 arrest in a cell and inhibits E2F1.

Embodiment 33: The bromodomain inhibitor for use of any one of Embodiments 1 to 32, wherein the method further comprises administering a PARP inhibitor to the subject.

Embodiment 34: The bromodomain for use of Embodiment 33, wherein the PARP inhibitor is selected from the group comprising olaparib, veliparib, rucaparib and BMN673.

Embodiment 35: The bromodomain inhibitor for use of any one of Embodiments 1 to 32, wherein the method further comprises administering a bromodomain inhibitor to the subject.

Embodiment 36: The bromodomain inhibitor for use of Embodiment 35, wherein the bromodomain inhibitor is selected from the group comprising JQ-1, OTX-015, I-BET151, CPI-0610, I-BET762, CPI203, PFI-1 and MS 436.

Embodiment 37: The bromodomain inhibitor for use of any one of embodiments 1 to 36, wherein the adenovirus, the CDK4/6 inhibitor, the PARP inhibitor and/or the bromodomain inhibitor are administered to the subject separately or as any combination.

Embodiment 38: The bromodomain inhibitor for use of any one of Embodiments 1 to 37, wherein cells of the tumor have a disruption of the CDK4/6 signaling pathway.

Embodiment 39: The bromodomain inhibitor for use of any one of Embodiments 1 to 38, wherein cells of the tumor have an uncontrolled G1-S transition of the cell cycle.

Embodiment 40: The bromodomain inhibitor for use of any one of Embodiments 1 to 38, wherein cells of the tumor have a loss of function mutation or a deletion in a gene selected from the group comprising RB1 gene, CDKN2A gene and CDKN2B gene.

Embodiment 41: The bromodomain inhibitor for use of any one of Embodiments 1 to 38, wherein cells of the tumor have an amplification of a gene and/or an activating mutation in a gene.

Embodiment 42: The bromodomain inhibitor for use of Embodiment 41, wherein the gene is selected from the group comprising CCND1, E2F1, E2F2, E2F3, CDK4 and CDK6.

Embodiment 43: The bromodomain inhibitor for use of Embodiment 41, wherein the gene is one coding for a component of a mitogenic signaling pathway.

Embodiment 44. The bromodomain inhibitor for use of Embodiment 43, wherein the mitogenic signaling pathway is selected from the group comprising the PI3K pathway and the MAPK pathway.

Embodiment 45. The bromodomain inhibitor for use of any one of Embodiment 1 to 44, wherein the cells of the tumor cells have a resistance to or are insensitive to one or several pharmaceutically active agents and/or radiation.

Embodiment 46: The bromodomain inhibitor for use of Embodiment 45, wherein the pharmaceutically active agent is a cytostatic.

Embodiment 47: The bromodomain inhibitor for use of claim 46, wherein the resistance is mediated by an ABC transporter.

Embodiment 48: The bromodomain inhibitor for use of claim 47, wherein the ABC transporter is selected from the group comprising MRP and MDR, in particular MDR-1.

Embodiment 49: The bromodomain inhibitor for use of any one of embodiments 45 to 48, wherein the resistance is a multiple resistance or polyresistance, particular a multiple or polyresistance against a cytostatic and/or radiation.

Embodiment 50: The bromodomain inhibitor for use of any one of Embodiments 1 to 49, wherein the cells of the tumor are Rb-positive.

Embodiment 51: The bromodomain inhibitor for use of any one of Embodiments 1 to 50, wherein the cells of the tumor have YB-1 in the nucleus.

Embodiment 52: The bromodomain inhibitor for use of any one of Embodiments 1 to 51, wherein the cells of the tumor have YB-1 in the nucleus after induction.

Embodiment 53: The bromodomain inhibitor for use of Embodiment 52, wherein the transport of YB-1 into the nucleus is triggered by at least one measure selected from the group comprising irradiation, administration of cytostatics and hyperthermia.

Embodiment 54: The bromodomain inhibitor for use of Embodiment 53, wherein the measure is applied to a cell, an organ or an organism, preferably an organism in need thereof, more preferably an organism suffering from the tumor.

Embodiment 55: The bromodomain inhibitor for use of any one of claims 1 to 54, wherein the tumor is selected from the group comprising bladder cancer, breast cancer, metastatic breast cancer (mBC), melanoma, glioma, pancreatic cancer, hepatocellular carcinoma, lung adenocarcinoma, sarcoma, ovarian cancer, renal cancer, prostate cancer, and leukemia.

The problem underling present invention is solved in a seventh aspect, which is also a first embodiment of such sixth aspect by nutlin or a nutlin derivative for use in the treatment and/or prevention of a diseases in a subject, more preferably a tumor or cancer, wherein the method comprises administering to the subject an adenovirus, a CDK4/6 inhibitor and a bromodomain inhibitor.

In the following, further embodiments of such sixth aspect are disclosed.

Embodiment 2: The nutlin or a nutlin derivative for use of Embodiment 1, wherein the adenovirus is an oncolytic adenovirus.

Embodiment 3: The nutlin or a nutlin derivative for use any one of Embodiments 1 and 2, wherein the adenovirus is replicating in a YB-1 dependent manner.

Embodiment 4: The nutlin or a nutlin derivative for use of Embodiment 3, wherein the adenovirus is replication deficient in cells which lack YB-1 in the nucleus, but is replicating in cells which have YB-1 in the nucleus.

Embodiment 5: The nutlin or a nutlin derivative for use of any one of Embodiments 2 to 4, wherein the adenovirus encodes an oncogene protein, wherein the oncogene protein transactivates at least one adenoviral gene, whereby the adenoviral gene is selected from the group comprising E1B55 kDa, E4orf6, E4orf3 and E3ADP.

Embodiment 6: The nutlin or a nutlin derivative for use of Embodiment 5, wherein the oncogene protein is E1A protein.

Embodiment 7: The nutlin or a nutlin derivative for use of Embodiment 6, wherein the E1A protein is capable of binding a functional Rb tumor suppressor gene product.

Embodiment 8: The nutlin or a nutlin derivative for use of Embodiment 6, wherein the E1A protein is incapable of binding a functional Rb tumor suppressor gene product.

Embodiment 9: The nutlin or a nutlin derivative for use of any one of Embodiments 6 to 8, wherein the E1A protein does not induce the localization of YB-1 into the nucleus.

Embodiment 10: The nutlin or a nutlin derivative for use of any one of Embodiments 5 to 9, wherein the oncogene protein exhibits one or several mutations or deletions compared to the wildtype oncogene protein E1A.

Embodiment 11: The nutlin or a nutlin derivative for use of Embodiment 10, wherein the deletion is one selected from the group comprising deletions of the CR3 stretches and deletions of the N-terminus and deletions of the C-terminus.

Embodiment 12: The nutlin or a nutlin derivative for use of any one of Embodiments 6 to 11, wherein the E1A protein is capable of binding to Rb.

Embodiment 13: The nutlin or a nutlin derivative for use of any one of Embodiments 6 to 12, wherein the E1A protein comprises one or several mutations or deletions compared to the wildtype oncogene protein, whereby the deletion is preferably a deletion in the CR1 region and/or CR2 region.

Embodiment 14: The nutlin or a nutlin derivative for use of Embodiment 13, wherein the E1A protein is incapable of binding to Rb.

Embodiment 15: The nutlin or a nutlin derivative for use of any one of Embodiments 1 to 14, wherein the virus is an adenovirus expressing E1A12 S protein.

Embodiment 16: The nutlin or a nutlin derivative for use of any one of Embodiments 1 to 15, wherein the virus is an adenovirus lacking expression of E1A13S protein.

Embodiment 17: The nutlin or a nutlin derivative for use of any one of Embodiments 1 to 16, wherein the virus is an adenovirus lacking a functionally active adenoviral E3 region.

Embodiment 18: The nutlin or a nutlin derivative for use of any one of Embodiments 1 to 17, wherein the virus is an adenovirus lacking expression of E1B 19 kDa protein.

Embodiment 19: The nutlin or a nutlin derivative for use of any one of Embodiments 1 to 18, wherein the virus is an adenovirus expressing an RGD motif at a fibre.

Embodiment 20: The nutlin or a nutlin derivative for use of any one of Embodiments 1 to 19, wherein the virus is an adenovirus serotype 5.

Embodiment 21: The nutlin or a nutlin derivative for use of any one of Embodiment 1 to 20, wherein the adenovirus is selected from the group comprising XVir-N-31, dl520, AdΔ24, AdΔ24-RGD, dl922-947, E1Ad/01/07, dl1119/1131, CB 016, VCN-01, E1Adl1107, E1Adl1101, ORCA-010, Enadenotucirev and viruses lacking an expressed viral oncogene which is capable of binding a functional Rb tumor suppressor gene product.

Embodiment 22: The nutlin or a nutlin derivative for use of Embodiment 21, wherein the adenovirus is XVir-N-31.

Embodiment 23: The nutlin or a nutlin derivative for use of Embodiment 21, wherein the adenovirus is dl520, wherein the adenovirual E3 region is functionally inactive.

Embodiment 24: The nutlin or a nutlin derivative for use of any one of Embodiment 21 to 23, wherein the adenovirus is dl520, wherein dl520 is lacking expression of E1B 19 kDa protein.

Embodiment 25: The nutlin or a nutlin derivative for use of any one of Embodiments 21 to 24, wherein the adenovirus is dl520 expressing an RGD motif at a fibre.

Embodiment 26: The nutlin or a nutlin derivative for use of any one of Embodiments 1 to 25, wherein the virus encodes YB-1.

Embodiment 27: The nutlin or a nutlin derivative for use of Embodiment 26, wherein the gene coding for YB-1 is under the control of a tissue-specific promoter, tumor-specific promoter and/or a YB-1 dependent promoter.

Embodiment 28: The nutlin or a nutlin derivative for use of Embodiment 27, wherein the YB-1 dependent promoter is the adenoviral E2 late promoter.

Embodiment 29: The nutlin or a nutlin derivative for use of any one of Embodiments 1 to 28, wherein the CDK4/6 inhibitor is a compound which reduces Rb phosphorylation in a cell, preferably a tumor cell.

Embodiment 30: The nutlin or a nutlin derivative for use of any one of Embodiments 1 to 29, wherein the CDK4/6 inhibitor is a compound which reduces Rb expression in a cell, preferably a tumor cell.

Embodiment 31: The nutlin or a nutlin derivative for use of any one of Embodiments 1 to 30, wherein the CDK4/6 inhibitor is selected from the group comprising palbociclib which is also referred to as PD 0332991, abemaciclib which is also referred to as LY-2835219, ribociclib which is also referred to as LEE011, Trilaciclib which is also referred to as G1T28, and Dinaciclib.

Embodiment 32: The nutlin or a nutlin derivative for use of any one of Embodiments 1 to 31, wherein the CDK4/6 inhibitor causes G1 arrest in a cell and inhibits E2F1.

Embodiment 33: The nutlin or a nutlin derivative for use of any one of Embodiments 1 to 32, wherein the method further comprises administering a PARP inhibitor to the subject.

Embodiment 34: The nutlin or a nutlin derivative for use of Embodiment 33, wherein the PARP inhibitor is selected from the group comprising olaparib, veliparib, rucaparib, Talazoparib and BMN673.

Embodiment 35: The nutlin or a nutlin derivative for use of any one of Embodiments 1 to 32, wherein the method further comprises administering a bromodomain inhibitor to the subject.

Embodiment 36: The nutlin or a nutlin derivative for use of Embodiment 35, wherein the bromodomain inhibitor is selected from the group comprising JQ-1, OTX-015, I-BET151, CPI-0610, I-BET762, CPI203, PFI-1 and MS 436.

Embodiment 37: The nutlin or a nutlin derivative for use of any one of embodiments 1 to 36, wherein the adenovirus, the CDK4/6 inhibitor, the PARP inhibitor, the bromodomain inhibitor and or the nutlin or nutlin derivative are administered to the subject separately or as any combination.

Embodiment 38: The nutlin or a nutlin derivative for use of any one of claims 1 to 37, wherein the nutlin derivative is selected form the group comprising NVP-HDM201, Idasanutlin, AM-8553, SAR405838, Nutlin-3a and AMG232.

Embodiment 39: The nutlin or a nutlin derivative for use of any one of claims 1 to 37, wherein the nutlin derivative is different from Nutlin-3a.

Embodiment 40: The nutlin or a nutlin derivative for use of any one of Embodiments 1 to 39, wherein cells of the tumor have a disruption of the CDK4/6 signaling pathway.

Embodiment 41: The nutlin or a nutlin derivative for use of any one of Embodiments 1 to 40, wherein cells of the tumor have an uncontrolled G1-S transition of the cell cycle.

Embodiment 42: The nutlin or a nutlin derivative for use of any one of Embodiments 1 to 40, wherein cells of the tumor have a loss of function mutation or a deletion in a gene selected from the group comprising RB1 gene, CDKN2A gene and CDKN2B gene.

Embodiment 43: The nutlin or a nutlin derivative for use of any one of Embodiments 1 to 40, wherein cells of the tumor have an amplification of a gene and/or an activating mutation in a gene.

Embodiment 44: The nutlin or a nutlin derivative for use of Embodiment 43, wherein the gene is selected from the group comprising CCND1, E2F1, E2F2, E2F3, CDK4 and CDK6.

Embodiment 45: The nutlin or a nutlin derivative for use of Embodiment 43, wherein the gene is one coding for a component of a mitogenic signaling pathway.

Embodiment 46. The nutlin or a nutlin derivative for use of Embodiment 45, wherein the mitogenic signaling pathway is selected from the group comprising the PI3K pathway and the MAPK pathway.

Embodiment 47. The nutlin or a nutlin derivative for use of any one of Embodiment 1 to 46, wherein the cells of the tumor cells have a resistance to or are insensitive to one or several pharmaceutically active agents and/or radiation.

Embodiment 48: The nutlin or a nutlin derivative for use of Embodiment 47, wherein the pharmaceutically active agent is a cytostatic.

Embodiment 49: The nutlin or a nutlin derivative for use of claim 48, wherein the resistance is mediated by an ABC transporter.

Embodiment 50: The nutlin or a nutlin derivative for use of claim 49, wherein the ABC transporter is selected from the group comprising MRP and MDR, in particular MDR-1.

Embodiment 51: The nutlin or a nutlin derivative for use of any one of embodiments 47 to 50, wherein the resistance is a multiple resistance or polyresistance, particular a multiple or polyresistance against a cytostatic and/or radiation.

Embodiment 52: The nutlin or a nutlin derivative for use of any one of Embodiments 1 to 51, wherein the cells of the tumor are Rb-negative.

Embodiment 53: The nutlin or a nutlin derivative for use of any one of Embodiments 1 to 52, wherein the cells of the tumor are Rb-positive.

Embodiment 54: The nutlin or a nutlin derivative for use of any one of Embodiments 1 to 53, wherein the cells of the tumor have YB-1 in the nucleus.

Embodiment 55: The nutlin or a nutlin derivative or for use of any one of Embodiments 1 to 54, wherein the cells of the tumor have YB-1 in the nucleus after induction.

Embodiment 56: The nutlin or a nutlin derivative for use of Embodiment 55, wherein the transport of YB-1 into the nucleus is triggered by at least one measure selected from the group comprising irradiation, administration of cytostatics and hyperthermia.

Embodiment 57: The bromodomain inhibitor for use of Embodiment 56, wherein the measure is applied to a cell, an organ or an organism, preferably an organism in need thereof, more preferably an organism suffering from the tumor.

The problem underlying the present invention is solved in an eighth aspect, which is also a first embodiment of such seventh aspect, by a combination therapy, wherein such combination therapy comprises administration to a subject in need thereof, of, among others, a) an adenovirus, in particular one as defined herein according to the third aspect, including any embodiment thereof; a CDK4/6 inhibitor, in particular one as defined herein according to the fourth aspect, including any embodiment thereof, and a PARP inhibitor, in particular one as defined herein according to the fourth aspect;

b) an adenovirus, in particular one as defined herein according to the third aspect, including any embodiment thereof; a CDK4/6 inhibitor, in particular one as defined herein according to the fourth aspect, including any embodiment thereof, and a bromodomain inhibitor, in particular one as defined herein according to the fifth aspect;

c) an adenovirus, in particular one as defined herein according to the third aspect, including any embodiment thereof; a CDK4/6 inhibitor, in particular one as defined herein according to the fourth aspect, including any embodiment thereof, and a nutlin or a nutlin derivative, in particular one as defined herein according to the sixth aspect;

d) an adenovirus, in particular one as defined herein according to the third aspect, including any embodiment thereof; a CDK4/6 inhibitor, in particular one as defined herein according to the fourth aspect, including any embodiment thereof, a bromodomain inhibitor, a bromodomain inhibitor, in particular one as defined herein according to the fifth aspect; and a nutlin or a nutlin derivative, in particular one as defined herein according to the sixth aspect;

e) an adenovirus, in particular one as defined herein according to the third aspect, including any embodiment thereof; a CDK4/6 inhibitor, in particular one as defined herein according to the fourth aspect, including any embodiment thereof, a bromodomain inhibitor, a bromodomain inhibitor, in particular one as defined herein according to the fifth aspect; and a PARP inhibitor, in particular one as defined herein according to the fifth aspect; and f) an adenovirus, in particular one as defined herein according to the third aspect, including any embodiment thereof; a CDK4/6 inhibitor, in particular one as defined herein according to the fourth aspect, including any embodiment thereof, a bromodomain inhibitor, a bromodomain inhibitor, in particular one as defined herein according to the fifth aspect; a PARP inhibitor, in particular one as defined herein according to the fifth aspect; and and a nutlin or a nutlin derivative, in particular one as defined herein according to the sixth aspect.

It is within the present invention that the various embodiments described in connection with the third aspect, including any embodiment thereof, the fourth aspect, including any embodiment thereof, the fifth aspect, including any embodiment thereof, and the sixth aspect, including any embodiment thereof, can be embodiments of a combination therapy according to the eighth aspect in its various forms, in particular as defined above as a), b), c), d), e) and f).

The problem underling present invention is solved in a ninth aspect, which is also a first embodiment of such seventh aspect by a method for the treatment and/or prevention of a diseases in a subject, more preferably a tumor or cancer, wherein the method comprises administering to the subject an adenovirus and a CDK4/6 inhibitor.

In the following, further embodiments of such ninth aspect are disclosed.

Embodiment 2: The method of Embodiment 1, wherein the adenovirus is an oncolytic adenovirus.

Embodiment 3: The method of any one of Embodiments 1 and 2, wherein the adenovirus is replicating in a YB-1 dependent manner.

Embodiment 4: The method of Embodiment 3, wherein the adenovirus is replication deficient in cells which lack YB-1 in the nucleus, but is replicating in cells which have YB-1 in the nucleus.

Embodiment 5: The method of any one of Embodiments 2 to 4, wherein the adenovirus encodes an oncogene protein, wherein the oncogene protein transactivates at least one adenoviral gene, whereby the adenoviral gene is selected from the group comprising E1B55 kDa, E4orf6, E4orf3 and E3ADP.

Embodiment 6: The method of Embodiment 5, wherein the oncogene protein is E1A protein.

Embodiment 7: The method of Embodiment 6, wherein the E1A protein is capable of binding a functional Rb tumor suppressor gene product.

Embodiment 8: The method of Embodiment 6, wherein the E1A protein is incapable of binding a functional Rb tumor suppressor gene product.

Embodiment 9: The method of any one of Embodiments 6 to 8, wherein the E1A protein does not induce the localization of YB-1 into the nucleus.

Embodiment 10: The method of any one of Embodiments 5 to 9, wherein the oncogene protein exhibits one or several mutations or deletions compared to the wildtype oncogene protein E1A.

Embodiment 11: The method of Embodiment 10, wherein the deletion is one selected from the group comprising deletions of the CR3 stretches and deletions of the N-terminus and deletions of the C-terminus.

Embodiment 12: The method of any one of Embodiments 6 to 11, wherein the E1A protein is capable of binding to Rb.

Embodiment 13: The method of any one of Embodiments 6 to 12, wherein the E1A protein comprises one or several mutations or deletions compared to the wildtype oncogene protein, whereby the deletion is preferably a deletion in the CR1 region and/or CR2 region.

Embodiment 14: The method of Embodiment 13, wherein the E1A protein is incapable of binding to Rb.

Embodiment 15: The method of any one of Embodiments 1 to 14, wherein the virus is an adenovirus expressing E1A12 S protein.

Embodiment 16: The method of any one of Embodiments 1 to 15, wherein the virus is an adenovirus lacking expression of E1A13S protein.

Embodiment 17: The method of any one of Embodiments 1 to 16, wherein the virus is an adenovirus lacking a functionally active adenoviral E3 region.

Embodiment 18: The method of any one of Embodiments 1 to 17, wherein the virus is an adenovirus lacking expression of E1B 19 kDa protein.

Embodiment 19: The method of any one of Embodiments 1 to 18, wherein the virus is an adenovirus expressing an RGD motif at a fibre.

Embodiment 20: The method of any one of Embodiments 1 to 19, wherein the virus is an adenovirus serotype 5.

Embodiment 21: The method of any one of Embodiment 1 to 20, wherein the adenovirus is selected from the group comprising XVir-N-31, dl520, AdΔ24, AdΔ24-RGD, dl922-947, E1Ad/01/07, dl1119/1131, CB 016, VCN-01, E1Adl1107, E1Adl1101, ORCA-010, Enadenotucirev and viruses lacking an expressed viral oncogene which is capable of binding a functional Rb tumor suppressor gene product.

Embodiment 22: The method of Embodiment 21, wherein the adenovirus is XVir-N-31.

Embodiment 23: The method of Embodiment 21, wherein the adenovirus is dl520, wherein the adenovirual E3 region is functionally inactive.

Embodiment 24: The method of any one of Embodiment 21 to 23, wherein the adenovirus is dl520, wherein dl520 is lacking expression of E1B 19 kDa protein.

Embodiment 25: The method of any one of Embodiments 21 to 24, wherein the adenovirus is dl520 expressing an RGD motif at a fibre.

Embodiment 26: The method of any one of Embodiments 1 to 25, wherein the virus encodes YB-1.

Embodiment 27: The method of Embodiment 26, wherein the gene coding for YB-1 is under the control of a tissue-specific promoter, tumor-specific promoter and/or a YB-1 dependent promoter.

Embodiment 28: The method of Embodiment 27, wherein the YB-1 dependent promoter is the adenoviral E2 late promoter.

Embodiment 29: The method of any one of Embodiments 1 to 28, wherein the CDK4/6 inhibitor is a compound which reduces Rb phosphorylation in a cell, preferably a tumor cell.

Embodiment 30: The method of any one of Embodiments 1 to 29, wherein the CDK4/6 inhibitor is a compound which reduces Rb expression in a cell, preferably a tumor cell.

Embodiment 31: The method of any one of Embodiments 1 to 30, wherein the CDK4/6 inhibitor is selected from the group comprising palbociclib which is also referred to as PD 0332991, abemaciclib which is also referred to as LY-2835219, ribociclib which is also referred to as LEE011, Trilaciclib which is also referred to as G1T28, and Dinaciclib.

Embodiment 32: The method of any one of Embodiments 1 to 31, wherein the CDK4/6 inhibitor causes G1 arrest in a cell and inhibits E2F1.

Embodiment 33: The method of any one of Embodiments 1 to 32, wherein the method further comprises administering a PARP inhibitor to the subject.

Embodiment 34: The method of Embodiment 33, wherein the PARP inhibitor is selected from the group comprising olaparib, veliparib, rucaparib and BMN673.

Embodiment 35: The method of any one of Embodiments 1 to 32, wherein the method further comprises administering a bromodomain inhibitor to the subject.

Embodiment 36: The method of Embodiment 35, wherein the bromodomain inhibitor is selected from the group comprising JQ-1, OTX-015, I-BET151, CPI-0610, I-BET762, CPI203, PFI-1 and MS 436.

Embodiment 37: The method of any one of embodiments 1 to 36, wherein the adenovirus, the CDK4/6 inhibitor, the PARP inhibitor and/or the bromodomain inhibitor are administered to the subject separately or as any combination.

Embodiment 38: The method of any one of Embodiments 1 to 37, wherein cells of the tumor have a disruption of the CDK4/6 signaling pathway.

Embodiment 39: The method of any one of Embodiments 1 to 38, wherein cells of the tumor have an uncontrolled G1-S transition of the cell cycle.

Embodiment 40: The method of any one of Embodiments 1 to 38, wherein cells of the tumor have a loss of function mutation or a deletion in a gene selected from the group comprising RB1 gene, CDKN2A gene and CDKN2B gene.

Embodiment 41: The method of any one of Embodiments 1 to 38, wherein cells of the tumor have an amplification of a gene and/or an activating mutation in a gene.

Embodiment 42: The method of Embodiment 41, wherein the gene is selected from the group comprising CCND1, E2F1, E2F2, E2F3, CDK4 and CDK6.

Embodiment 43: The method of Embodiment 41, wherein the gene is one coding for a component of a mitogenic signaling pathway.

Embodiment 44: The method of Embodiment 43, wherein the mitogenic signaling pathway is selected from the group comprising the PI3K pathway and the MAPK pathway.

Embodiment 45: The method of any one of Embodiment 1 to 44, wherein the cells of the tumor cells have a resistance to or are insensitive to one or several pharmaceutically active agents and/or radiation.

Embodiment 46: The method of Embodiment 45, wherein the pharmaceutically active agent is a cytostatic.

Embodiment 47: The method of claim 46, wherein the resistance is mediated by an ABC transporter.

Embodiment 48: The method of claim 47, wherein the ABC transporter is selected from the group comprising MRP and MDR, in particular MDR-1.

Embodiment 49: The method of any one of embodiments 45 to 48, wherein the resistance is a multiple resistance or polyresistance, particular a multiple or polyresistance against a cytostatic and/or radiation.

Embodiment 50: The method of any one of Embodiments 1 to 49, wherein the cells of the tumor are Rb-positive.

Embodiment 51: The method of any one of Embodiments 1 to 50, wherein the cells of the tumor have YB-1 in the nucleus.

Embodiment 52: The method of any one of Embodiments 1 to 51, wherein the cells of the tumor have YB-1 in the nucleus after induction.

Embodiment 53: The method of Embodiment 52, wherein the transport of YB-1 into the nucleus is triggered by at least one measure selected from the group comprising irradiation, administration of cytostatics and hyperthermia.

Embodiment 54: The method of Embodiment 53, wherein the measure is applied to a cell, an organ or an organism, preferably an organism in need thereof, more preferably an organism suffering from the tumor.

Embodiment 55: The method of claims 1 to 54, wherein the tumor is selected from the group comprising bladder cancer, breast cancer, metastatic breast cancer (mBC), melanoma, glioma, pancreatic cancer, hepatocellular carcinoma, lung adenocarcinoma, sarcoma, ovarian cancer, renal cancer, prostate cancer, and leukemia.

In a tenth aspect, the present invention also relates to the use of a composition for the manufacture of a medicament, wherein the composition is a composition as disclosed in connection with the first aspect of the present invention, including any embodiment thereof, and the medicament is for the treatment and/or prevention of a disease as specified in connection with the second aspect of the present invention, including any embodiment thereof.

In an eleventh aspect, the present inventions also related to the use of an adenovirus for the manufacture of a medicament, wherein the adenovirus is an adenovirus as disclosed in connection with the third aspect of the present invention, including any embodiment thereof, and the medicament is for the treatment and/or prevention of a disease as specified in connection with the third aspect of the present invention, including any embodiment thereof.

In a twelfth aspect, the present inventions also related to the use of a CDK4/6 inhibitor for the manufacture of a medicament, wherein the CDK4/6 inhibitor is a CDK4/6 inhibitor as disclosed in connection with the fourth aspect of the present invention, including any embodiment thereof, and the medicament is for the treatment and/or prevention of a disease as specified in connection with the fourth aspect of the present invention, including any embodiment thereof.

In an $13^{th}$ aspect, the present inventions also related to the use of a PARP inhibitor for the manufacture of a medicament, wherein the PARP inhibitor is a PARP inhibitor as disclosed in connection with the fifth aspect of the present invention, including any embodiment thereof, and the medicament is for the treatment and/or prevention of a disease as specified in connection with the fifth aspect of the present invention, including any embodiment thereof.

In a $14^{th}$ aspect, the present inventions also related to the use of a bromodomain inhibitor for the manufacture of a medicament, wherein the bromodomain inhibitor is a bromodomain inhibitor as disclosed in connection with the sixth aspect of the present invention, including any embodiment thereof, and the medicament is for the treatment and/or prevention of a disease as specified in connection with the sixth aspect of the present invention, including any embodiment thereof.

In a $15^{th}$ aspect, the present inventions also related to the use of nutlin or a derivative thereof for the manufacture of a medicament, wherein the nutlin or nutlin derivative is nutlin or a nutlin derivative as disclosed in connection with the seventh aspect of the present invention, including any embodiment thereof, and the medicament is for the treatment and/or prevention of a disease as specified in connection with the seventh aspect of the present invention, including any embodiment thereof.

In an embodiment of each and any aspect as disclosed herein, including any embodiment thereof, a CDK4/6 inhibitor is an agent which inhibits or is capable of inhibiting CDK4/6 thus causing an arrest of an accordingly treated cell in the G1 phase.

In an embodiment of each and any aspect of the present invention, including any embodiment thereof, the bromodomain inhibitor is a bivalent bromodomain inhibitor, more preferably the bromodomain inhibitor is AZD5153 of the following formula

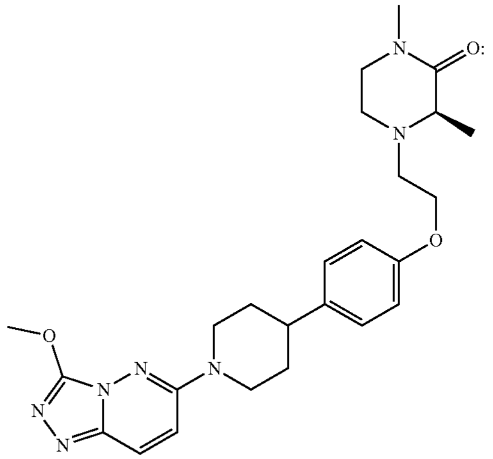
In an embodiment of each and any aspect of the present invention, including any embodiment thereof, the bromodomain inhibitor is a BET degrader, preferably the bromodomain inhibitor is selected from the group comprising dBET6 of the following formula and ARV771 of the following formula:
General Structure of BET-Degraders
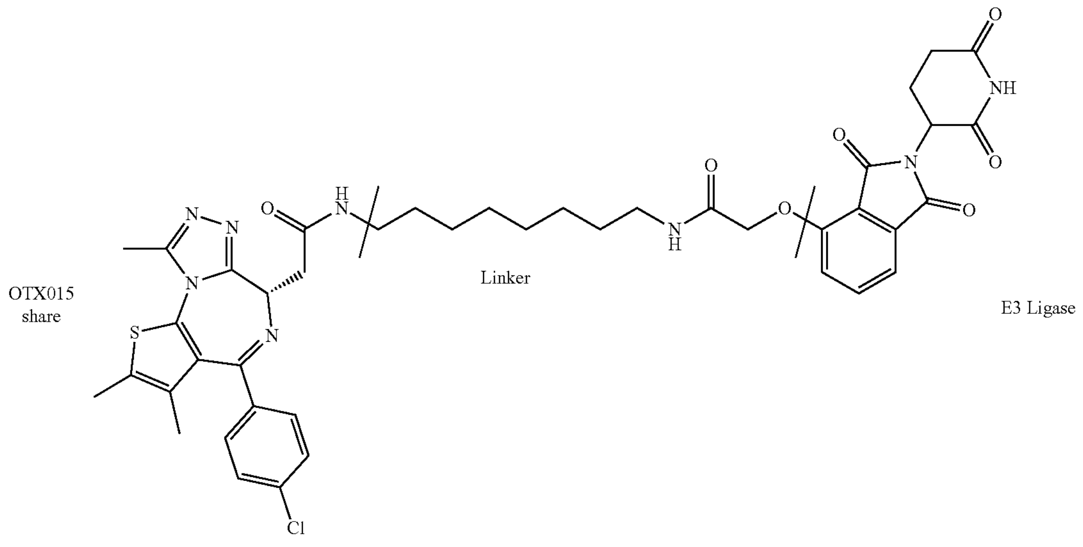
BET-degrader dBET6

-continued

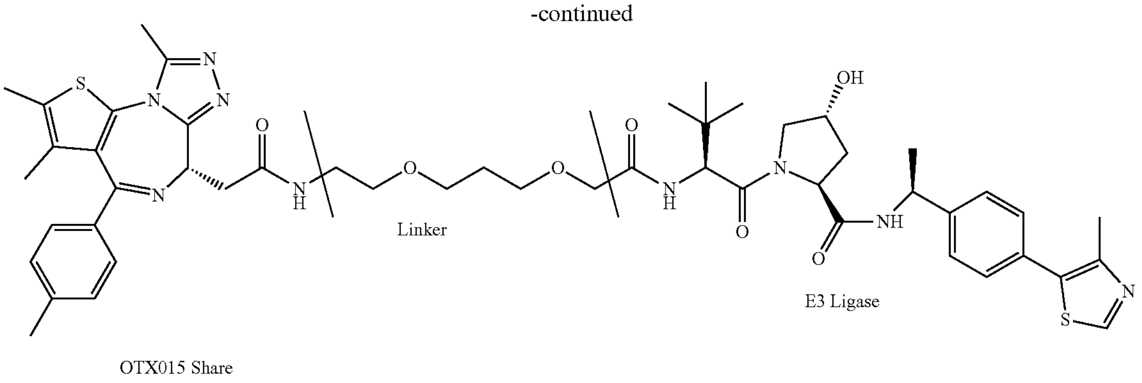

BET-degrader ARV-771

Marcel Scheepstra, Koen F.W. Hekking, Luc van Hijfte, Rutger H.A. Folmer.Bivalent Ligands for Protein Degradation in Drug Discovery. Computational and Structural Biotechnology Journal 17 (2019) 160-176.

(see, e.g. Scheepstra M et al. (Computational and Structural Biotechnology Journal 17(2019) 160-179).

It will be acknowledged by a person skilled in the art that each and any embodiment of one aspect of the present invention is also an embodiment of each and any of the other aspects of the present invention, including any embodiment thereof.

Without wishing to be bound by any theory, the present inventors have surprisingly found that combining an oncolytic virus, preferably an oncolytic adenovirus, with a CDK4/6 inhibitor increases the efficacy of tumor therapy based on such oncolytic adenovirus. More specifically, the CDK4/6 inhibitor is assumed to inhibit E2F1 (also referred to as E2F-1 herein) thus reducing its effective concentration, preferably in tumor cells, and synchronizes G1 arrest in cells. Because of this, more infected cells can complete the entire viral life cycle.

Based on the evidence and insights provided herein, a person skilled in the art will understand that any—mutant—adenovirus is suitable for use in the practicing of the instant invention which allows that at least as little as 10%, 20% or 30% of wild type expression and, respectively, activity of E1B55K and E4orf6 is achieved by such adenovirus. It will be appreciated by a person skilled in the art that such mutant adenovirus can be generated by modifying E1A. Exemplary mutant adenoviruses are adenovirus XVir-N-31, dl520, AdΔ24, AdΔ24-RGD, dl922-947, E1Ad/01/07, dl1119/1131, CB 016, VCN-01, E1Adl1107, E1Adl1101, ORCA-010, Enadenotucirev and viruses lacking an expressed viral oncogene which is capable of binding a functional Rb tumor suppressor gene product.

Eponymous for adenoviruses is the first isolation of the virus in human tonsils and adenoid tissue in 1953 by Wallace P. Rowe and Robert J. Huebner (Rowe et al., 1953). The family of Adenoviridae comprises five genera, namely Mastadenoviruses, Aviadenoviruses, Siadenoviruses, Atadenoviruses and Ichtadenoviruses (Modrow, 2013). Due to their oncogenicity in newborn rodents, they can be classified into seven subgroups HAdV-A to HAdV-G (Boulanger and Blair, 1991) with altogether 62 serotypes. Thereby, research on oncolytic virotherapy is mainly focusing on Mastadenovirus Type C serotype 5.

The uncoated icosahedral capsid with a size of 80 to 110 nm is comprised of 252 capsomers, that consist of 12 pentons, assembled of a penton basis and spike-like protein structures, called fibers, on the vertices of the capsid and 249 faces, called hexons (Modrow, 2013). The whole lifecycle of adenoviruses, can be subdivided into an early phase with cell entry, nuclear translocation of the viral genome, transcription and translation of early genes and the late phase with transcription and translation of late genes. Late proteins are thereby mainly responsible for assembly of structural proteins and maturation of virions (Russell, 2000). In permissive cells, the early phase takes about 6-8 hours with a following late phase of about 4-6 hours. Attachment occurs via interaction of a knob structure, that is present on every end of the fiber structures with a receptor on the target cells at least for the adenoviruses HAdV-A, -C, -E and -F. Since this receptor was detected as the same one, that is responsible for coxsackie B virus adsorption, the receptor is called coxsackievirus and adenovirus receptor (CAR) (Bergelson, 1997). Additionally, binding on the surface of the target cell is supported by "bridge molecules", soluble proteins in bodily fluids like blood coagulation factors VII and X, that mediates the binding of the fiber proteins of certain adenovirus types (Modrow, 2013).

After this adsorption step, an RGD-motif (arginine-glycine-aspartic acid) in the penton base interacts with heterodimeric integrins αvβ3 or αvβ5, that function as co-receptors in this process. This interaction results in internalization of the virus (Wickham et al., 1993). Subsequently, endocytosis via clathrin-mediated internalization in the cytoplasmic membrane occurs and the virus is present in endosomes. After acidification of the endocytic vesicles, the viral fiber protein changes its conformation with resulting destruction of the endosomal membrane (Greber et al., 1996). Viral particles are now free in the cytoplasm. Via binding of residual particles on dyneins of microtubules, the viral genome is transferred into the nucleus (Modrow, 2013).

The genome of adenoviruses consists of a double-stranded, linear DNA of 36-38 kb length. By interaction of two terminal protein (TP) molecules, that are covalently linked to both 5' ends, a quasi-circular state is formed (Modrow, 2013). In general, five coding regions of the adenoviral genome can be subdivided into the early genes E1-E4, active mainly in the early phase of infection and the late genes (L1-L5), that encode proteins mainly necessary for viral particle formation (Modrow, 2013).

Adenoviral replication is especially dependent on the expression of the early viral gene E2, which is strongly induced by the large E1A protein (E1A13S). The first viral gene post infection to be transcribed is early region 1A (E1A). The primary E1A transcript is processed by differential splicing to yield five distinct messages with sedimentation coefficients of 13S, 12S 11S, 10S, and 9S. The 13S and 12S mRNAs are the most abundant at early times during infection, while the 9S mRNA is the most abundant at late times. The 11S and 10S mRNA are minor species that become more abundant at late times after infection. The 13S, 12S, 11S, 10S and 9S E1A mRNA code for 289 residue (R), 243R, 217R, 171R and 55R proteins respectively, all of which are detectable in vivo with the exception of the 9S product which has only been detected in vitro. In general, adenoviral gene expression is highly regulated in course of infection with a high degree of complexity. Thereby, transcription of the E2 genes which products encode for the viral DNA polymerase and other proteins necessary for efficient viral replication is under control of two promoters, the E2-early and E2-late promoter.

Due to its two overlapping transcriptional control regions, the E2-early promoter can be subdivided into the major promoter starting at position +1 and the minor promoter starting at position −26, both containing a TATA motif (Swaminathan and Thimmapaya, 1996). These motifs serve as binding sites for TATA box-binding proteins (TBP). Moreover, one binding site for the activating transcription factor (ATF) between positions −68 and −77 and two E2F1/DP-1 binding sites (TTTCGCGC), aligned in inverted orientation with respect to each other, are located at position −35 and −63 of the major E2-early promoter (Swaminathan and Thimmapaya, 1996). The activation of the E2-early promoter through E1A is mainly dependent on the two E2F1-binding sites localized in the major promoter part.

At intermediate stages of infection, after about 6 hpi (hours past infection), expression of E2 genes is controlled by the E2-late promoter. At position nt −33 to −22 of its 157-bp sequence, there is a TATA box, that can be bound and activated by cellular TBP (Swaminathan and Thimmapaya, 1996). Moreover, two SP1 recognition sites and three CCAAT boxes are characteristic for the E2-late promoter.

Since it was shown, that the cellular factor YB-1 is able to bind to inverted CCAAT boxes, interaction between the Y-box binding protein 1 (YB-1) and the E2-late promoter was investigated. Holm et al. showed in 2002, that there is in fact a specific interaction of YB-1 with the Y-boxes (inverted CCAAT-boxes), present in the E2-late promoter with ability to control the activity of this promoter (Holm et al., 2002). To exert its transactivating activity, YB-1 has to be translocated into the nucleus via the adenoviral complex E1B-55k/E4-orf6. These early viral genes are expressed after transactivation of E1A-13S (Frisch and Mymryk, 2002).

The cellular factor YB-1, encoded by the YBX1 gene, is a cold shock domain bearing DNA-binding protein with multiple functions in transcription, splicing, translational control and repair of DNA damages (Kohno et al., 2003). Moreover, it plays an important role in drug-resistance, due to its activation of MDR1 and MRP1 genes that are involved in the development of a multidrug-resistant phenotype in cancer cells (Mantwill et al., 2006). YB-1 expression is induced with subsequent nuclear transport through exposure of extrinsic stress factors like adenoviral infection, chemotherapy or UV radiation (Mantwill et al., 2006).

Transcriptional activation of adenovirus early genes and late genes is pivotal to the viral life cycle. Briefly, the viral life cycle is initiated by the activation of E1A transcription, followed by a cascade of activation of E2, E3 and E4 genes. Finally, the major late promoter (MLP) is activated to coordinate the expression of capsid and accessory proteins involved largely in genome encapsidation (Turner et al 2015). To overcome the block to viral DNA replication present in non-proliferating cells, the virus expresses the early 1A proteins (E1A). These immediate early proteins drive cells into S-phase and induce expression of all other viral early genes. During infection, several E1A isoforms are expressed with proteins of 289, 243, 217, 171, and 55 residues being present for human adenovirus type 5. In the context of infection, the primary driver of viral gene expression is the large E1A 289R protein (Radko et al 2015).

Upon infection, expression of the adenoviral E1A protein promotes cell cycle progression from G0/G1 phase into S-Phase and viral replication even in terminally differentiated epithelial cells, the major target of human adenoviruses. This process is considered to be essential for adenoviral life cycle.

Adenoviruses have been designed to infect, replicate and kill cancer cells while sparing normal cells. Following infection and replication in tumor cells, oncolytic viruses kill the cells, releasing virions for subsequent cycles of amplification. To achieve replication only into tumor cells, two kinds of genetic modifications have been made, leading to three subclasses of oncolytic adenovirus (also referred to as CRAd herein) have been designed all of which may be used in the practicing of the present invention. Furthermore, oncolytic adenoviruses suitable for use in the practicing of the present invention are, among others, described in WO 2003/099859.

Type I CRAd are characterized by mutations or deletions in the E1 region of the genome, interfering with the inactivation of cell cycle regulators such as p53 and retinoblastoma protein (Rb). As a consequence, type I CRAds replicate in actively dividing tumor cells. For example, Onyx-015, also known as dl1520, which is unable to express the E1B-55 kDa protein, is unable to inactivate p53 and avoid p53-induced cell cycle arrest. Several studies attributed the molecular basis of Onyx-015 selectivity to the lack of expression of p53 or one of genes involved in p53 pathway. However, O'Shea et al. showed that late viral RNA export, rather than p53 inactivation, determines Onyx-015 virus selectivity. Other type I CRAds with deletions in the E1A region are unable to bind Rb and trigger S phase entry. For example, dl922-947 and A24 contain a 24 nucleotide deletion in CR2 domain of E1A region, abrogating E1A-Rb interaction. As a result, these viruses replicate mainly in tumor cells where free, unbound E2F1 is available.

Another way to restrict adenoviral replication to tumor cells is to regulate the transcription of viral genes required for viral replication. In type II CRAds, the genome is placed under the control of a tumor-specific promoter. Those promoters were derived from genes known to be preferentially expressed in some tumors compared to normal tissue (e.g., telomerase or cyclo-oxygenase II); or that are overexpressed in tumors (e.g., prostate specific antigen, PSA or α-foetoprotein, AFP) compared to normal tissues. In type III CRAds such as XVir-N-31 (Ad-Delo3-RGD) is characterized by deletion of the transactivation domain CR3 in the E1A13S protein. XVir-N-31 is replication defective adenoviruses in normal cells. XVir-N-31 restores its replication competence by the presence of the cellular multifunctional protein YB-1 in the nucleus. Accordingly, CRAds are only capable to replicate in tumor cells and thus ultimately lysing them. Neither mutations of p53, nor ras nor RB are effective to complement the replication deficiency of XVir-N-31. XVir-N-31 lack E1A13S, consequently the E1B55k protein and the E4orf6 protein are not expressed. This deficiency is complemented by the presence of YB-1 in the nucleus of tumor cells which triggers the expression of E1B55k and E4orf6 independently of E1A13S. Once induced by the presence of YB-1 in the nucleus, E1B55k and E4orf6 transfer further cellular YB-1 into the nucleus propelling viral replication.

The cell cycle progresses sequentially through the gap 1 (G1), synthesis (S), gap 2 (G2) and mitosis (M) stages. This progression is regulated via a complex signaling network. The CDK (cyclin-dependent kinase) proteins, CDK1, CDK2, CDK4 and CDK6, are major regulators of cell cycle progression when complexed with specific cyclin proteins. Constitutive expression of CDKs and temporal control of various cyclins enables the regulation of specific cell cycle phases by distinct cyclin-CDK complexes. CDK activity is negatively regulated by several inhibitory proteins. The various aspects of CDK biology and function have been previously reviewed comprehensively.

CDK4 and CDK6, which show structural and functional homology, regulate the transition of quiescent cells in the G1 phase into the S phase when complexed with cyclin D proteins. Cyclin D proteins have three subtypes, cyclin D1-3, and accumulate in the presence of mitogenic stimuli. Negative regulators of CDK4/6 include the inhibitor of CDK4 (INK4) proteins, p161NK4A, p151NK4B, p181NK4C and p191NK4D, which inhibit CDK4/6 activity either by reducing their binding with cyclin D1 or by directly occupying their catalytic domains. The kinase activity of CDK4/6 leads to the phosphorylation of members of the retinoblastoma (Rb) protein family including Rb, p107 and p130, which results in their functional inactivation. In quiescent cells, active hypophosphorylated Rb binds to members of the E2F1 transcription factor family that form a complex with DP-1/2, together with other co-repressors and suppresses E2F1 function (Rubin et al 2005). Upon phosphorylation, Rb dissociates from this complex and allows the transcription of E2F1 target genes including cyclin A, cyclin E and DHFR, among others, which are required for the transition of the cell cycle into the S phase. Hence, inhibition of CDK4/6 activity leads to Rb dephosphorylation and repression of E2F1 activity, which promotes a G0/G1 arrest. This has fueled the development of CDK4/6 inhibitors as target therapy in cancer cells.

The disruption of the CDK4/6-Rb signalling pathway and an uncontrolled G1-S transition of the cell cycle is a common feature of cancer cells. This can occur due to various molecular alterations including loss of function mutations or deletions of the RB1 gene (encoding for Rb), CDKN2A (encoding for p16INK4A and p14ARF) or CDKN2B (encoding for p15INK4B). Such deregulation can also result from amplification or activating mutations in CCND1 (encoding for cyclin D1), E2F1-3, CDK4, CDK6 or components of various mitogenic signaling pathways such as the PI3K or MAPK pathways.

Several ATP-competitive small molecule CDK inhibitors have been developed. However, first generation inhibitors such as flavopiridol are non-selective and can inhibit multiple CDKs which might result in limited efficacy and high toxicity. Next generation CDK4/6 inhibitors display high selectivity and include palbociclib (PD-0332991 from Pfizer), abemaciclib (LY-2835219 from Eli Lilly) and ribociclib (LEE011 from Novartis) and Trilaciclib (G1T28). These CDK4/6 inhibitors have been tested pre-clinically in in vitro and in vivo models of several cancer entities including leukemia, breast cancer, melanoma, glioma, pancreatic cancer, hepatocellular carcinoma, lung adenocarcinoma, sarcoma, ovarian cancer, renal cancer, prostate cancer and metastatic breast cancer (mBC). In most studies they have demonstrated a consistent molecular and functional phenotype with a dose-dependent reduction in Rb phosphorylation, protein expression and transcription of E2F1 target genes, which correlates with a G0/G1 arrest and inhibition of cell proliferation. Additionally, all these reports demonstrate that Rb expression is a pre-requisite for sensitivity to these inhibitors.

CDK4/6 inhibitors such as PD-0332991, result in a dose dependent reduction in total Rb protein that correlated with a decrease in phosphorylated Rb. This decrease in total Rb correlates partially with a reduction in RB1 transcript levels and transcription of E2F1 target genes CCNA2 and CCNE2. Also, E2F1 expression level is significantly downregulated.

CDK4/6 inhibitors suitable for use in the practicing of the present invention are disclosed in FIG. 25.

As evident from the example part, any CDK4/6 inhibitor is suitable for use in combination with a virus, preferably an adenovirus and more preferably an oncolytic adenovirus, whereby the CDK4/6 inhibitor causes G1 arrest of cells and inhibits E2F1, more specifically, E2F1 activity.

It will be appreciated by a person skilled in the art that any CDK4/6 inhibitor is used in a therapeutically effective concentration.

PARP1 is a protein that is important for repairing single-strand breaks ('nicks' in the DNA). In mammals, 17 PARP family members have been discovered, and only 6 of these synthesize poly ADP-ribose (pADPr). PARP1, PARP2, and PARP3 have roles in DNA repair. PARP1 binds to DNA that has suffered from single-stranded breaks (SSBs) and double-stranded breaks (DSBs). PARP1 then undergoes a conformational change that aligns key amino acid residues in the active site, thereby increasing its activity. Once PARP1 is activated, it synthesizes pADPr, which binds to proteins and alters their function. pADPr is rapidly degraded by pADPr glycohydrolase to ensure that the levels of the pADPr present are reflective of DNA damage and that the response to pADPr is terminated following DNA repair.

By inhibiting DNA repair pathways, PARP1 inhibitors cause an increase in single-stranded breaks within DNA. This DNA damage is unrepaired and carried into daughter cells following replication, as BER is no longer occurring. This leads to an increase in DSBs in tumors that have BRCA1 and BRCA2 mutations (Scott et al. 2015, J Clin Oncol., 33(12): 1397-140). The chemical structures of PARP inhibitors including the PARP drug candidates rucaparib, veliparib and olaparib are shown in FIG. 26 and described in Antolin and Mestres 2014, Oncotarget, 30; 5(10):3023-8, including the benzamide moiety that characterizes all PARP inhibitor structures.

In addition, it is well established that YB-1 potentiates PARP activity and decreases the efficacy of PARP1 inhibitors (Alemasova et al. 2018, Oncotarget, 34, 23349-65), suggesting that YB-1 dependent oncolytic adenovirus in combination with both CDK 4/6 Inhibitors and PARP-Inhibitors will work synergistically in cancer cell killing. Olaparib and BMN673 (Talazolarib developed from Pfizer, USA, Clin Cancer Res. 2013, 15; 19(18):5003-15) are example of PARP-Inhibitors.

It will be appreciated by a person skilled in the art that any PARP inhibitor is used in a therapeutically effective concentration.

CDK4/6 inhibitors suitable for use in the practicing of the present invention are disclosed in FIG. 25.

Aberrations in the epigenetic landscape are a hallmark of cancer and acetylation of lysine residues is a post-translational modification with broad relevance to cellular signaling and disease biology. Enzymes that 'write' (histone acetyltransferases, HATs) and 'erase' (histone deacetylases, HDACs) acetylation sites are an area of extensive research in current drug development. Recruitment of proteins to macromolecular complexes by acetylated lysine residues is mediated by bromodomains (BRDs), which are evolutionarily highly conserved protein-interaction modules that recognise ε-N-lysine acetylation motifs. The conserved BRD fold contains a deep, largely hydrophobic acetyl lysine binding site, which represents an attractive pocket for the development of small, pharmaceutically active molecules. Proteins that contain BRDs have been implicated in the development of a large variety of diseases.

Recently, two highly potent and selective inhibitors that target BRDs of the BET (bromodomains and extra-terminal) family provided compelling data supporting targeting of these BRDs in cancer. The BET (bromodomain and extra-terminal domain) subfamily of bromodomain proteins, composed of BRD2, BRD3, BRD4, and BRDT, perform diverse roles in regulating transcription by RNA polymerase II (POLII) and are an exciting new class of epigenetic drug targets. These proteins facilitate the initiation and elongation phases of transcription by binding to activated chromatin at acetylated lysine residues. The recognition of activated chromatin by these so-called epigenetic "readers" promotes the recruitment of the RNA polymerase II complex to sites of active transcription. The BRD4/P-TEFb interaction is important for rapid transcriptional re-initiation after mitosis (Muller et al., 2011, Expert Rev. Mol. Medicine, 13, e19). P-TEFb was identified and purified as a factor needed for the generation of long run-off transcripts using an in vitro transcription system derived from *Drosophila* cells. It is a cyclin dependent kinase containing the catalytic subunit, Cdk9, and a regulatory subunit, cyclin T in *Drosophila*. In humans there are multiple forms of P-TEFb which contain Cdk9 and one of several cyclin subunits, cyclin T1, T2, and K. P-TEFb associates with other factors including the bromodomain protein BRD4, and is found associated with a large complex of proteins called the super elongation complex (Yang Z, et al., 2005. Mol Cell; 19:535-45; Fu et al., 1999, J Biol Chem., 274:34527-30).

JQ-1 (thieno-triazolo-1-4-diazepine) is a potent inhibitor of the BET family of bromodomain proteins which include BRD2, BRD3, BRD4 (Filippakopoulos et al., 2010 Nature 468, 1067-1073). JQ-1 prevent interaction between the bromodomain and the acetyl group, causing the downregulation of certain genes. Further BET bromodomain Inhibitors including OTOX15, BAY1238097, GSK2820151, I-BET762 and PLX51107 have been described (Perez-*Salvia* and Esteller 2017, EPIGENETICS, 12, 323-339; Brandt et al., 2015ACS Chem. Biol., 10, 22-39). JQ-1 is structurally related to benzodiazepines. The formula is $C_{23}H_{25}ClN_4O_2S$.

Recently, it has been shown that the BET inhibitor JQ-1 facilitates adenovirus infection and adenoviral vector-mediated gene delivery. Treatment of cells with JQ-1 induces an increase in BRD4 association with CDK9, a subunit of P-TEFb of transcription elongation. However, as stated in the paper, further studies are required to delicate the mechanism by which BED4 utilizes to regulate adenovirus infection and transgene expression (Baojie Lv et al 2018, Scientific reports, 8, 11554). Importantly viral replication and virus transcription were not investigated. However, it is known, that CDK9 stimulates released of paused polymerase and activates transcription by increasing the number of transcribing polymerases and thus the amount of mRNA synthesis per time (Gressel et al. 2017, eLife, 6, e29736). In addition, it was shown, that BET inhibitor resistance can be overcome by CDK 4/6 inhibitors (Jin et al. 2018, Mol Cell; 71(4):592-605). Recently it was demonstrated a dramatic increase in P-TEFb-Brd4 interaction from late mitosis to early G1 phases of cell cycle and active recruitment of P-TEFb to the chromosomes, followed by initiation of transcription of key genes for G1 progression. Importantly, depletion of Brd4 abrogated the whole process by reducing transcription of essential G1 genes, leading to G1 cell cycle arrest and apoptosis (Yang et al., 2008, Mol Cell Biol., 28:967-976, Kohoutek, 2009, Cell Division, 4. 19).

However, nothing is known about using YB-1 dependent oncolytic adenoviruses in conjunction with CDK 4/6 inhibitors and BET inhibitors.

It will be appreciated and is within the present invention that other bromodomain inhibitors will be equally suitable for use in triple therapy using a virus, preferably an adenovirus, more preferably an oncolytic adenovirus such as XVir-N-31, and a CDK4/6 inhibitor.

It will be appreciated by a person skilled in the art that any bromodomain (Bet) inhibitor is used in a therapeutically effective concentration.

Bromodomain inhibitors suitable for use in the practicing of the present invention are disclosed in FIG. 27.

The role of MDM2 on p53 and E2F1

The p53 and retinoblastoma (Rb) proteins are two key tumor suppressors. Mutations in one or both are found in all human cancer tumors and both have been extensively studied as potential therapeutic targets in drug development programs. As p53 and E2F1 are pivotal regulators of cell proliferation and viability (cell death), their abundance and activity are tightly regulated. The Mouse Double Minute 2 protein (MDM2) also known as E3 ubiquitin-protein ligase seems to regulate both MDM2-p53 and the Rb-E2F1 pathway. Since Rb and p53 are not able to interact directly, it is suggested that MDM2 is a bridge between Rb and p53 (Polager and Ginsberg, Nat Rev Cancer 2009, 9, 738-48). Further supporting the role of MDM2 as an oncogene, several human tumor types have been shown to have increased levels of MDM2, including soft tissue sarcomas and osteosarcomas as well as breast tumors. The MDM2 oncoprotein ubiquitinates and antagonizes p53 but may also carry out p53-independent functions. MDM2 directly binds to p53 and inhibits its transcriptional activity. In addition, as a p53-selective E3 ubiquitin ligase, MDM2 promotes p53 ubiquitylation and targets it for proteasomal degradation (Eischem et al, Hum. Mutant. 20014, 35, 728-737). However, there exist evidence that MDM2 also is required for survival of p53-deficient cancer cells (Feeley et al, Cancer Res 2017, 77, 3823-3833).

In line with a positive effect of MDM2 on the E2F1 pathway, MDM2 can physically interact with Rb, E2F1 and the heterodimeric partner of E2F1, DP1, to promote the G1/S cell cycle transition. Accordingly, MDM2 interaction with E2F1 or DP1 can stimulate transcription of E2F1 target genes that are involved in cell cycle progression. Moreover, targeting of E2F1 for degradation by the F-box protein SKP2 is antagonized by the binding of MDM2. Thus, there exists evidence that MDM2 binding increases E2F1 stability (Zhang et al. Oncogene 2005, 24, 7238-7247), while MDM2 inhibition is associated with a decrease of E2F1 protein level. MDM2, like many other oncoproteins, binds selectively to the hypo-phosphorylated Rb. The interaction between MDM2 and Rb inhibits the Rb-E2F1 complexes formation resulting in suppression of Rb function. In addition, the interaction between RB and MDM2 causes MDM2-mediated Rb degradation. The current facts seem to confirm that MDM2 also (besides p53) is a key negative regulator of Rb (Shi and Gu, Genes Cancer. 2012, 3: 240-248; Yap et al., Oncogene 1999, 18, 7681-7689, Wu et al., JBC 2009, 284, 26315-26321).

Nutlin-3

Nutlins are cis-imidazoline analogs, which inhibit the interaction between MDM2 and tumor suppressor p53. Nutlin-3 is the compound most commonly used in anti-cancer studies. Nutlin small molecules occupy p53 binding pocket of MDM2 and effectively disrupt the p53-MDM2 interaction that leads to activation of the p53 pathway in p53 wild-type cells. In response to nutlin-3 treatment, p53 cancer cells undergo either cell cycle arrest (G0/G1 or G2/S) ore apoptosis. In addition, nutlin-3 can induce differentiation and cellular senescence. It was shown that an array of factors affects the outcome of Nutlin-3 treatment, including the single nucleotide polymorphism of MDM2, MDM4, p73, ATM, and E2F1. Activation of p53 up-regulates p21 and MDM2, both of which are important regulators for Rb. Recently it was shown that Nultin-3 affects both Rb and E2F1 protein levels and Rb phosphorylation negatively, which significantly affect the cellular responses to Nutlin-3 (Du et al., JBC 2009, 284, 26315-26321).

Although previous studies suggested that the tumorigenicity of MDM2 is due to its negative regulation of p53, the p53-independent interactions may be equally as important. During recent studies utilizing MDM2 inhibitors, it was noted that E2F transcription factor 1 (E2F1) was down regulated upon inhibition of MDM2, regardless of the p53 status of the cancer. One publication describes the used of antisense RNA to inhibit MDM2 function. They concluded that MDM2 has a role in prostate cancer growth via p53-dependent and p53-independent mechanisms. Furthermore, they show that Bcl2, Rb, pRb and E2F1 protein levels were decreased, whereas p21 was increased (Zhang et al 2003, PNAS 2003, 100, 11636-11641). However, it was shown that MDM2 prolongs the half-life of the E2F1 protein by inhibiting its ubiquitination. MDM2 displaces SCF(SKP2), the E2F1 E3 ligase. Direct binding between MDM2 and E2F1 is necessary for the negative effects of MDM2 on E2F1 ubiquitination, and deletion of the MDM2 nuclear localization signal does not result in loss of the ability to increase the E2F1 protein level. The downregulation of E2F1 upon MDM2 inhibition was not due to either pRB or p14(Arf). In addition, E2F1 was responsible for at least part of the inhibition of cell proliferation induced by MDM2 knockdown. In conclusion, the present study provides evidence that stabilization of the E2F1 protein is likely another p53-independent component of MDM2-mediated tumorigenesis (Zhang et al., Oncogene 2005, 24, 7238-7247).

Clearly the Rb-E2F1 and MDM2-p53 pathways, along with the multifaceted crosstalk between them, are crucial regulators of cell cycle progression and viability. Clinical studies using MDM2-targeting drugs, however, have currently not met the initial expectations, at least not when used as single drugs. This has spurred the search for optimized combinations of MDM2 inhibitors with other cancer drugs.

Several derivatives of nutlin, have been developed and progressed into human studies (FIG. 1). These compounds are thought to work best on tumors that contain normal or "wild-type" p53. However, recent results suggest that E2F1 transcriptionally activity is a critical determinant MDM2 antagonist-induced apoptosis and p73 is important for E2F1 mediated apoptosis induced by Nutlin-3 (Burgess et al., Frontiers in Oncology 2016, 6, article 7; Skalniak et al., 2019, 29, 151-170; Kitagawa et al., Oncogene 2008, 27, 5303-5314).

Nutlin and derivatives thereof(NVP-HDM201, Idasanutlin, AM-8553, SAR405838, Nutlin-3a, AMG232) are shown in FIG. 43.

The tumours which can in particular be treated by the viruses and thus combinations of the present invention described herein are preferably those tumours which are selected from the group comprising tumours of the nervous system, ocular tumours, tumours of the skin, tumours of the soft tissue, gastrointestinal tumours, tumours of the respiratory system, tumour of the skeleton, tumours of the endocrine system, tumours of the female genital system, tumours of a mammary gland, tumours of the male genital system, tumours of the urinary outflow system, tumours of the haematopoietic system including mixed and embryonic tumours, and leukemia. It is within the present invention that these tumours are in particular resistant tumours as in particular defined herein.

The group of tumors of the nervous system preferably comprises:

1. Tumors of the skull as well as of the brain (intracranial), preferably astrocytoma, oligodendroglioma, meningioma, neuroblastoma, ganglioneuroma, ependymoma, schwannoglioma, neurofibroma, haemangioblastoma, lipoma, craniopharyngioma, teratoma and chordoma;

2. Tumors of the spinal cord and of the vertebral canal, preferably glioblastoma, meningioma, neuroblastoma, neurofibroma, osteosarcoma, chondrosarcoma, haemangiosarcoma, fibrosarcoma and multiple myeloma; and 3. Tumors of the peripheral nerves, preferably schwannoglioma, neurofibroma, neurofibrosarcoma and perineural fibroblastoma.

The group of the ocular tumors preferably comprises:

1. Tumors of the eyelids and of the lid glands, preferably adenoma, adenocarcinoma, papilloma, histiocytoma, mast cell tumor, basal-cell tumor, melanoma, squamous-cell carcinoma, fibroma and fibrosarcoma;

2. Tumors of the conjunctiva and of the nictitating membrane, preferably squamous-cell carcinoma, haemangioma, haemangiosarcoma, adenoma, adenocarcinoma, fibrosarcoma, melanoma and papilloma; and 3. Tumors of the orbita, the optic nerve and of the eyeball, preferably retinoblastoma, osteosarcoma, mast cell tumor, meningioma, reticular cell tumor, glioma, schwannoglioma, chondroma, adenocarcinoma, squamous-cell carcinoma, plasma cell tumor, lymphoma, rhabdomyosarcoma and melanoma.

The group of skin tumors preferably comprises:

Tumors of the histiocytoma, lipoma, fibrosarcoma, fibroma, mast cell tumor, malignant melanoma, papilloma, basal-cell tumor, keratoacanthoma, haemangiopericytoma, tumors of the hair follicles, tumors of the sweat glands, tumors of the sebaceous glands, haemangioma, haemangiosarcoma, lipoma, liposarcoma, malignant fibrous histiocytoma, plasmacytoma and lymphangioma.

The group of tumors of the soft-tissues preferably comprises:

Tumors of the alveolar soft-tissue sarcoma, epithelioid cell sarcoma, chondrosarcoma of the soft-tissue, osteosarcoma of the soft-tissues, Ewing's sarcoma of the soft-tissues, primitive neuroectodermal tumors (PNET), fibrosarcoma, fibroma, leiomyosarcoma, leiomyoma, liposarcoma, malignant fibrous histiocytoma, malignant haemangiopericytoma, haemangioma, haemangiosarcoma, malignant mesenchymoma, malignant peripheral nerve sheath tumor (MPNST, malignant schwannoglioma, malignant melanocytic schwannoglioma, rhabdomyosarcoma, synovial sarcoma, lymphangioma and lymphangiosarcoma.

The group of gastrointestinal tumors preferably comprises:

1. Tumors of the oral cavity and of the tongue, preferably squamous-cell carcinoma, fibrosarcoma, Merkel cell tumor, inductive fibroameloblastoma, fibroma, fibrosarcoma, viral papillomatosis, idiopathic papillomatosis, nasopharyngeal polyps, leiomyosarcoma, myoblastoma and mast cell tumor;

2. Tumors of the salivary glands, preferably adenocarcinoma;

3. Tumors of the oesophagus, preferably squamous-cell carcinoma, leiomyosarcoma, fibrosarcoma, osteosarcoma, Barrett carcinoma and paraoesophageal tumors;

4. Tumors of the exocrine pancreas, preferably adenocarcinoma; and

5. Tumors of the stomach, preferably adenocarcinoma, leiomyoma, leiomyosarcoma and fibrosarcoma.

The group of the tumors of the respiratory system preferably comprises:

1. Tumors of the nose and nasal cavity, of the larynx and of the trachea, preferably squamous-cell carcinoma, fibrosarcoma, fibroma, lymphosarcoma, lymphoma, haemangioma, haemangiosarcoma, melanoma, mast cell tumor, osteosarcoma, chondrosarcoma, oncocytoma (rhabdomyoma), adenocarcinoma and myoblastoma; and 2. Tumors of the lung, preferably squamous-cell carcinoma, fibrosarcoma, fibroma, lymphosarcoma, lymphoma, haemangioma, haemangiosarcoma, melanoma, mast cell tumor, osteosarcoma, chondrosarcoma, oncocytoma (rhabdomyoma), adenocarcinoma, myoblastoma, small-cell carcinoma, non-small cell carcinoma, bronchial adenocarcinoma, bronchoalveolar adenocarcinoma and alveolar adenocarcinoma.

The group of the skeleton tumors preferably comprises: osteosarcoma, chondrosarcoma, parosteal osteosarcoma, haemangiosarcoma, synovial cell sarcoma, haemangiosarcoma, fibrosarcoma, malignant mesenchymoma, giant-cell tumor, osteoma and multilobular osteoma.

The group of the tumors of the endocrine system preferably comprises:

1. Tumors of the thyroid gland/parathyroid, preferably adenoma and adenocarcinoma;

2. Tumors of the suprarenal gland, preferably adenoma, adenocarcinoma and pheochromocytoma (medullosuprarenoma);

3. Tumors of the hypothalamus/hypophysis, preferably adenoma and adenocarcinoma;

4. Tumors of the endocrine pancreas, preferably insulinoma (beta cell tumor, APUDom) and Zollinger-Ellison syndrome (gastrin secernent tumor of the delta cells of the pancreas); and 5. as well as multiple endocrine neoplasias (MEN) and chemodectoma.

The group of the tumors of the female sexual system tumors preferably comprises:

1. Tumors of the ovaries, preferably adenoma, adenocarcinoma, cystadenoma, and undifferentiated carcinoma;

2. Tumors of the uterine, preferably leiomyoma, leiomyosarcoma, adenoma, adenocarcinoma, fibroma, fibrosarcoma and lipoma;

3. Tumors of the cervix, preferably adenocarcinoma, adenoma, leiomyosarcoma and leiomyoma;

4. Tumors of the vagina and vulva, preferably leiomyoma, leiomyosarcoma, fibroleiomyoma, fibroma, fibrosarcoma, polyps and squamous-cell carcinoma.

The group of tumors of the mammary glands preferably comprises:

fibroadenoma, adenoma, adenocarcinoma, mesenchymal tumora, carcinoma, carcinosarcoma.

The group of the tumors of the male sexual system preferably comprises:

1. Tumors of the testicles, preferably seminoma, interstitial-cell tumor and Sertoli cell tumor;

2. Tumors of the prostate, preferably adenocarcinoma, undifferentiated carcinoma, squamous-cell carcinoma, leiomyosarcoma and transitional cell carcinoma; and 3. Tumors of the penis and the external genitals, preferably mast cell tumor and squamous-cell carcinoma.

The group of tumors of the urinary outflow system preferably comprises:

1. Tumors of the kidney, preferably adenocarcinoma, transitional cell carcinoma (epithelial tumors), fibrosarcoma, chondrosarcoma (mesenchymal tumors), Wilm's tumor, nephroblastoma and embryonal nephroma (embryonal pluripotent blastoma);

2. Tumors of the ureter, preferably leiomyoma, leiomyosarcoma, fibropapilloma, transitional cell carcinoma;

3. Tumors of the urinary bladder, preferably transitional cell carcinoma, squamous-cell carcinoma, adenocarcinoma, botryoid (embryonal rhabdomyosarcoma), fibroma, fibrosarcoma, leiomyoma, leiomyosarcoma, papilloma and haemangiosarcoma; and 4. Tumors of the urethra, preferably transitional cell carcinoma, squamous-cell carcinoma and leiomyosarcoma.

The group of tumors of the haematopoietic system preferably comprises:

1. Lymphoma, lymphatic leukemia, non-lymphactic leukemia, myeloproliferative leukemia, Hodgkin's lymphoma, Non-Hodgkin's lymphoma.

The group of the mixed and embryonal tumors preferably comprises:

Haemangiosarcoma, thymoma and mesothelioma.

Preferably, these tumors are selected from the group comprising breast cancer, ovary carcinoma, prostate carcinoma, osteosarcoma, glioblastoma, melanoma, small-cell lung carcinoma and colorectal carcinoma. Further tumors are those which are resistant as described herein, preferably those which are multiple resistant, particularly also those tumors of the group described above.

It is also within the present invention that subjects to which the combination of the invention is to be administered are identified and screened, respectively. Such identification of patients who may benefit from the present invention in its diverse aspects, is based on the detection of YB-1 in the nucleus of a sample of a subject.

In an embodiment, the examination of the tumor tissue is done by using an agent which is selected from the group comprising antibodies against YB-1, aptamers against YB-1 and spiegelmers against YB-1 as well as anticalines against YB-1. Basically, the same means can be produced for the corresponding markers and used accordingly. The manufacture of antibodies, in particular monoclonal antibodies, is known to the ones skilled in the art. A further means for specific detection of YB-1 or the markers, are peptides which bind with a high affinity to the target structures, in the present case YB-1 or said markers. In the prior art methods are known such as phage-display in order to generate such peptides. Typically, a peptide library is taken as a starting point, whereby individual peptides have a length of from 8 to 20 amino acids and the size of the library is about 102 to 1018, preferably 108 to 1015 different peptides. A special form of target molecule binding polypeptides are the so-called anticalines which are, for example, described in German patent application DE 197 42 706.

A further means for specific binding of YB-1 or the corresponding markers disclosed herein and thus for the detection of cell cyclus independent localisation of YB-1 in the cellular nucleus, are the so-called aptamers, i.e. D-nucleic acids which are present either as RNA or DNA either as a single strand or a double strand and specifically bind to the target molecule. The generation of aptamers is, for example, described in European patent EP 0 533 838. A special form of aptamers are the so-called aptazymes, which, for example, are described by Piganeau, N. et al. (2000), Angew. Chem. Int. Ed., 39, no. 29, pages 4369-4373. These are special embodiments of aptamers insofar as they comprise apart from the aptamer part a ribozyme part and get catalytically active upon binding or release of the target molecule binding to the aptamer part and cleave a nucleic acid substrate which goes along with the generation of a signal.

A further form of aptamers are the so-called spiegelmers, i. e. target molecule binding nucleic acids which are made of L-nucleic acids. The method for the manufacture of such spiegelmers is, for example, described in WO 98/08856.

The sample of the tumor tissue can be obtained by puncture or through surgery. The assessment whether YB-1 is localised in the nucleus independent from the cell cycle, is frequently done by using microscopic techniques and/or immuno histoanalysis, preferably using the antibody or any of the other aforementioned means. Further means for detecting YB-1 in the nucleus and in particular for detecting that YB-1 is located there independent from the cell cycle, are known to the one skilled in the art. For example, the localisation of YB-1 can be easily detected in stained tissue sections when screening them. The frequency of the presence of YB-1 in the nucleus already indicates that the localisation is independent from the cell cycle. A further option for cell cycle independent detection of YB-1 in the nucleus resides in the staining against YB-1 and detection whether YB-1 is localised in the nucleus and determination of the phase of the cells. This as well as the detection of YB-1 may also be performed by using the afore-mentioned means directed against YB-1. The detection of the means is done by methods known to the one skilled in the art. By said agents specifically binding to YB-1 and not to any other structures within the sample to be analysed, particularly the cells, their localisation and because of their specific binding to YB-1 also the localisation of YB-1 can be detected and established by a suitable labelling of the means. Methods for the labelling of said means are known to the ones skilled in the art.

In the following, the present invention shall be further illustrated by reference to the figures and samples from which new features, embodiments and advantages may be taken.

FIG. 1 a is a bar diagram showing relative absorbance as an indicator of cell viability for XVir-N-31 (XVir), wild type adenovirus (WT) and control (Ctrl) when used in combination with CDK4/6 inhibitors LY (LY-2835219), PD (PD-032991) or LEE (LEE011).

FIG. 1*b* is a bar diagram showing viral titre for XVir-N-31 (XVir) and wild type adenovirus (WT) when combined with CDK4/6 inhibitors LY (LY-2835219), PD (PD-032991) or LEE (LEE011).

FIG. 1*c* is a bar diagram showing relative fiber DNA for XVir-N-31 (XVir) and wild type adenovirus (WT) when combined with CDK4/6 inhibitors LY (LY-2835219), PD (PD-032991) or LEE (LEE011).

FIG. 2 depicts the result of a Western blot analysis.

FIGS. 3*a-d* are bar diagrams.

FIGS. 4*a-d* are bar diagrams.

Figure 9A:
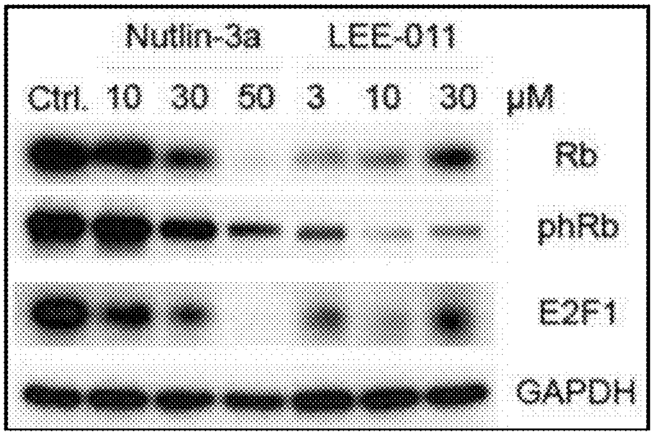
Figure 9B:
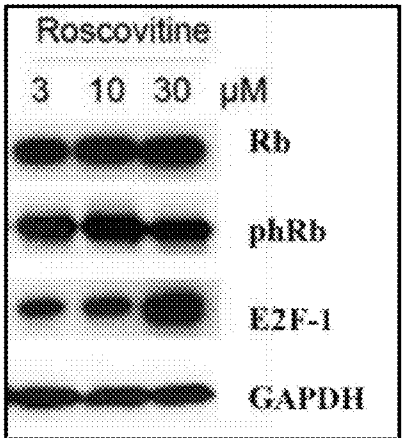
Figure 9C:
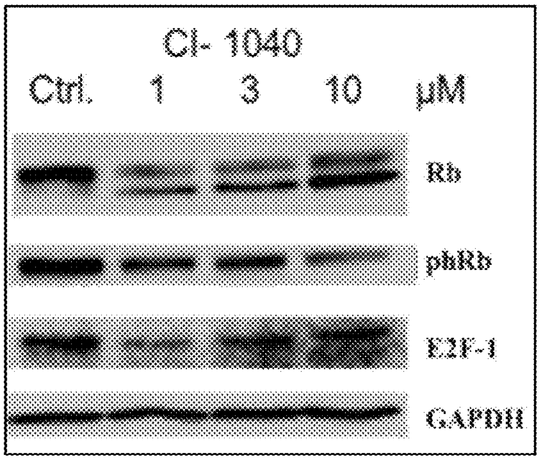

FIGS. 9A-C show the result of a Western blot analysis of UMUC cells treated with indicated concentrations of Nutlin-3a and LEE011 (Ribociclib) (FIG. 9A), Roscovitine (FIG. 9B) and CI-1040 (FIG. 9C); Rb means retinoblastoma protein; phRB means phosphorylated retinoblastoma protein; E2F1 means transcription factor E2F1; and GAPDH served as loading control.

Figure 10:
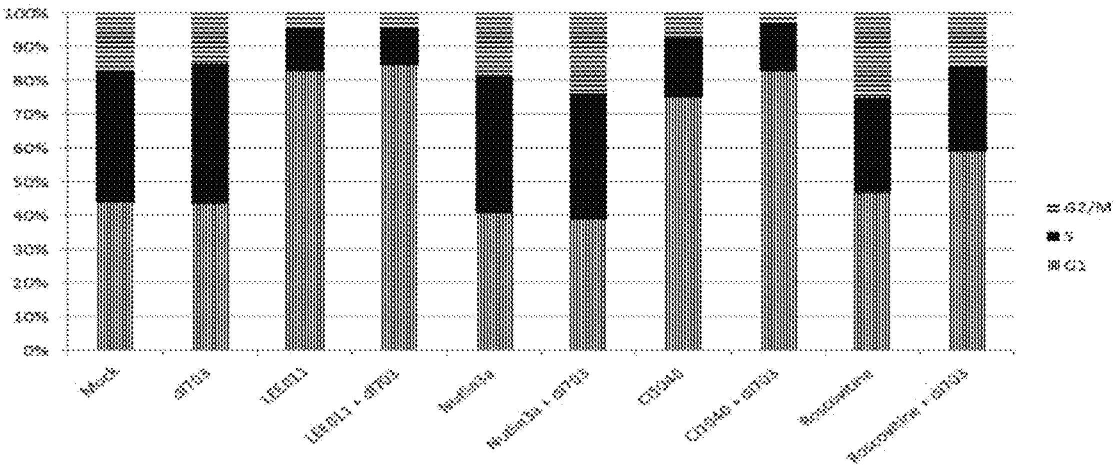

FIG. 10 is a bar diagram showing cell cycle distribution in UMUC3 cells, measured 48 hours post treatment, whereby the concentrations of the CDK4/6 inhibitors was as follows: Roscovetine: 10 μM, CI-1040: 1 μM, Nutlin-3a: 10 μM, and LEE011: 10 μM.

Figure 11:
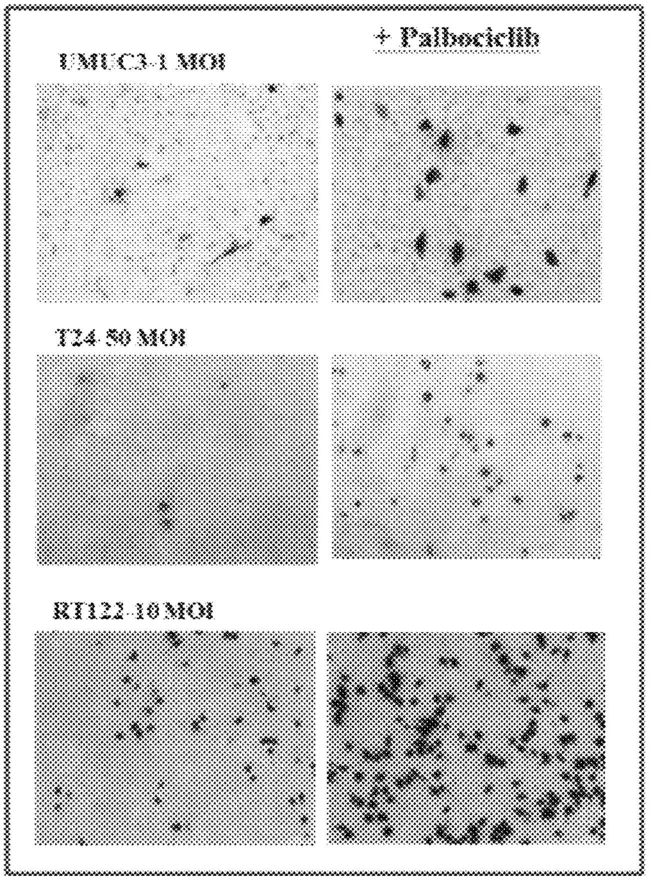

FIG. 11 is a panel of microscopic images showing adenovirus hexon gene expression with and without Palbociclib treatment.

Figure 12:
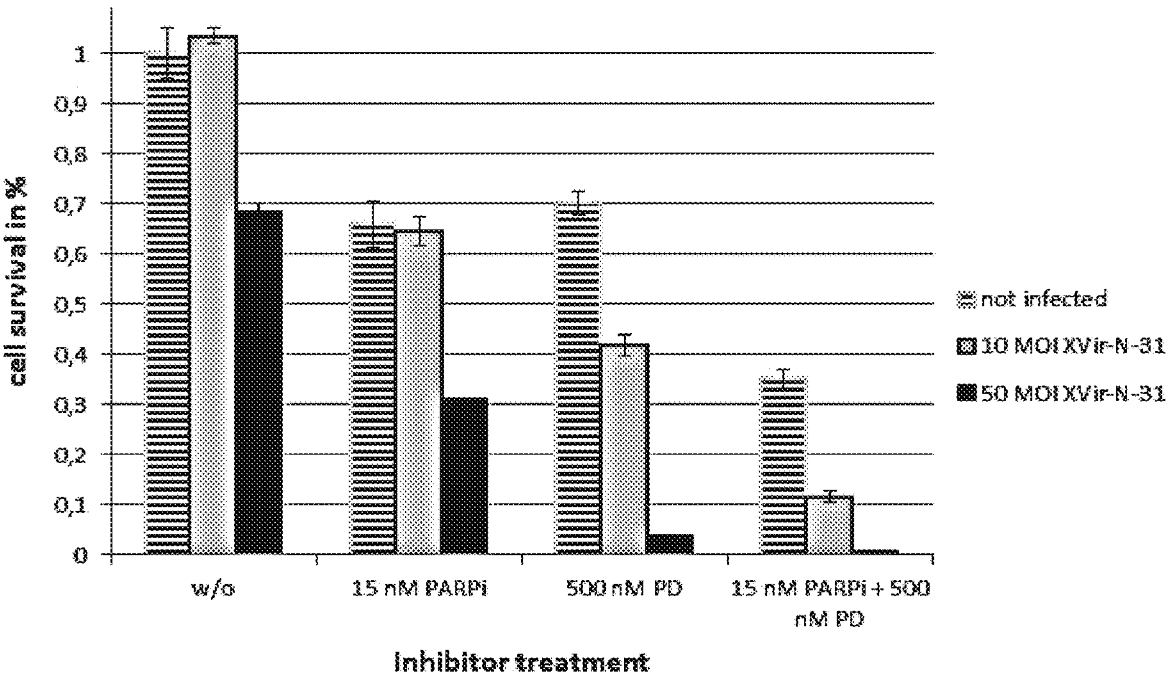

FIG. 12 is a bar diagram showing the result of a potency assay of T24 cells exposed to XVir-N-31 alone, with 15 nM PARP inhibitor PARPi, 500 nM PD (Palbociclib) or a combination of 15 nM PARPi and 500 nM PD, as percentage cell survival, whereby the cells were either not infected (left column), infected with an MOI of 10 (middle column) or an MOI of 50 (right column).

Figure 13:
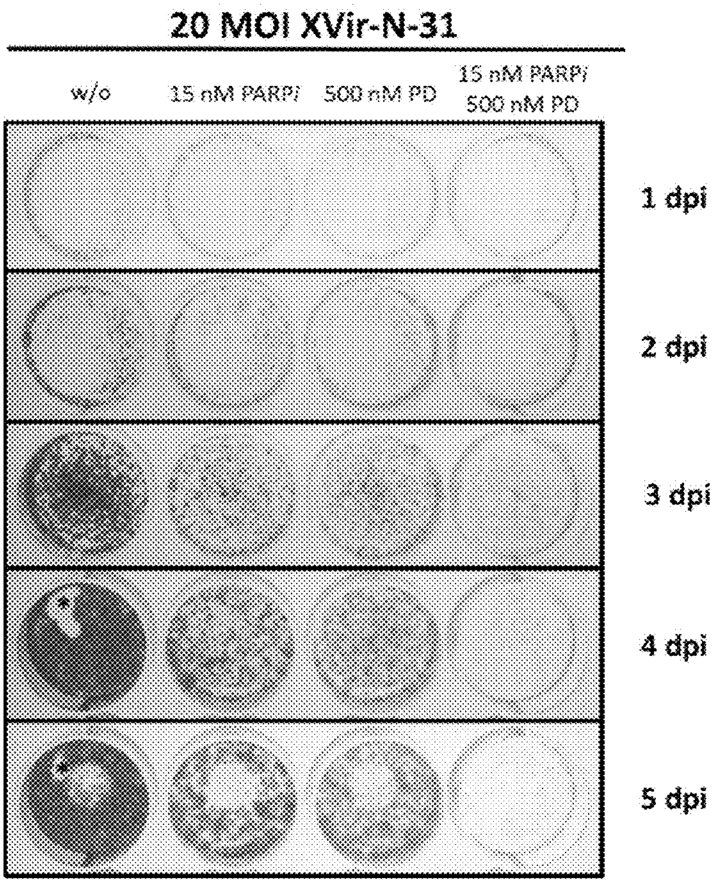

FIG. 13 is a panel of pictures showing cultures of SRB-stained T24 cells after treatment with XVir-N-31 (20 MOI), XVir-N-31 and 15 nM PARPi, XVir-N-31 and 500 nM PD, and XVir-N-31, 15 nM PARPi and 500 nM PD, 1 dpi, 2 dpi, 3 dpi, 4 dpi, 5 dpi and 6 dpi.

Figure 14:
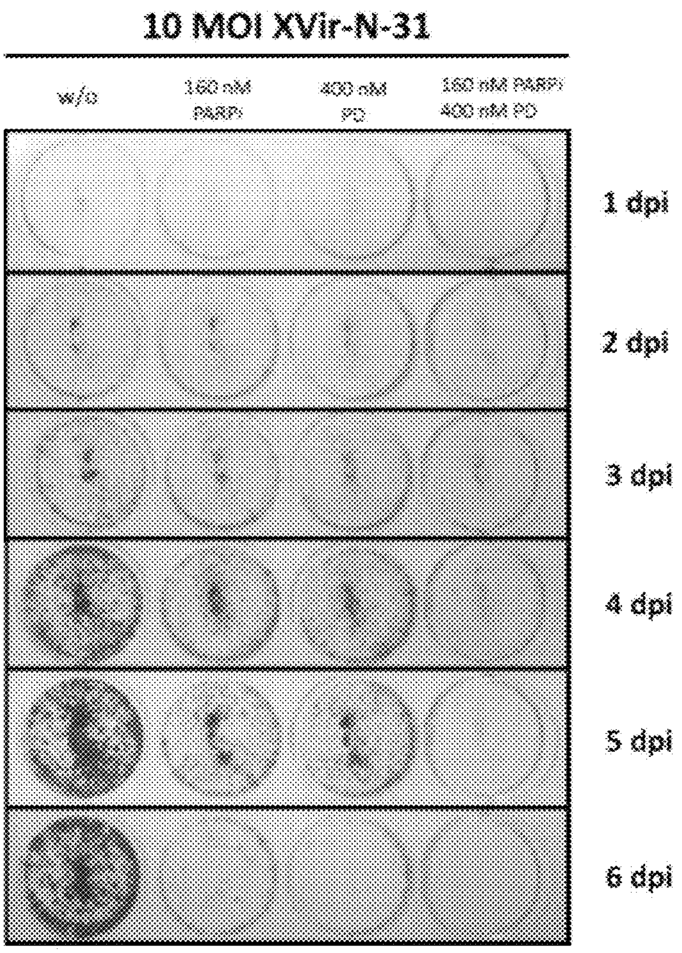

FIG. 14 is a panel of pictures showing cultures of SRB-stained UMUC cells after treatment with XVir-N-31 (10 MOI), XVir-N-31 and 160 nM PARPi, XVir-N-31 and 400 nM PD, and XVir-N-31, 160 nM PARPi and 400 nM PD, 1 dpi, 2 dpi, 3 dpi, 4 dpi, 5 dpi and 6 dpi.

Figure 15:
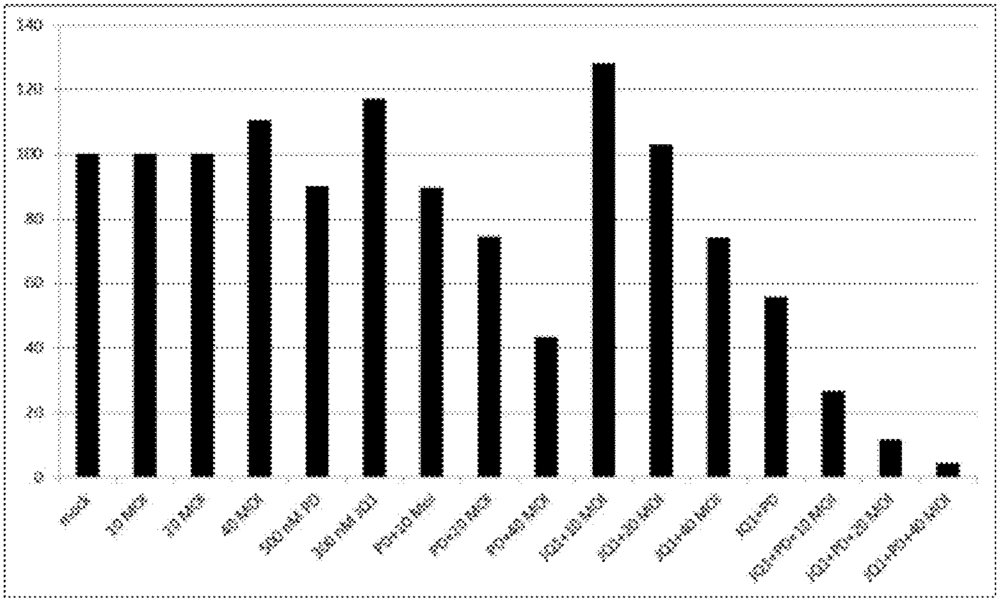

FIG. 15 is a bar diagram showing the result of a potency assay on T24 cells 5 days post infection with XVir-N-31, the CDK 4/6 inhibitor Palbociclib and the bromodomain inhibitor JQ-1; Y-axis: survival of cells in %.

Figure 16:
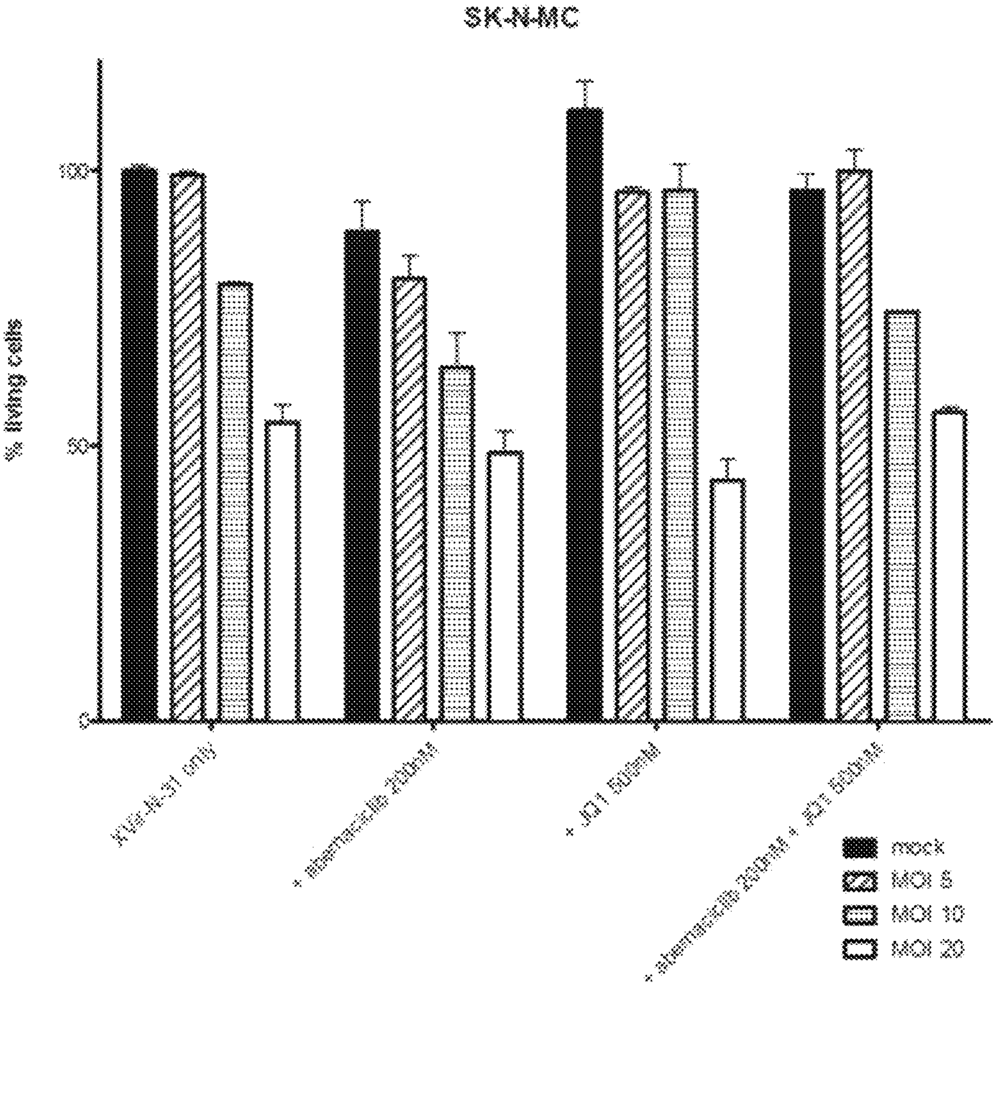

FIG. 16 is a bar diagram showing the result of a potency assay of SK-N-MC cells 5 days after exposure to XVir-N-31 alone, with 200 nM abemaciclib, 500 nM JQ-1 or a combination of 200 nM abemaciclib and 500 nM JQ-1, as percentage cell survival, whereby the cells were either not infected or infected with an MOI of 5, 10 or 20.

Figure 17:
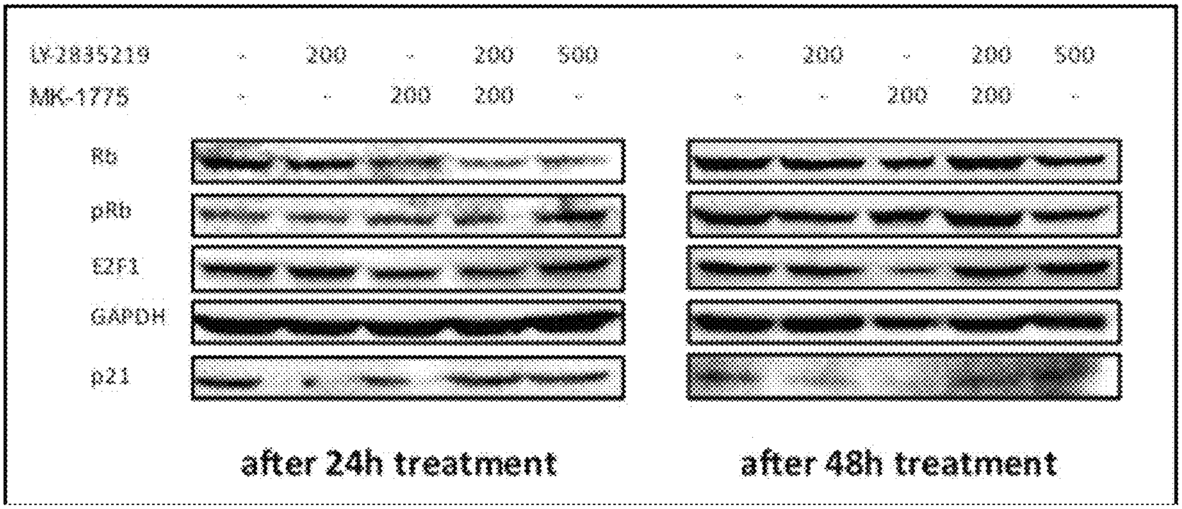

FIG. 17 shows the result of a Western blot analysis of SK-N-MC cells treated with indicated concentrations of CDK 4/6 Inhibitor LY-2835219 (Abemaciclib) and the Wee-Inhibitor MK-1775 (Adavosertib) 24 and 48 Hours post treatment; Rb means retinoblastoma protein; phRB means phosphorylated retinoblastoma protein; E2F1 means transcription factor E2F1; and GAPDH served as loading control.

Figure 18:
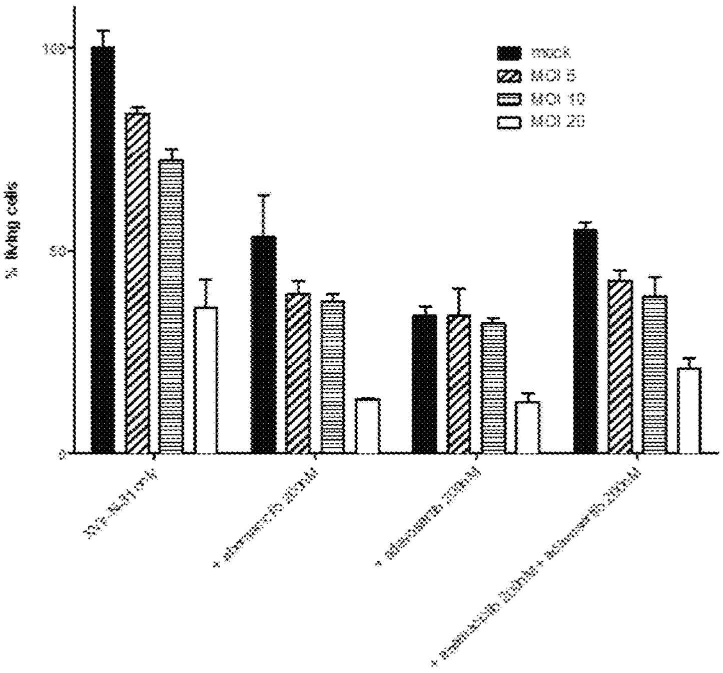

FIG. 18 shows the result of a potency assay on SK-N-MC cells 5 days post infection with XVir-N-31, the CDK 4/6 inhibitor Abemaciclib and Adavosertib (Wee-inhibitor MK-1775) expressed as percentage of living cells.

Figure 19:
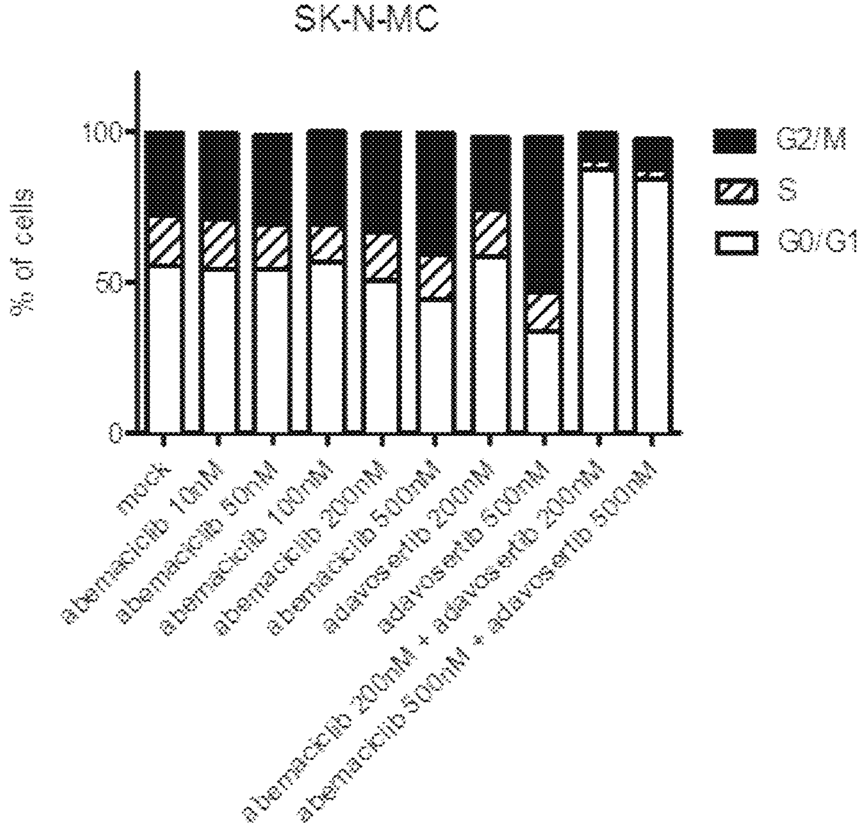

FIG. 19 shows cell cycle distribution after treatment of SK-N-MC cells with the indicated inhibitors.

Figure 20:
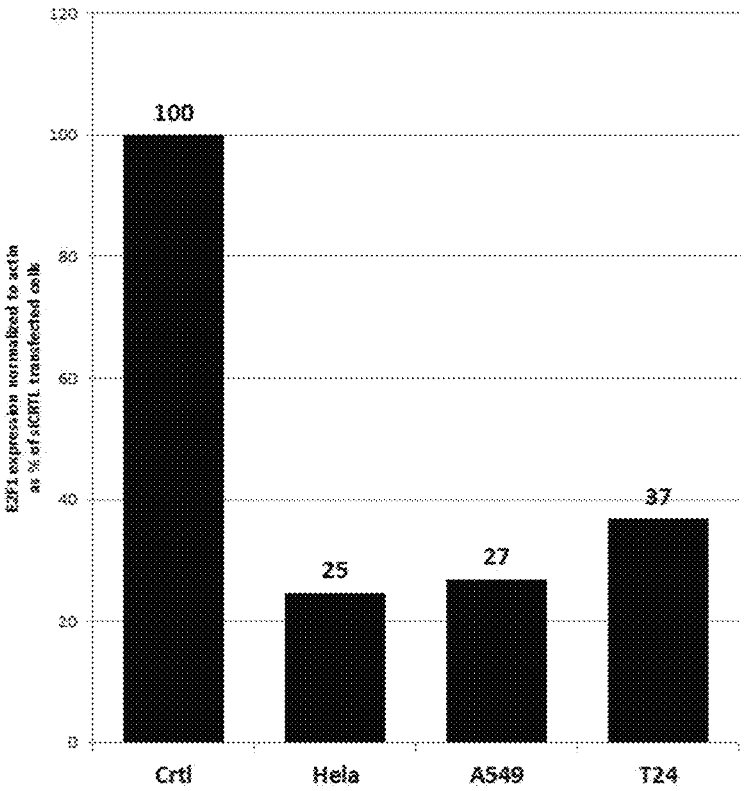

FIG. 20 is a bar diagram showing the effect of E2F1 directed siRNA on E2F1 expression in various cell lines; Y axis: E2F1 expression normalized to actin as % of siCTRL transfected cells.

FIG. 21 is a bar diagram showing that E2F1 inhibition causes increased E2-early expression in T24 cells treated with siRNA-E2F1; Y axis: adenoviral gene expression normalized to actin (in % of siCTRL).

FIG. 22 is a scheme showing location of the primers for determining adenovirus E2-early expression.

FIG. 23 is a representation of the nucleotide sequence of the wild type E2 early promoter adenovirus (above) and a mutant E2 early promoter having mutations at the E2F1-binding sites (below).

Figure 24:
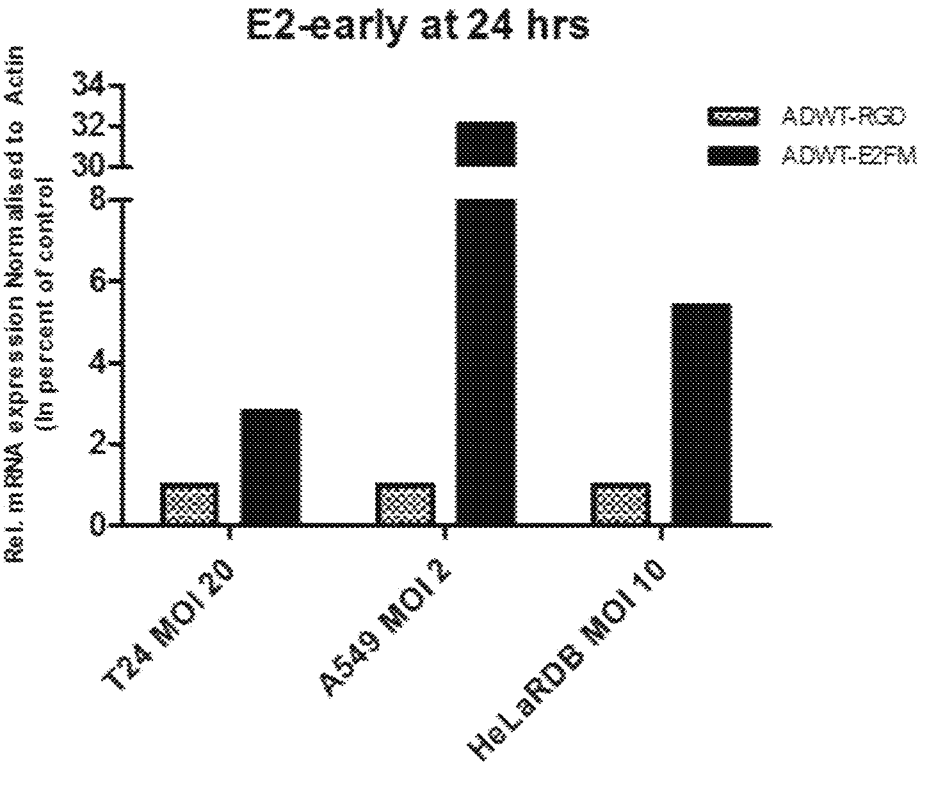

FIG. 24 is a bar diagram showing RNA expression in AdWT-RGD and AdE2Fm (also containing the RGD motive in the fibre) infected T24 cells obtained by RT-qPCR at 24 hours post infection; AD-WT gene expression was set to 100%.

Figure 25A:
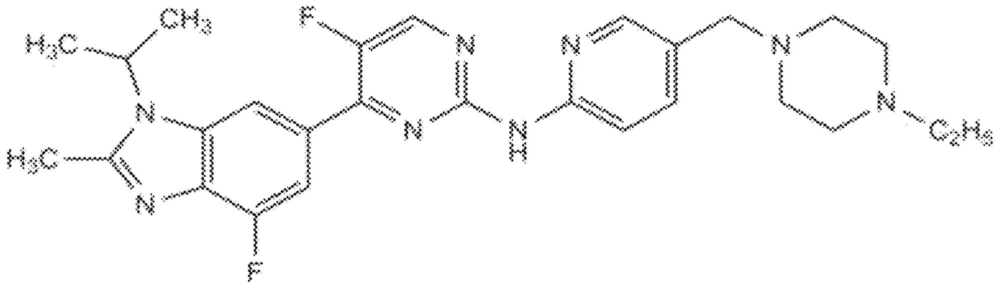
Figure 25A:
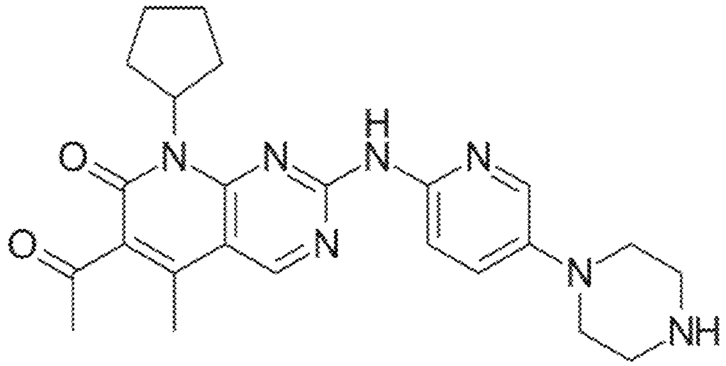
Figure 25A:
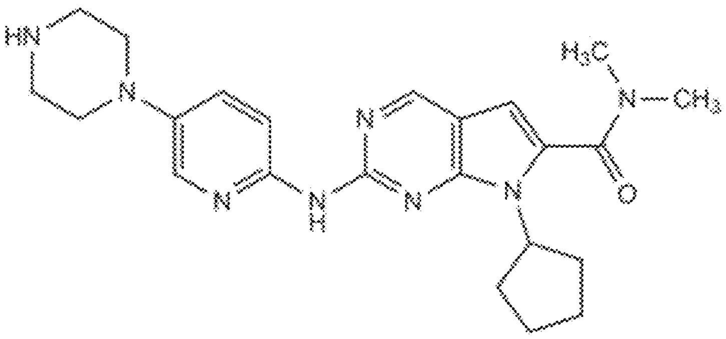
Figure 25B:
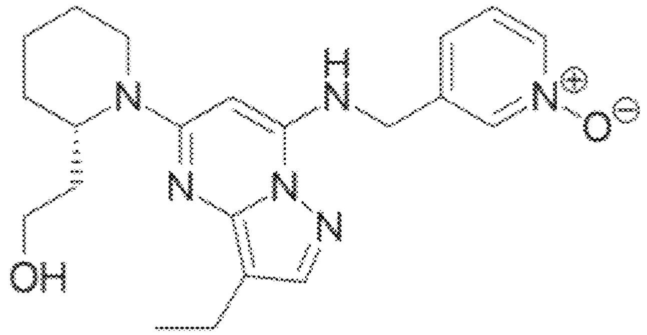

FIG. 25A-B shows various CDK4/6 inhibitors suitable for use in the instant invention.

Figure 26A:
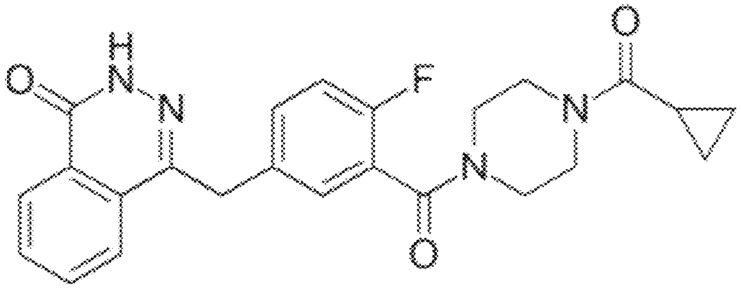
Figure 26A:
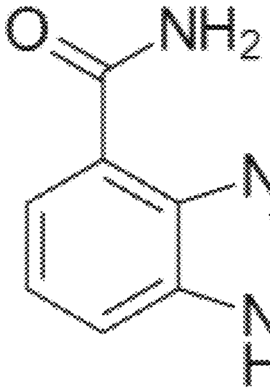
Figure 26A:
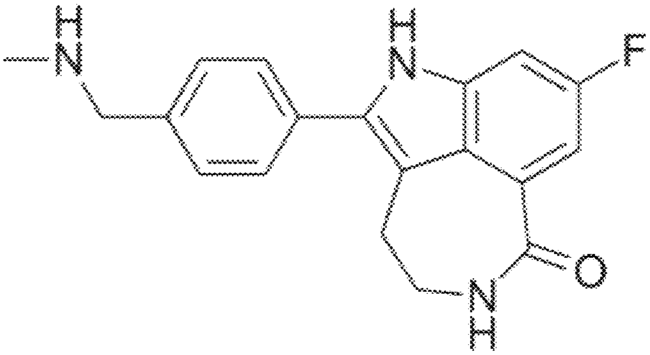
Figure 26B:
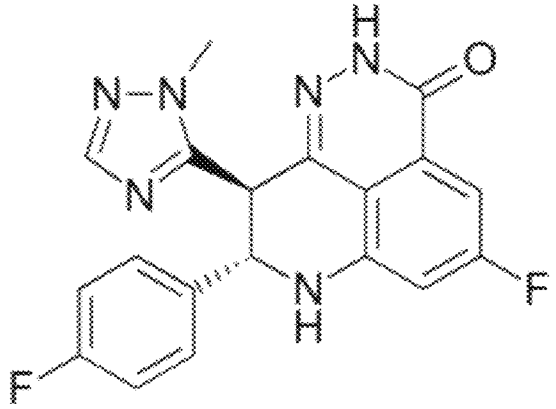

FIG. 26A-B shows various PARP inhibitors suitable for use in the instant invention.

Figure 27A:
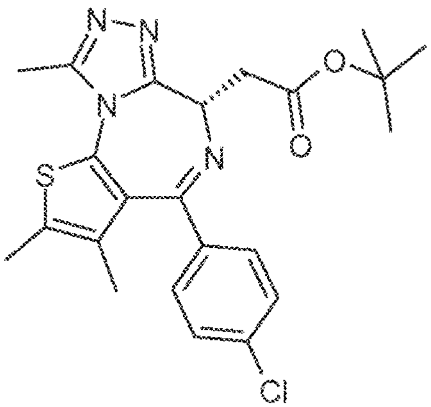
Figure 27A:
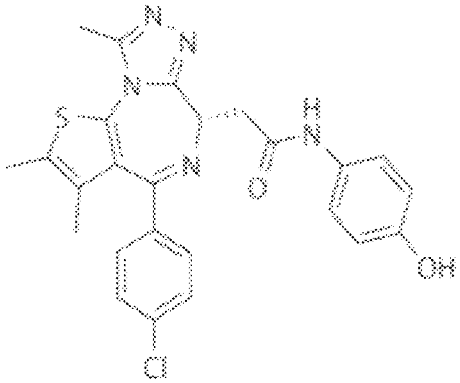
Figure 27B:
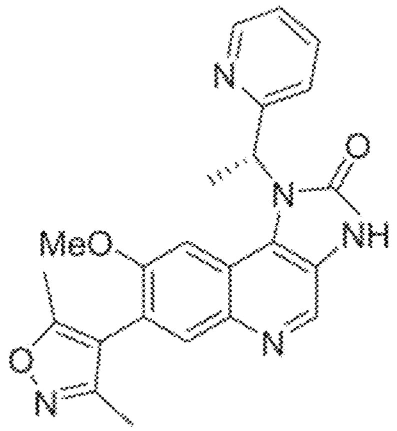
Figure 27B:
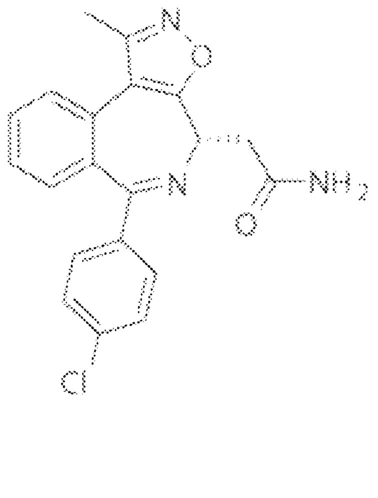
Figure 27C:
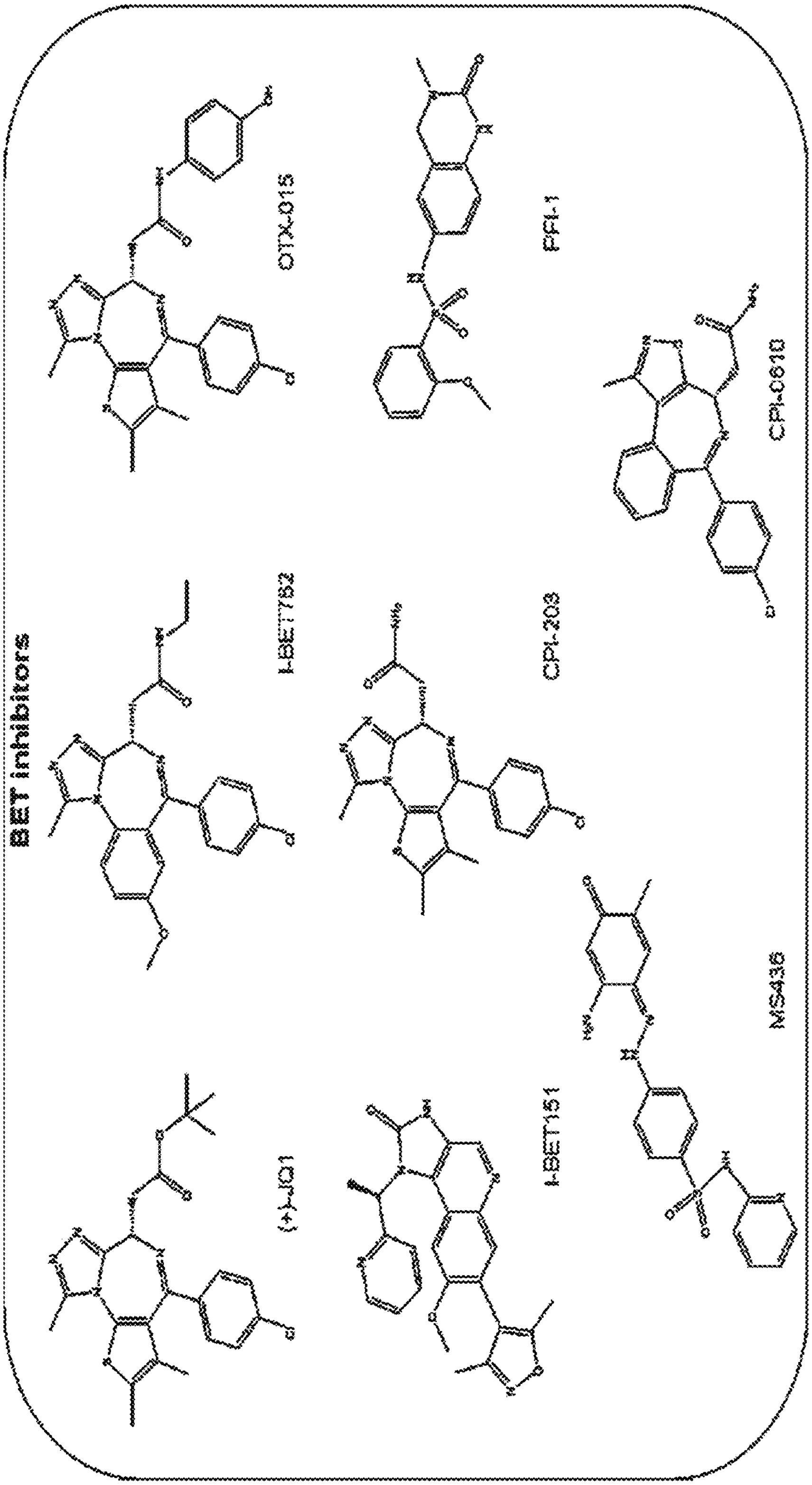

FIG. 27A-C shows various Bet inhibitors suitable for use in the instant invention.

Figure 28:
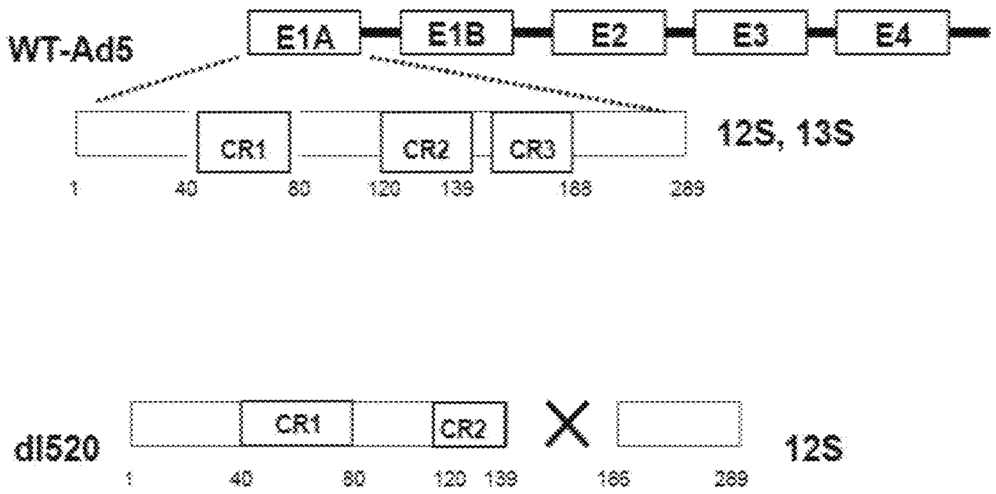

FIG. 28 shows the structure of WT-Ad5 and adenovirus dl520 which is an oncolytic adenovirus expressing only the E1A12 protein, through deletion of the CR3-domain of the E1 A gene.

Figure 29:
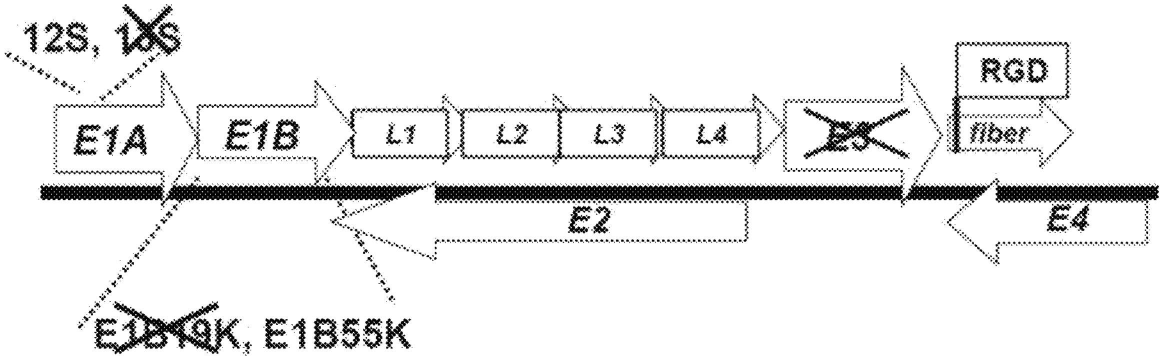

FIG. 29 shows the structure of XVir-N-31 which is characterized by deletion of the E1B19K protein, deletion of 2 kb in E3-region, deletion des E1A13S Protein, and introducing a RGD motif the fiber protein.

Figure 30:
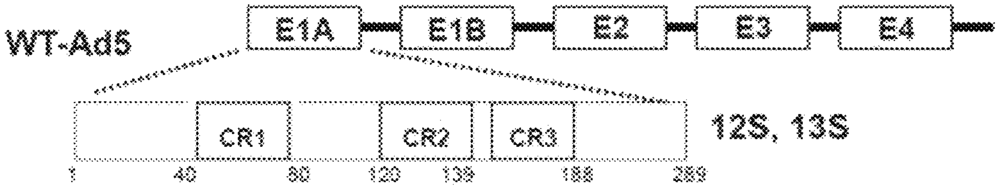
Figure 30:
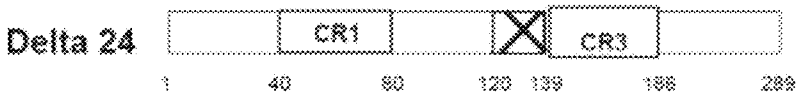

FIG. 30 shows the structure of Ad-Delta 24 and Ad-Delta 24-RGD which are also described by Kleijn et al. (Kleijn et al., PLoS One. 2014; 9(5): e97495), and characterized by deletion of the CR2-domain of the E1A gene; it replicate only in tumor cells with deregulated retinoblastoma-pathway (Rb). Ad-Delta 24-RGD contains in addition a RGD motive in the fiber knob, as shown in XVir-N-31. Please note the oncolytic adenovirus dl922-947 is similar to delta24, since the deletion in this virus also is located in the E1A-CR2 domain and is affecting RB-binding (retinoblastoma protein).

Figure 31:

FIG. 31 shows the structure of VCN-01 which is a replication-competent adenovirus specifically engineered to replicate in tumors with a defective RB pathway, presents an enhanced infectivity through a modified fiber and an improved distribution through the expression of a soluble hyaluronidase (Pascual-Pasto et al. Sci Transl Med. 2019, 11 476). The deletion in E1A in VCN-01 is similar to the deletion in delta24 (deletion of the CR2-domain in E1A). Further, the expression of this E1A protein is regulated by introducing E2F1 binding sites in the E1A promoter. In addition, it contains an RGD motif in the fiber knob and expresses a soluble hyaluronidase (Martínez-Vélez et al. 2016, Clin Cancer Res. 1; 22(9):2217-25. The Oncolytic Adenovirus VCN-01 as Therapeutic Approach Against Pediatric Osteosarcoma).

Figure 32:
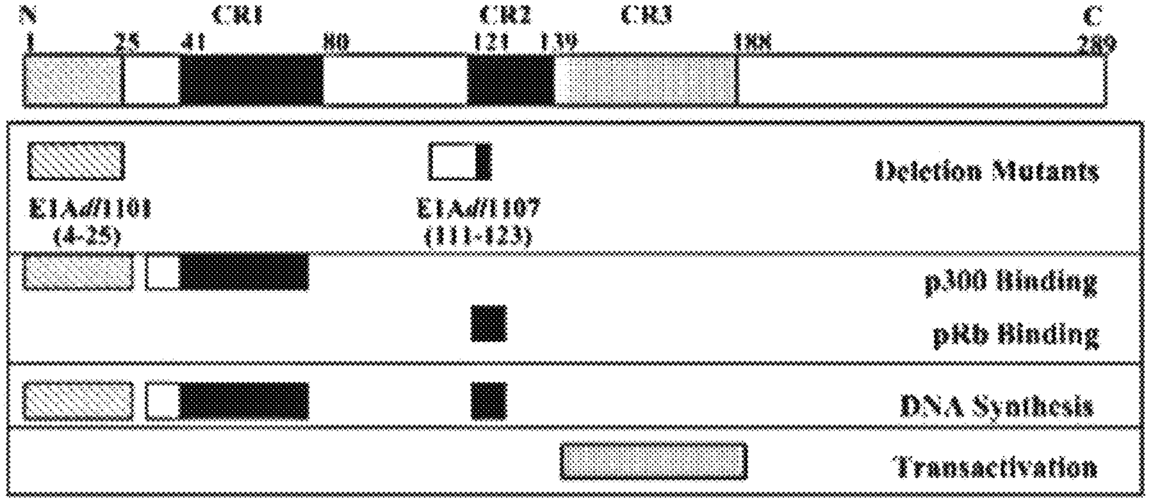

FIG. 32 shows the structure of E1Adl1107 and E1Adl1101, whereby the deletion of these two oncolytic adenoviruses affects binding to p300 (Histone acetyltransferase p300 also known as p300 HAT or E1A-associated protein p300) or pRb (retinoblastoma protein. (Howe et al., MOLECULAR THERAPY 2000, 2, 485-495)

Figure 33:
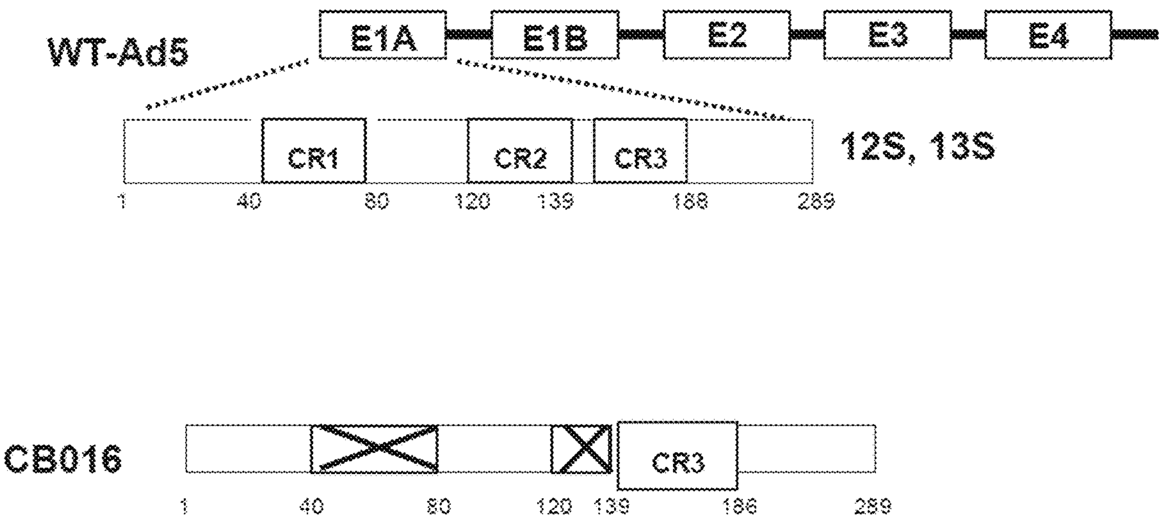

FIG. 33 shows the structure of oncolytic adenovirus CB016 (and the one of wild type adenovirus 5 (WT-Ad5), where deletion in the E1A-CR2 domain is similar as in Ad-Delta 24. In addition, CB016 contains a deletion in the CR1 domain. In addition, it contains either an RGD motif in the fiber or a fiber from serotype 3 (LaRocca et al., Oral Oncol. 2016, 56, 25-31).

Figure 34:
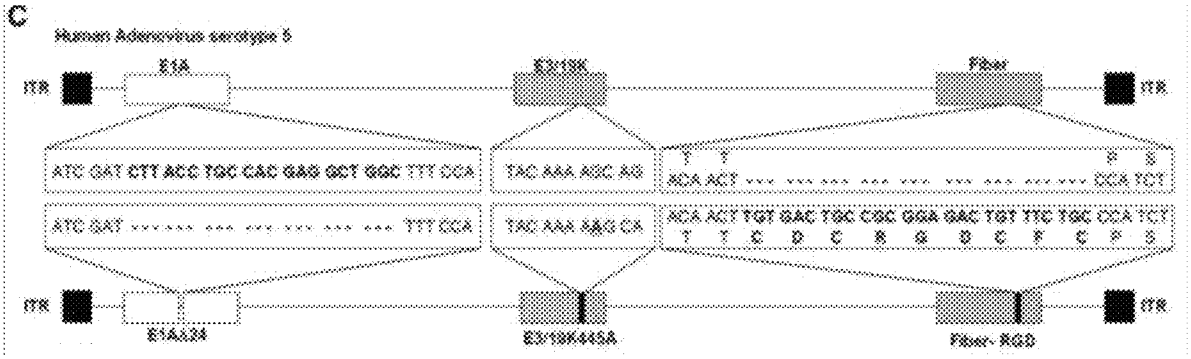

FIG. 34 shows the structure of adenovirus ORCA-010 which contains an E1AΔ24 deletion in the E1A CR2-domain, the potency-enhancing T1 mutation in the E3/19K protein, and the infectivity-enhancing fiber RGD modification (Dong et al., Hum Gene Ther. 2014 Oct. 1; 25(10): 897-904).

Figure 35:
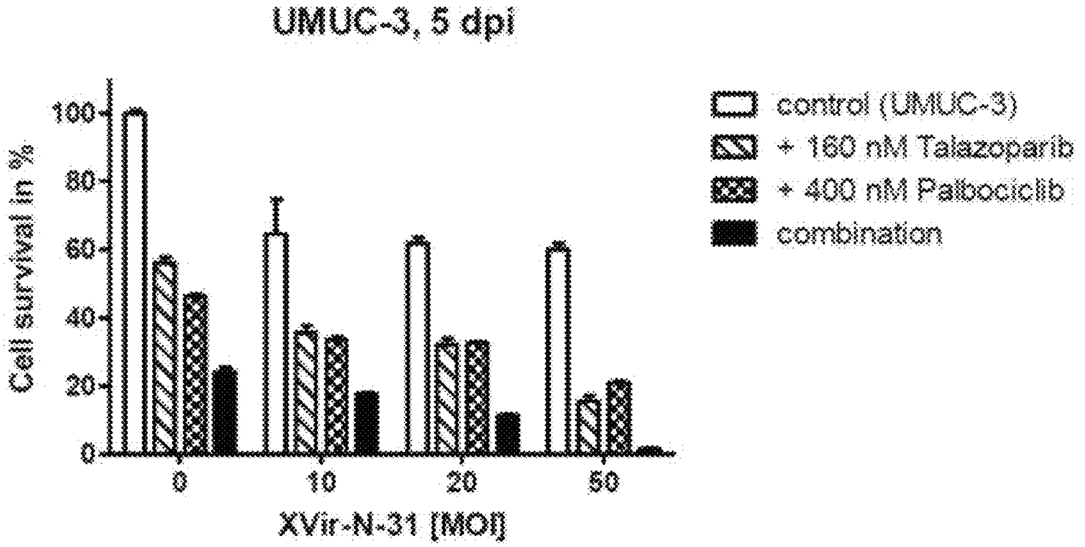

FIG. 35 is a bar diagram showing the results of a potency assay expressed as cell survival in % to determine cell killing effect of XVir-N-31 alone or in combination with Palbociclib alone, with Talazoparib alone or both Palbociclib and Talazoparib ("combination") in UMUC-3 cells 5 days post infection (5 dpi), whereby MOI of XVir-N-31 was 10, 20 or 50.

Figure 36:
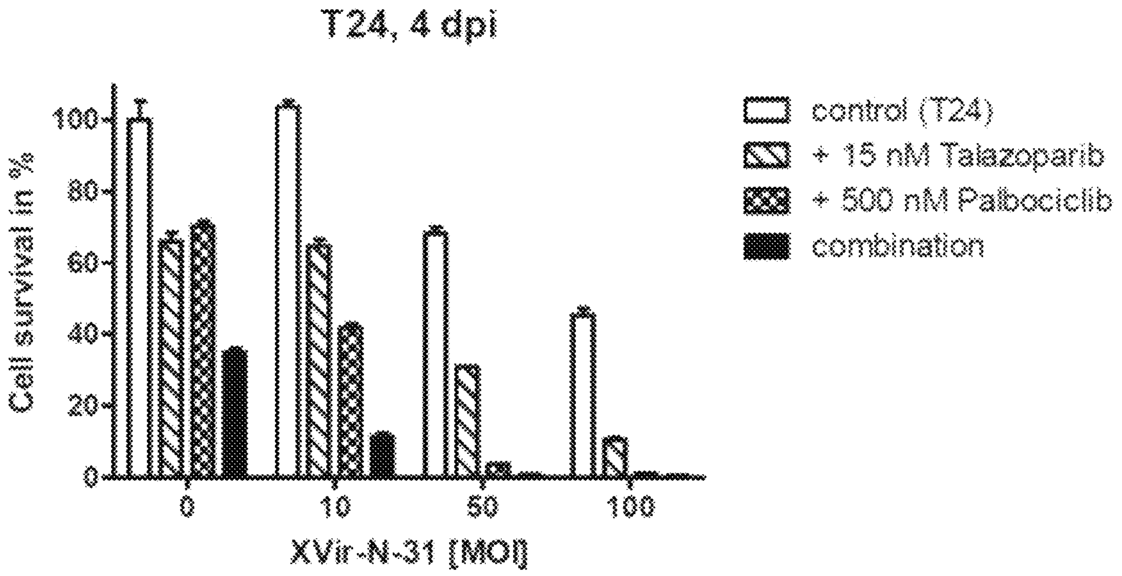

FIG. 36 is a bar diagram showing the results of a potency assay expressed as cell survival in % to determine cell killing effect of XVir-N-31 alone or in combination with Palbociclib alone, with Talazoparib alone or both Palbociclib and Talazoparib ("combination") in T24 cells 4 days post infection (4 dpi), whereby MOI of XVir-N-31 was 10, 50 or 100.

Figure 37:
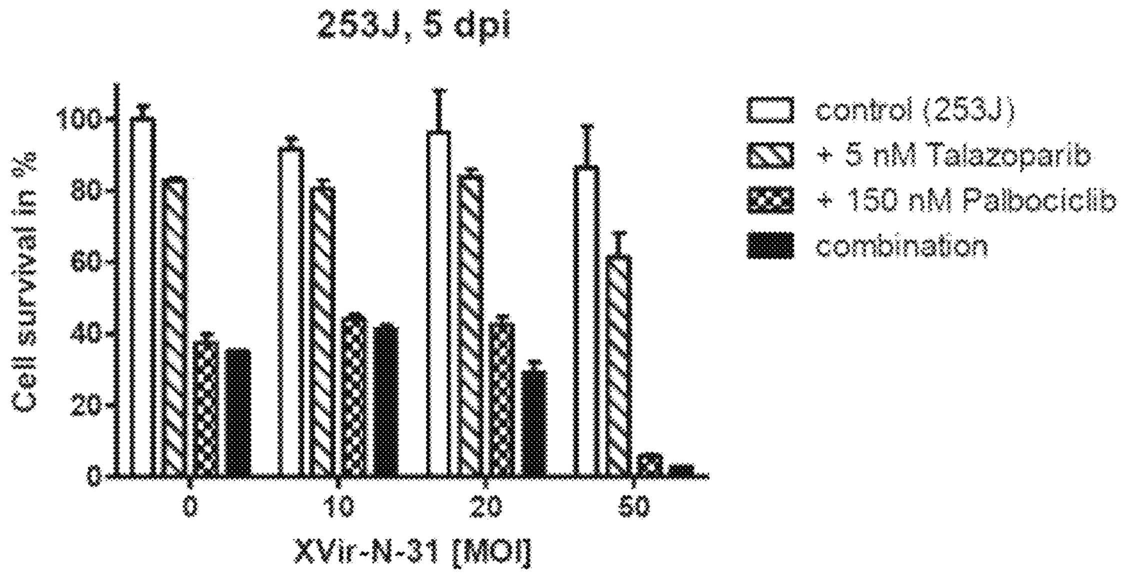

FIG. 37 is a bar diagram showing the results of a potency assay expressed as cell survival in % to determine cell killing effect of XVir-N-31 alone or in combination with Palbociclib alone, with Talazoparib alone or both Palbociclib and Talazoparib ("combination") in 253J cells 5 days post infection (5 dpi), whereby MOI of XVir-N-31 was 10, 20 or 50.

Figure 38:
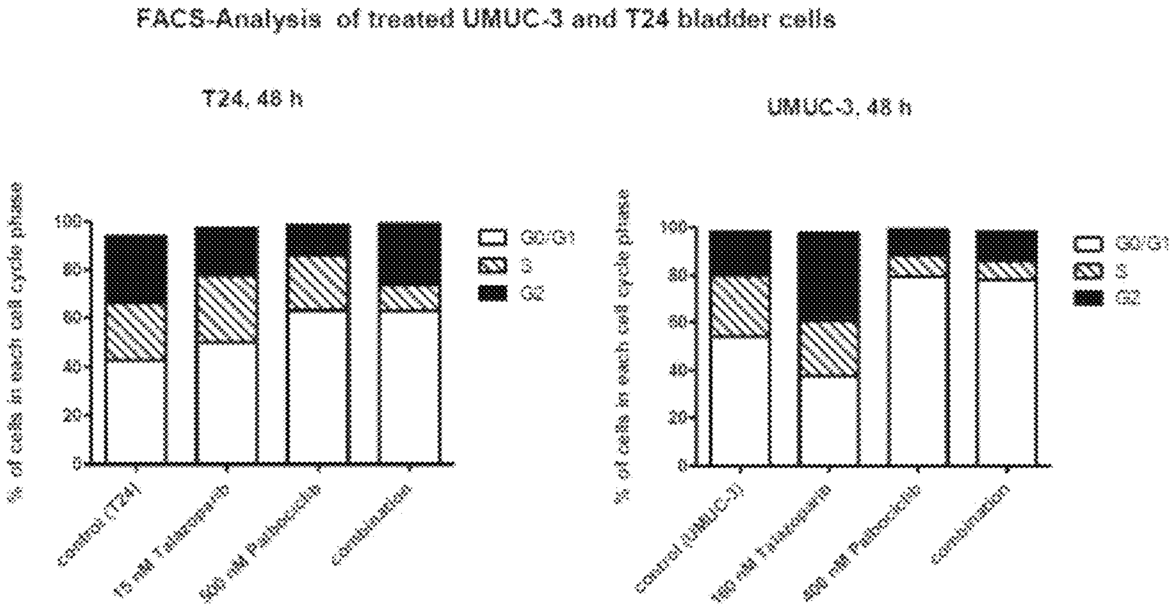

FIG. 38 is a bar diagram showing the % of cells in cell cycle phases G0/G1, S and G2 of T24 cells (left) and UMUC-3 cells (right), 48 hours post infection with Talazoparib alone, Palbociclib alone or both Talazoparib and Palbociclib ("combination").

Figure 39:
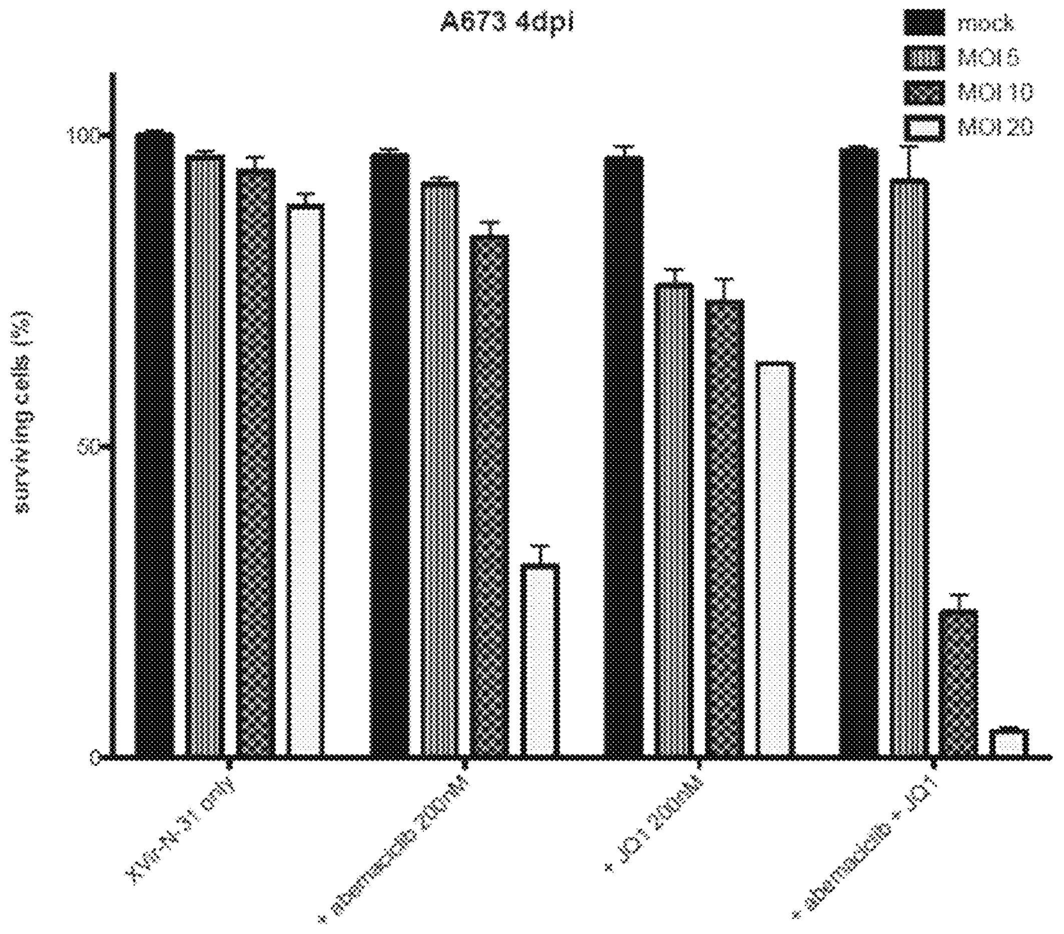

FIG. 39 is a bar diagram showing the percentage of surviving cells in a potency assay on A673 cells 4 days post infection with XVir-N-31 at 5, 10 and 20 MOI, the CDK 4/6 inhibitor Abemaciclib at 200 nM and the bromodomain inhibitor JQ-1 at 200 nM.

Figure 40:
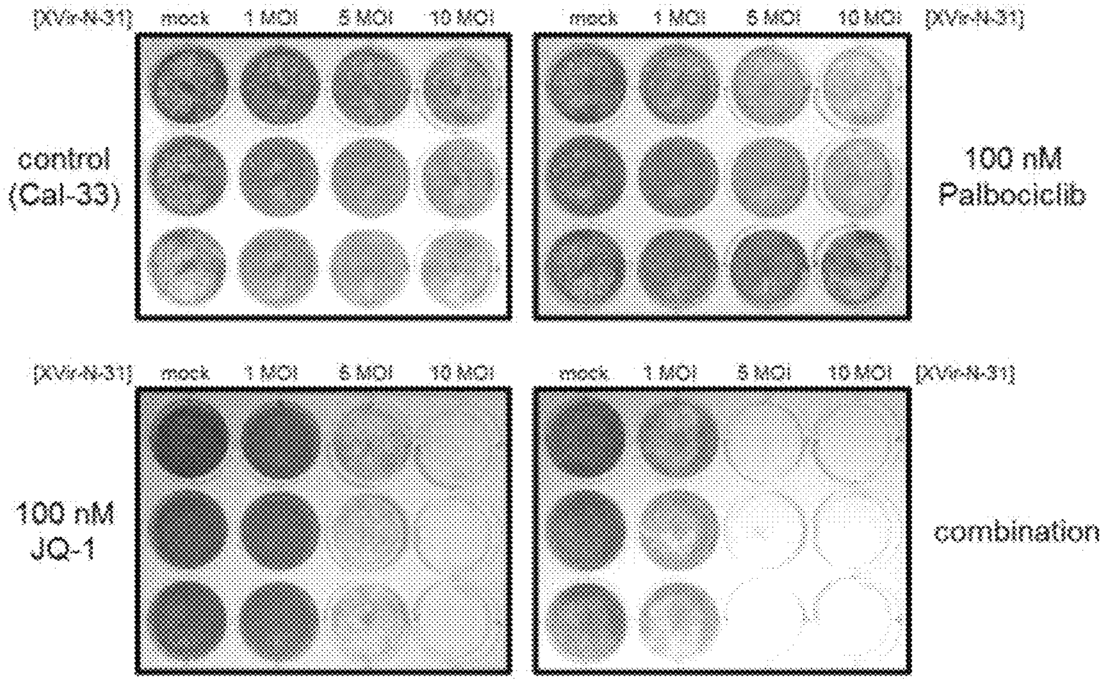

FIG. 40 is a panel of pictures showing cultures of SRB-stained Cal-33 cells after treatment with XVir-N-31 (1, 5 and 10 MOI), 100 nM Palbociclib alone, 100 nM JQ-1 alone or in combination (both Palbociclib and JQ-1) 4 days post infection.

Figure 41:
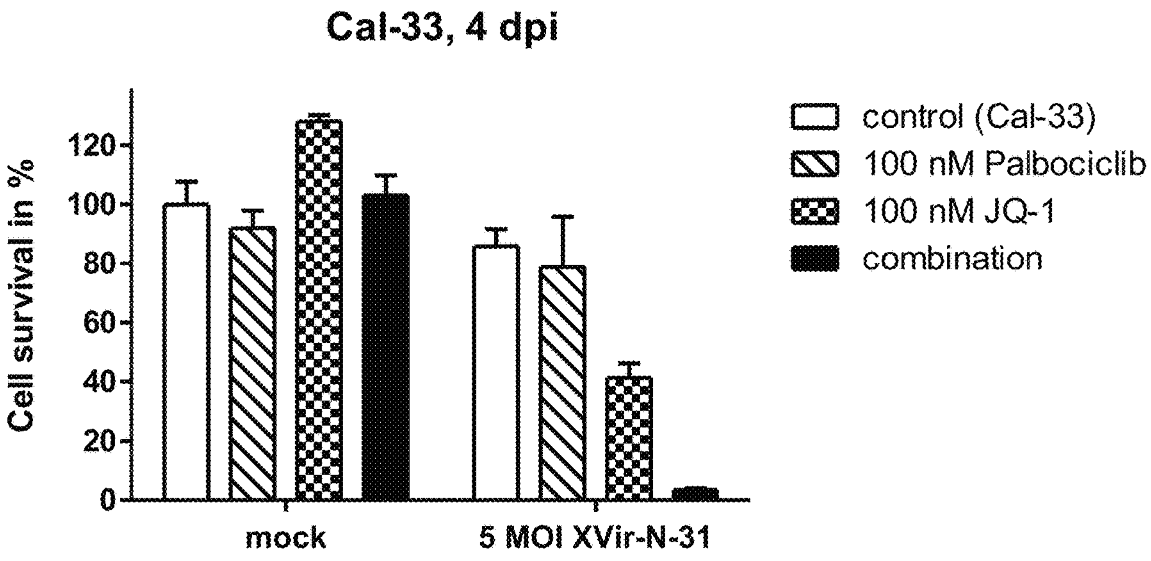

FIG. 41 is a bar diagram showing the result of the potency test as depicted in FIG. 40 expressed as cell survival in % 4 days after infection of Cal-33 cells at an XVir-N-31 MOI of 5 using 100 nM Palbociclib, 100 nm JQ-1 or a combination of both Palbociclib and JQ-1.

Figure 42A:
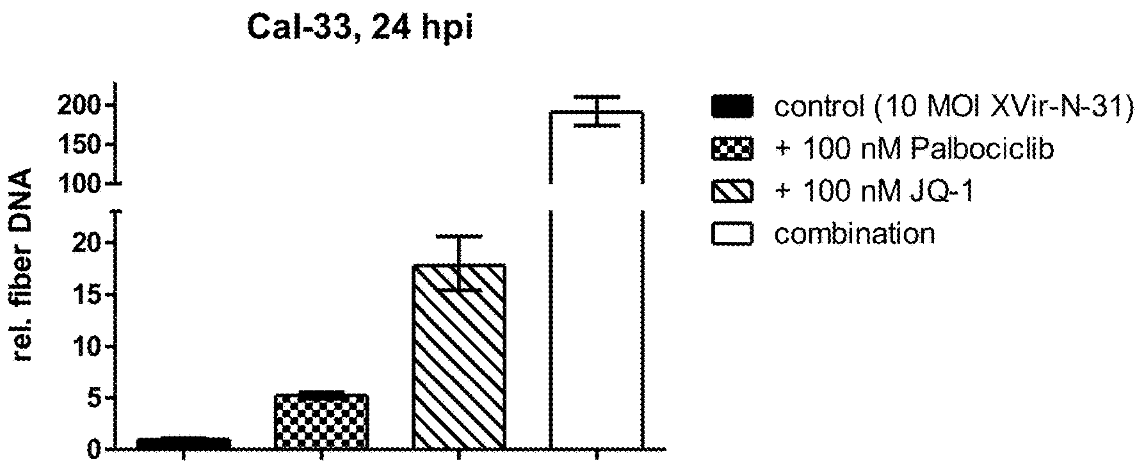
Figure 42B:
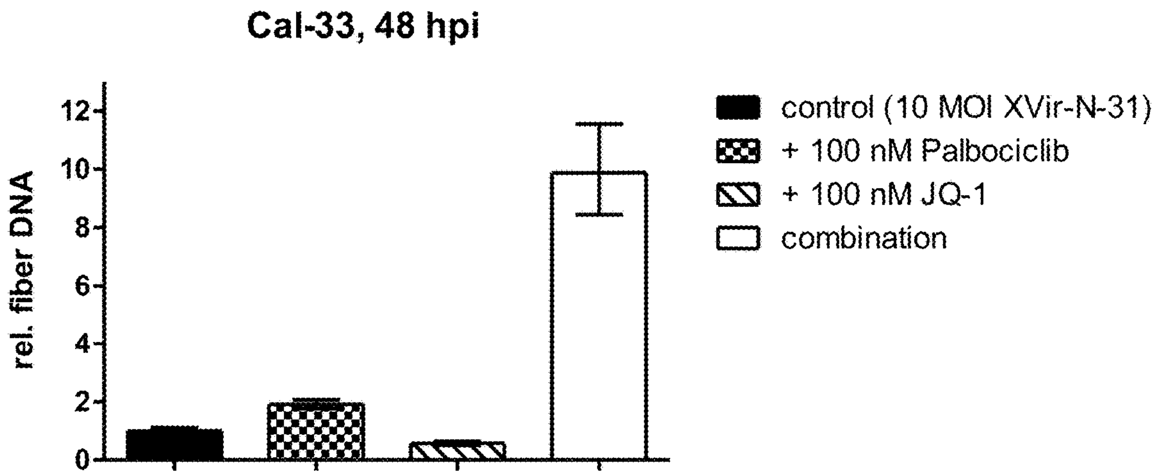
Figure 43A:
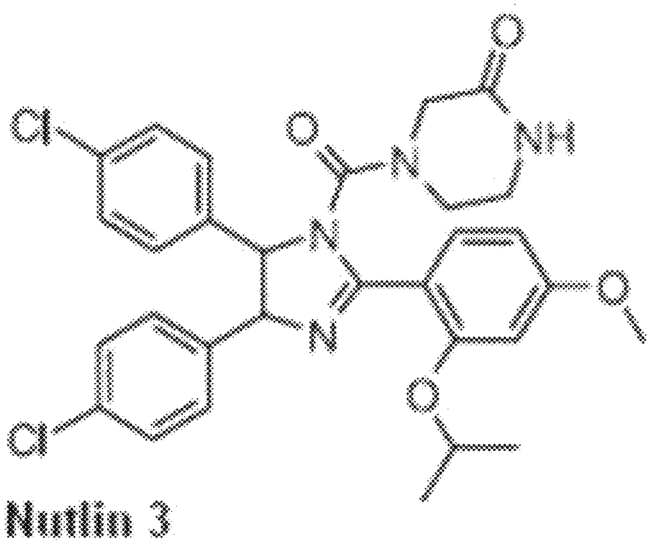
Figure 43A:
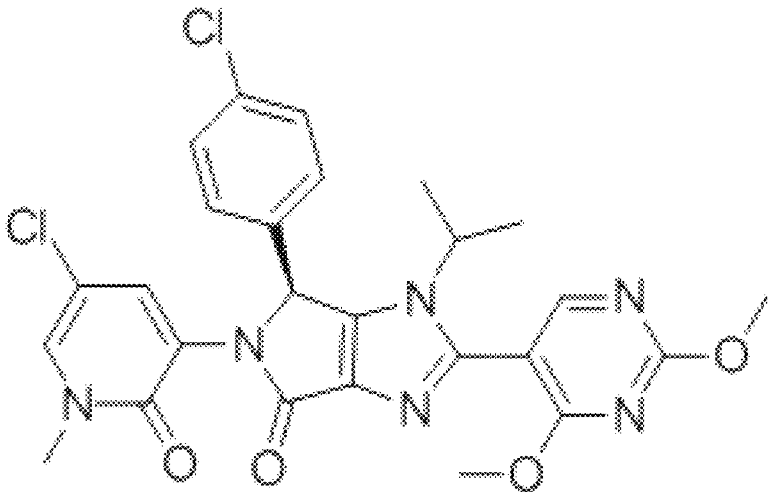
Figure 43B:
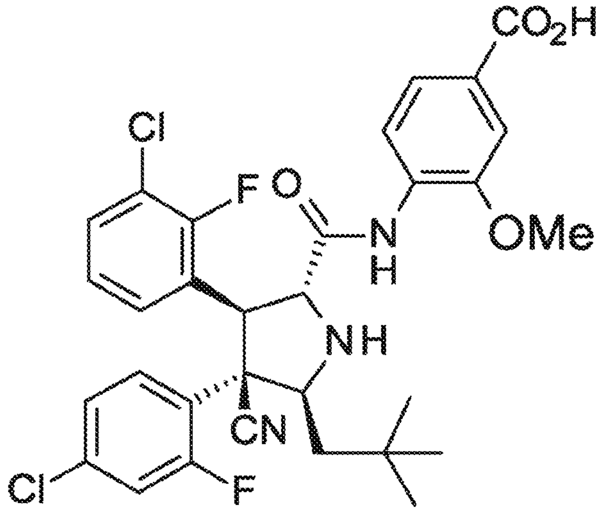
Figure 43B:
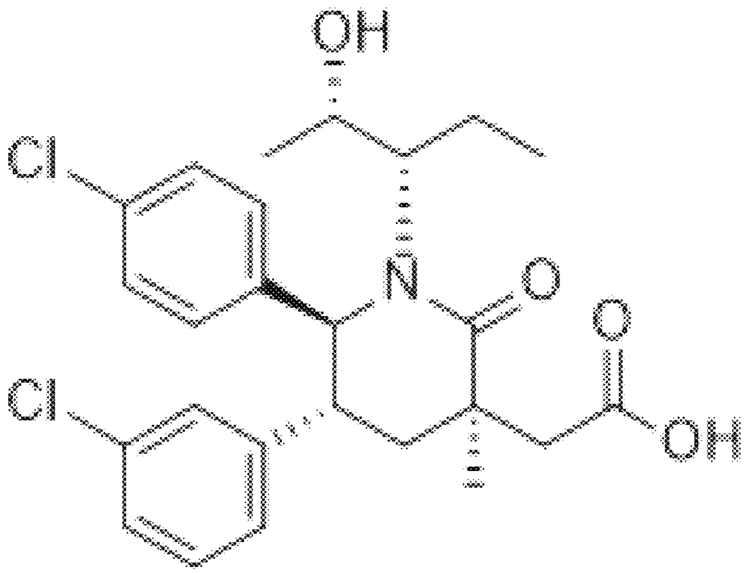
Figure 43C:
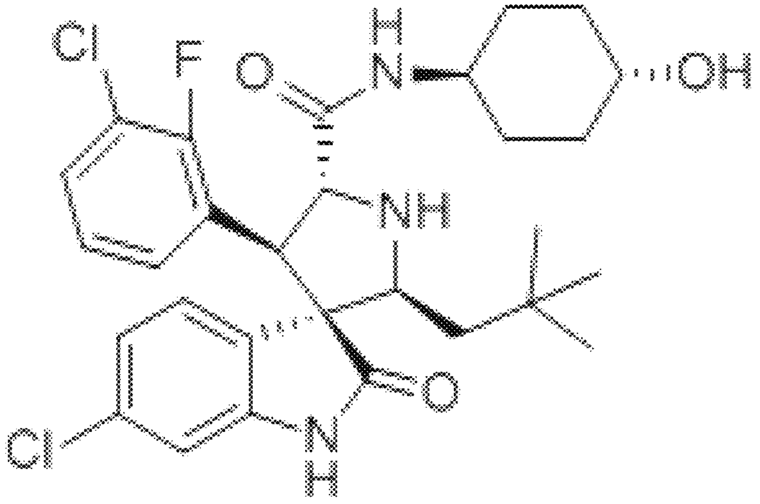
Figure 43C:
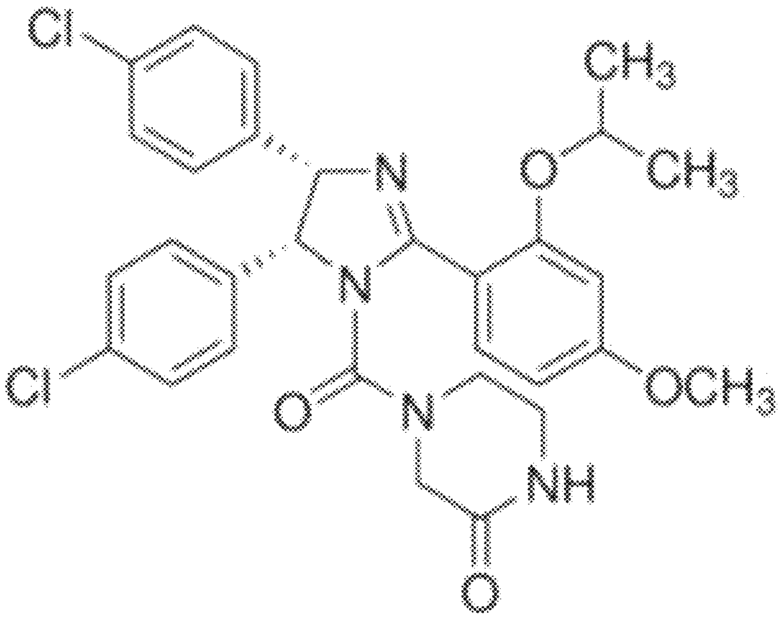
Figure 43D:
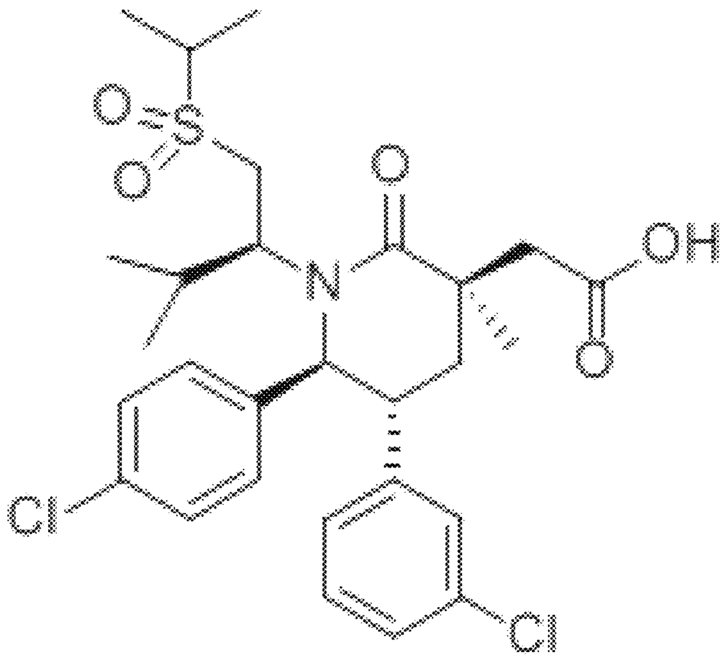

FIG. 42(A,B) are bar diagrams showing XVir-N-31 replication expressed as "relative fibre" in Cal-33 cells 24 hours (FIG. 42A) and 48 hours (FIG. 42B) after infection. MOI was 10, Palbociclib concentration was 100 nM and JQ-1 concentration was equally 100 nM.

FIG. 43A-D shows nutlin and derivatives thereof, namely NVP-HDM201, Idasanutlin, AM-8553, SAR405838, Nutlin-3a, AMG232.

Figure 44:
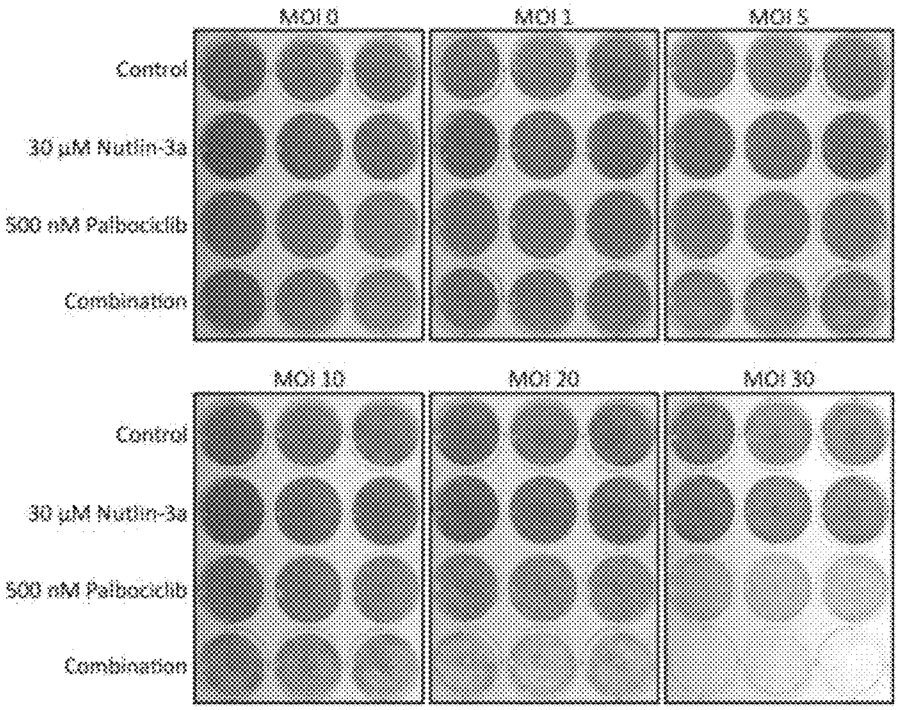

FIG. 44 is a panel of pictures showing cultures of SRB-stained T24 cells after treatment with XVir-N-31 alone, XVir-N-1 with 30 μM Nutlin-3a, XVir-N-31 with 500 nM Palbociclib and XVir-N-31 with both Nutlin-3a and Palbociclib, whereby the MOI of XVir-N-31 is 0, 1, 5, 10, 20 or 30.

Figure 45:
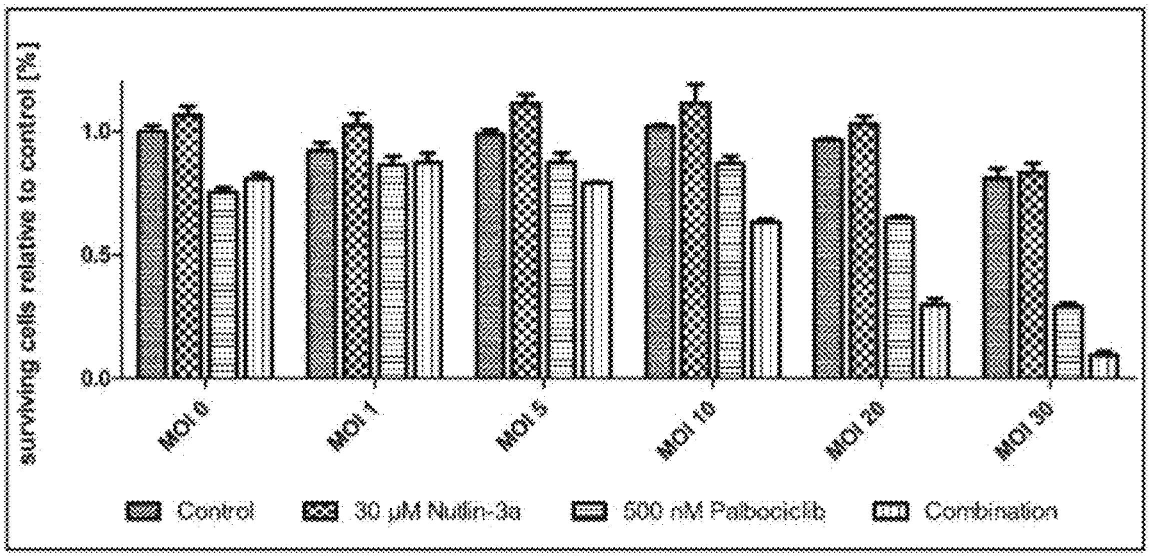

FIG. 45 is a bar diagram showing the result of the potency test as depicted in FIG. 44 expressed as surviving cells relative to control in %.

Figure 46:
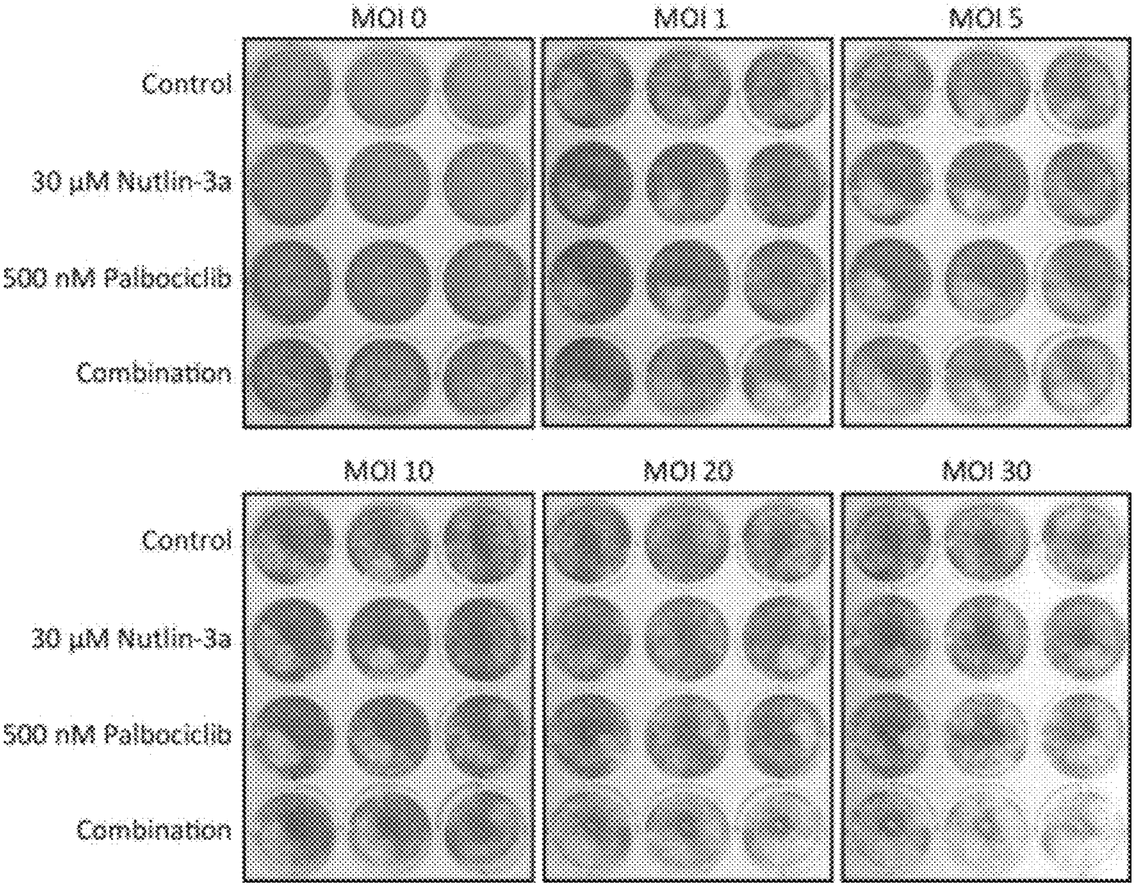

FIG. 46 is a panel of pictures showing cultures of SRB-stained T24shRb cells after treatment with XVir-N-31 alone, XVir-N-1 with 30 μM Nutlin-3a, XVir-N-31 with 500 nM Palbociclib and XVir-N-31 with both Nutlin-3a and Palbociclib, whereby the MOI of XVir-N-31 is 0, 1, 5, 10, 20 or 30.

Figure 47:
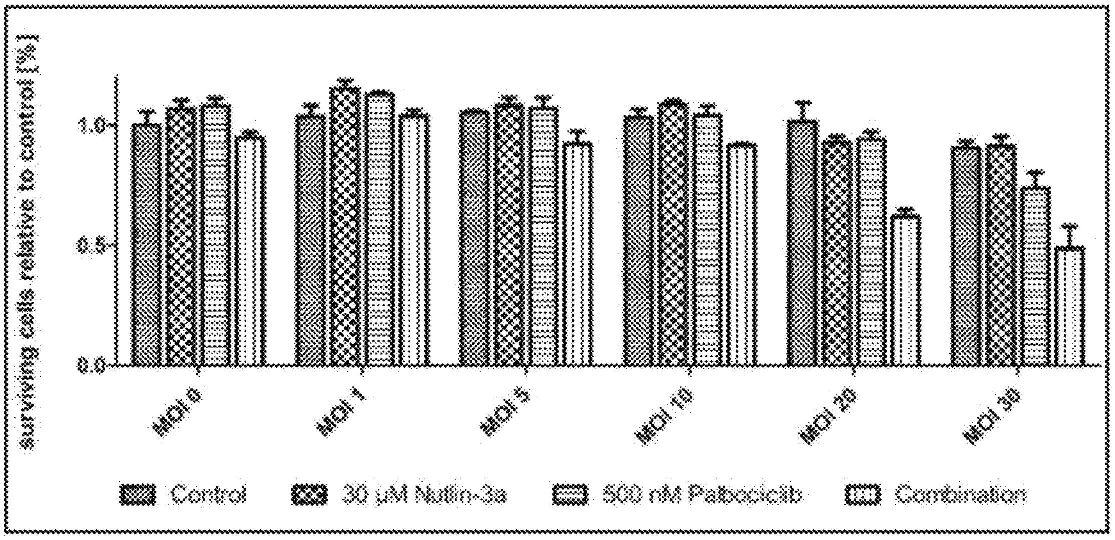

FIG. 47 is a bar diagram showing the result of the potency test as depicted in FIG. 46 expressed as surviving cells relative to control in %.

Figure 48:
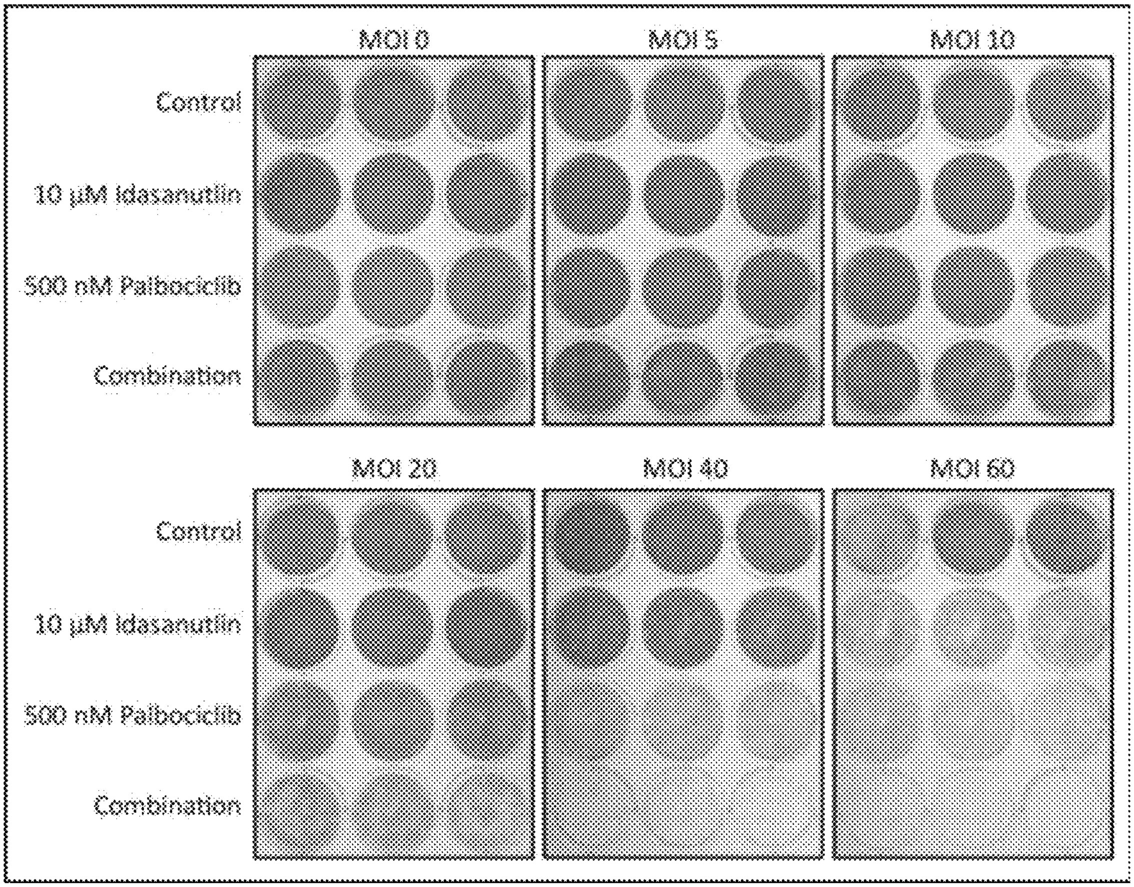

FIG. 48 is a panel of pictures showing cultures of SRB-stained T24 cells after treatment with XVir-N-31 alone, XVir-N-1 with 10 μM Isadanutlin, XVir-N-31 with 500 nM Palbociclib and XVir-N-31 with both Isadanutlinand Palbociclib, whereby the MOI of XVir-N-31 is 0, 5, 10, 20, 40 and 60.

Figure 49:
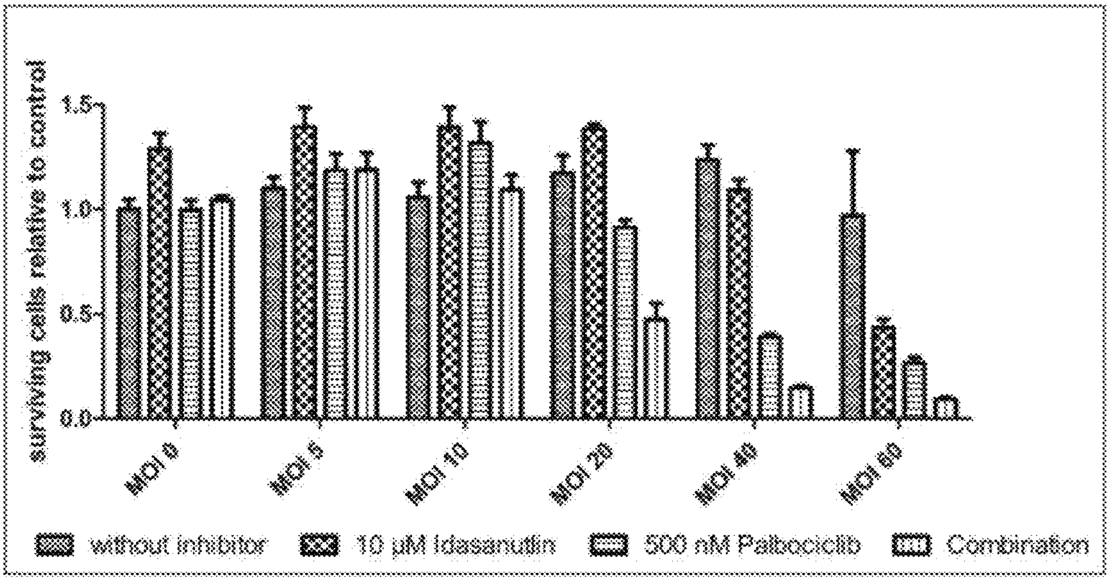

FIG. 49 is a bar diagram showing the result of the potency test as depicted in FIG. 48 expressed as surviving cells relative to control in %.

Figure 50:
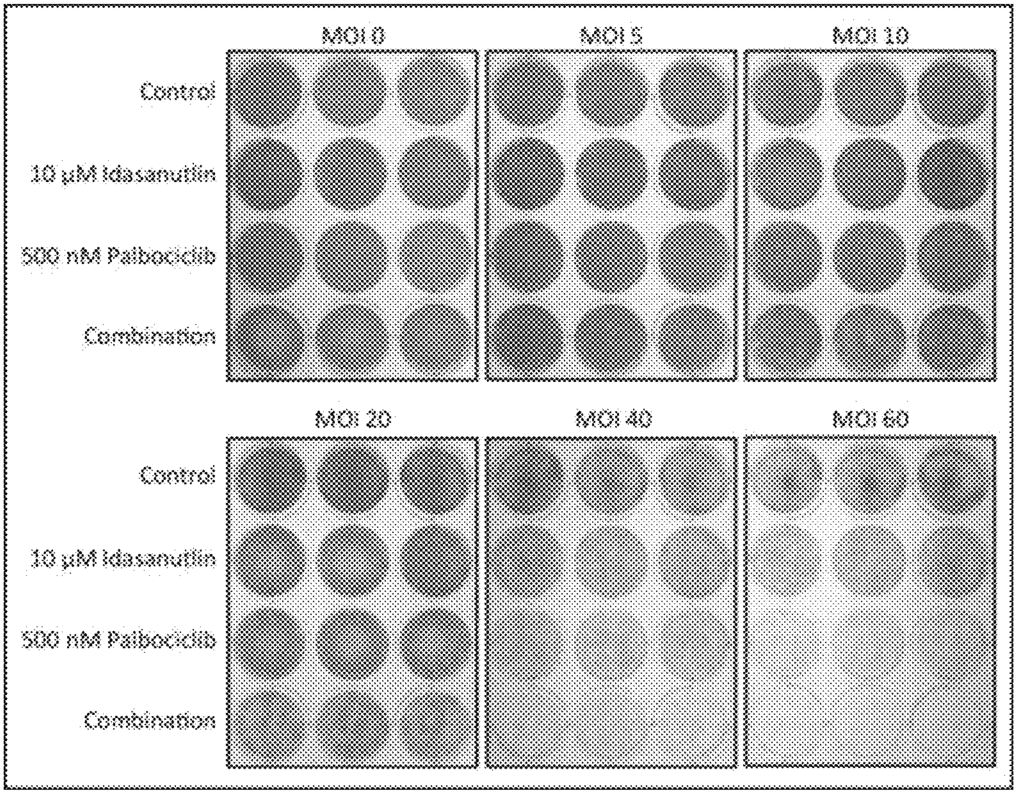

FIG. 50 is a panel of pictures showing cultures of SRB-stained T24shRb cells after treatment with XVir-N-31 alone, XVir-N-1 with 10 μM Idasanutlin, XVir-N-31 with 500 nM Palbociclib and XVir-N-31 with both Idasanutlin and Palbociclib, whereby the MOI of XVir-N-31 is 0, 5, 10, 20, 40 and 60.

Figure 51:
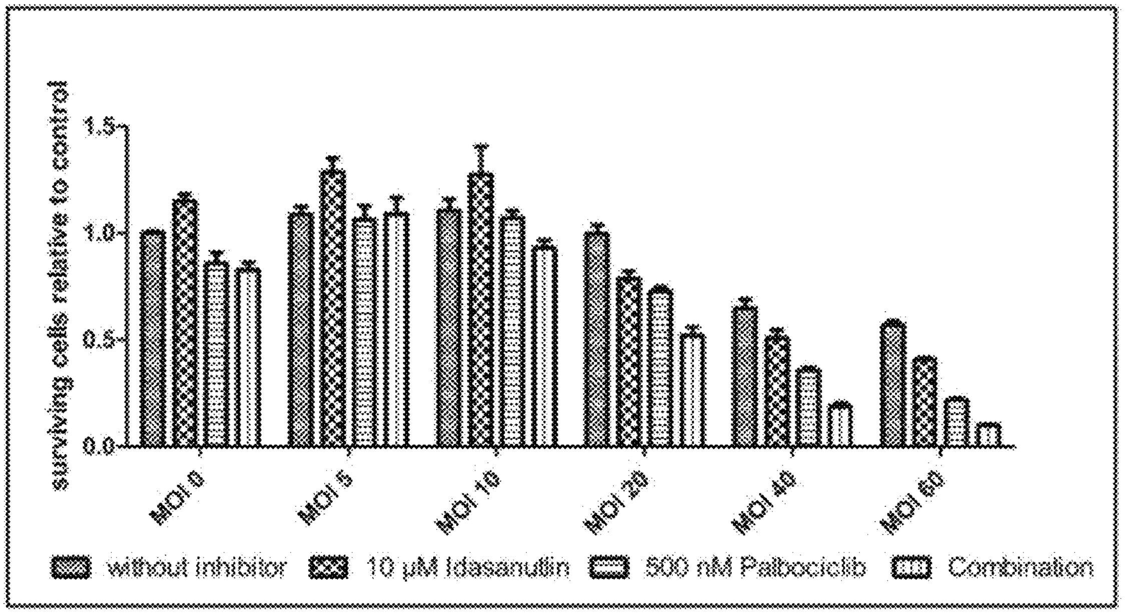

FIG. 51 is a bar diagram showing the result of the potency test as depicted in FIG. 50 expressed as surviving cells relative to control in %.

Figure 52:
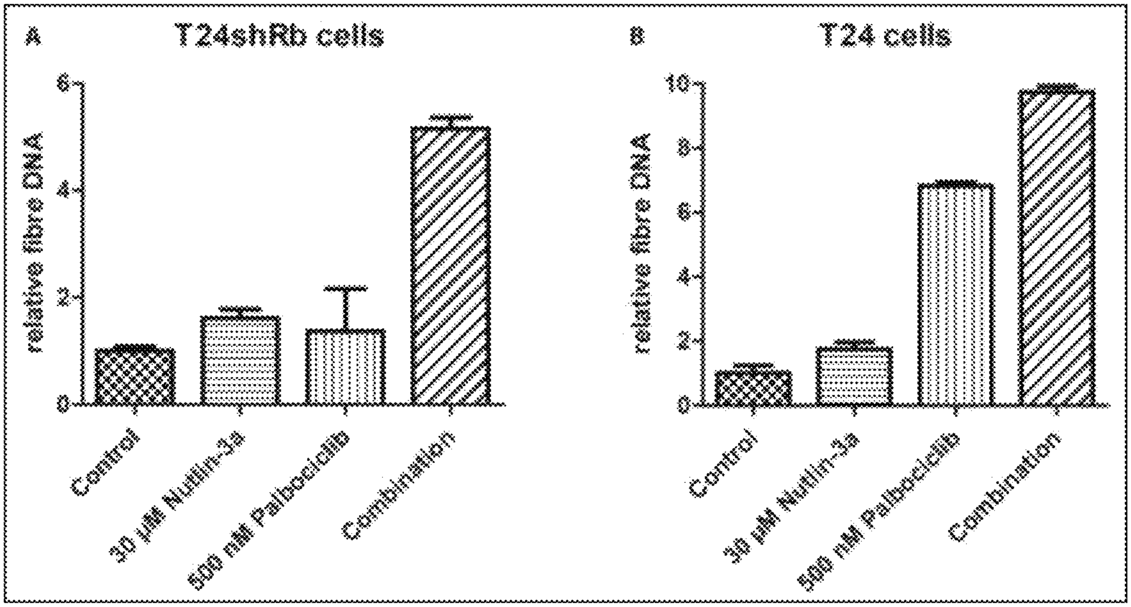

FIG. 52 is bar diagrams showing XVir-N-31 replication expressed as "relative fibre" in T24shRb cells (left) and T24 cells (right) after 24 hours and 48 hours, respectively. MOI was 20, Palbociclib concentration was 500 nM and Nutlin-3a concentration was 30 μM.

Figure 53:
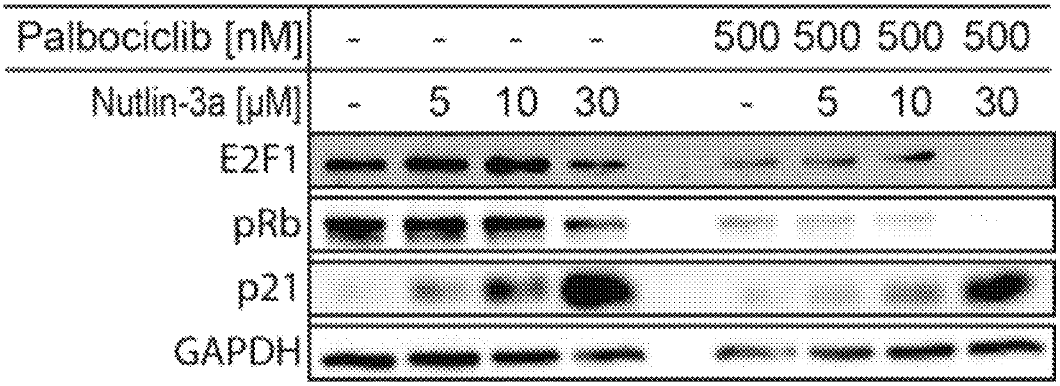

FIG. 53 shows the result of a Western Blot analysis.

Figure 54:
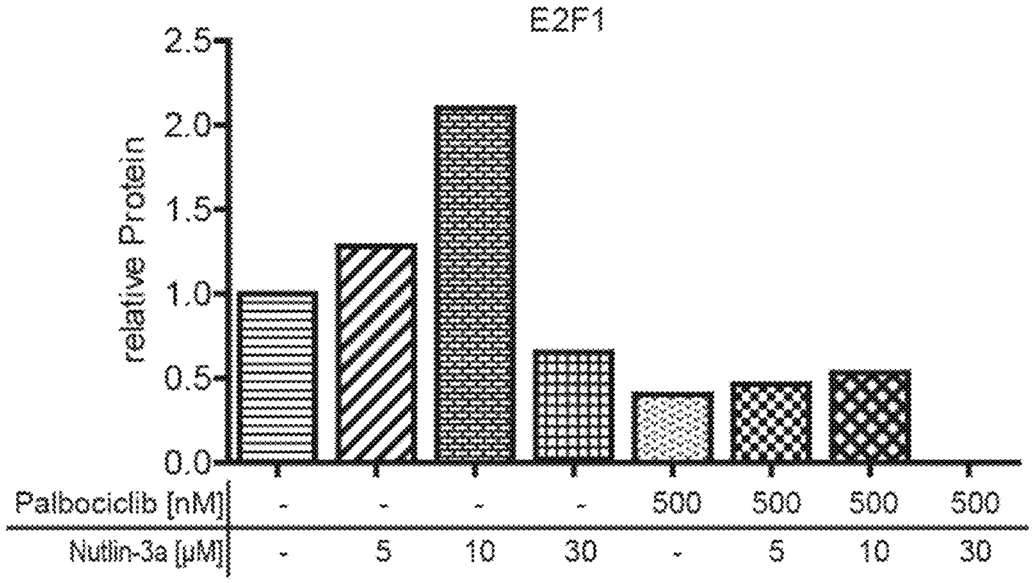

FIG. 54 is a bar diagram showing relative amount of E2F1 protein upon exposure of T24shRB cells to Palbociclib, Nutlin-3a or a combination of both.

Figure 55A:
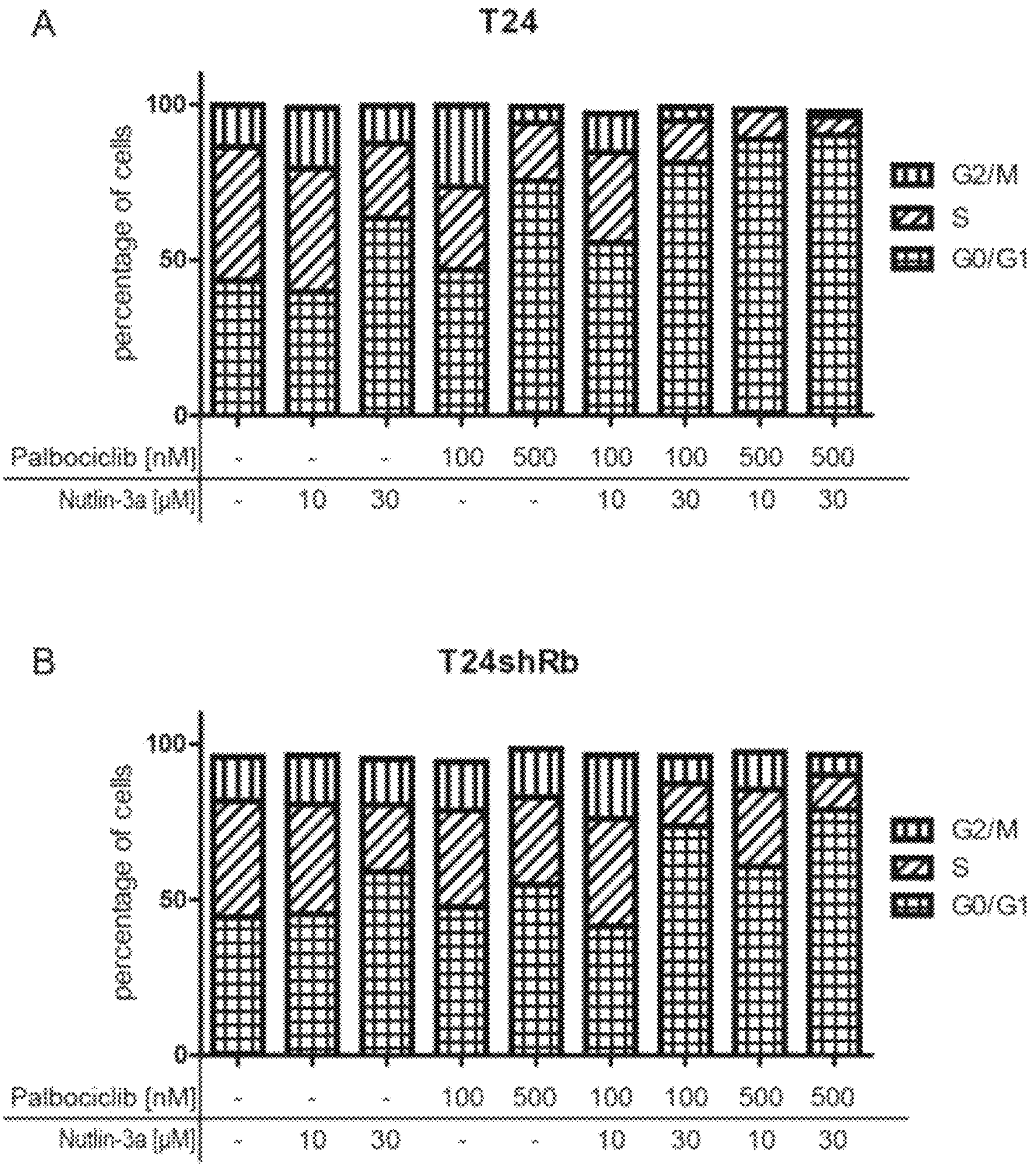
Figure 55B:
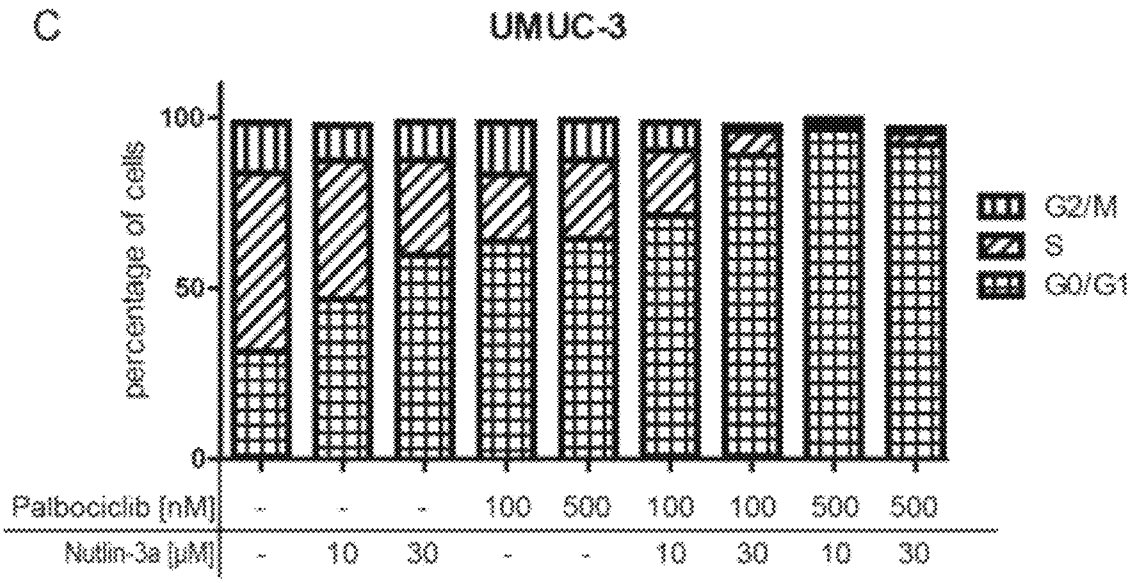

FIGS. 55A-B are bar diagrams showing the % of cells in cell cycle phases G0/G1, S and G2 of T24 cells (A), T24shRb cells (B), UMUC-3 cells (C) and RT112 cells (D) upon exposure of the cells to Palbociclib, Nutlin-3a or a combination of both at the indicated concentrations.

Figure 56A:
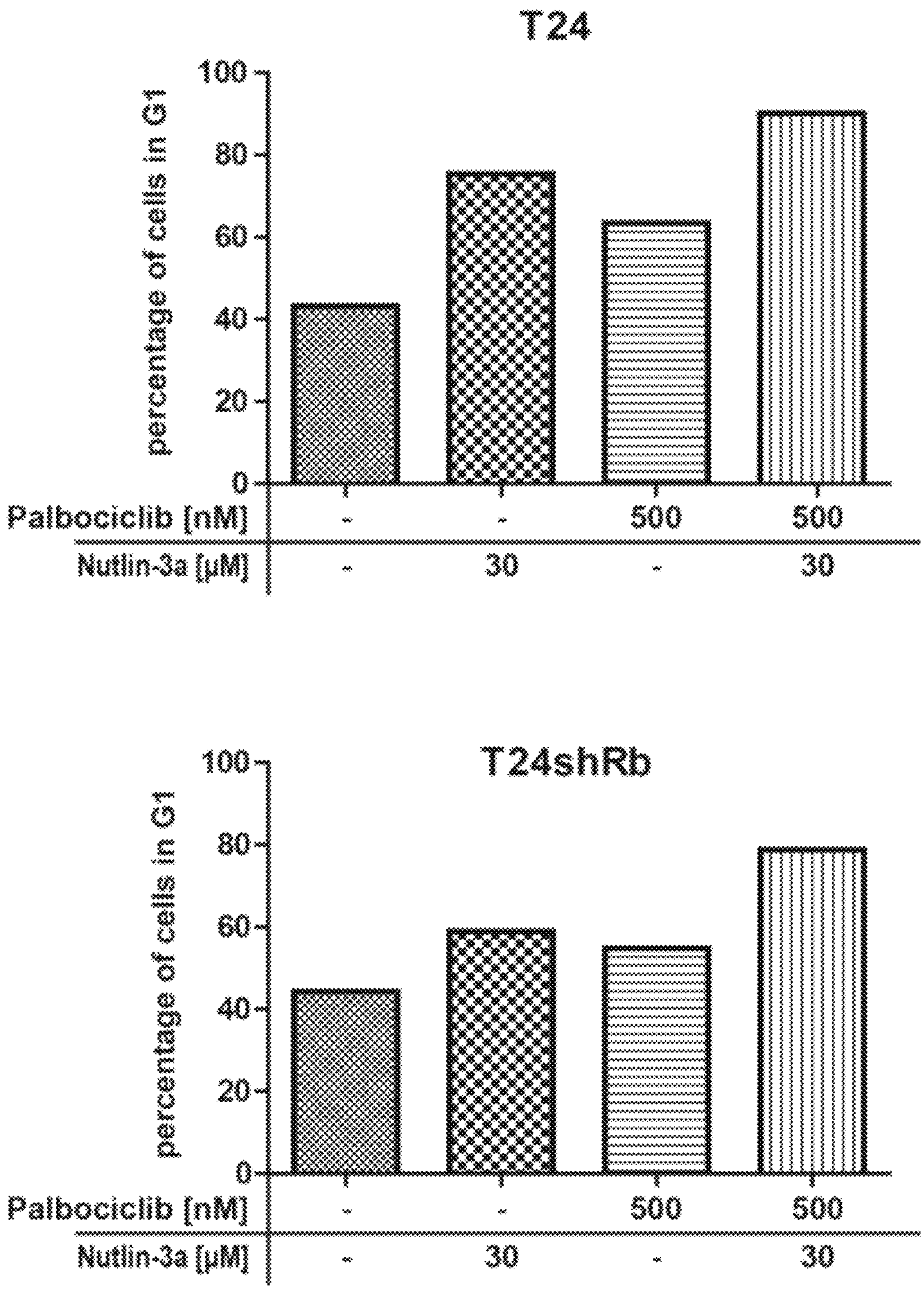
Figure 56B:
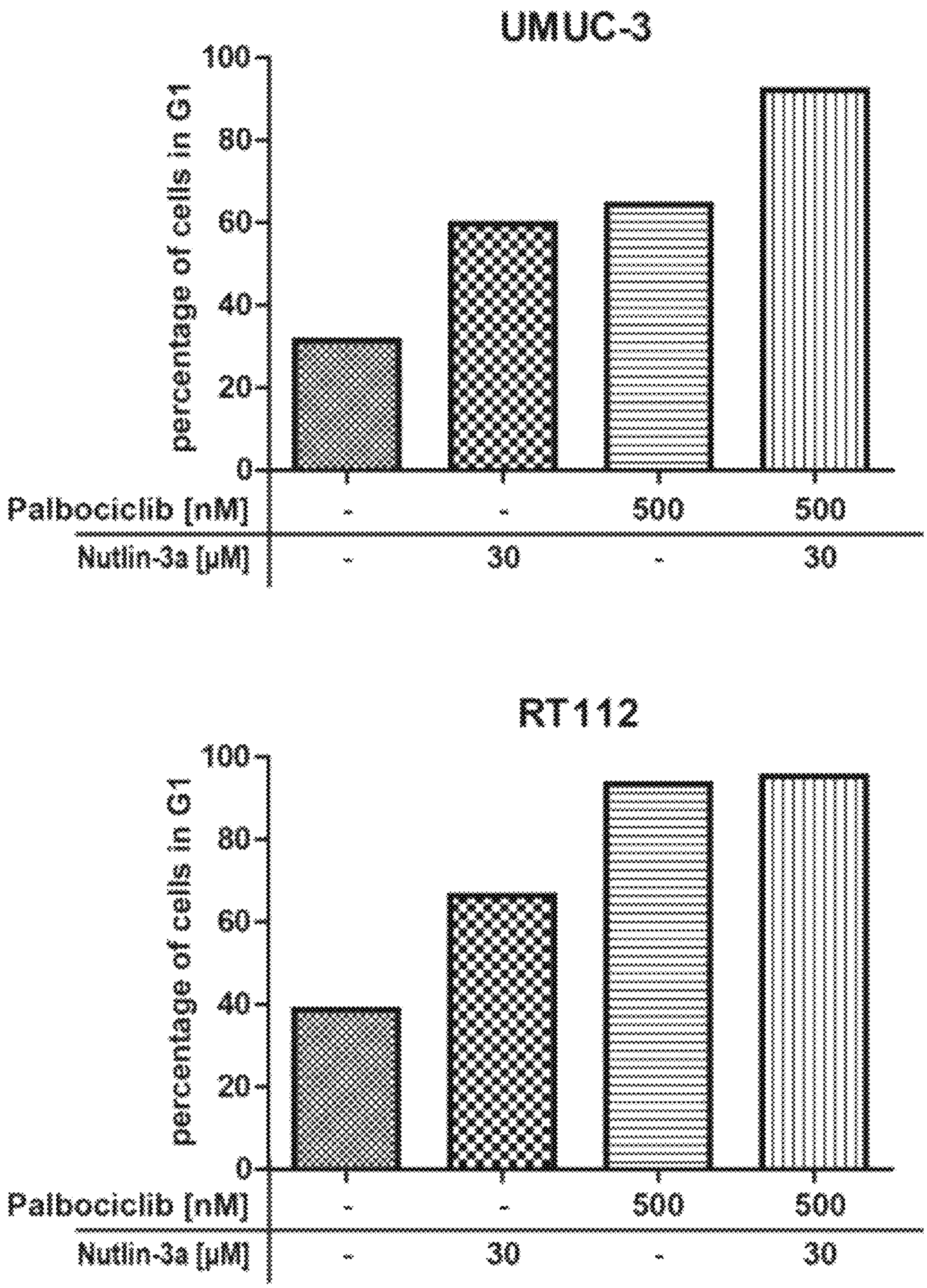

FIGS. 56A-B are bar diagrams showing the % of cells in cell cycle phase G1 of T24 cells (A), T24shRb cells (B), UMUC-3 cells (C) and RT112 cells (D) upon exposure of the cells to Palbociclib, Nutlin-3a or a combination of both at the indicated concentrations.

Figure 57:
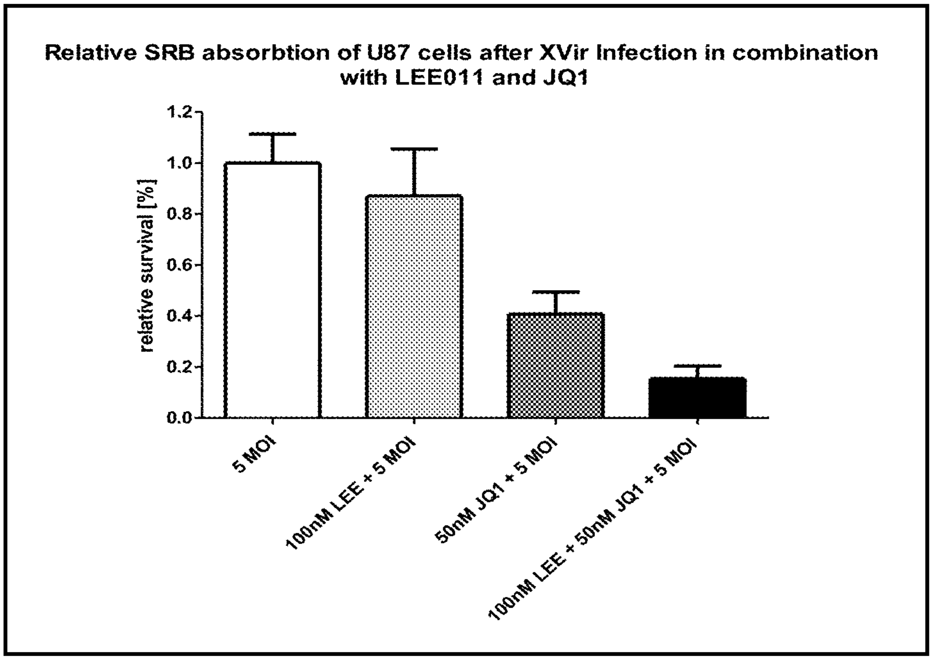

FIG. 57 is a bar diagram indicating relative survival of U87 cells post XVir-N-31 infection with 100 nM Ribociclib (LEE also referred to as LEE011), with 100 nMJQ1 and with both 100 nM Ribociclib (LEE) and 100 nMJQ1, with MOI for XVir-N-31 being 5.

Figure 58:
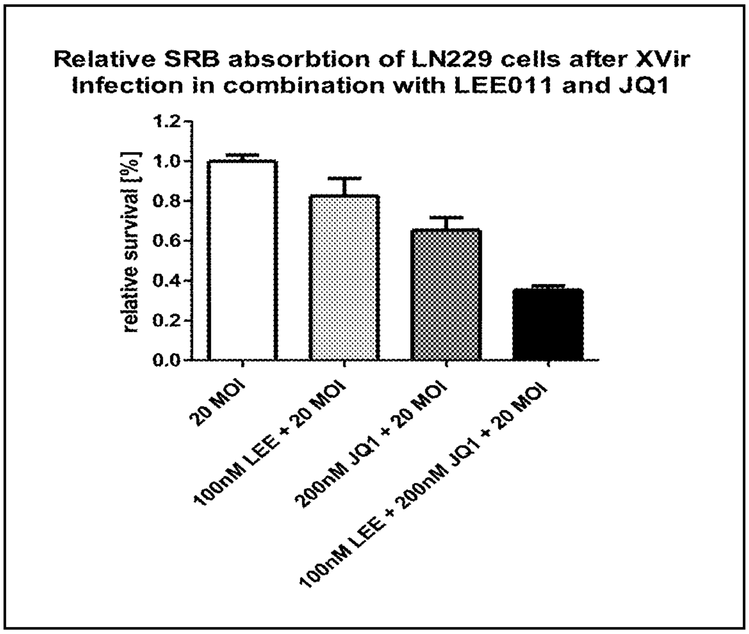

FIG. 58 is a bar diagram indicating relative survival of LN229 cells post XVir-N-31 infection with 100 nM Ribociclib (LEE also referred to as LEE011), with 200 nMJQ1 and with both 100 nM Ribociclib (LEE) and 200 nMJQ1, with MOI for XVir-N-31 being 20.

Figure 59:
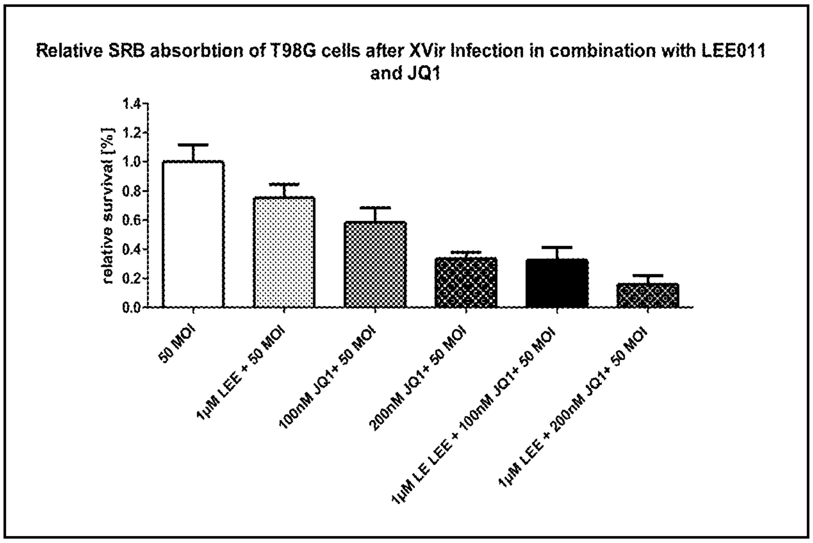

FIG. 59 is a bar diagram indicating relative survival of T98G cells post XVir-N-31 infection with 1 μM Ribociclib (LEE also referred to as LEE011), with 200 nMJQ1 and with both 100 nM Ribociclib (LEE) and 200 nMJQ1, with MOI for XVir-N-31 being 50.

Figure 60:
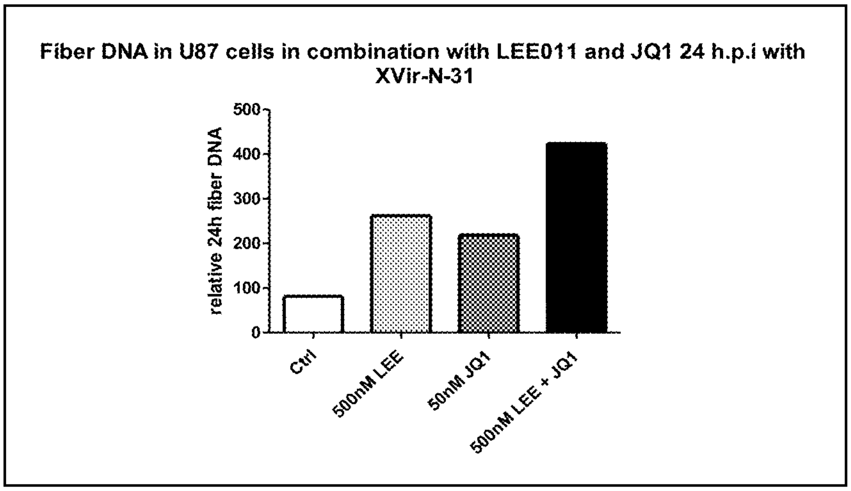

FIG. 60 is a bar diagram indicating relative amount of adenovirus XVir-N-31 fiber DNA in U87 cells when exposed to Ribociclib (LEE) (500 nM), JQ1 (50 nM) or a combination of Ribociclib (500 nM) and JQ1 24 (50 nM) 24 hours post infection (h.p.i.) with XVir-N-31.

Figure 61:
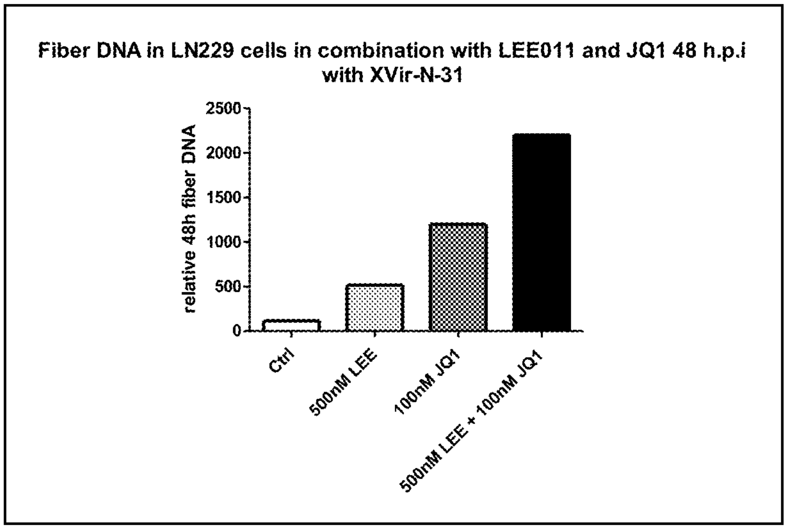

FIG. 61 is a bar diagram indicating relative amount of adenovirus XVir-N-31 fiber DNA in LN229 cells when exposed to Ribociclib (LEE) (500 nM), JQ1 (100 nM) or a combination of Ribociclib (500 nM) and JQ1 (100 nM) 48 hours post infection (h.p.i.) with XVir-N-31.

Figure 62:
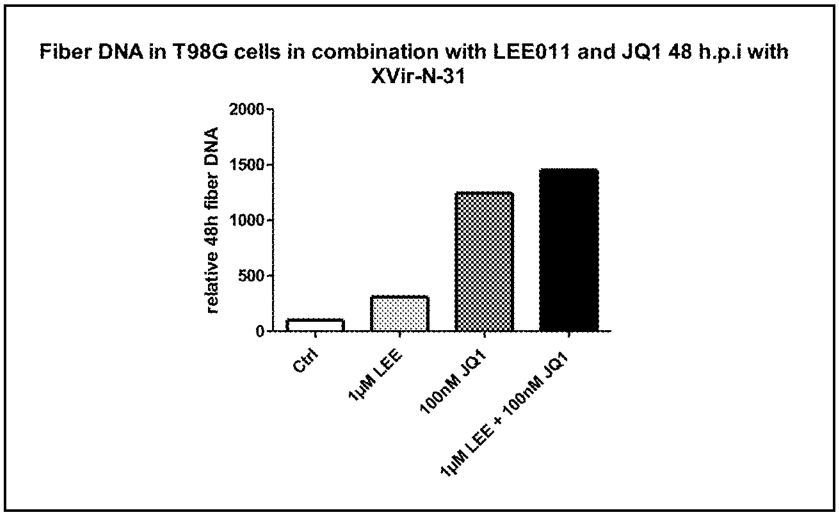

FIG. 62 is a bar diagram indicating relative amount of adenovirus XVir-N-31 fiber DNA in T98G cells when exposed to Ribociclib (LEE) (1 μM), JQ1 (100 nM) or a combination of Ribociclib (1 μM) and JQ1 (100 nM) 48 hours post infection (h.p.i.) with XVir-N-31.

Figure 63:
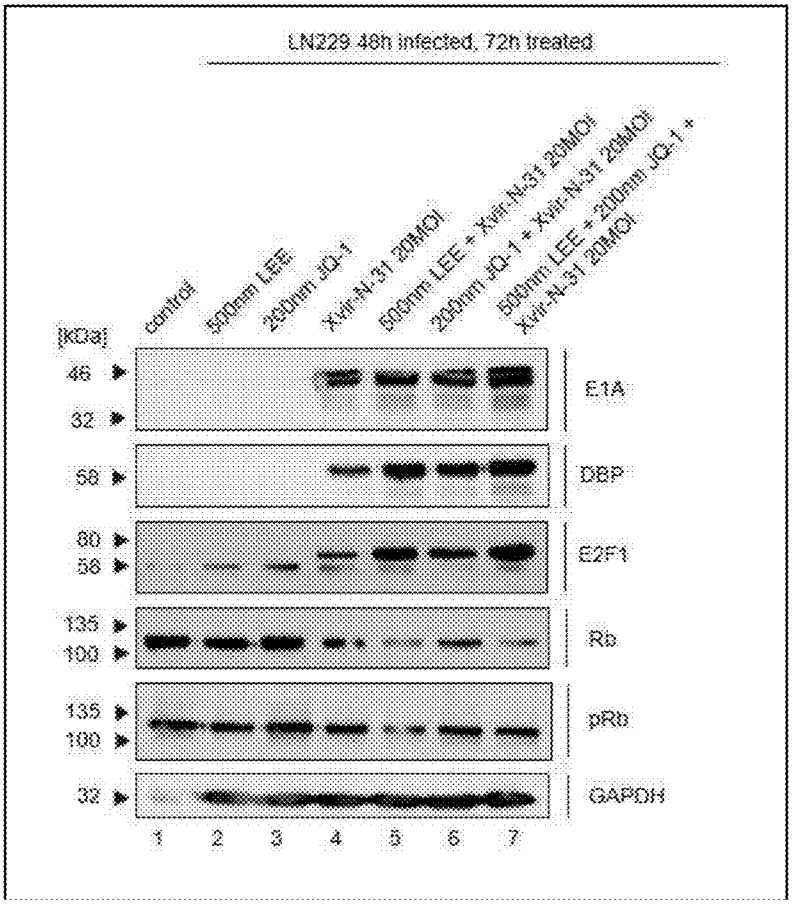

FIG. 63 shows the result of a Western blot analysis of LN229 cells 24 hours post infection with XVir-N-31 (MOI 20) upon exposure to 500 nM LEE, 200 nM JQ-1 or a combination of both 500 nM LEE and 200 nm JQ-1.

Figure 64:
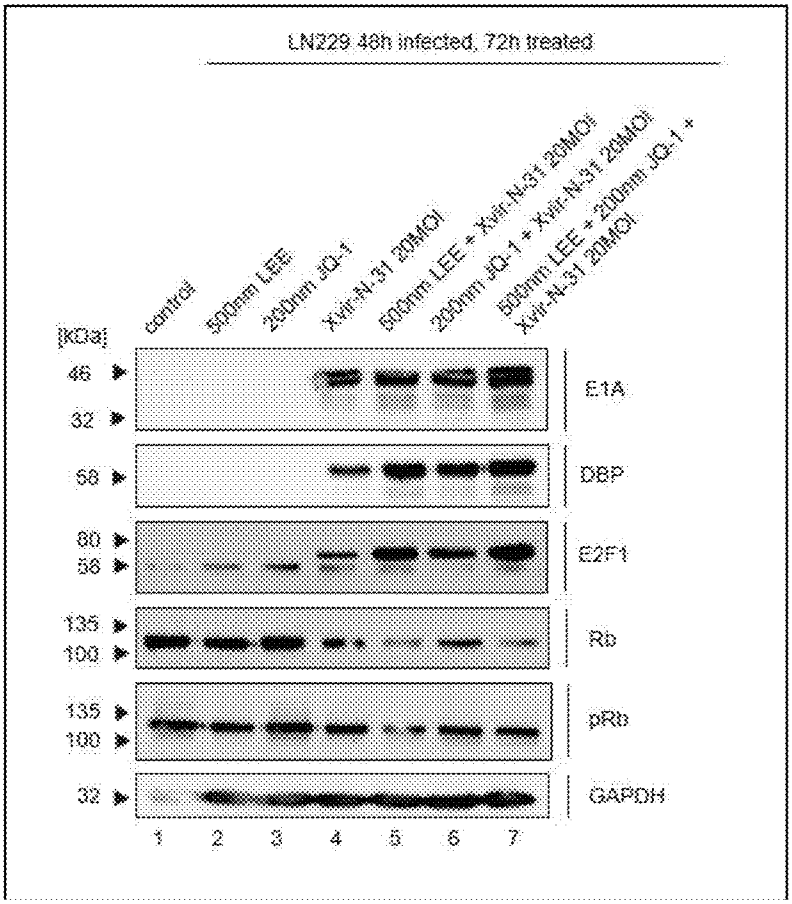

FIG. 64 shows the result of a Western blot analysis of LN229 cells 48 hours post infection with XVir-N-31 (MOI 20) upon exposure to 500 nM LEE, 200 nM JQ-1 or a combination of both 500 nM LEE and 200 nm JQ-1.

Figure 65:
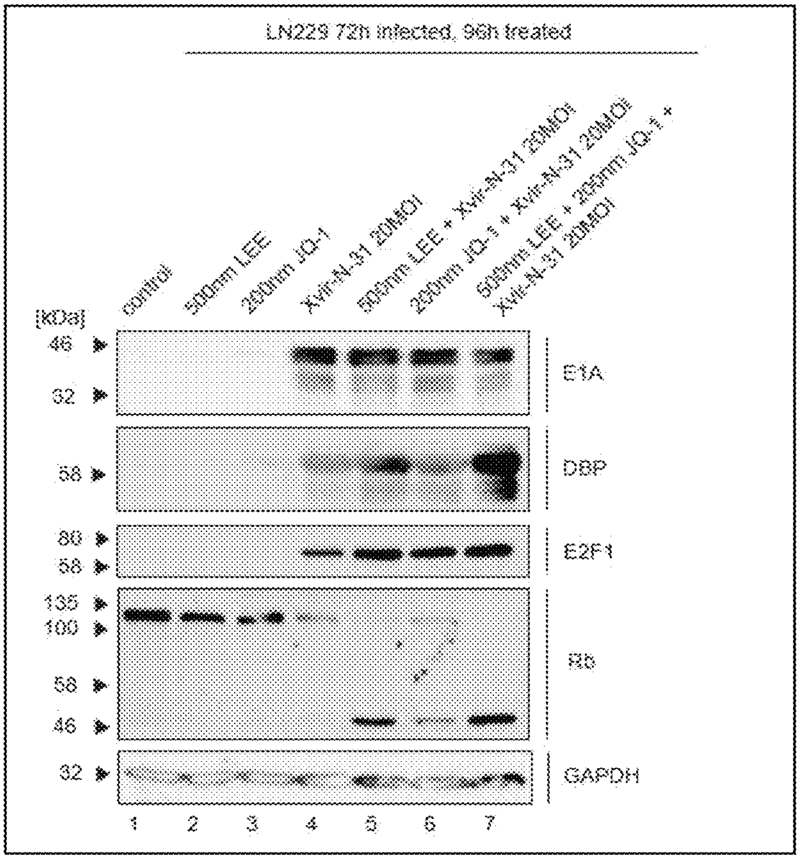

FIG. 65 shows the result of a Western blot analysis of LN229 cells 72 hours post infection with XVir-N-31 (MOI 20) upon exposure to 500 nM LEE, 200 nM JQ-1 or a combination of both 500 nM LEE and 200 nm JQ-1.

Figure 66:
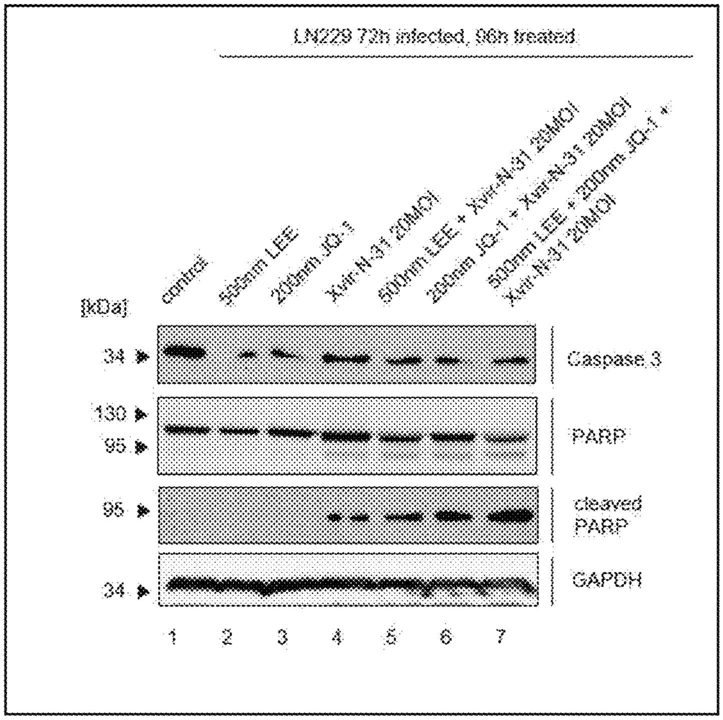

FIG. 66 shows the result of a Western blot analysis of LN229 cells 72 hours post infection with XVir-N-31 (MOI 20) upon exposure to 500 nM LEE, 200 nM JQ-1 or a combination of both 500 nM LEE and 200 nm JQ-1.

Figure 67:
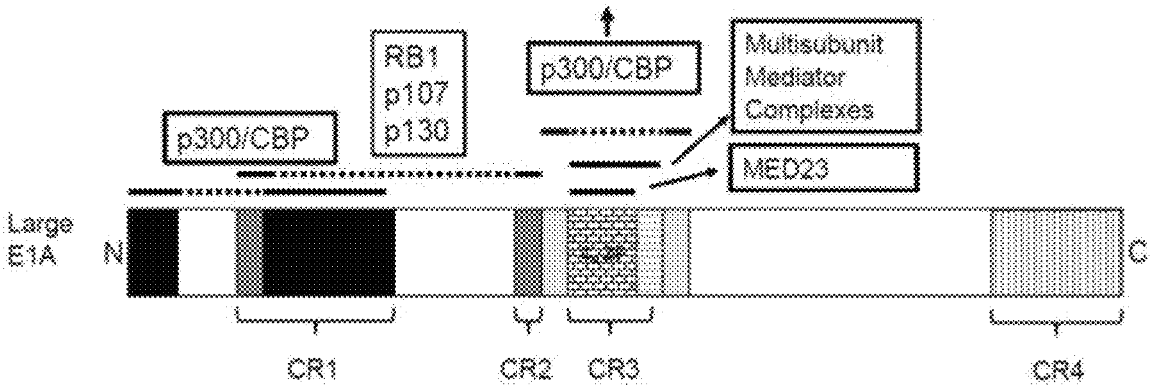

FIG. 67 is an illustration of interacting partners of E1A and location of the conserved region CR1-CR4.

Figure 68:
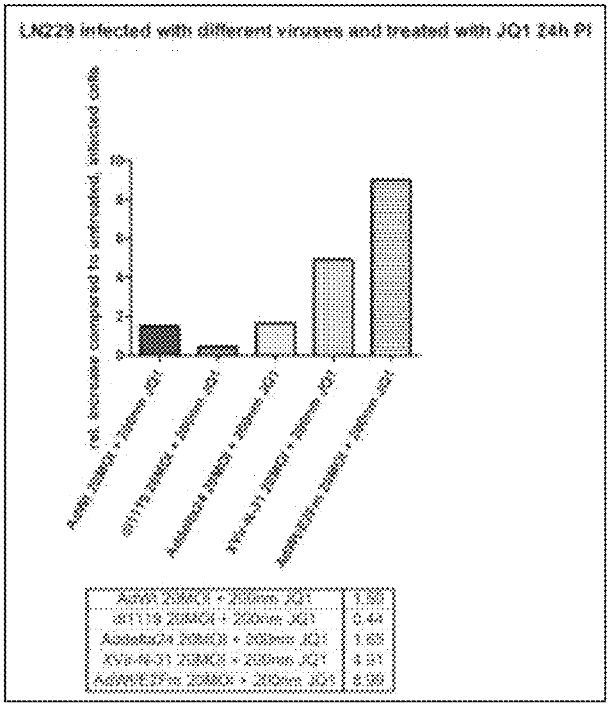

FIG. 68 is a bar diagram showing the relative increase of adenovirus DNA in LN229 cells 24 hours post infection (PI) of adenoviruses AdWT, dl119, Ad delta 24, XVir-N-31 and AdWT/E2Fm (MOI 20) upon JQ-1 treatment (200 nm).

Figure 69:
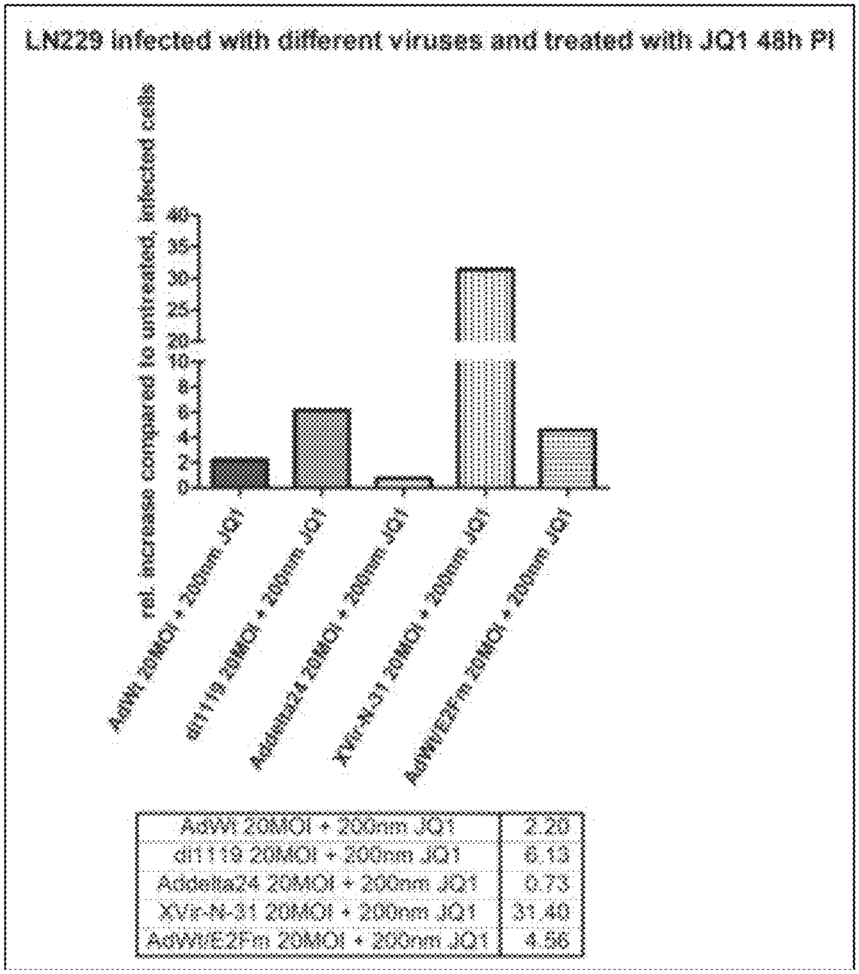

FIG. 69 is a bar diagram showing the relative increase of adenovirus DNA in LN229 cells 48 hours post infection (PI) of adenoviruses AdWT, dl1119, Ad delta 24, XVir-N-31 and AdWT/E2Fm (MOI 20) upon JQ-1 treatment (200 nm).

Figure 70:
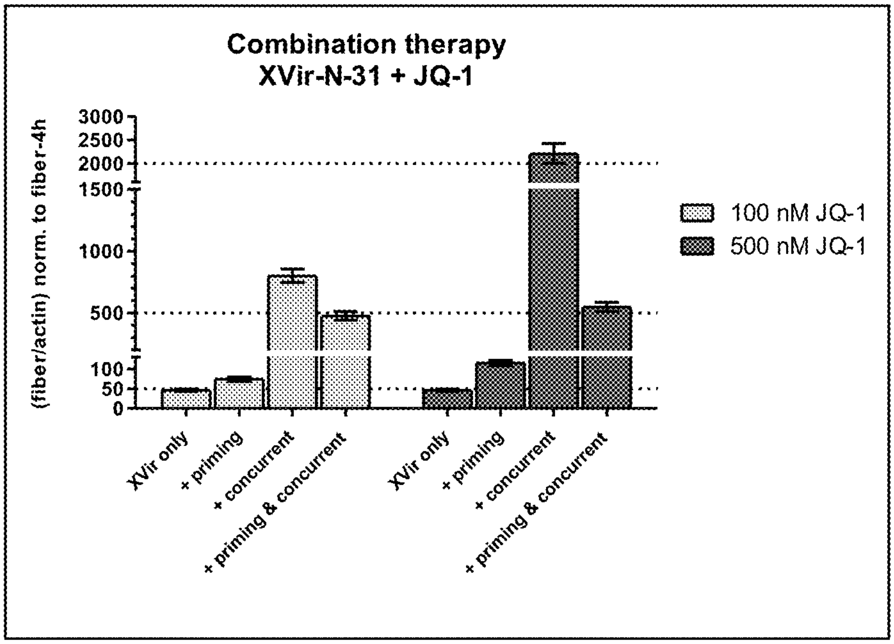

FIG. 70 is a diagram showing quantified fibre DNA in UMUC-3 cells (expressed as fibre/actin) normalized to fibre at 4 hours) 24 hours post infection with XVir-N-31 after priming or concurrent treatment with with either 100 nM JQ-1 (left) or 500 nM JQ-1 (right).

Figure 71:
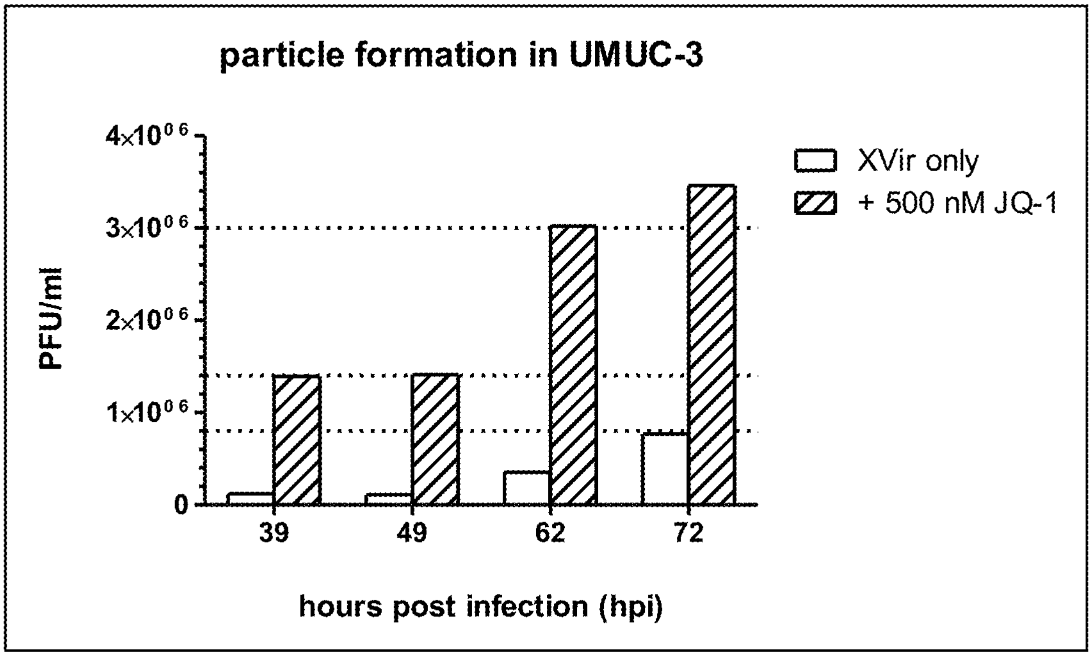

FIG. 71 is a diagram indicating particle formation of XVir-N-31 (expressed as PFU/ml) in UMUC-3 cells at 39, 49, 62 or 72 hours post infection (hpi) with and without 500 nM JQ-1.

Figure 72:
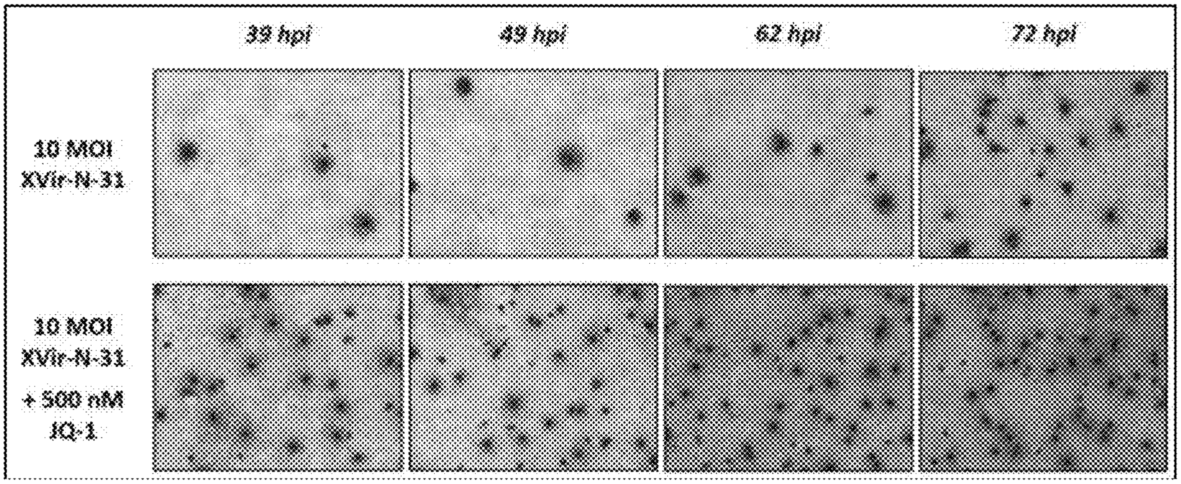

FIG. 72 is a panel of bright-field photomicrographs of XVir-N-31 infected cells (MOI of 10) after hexon titer test 39, 49, 62 or 72 hours post infection (hpi) without (upper row) and 500 nM JQ-1 (lower row).

Figure 73:
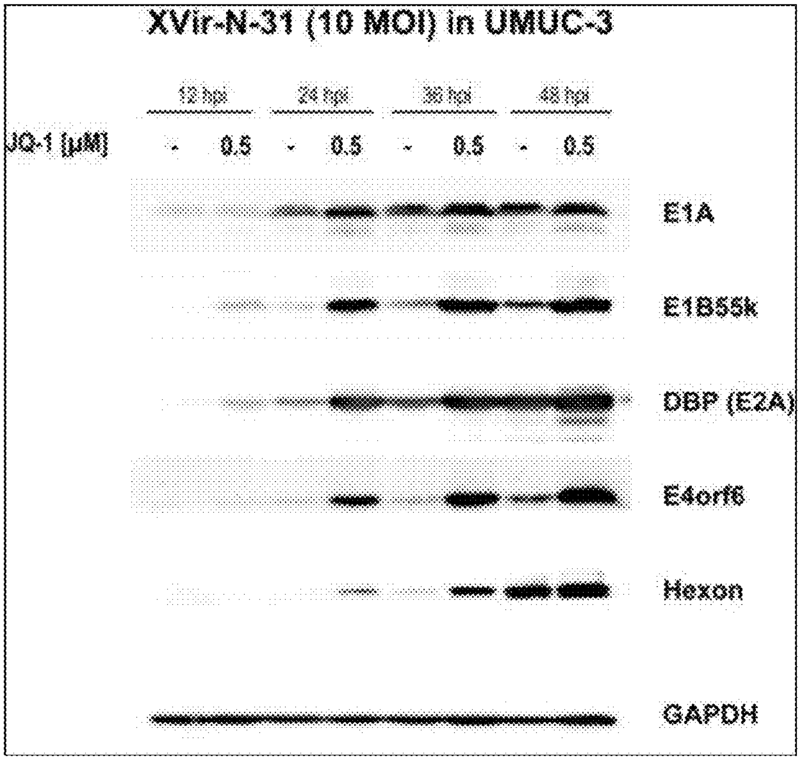

FIG. 73 is a Western blot analysis of UMUC-3 cells upon treatment with XVir-N-31 with or without 500 nM JQ-1 at 12 hours post infection, 24 hours post infection, 36 hours post infection and 48 hours post infection illustrating quantified viral expression kinetics.

Figure 74:
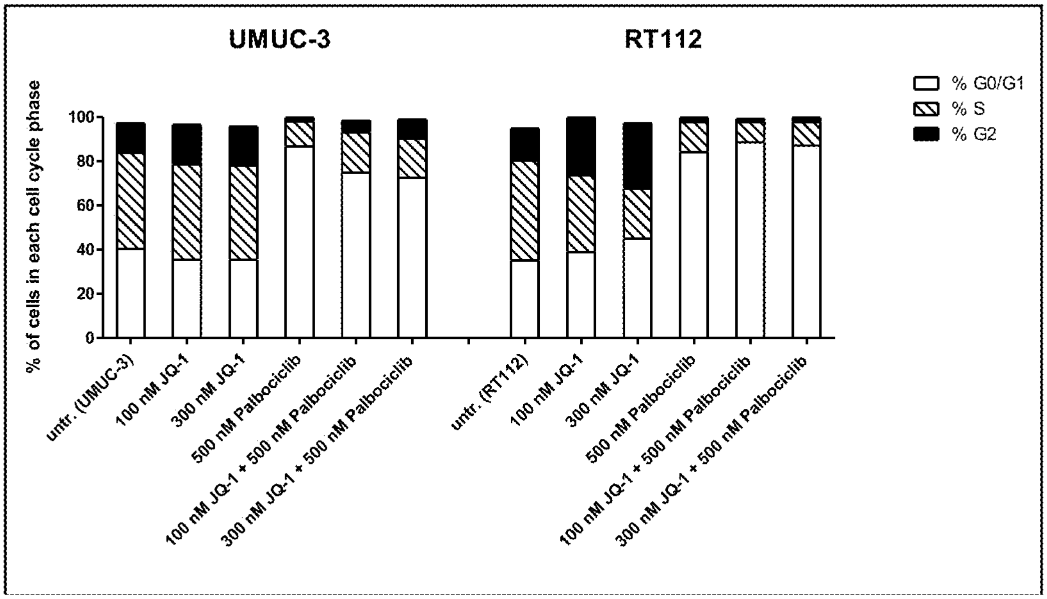

FIG. 74 is a bar diagram showing the percentage of UMUC-3 cells (left) and RT112 cells (right) in G0/G1 phase, S phase and G2 phase under the influence of 100 nM JQ-1, 300 nM JQ-1, 500 nM Palbociclib, a combination of 100 nM JQ-1 and 500 nM Palboccilib, and a combination of 300 nM JQ-1 and 500 nM Palbociclib.

Figure 75:
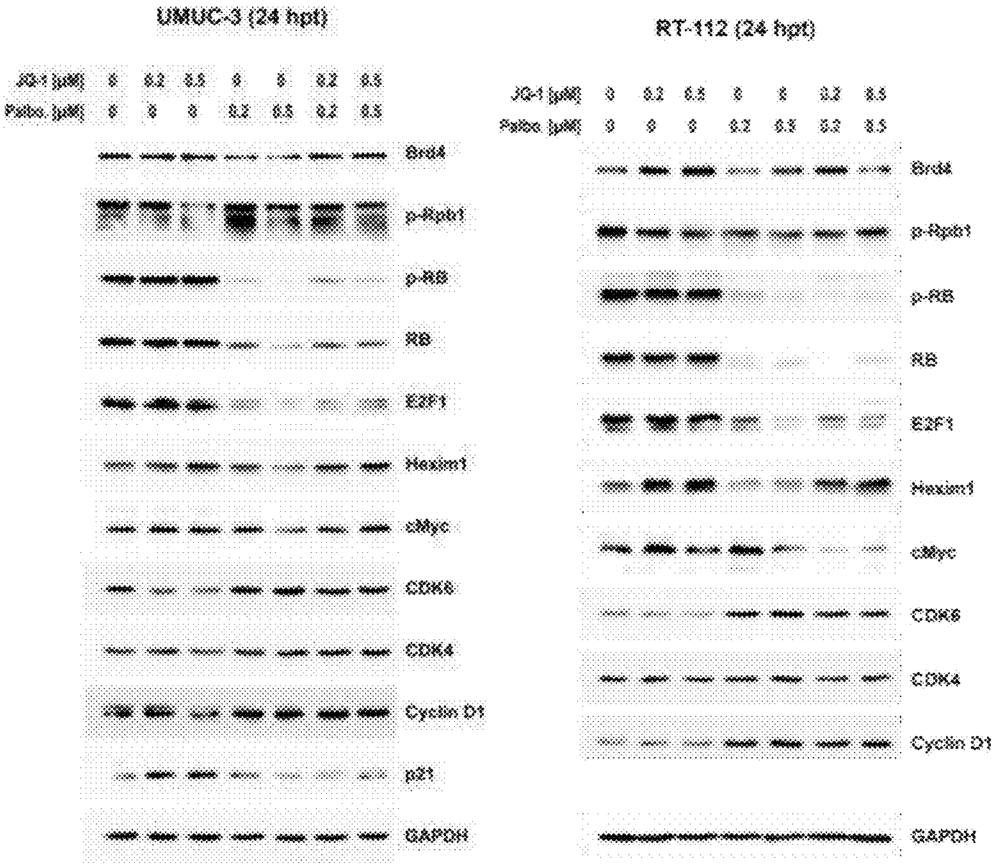

FIG. 75 shows the result of a Western blot analysis of UMUC-3 cells (left) and RT-112 cells (right) upon exposure to JQ-1 and/or Palbociclib at 0, 0.2 μM, and 0.5 μM 24 hours post treatment.

Figure 76:
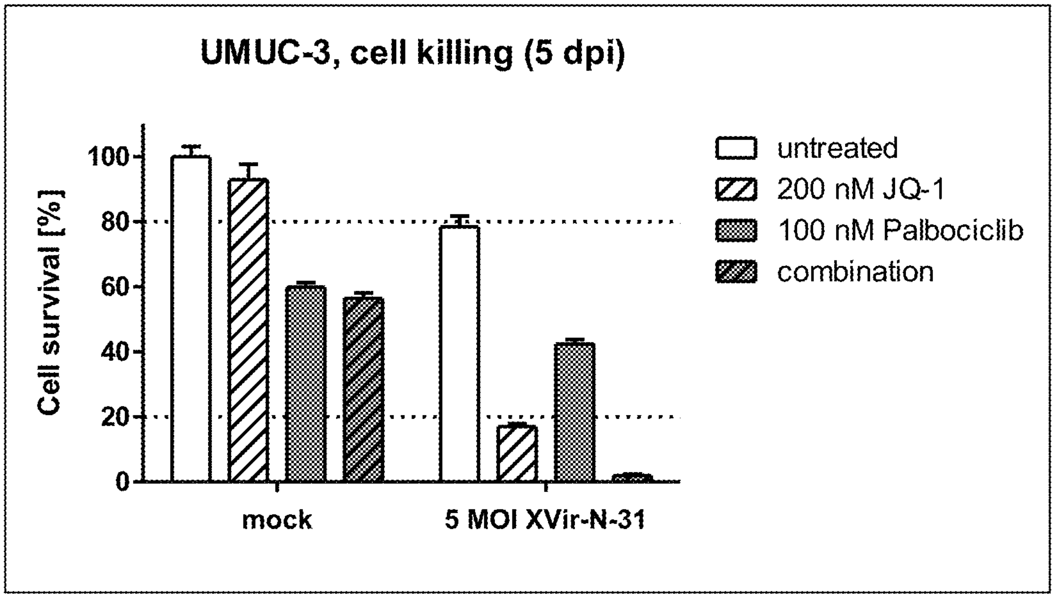

FIG. 76 is a bar diagram showing the effect of XVir-N31 (MOI of 5) on the killing of UMUC-3 cells upon treatment with 200 nM JQ-1, 100 nM Palbociclib, and a combination of 200 nM JQ-1 and 100 nM Palbociclib, each five days post infection.

Figure 77:
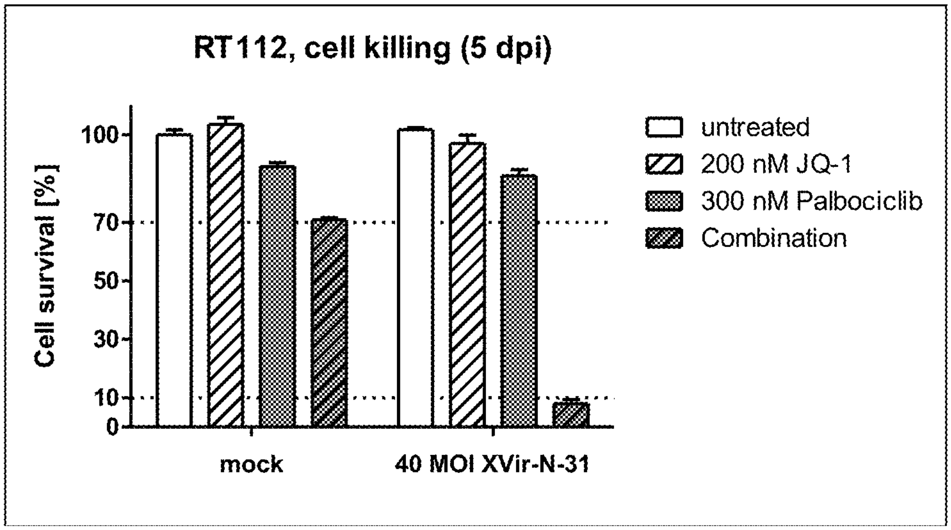

FIG. 77 is a bar diagram showing the effect of XVir-N31 (MOI of 40) on the killing of RT112 cells upon treatment with 200 nM JQ-1, 300 nM Palbociclib, and a combination of 200 nM JQ-1 and 300 nM Palbociclib, each five days post infection.

Figure 78:
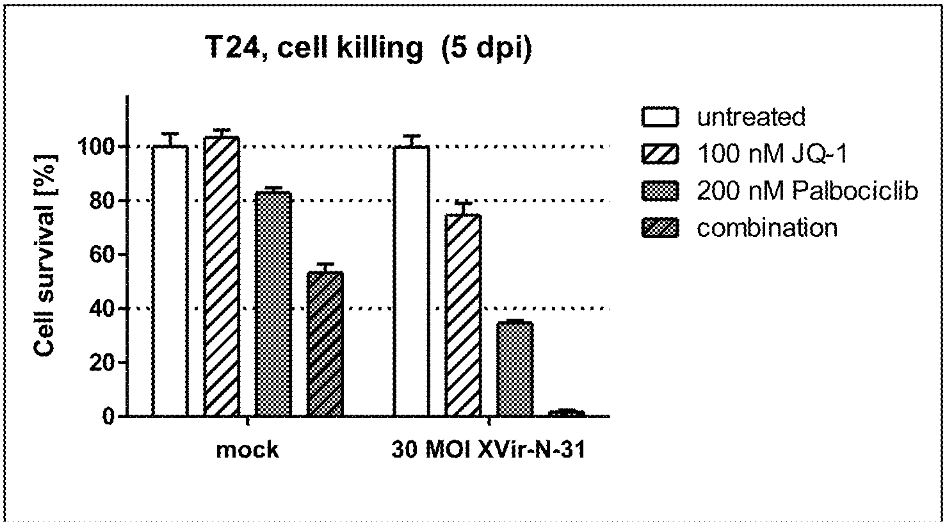

FIG. 78 is a bar diagram showing the effect of XVir-N31 (MOI of 40) on the killing of T24 cells upon treatment with 100 nM JQ-1, 200 nM Palbociclib, and a combination of 100 nM JQ-1 and 200 nM Palbociclib, each five days post infection.

Figure 79:
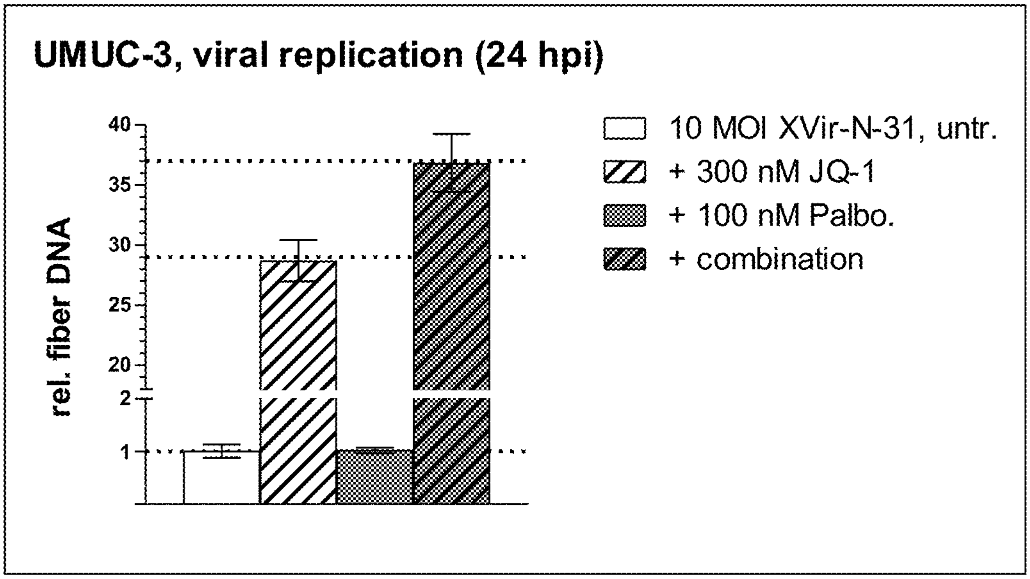

FIG. 79 is a bar diagram showing replication of XVir-N-31 in UMUC-3 cells 24 hours post infection with XVir-N-31 (MOI of 10) after priming and concurrent treatment with JQ-1 (300 nM), Palbociclib (100 nM) or a combination of both JQ-1 (300 nM) and Palbociclib (100 nM), whereby replication of XVir-N-31 is quantified as relative fiber DNA level.

Figure 80:
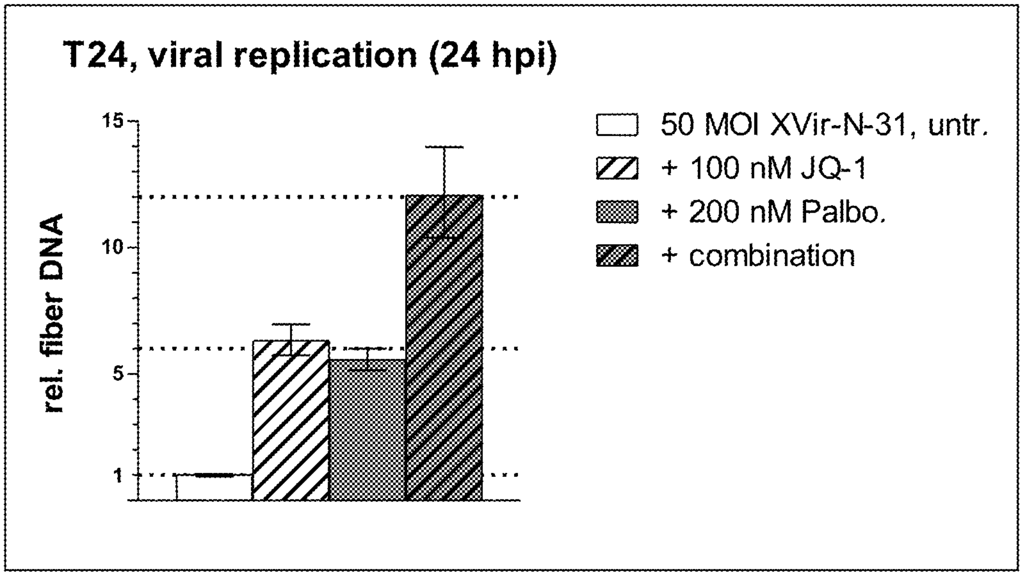

FIG. 80 is a bar diagram showing replication of XVir-N-31 in T24 cells 24 hours post infection with XVir-N-31 (MOI of 50) after priming and concurrent treatment with JQ-1 (100 nM), Palbociclib (200 nM) or a combination of both JQ-1 (100 nM) and Palbociclib (200 nM), whereby replication of XVir-N-31 is quantified as relative fiber DNA level.

Figure 81:
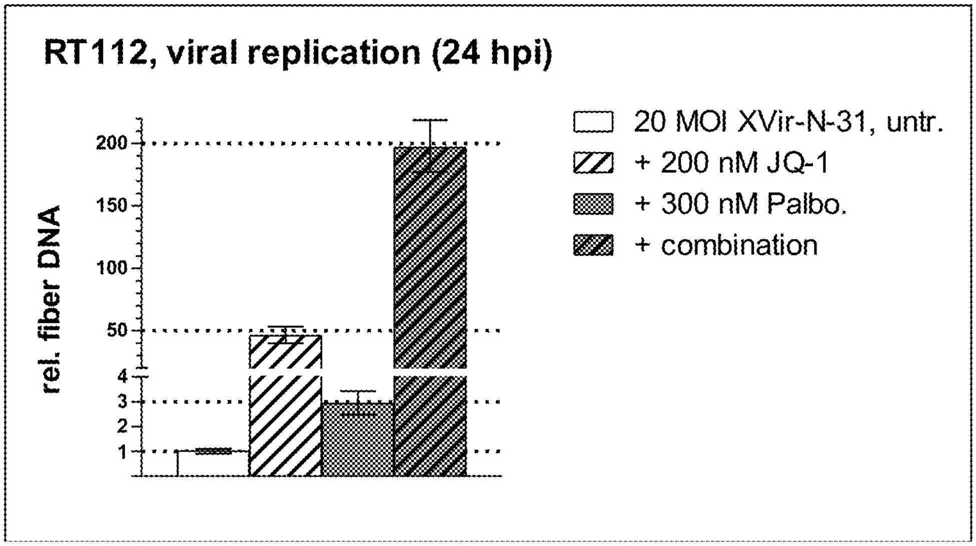

FIG. 81 is a bar diagram showing replication of XVir-N-31 in RT112 cells 24 hours post infection with XVir-N-31 (MOI of 20) after priming and concurrent treatment with JQ-1 (200 nM), Palbociclib (300 nM) or a combination of both JQ-1 (200 nM) and Palbociclib (300 nM), whereby replication of XVir-N-31 is quantified as relative fiber DNA level.

Figure 82:
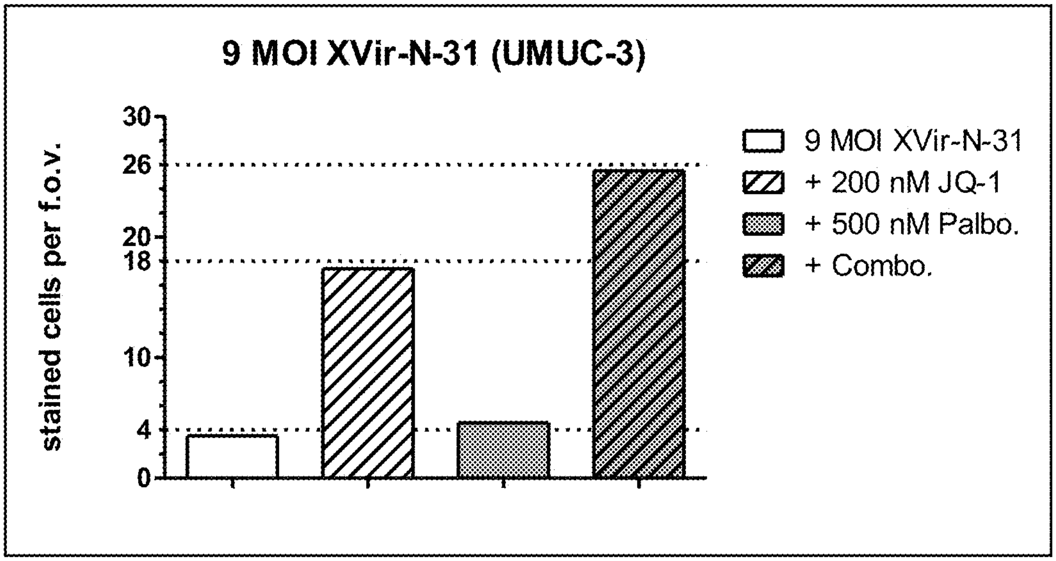

FIG. 82 is a bar diagram illustrating quantitative average production of virus producing UMUC-3 cells infected with XVir-N-31 (MOI of 9) with 200 nM JQ-1, with 500 nM Palbociclib or a combination of both 200 nM JQ-1 and 500 nM Palbociclib, whereby quantification of average production is indicated as stained cells per field of view (f.o.v).

Figure 83:
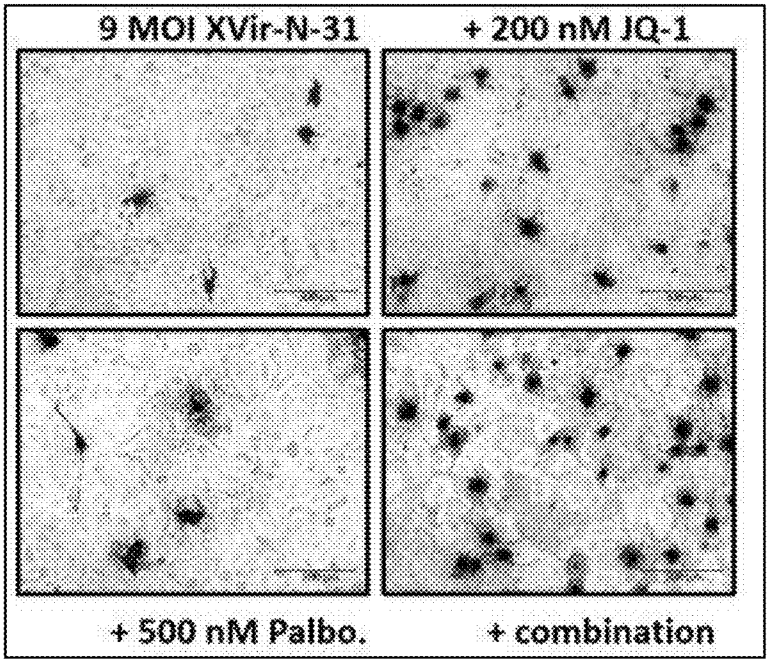

FIG. 83 is a panel of bright-field photomicrographs of XVir-N-31 infected UMUC-3 cells (MOI of 9) after hexon titer test, whereby the cells were infected with XVir-N-31 alone, a combination of XVir-N-31 and 200 nM JQ-1, a combination of XVir-N-31 and 500 nM Palbociclib, or a combination of XVir-N-31, 200 nM of JQ-1 and 500 nM of Palbociclib.

Figure 84:
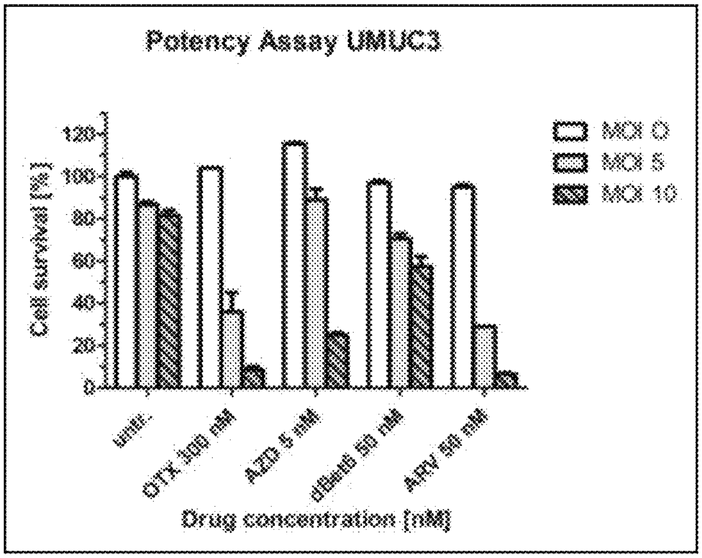

FIG. 84 is a bar diagram indicating relative survival of UMUC-3 cells post infection with XVir-N-31 (at MOIs of 0, 5 and 10) in combination with indicated BET inhibitors OTX (300 nM), AZD (5 nM), dBet6 (50 nM) and ARV (50 nM).

Figure 85:
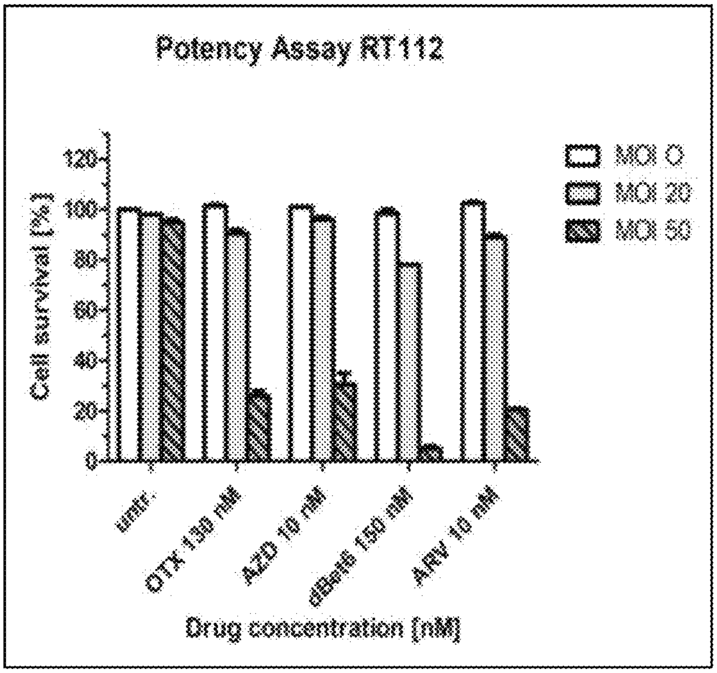

FIG. 85 is a bar diagram indicating relative survival of RT112 cells post infection with XVir-N-31 (at MOIs of 0, 20 and 50) in combination with indicated BET inhibitors OTX (130 nM), AZD (10 nM), dBet6 (150 nM) and ARV (10 nM).

Figure 86:
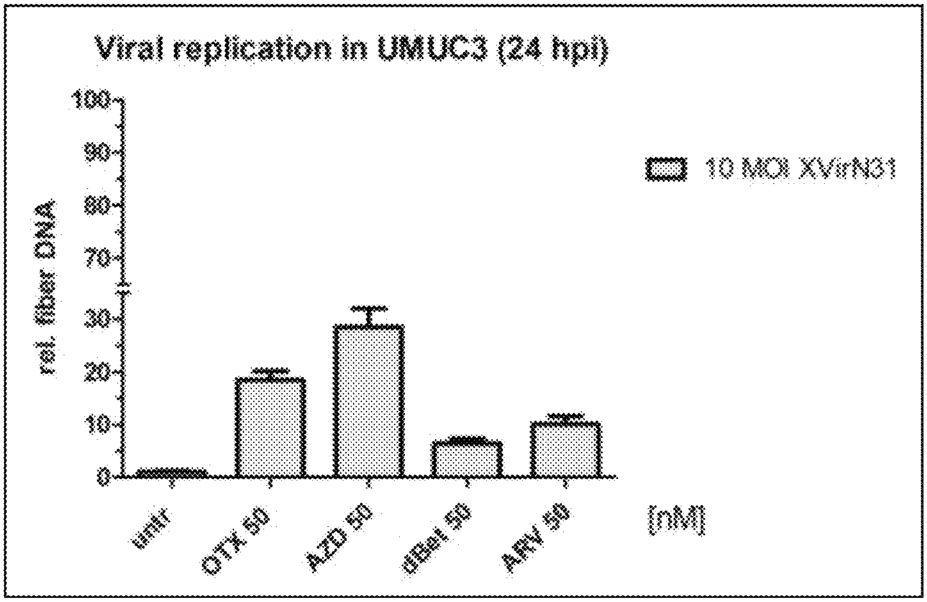

FIG. 86 is a bar diagram indicating viral replication in UMUC-3 cells 24 hours post infection with XVir-N-31 (MOI of 10) in combination with indicated BET inhibitors (OTX: 50 nM; AZD: 50 nM, dBet: 50 nM, and ARV: 50 nM).

Figure 87:
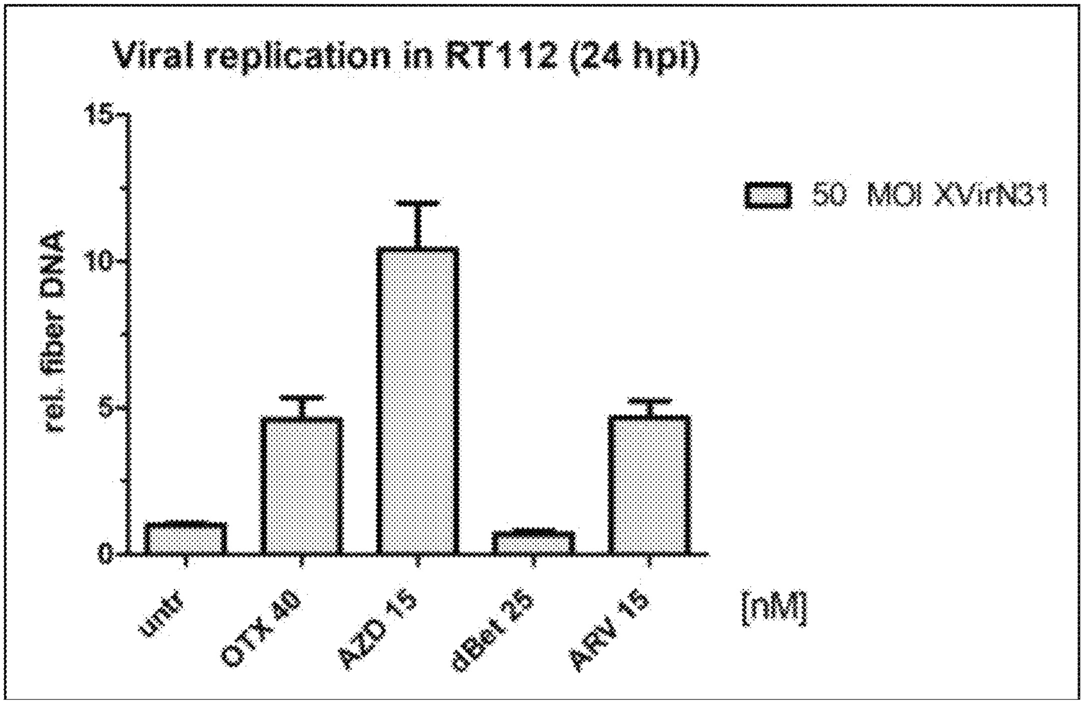

FIG. 87 is a bar diagram indicating viral replication in RT112 cells 24 hours post infection with XVir-N-31 (MOI of 50) in combination with indicated BET inhibitors (OTX: 40 nM; AZD: 15 nM, dBet: 25 nM, and ARV: 15 nM).

Figure 88:
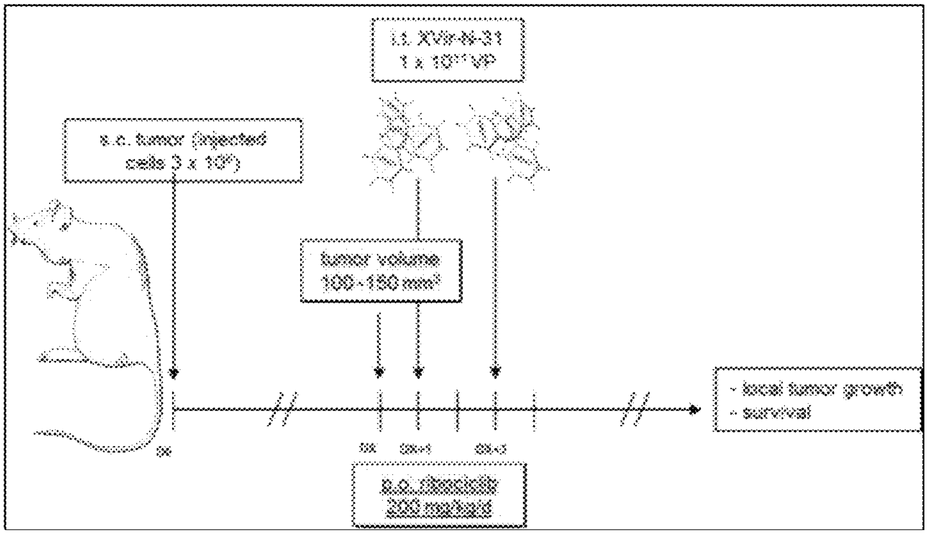

FIG. 88 is an illustration of the animal studies indicating the dosing and scheduled application of XVir-N-31 and Ribociclib. Ribociclib succinate (LEE011) was administered daily at 200 mg/kg/body weight by oral gavage for a total of 5 days (day X until X+4). Dissolvent without LEE011 was applied in PBS and XVir-N-31 only animals. XVir-N-31 was injected into the tumor twice at day X+1 and X+3. All control animals, which did not receive XVir-N-31, received i.t. PBS injections, respectively.

Figure 89:
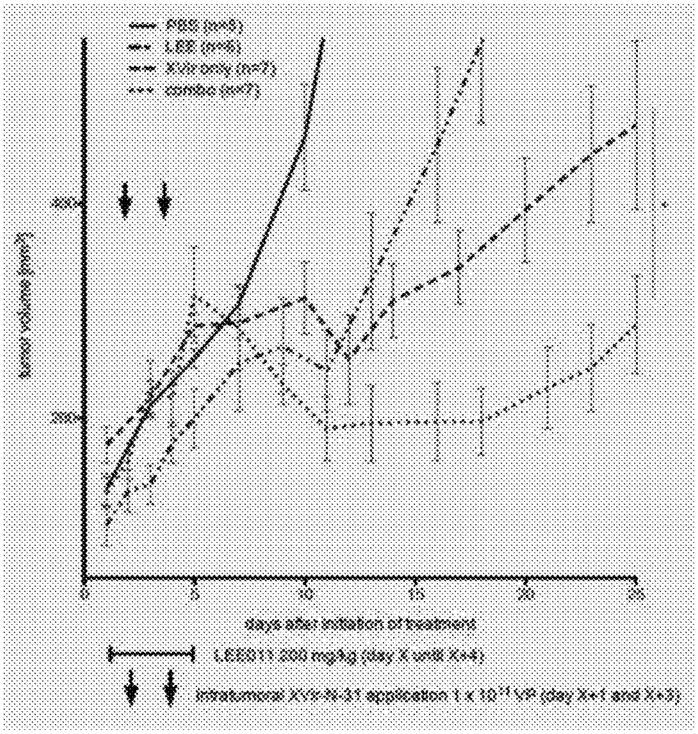

FIG. 89 is a diagram showing volume growth curves of various treatment groups (PBS, LEE, XVir only and combo); each data point shows the mean f tumor size at indicated days after initiation of treatment.

Figure 90:
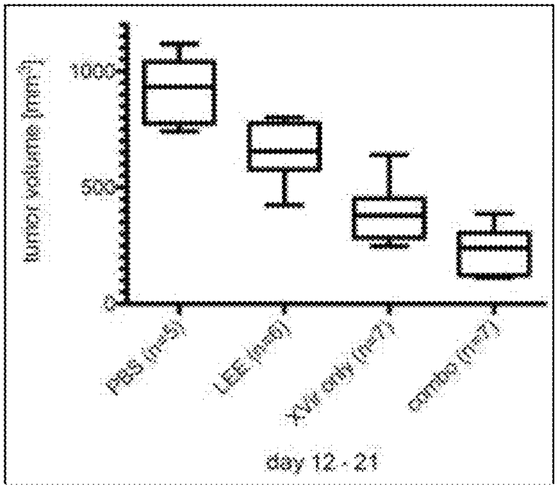

FIG. 90 is a box plot diagram showing tumor volume [$mm^3$] for the various treatment groups (PBS number of animals=5), LEE (PBS number of animals=6), XVir only (PBS number of animals=7) and combo (PBS number of animals=7)) at day 12-21 after initiation of treatment.

Figure 91:
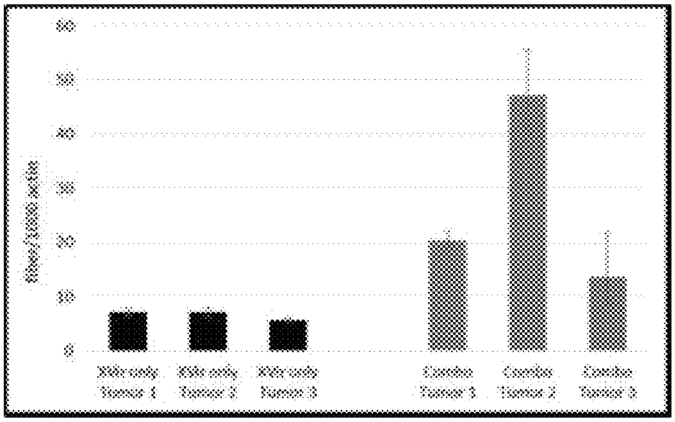

FIG. 91 is a bar diagram showing viral genomes in tumors (expressed as fiber/1000 actin) of representative animals receiving combination treatment compared to XVir-N-31 only treatment; assessment 2 days after second i.t. injection of XVir-N31.

EXAMPLE 1: MATERIALS AND METHODS

Cell Culture

Human bladder cancer cell lines were cultured under subconfluent conditions in RPMI or DMEM medium (Biochrom AG) at 5% or 10% CO2, respectively, supplemented with 10% FBS (Biochrom AG) and 1% NEA (Biochrom AG). Depending on the cell line and experimental conditions, 0.2-1×106, 0.5-1×105, 0.25-0.5×105, and 500-700 cells were seeded in 10 cm, 6-well, 12-well and 96-well formats, respectively.

Cell Lines

HeLaP

HeLa P cells (ATCC CCL-2) are epithelial cells from cervical adenocarcinoma named after the patient Henrietta Lacks. This cell line is the most widely distributed and oldest cell line (Rahbari et al., 2009), since it was the first permanent cell line, established in 1951 (Gey et al., 1952). Cultivation occurred in DMEM (10% FBS, 1% PS) under 10% CO2 conditions at 37° C.

HeLaRDB

HeLaRDB is a sub-cell line of the HeLaP-cell line, with resistance to daunoblastin based on overexpression of the glycoprotein P. The resistance was achieved through cultivation with medium containing this anthracycline. This cytostatic agent intercalates in double-stranded DNA sequences and inhibits cellular transcription and replication (Mizuno et al., 1975). As a result of the stress reactions, caused by daunoblastin treatment, the cellular factor YB-1 shows higher nuclear localization in comparison to the parental cell line (Holm et al., 2004). To maintain the resistance against daunoblastin, the cells were cultured in DMEM (10% FBS, 1% PS) containing 0.25 μg/ml daunoblastin under 10% CO2 conditions at 37° C. every 14 days.

A549

A549 cells (ATCC CCL-185) were isolated in 1972 from an adenocarcinoma in the human alveolar basal (Giard et al., 1973). Cultivation occurred in Dulbecco's MEM (10% FBS and 1% PS) at 37° C. and 10% CO2.

T24

T24 cells (ATCC HTB-4) derived 1970 of a primary human urinary bladder carcinoma (Bubenik, Baresovi et al., 1973). Due to a point mutation in the HRAS gene (Reddy et al., 1982), the MAPK and PI3K pathway is activated. Moreover, an additional mutation in the gene locus of the tumor suppressor gene p53 is present in this cell line (Pinto-Leite et al., 2014). The cells were cultivated with RPMI containing 10% FCS, 1% PS and 1% non-essential amino acids at 37° C. under 5% CO2 conditions.

HEK293

HEK293 cells (ATCC CRL-1573) are human embryonic kidney cells isolated in 1973. Due to a stabile transfection of a 4.5 kb-sized part of the genome of adenoviral serotype 5, which includes the whole E1 region (Graham and Smiley, 1977), this cell line is used for production of E1-deficient adenoviruses and for measurement of virus titer.

TABLE 1

| Primer | | | |
|---|---|---|---|
| Name Company | Forward primer | Reverse primer | |
| Fiber Eurofins | AAGCTAGCCCTGCAAACATCA | CCCAAGCTACCAGTGGCAGTA | (SEQ ID NO: 1) |
| E2 early Invitrogen | CCGTCATCTCTACAGCCCAT | GGGCTTTGTCAGAGTCTTGC | (SEQ ID NO: 2) |
| E2 late Invitrogen | CTTCCTAGCGACTTTGTGCC | GTCAGAGTGGTAGGCAAGGT | (SEQ ID NO: 3) |
| E1A 12S Metabion | CGACGAGGATGAAGTCCTGTGTCTG | CTCAGGATAGCAGGCGCCAT | (SEQ ID NO: 4) |
| E1A 12S short Metabion | GAGGATGAAGTCCTGTGT | CTCAGGATAGCAGGCGCCAT | (SEQ ID NO: 5) |
| E1A 13S Metabion | TGTTTGTCTACAGTCCTGTGTCTG | CTCAGGATAGCAGGCGCCAT | (SEQ ID NO: 6) |
| E1A 13S short Metabion | TTGTCTACAGTCCTGTGT | CTCAGGATAGCAGGCGCCAT | (SEQ ID NO: 7) |
| E4orf6 Metabion | TCCCTCCCAACA CACAGAGT | GACAGGAAACCG TGTGGAAT | (SEQ ID NO: 8) |
| Rb Life Techno. | AGCAACCCTCCTAAACCACT | TGTTTGAGGTATCCATGCTATCA | (SEQ ID NO: 9) |
| E2F1 Life Technology | ACGCTATGAGACCTCACTGAA | TCCTGGGTCAACCCCTCAAG | (SEQ ID NO: 10) |
| E2F2 Life Technology | CGTCCCTGAGTTCCCAACC | GCGAAGTGTCATACCGAGTCTT | (SEQ ID NO: 11) |
| GAPDH MWG | TGGCATGGACTGTGGTCATGAG | ACTGGCGTCTTCACCACCATGG | (SEQ ID NO: 12) |
| Actin Eurofins | TAAGTAGGTGCACAGTAGGTCTGA | AAAGTGCAAAGAACACGGCTAAG | (SEQ ID NO: 13) |
| L4 33K Eurofins | GAACCAGGGCCGCCCATACTG | GGGCTTTGTCAGAGTCTTGC | (SEQ ID NO: 14) |
| L4 22K Eurofins | CCGTTAGCCCAAGAGCAAC | CGGCCGTGATGGTAGAGAAG | (SEQ ID NO: 15) |
| L4HexAss Eurofins | CTGTGGTACTTCCCAGAGAC | CAGGTGAGTTATACCCTGCC | (SEQ ID NO: 16) |

Virus Characteristics

Ad-WT+AdWT-RGD Wildtype Mastadenovirus, Type C, Serotype 5 and ADWT with additional RGD-fiber motif AdWT-E2F1mut. Mastadenovirus, Type C, Serotype 5, mutations in both E2F1 binding sites of the E2-early promoter with additional RGD-fiber motif and a 2,7 kb-sized deletion in the E3 region (ΔE3)

XVir-N-31 Mastadenovirus, Type C, Serotype 5 with deletions in the E1B-region (1.716-1915, 200 bp), E3-region (28.132-30.813) and 12 base deletion in the E1A-region. Replicates in cancer cells only displaying nuclear YB-1 expression.

XVir-N-31/E2F1M Mastadenovirus, Type C, Serotype 5 with deletions in the E1B-region (1.716-1915, 200 bp), E3-region (28.132-30.813) and 12 base deletion in the E1A-region. Replicates in cancer cells only displaying nuclear YB-1 expression. mutations in both E2F1 binding sites of the E2-early promoter with additional RGD-fiber motif and a 2,7 kb-sized deletion in the E3 region (ΔE3)

| Target gene | siRNA construct | Manufacturer |
|---|---|---|
| Control | Control (non-sil.) siRNA, 20 μM | Qiagen, the Netherlands |
| E2F1 | E2F1 (SASI_Hs01_00162220), 10 μM | Sigma, Merck, Germany |
| YB-1 | YBX1 siRNA FlexiTube, 10 μM | Qiagen, the Netherlands |

Methods siRNA Transfection

Downregulation of certain genes was performed using siRNA transfection. Thereby, 5 μl Lipofectamin RNAiMAX (Thermo Fischer) reagent was added to 150 μl of Opti-MEM in one tube and 36 pmol of siRNA was combined with 150 μl of Opti-MEM in another tube. After combining the contents of both tubes and brief vortexing, the solution was incubated for 5 minutes at room temperature. 250 μl of the siRNA-lipid complex was then added to the 250.000-1.000.000 cells, seeded in 6-well plates on the previous day without changing the medium, reaching a final concentration of siRNA of 30 pmol per well. After 48 hours of incubation at 37° C. at 10% CO2 conditions, infection or lysation took place.

RNA-Quantification in Combination with siRNA

RNA was also quantified in cells were virus was combined with siRNA transfection. Thereby, 125.000 cells were seeded and transfected on the following day with 30 pmol of siRNA-construct of Ctrl-, YB-1-, and E2F1-siRNA. After 48 hours of incubation, infection took place and lysation occurred 24 hours post infection. The lysates were stored at −20° C.

RNA Isolation

Cells were rinsed with PBS and lysed with lysis buffer (mirVana miRNA isolation kit, Life Technologies) and transferred into 1.5 ml reaction tube. 50 μl of homogenate additive (mirVana miRNA isolation kit, Life Technologies) was added to the lysates, resuspended and incubated for 10 minutes on ice. 500 μl of acid-phenol-chloroform was added, vortexed for approximately 30 seconds and incubated for 2 minutes on ice. After centrifugation for 5 minutes at room temperature at 14.000 g, the aqueous and organic phases are separated. The upper aqueous phase was transferred to a new snap cap and combined and inverted with the equal amount of Isopropanol. After incubation for 10 minutes at room temperature the samples were centrifuged at 4° C. and 14.000 g for 30 minutes. Subsequently the supernatant was removed and the RNA pellet was washed with 1 ml 75% ethanol. The samples were briefly centrifuged at 7500 g for 5 minutes at 4° C. After removing the supernatant, the air dried pellet was solved in 20 μl nuclease-free water and incubated for 10 minutes at 55° C. and 500 rpm in a thermomixer. Subsequently the RNA concentrations were measured via spectrophotometral measurement. To avoid amplification of ruts of DNA, a DNAse digestion was performed. Thereby the Deoxyribonuclease I, Amplification Grade-Kit by Invitrogen by life technologies was used. To 1 μg RNA, 1 μl 10×DNAse I Reaction buffer and 1 μl DNAse I are added and filled with DEPC-treated water to an end volume of 10 μl and incubated for exactly 15 minutes at room temperature. By adding 1 μl of 25 mM EDTA solution, the DNase I is inactivated and thereby the process of DNAse digestion is stopped. The samples were incubated for 10 minutes at 65° C. and were then used for reverse transcription.

Reverse Transcription

To rewrite RNA to cDNA the High capacity cDNA Reverse Transcription Kit (Thermo Scientific) was used. 2 μg RNA of the DNA digested samples were added to Mastermix containing transcription buffer, 100 mM dNTPs and RNAse inhibitor in PCR soft tubes. Thereby it had to be considered, that the RNA transcribed via the E2-early and E2-late promoter could not be rewritten by random primers, usually used for reverse transcription, because these random primers would bind to both strands of the double-stranded adenoviral genome. Therefor, the rewriting from RNA to cDNA for the samples used for the E2-early and E2-late quantification was performed by using the specific E2-early reverse primer (Table 1). For the housekeeping gene actin, that was used to normalize the results, the random primer was used.

DNA-Replication Analysis

To investigate viral replication within infected cells DNA-replication analysis was performed. 125.000 cells were seeded in 6-well plates and infected with 10-20 MOI. After 2 respectively 8, 12, 24, 36 and 48 hours post infection, lyzation took place. Thereby, the medium was removed and the adherent cells were washed with 1 ml PBS. After adding 200 μl DNA-lysis buffer, the adherent cells were detached from the plate using a cell scraper. The lysate was then transferred into a snap cap. 3 μl of the enzyme proteinase K was added and incubated at the 56° C. and 550 rpm at a thermomixer overnight. On the following day, DNA isolation was performed.

DNA Isolation

For purification of DNA, 200 μl phenol-chloroform-isoamylalcohol was added to the lysate. After vortexing and subsequent incubation for 5 minutes on ice, a phase separation was achieved by centrifugation for 3 minutes at 16430 g at 4° C. The upper aqueous phase was transferred to a new snap cap, containing 200 μl chloroform and 20 μl cresol red in 10 mM TrisCl for a better visualization of the phases. After vortexing and incubation for 5 minutes for 5 minutes on ice, centrifugation for 3 minutes at 16430 g at 4° C. took place. Again, the upper aqueous phase was combined with 800 μl ethanol and 50 μl 3M sodium acetate solution. 2 μl Glycogen was added, to achieve a better precipitation. After short inversion of the tube, the solution was centrifuged for 30 minutes at 16430 g at 4° C. Subsequently, the DNA pellet was covered by 400 μl 70% ethanol and incubated for 10 minutes at room temperature. After centrifugation for 7 minutes at 4760 g at room temperature, the DNA pellets were dried for about 5-10 minutes at 37° C. Subsequently, the pellets were dissolved in 100 μl 0,1×TE-buffer and shaken at 40° C. at 400 rpm for approximately 3 hours.

When the DNA was completely dissolved, the DNA concentration was measured by means of a spectrophotometer using 2 μl of DNA solution for the measurement and 0,1×TE-buffer as a blank solution. The DNA was then stored at 4° C.

qPCR

For further quantification real time quantitative PCR were used. 5 μl of Template DNA respectively cDNA was used in a final concentration of 10 ng/1. qPCR was performed using 10 μl Mastermix GoTaq qPCR (Promega Corporation) (7,5 μl Mastermix, 1,5 μl primer, 1 μl H2O) and 5 μl DNA template in a 96-well plate pipetted as duplicates. Relative quantification was performed using the comparative CT method with two normalizer genes. The plate was closed via a foil and centrifuged at room temperature for 2 minutes at 220 g. Then the plate was incubated following a certain temperature-time-program in the thermal cycler. Primer used are listed in table 1. Reactions were carried out on a CFX96 Real-Time PCR detection system (Bio-Rad Laboratories).

qPCR Cycling Conditions

Fiber: 94° C. for 2 minutes, 94° C. for 15 seconds, 60° C. for 15 seconds and 72° C. for 15 seconds, for 45 cycles Other viral genes: 94° C. for 1.5 minutes, 94° C. for 15 seconds, 58° C. for 15 seconds and 72° C. for 15 seconds, for 45 cycles Rb: 94° C. for 2 minutes, 94° C. for 15 seconds, 60° C. for 30 seconds and 72° C. for 1 minute, for 44 cycles E2F1s: 95° C. for 2 minutes, 95° C. for 15 seconds, 60° C. for 30 seconds and 72° C. for 30 seconds, for 40 cycles Protein Isolation Cells were lysed using an 1% SDS buffer, to achieve the disruption of the nuclear membrane. To avoid denaturation of the proteins, the whole process was performed on ice. After suctioning the medium, the cells were washed twice with cold PBS. The adherent cells of one well of a duplicate approach was lysed with 200 μl of 1% SDS buffer and scraped by means of a cell scraper. The lysate was then transferred to the other well of the duplicate approach and again scraped. The lysate of both wells combined, was then transferred in a snap cap tube. Subsequently the lysates were treated with a syringe, to destroy the viscous DNA and centrifuged for 30 minutes at 4° C. with 31000 rpm. Because the proteins are present in the supernatant, the supernatant was transferred into a new snap cap tube and used for further steps.

Protein Quantification

To quantify the amount of protein, the bicinchoninic acid (BCA) assay by means of the Pierce™ BCA Protein Kit was performed. Thereby 112,5 μl of the BCA solution A+B (50:1) and 12,5 μl of the sample were added into one well of a 96-well plate and incubated for 30 minutes at 37° C. Dependent on the protein concentration, a staining of the solution resulted. By means of a standard series with known protein concentrations, the protein concentrations of the samples were determined by photometric measurement at 562 nm in the microplate reader.

SDS Gel Electrophoresis

To separate the proteins in subsequent sodium dodecyl sulfate polyacrylamide gel electrophoresis, the calculated amounts of lysate and lysis buffer were mixed with 15 μl loading buffer-DDT-Mixture (6:1). The protein loading substances were then cooked for five minutes at 100° C. 5 μl of the color protein standard and 40 μl of the samples were then loaded onto the gel. For protein separation with detection of viral proteins a 10% gel was used. To study the downregulated genes via siRNA, 12% gels were used. The composition of the resolving and stacking gels are listed in section Buffers and solutions. For approximately 20 minutes the gel was running in TGS-Buffer at 90 V to concentrate all proteins in one band. Subsequently the gels run for approximately 60 minutes at 150 V in TGS-Buffer, to separate the proteins by size.

Western Blot

To transfer the proteins from the gel onto a membrane it was blotted using the western blot technique. To activate the hydrophobic PVDF-membrane, it was incubated for about 2 minutes in methanol. Subsequently, the membrane together with the sponges, filter papers and the gel were deposit in blotting buffer. By means of electrophoresis for approximately two hours at 100V at 4° C., the proteins were transferred on the membrane in blotting buffer. To avoid unspecific antibody binding, the membrane was blocked rotating for one hour at room temperature in 10 ml 5% milk powder in TBST for analyzing cellular proteins respectively in 5 ml 5% BSA-TBST for the subsequent use of antibodies detecting viral proteins. After washing the membrane five times in TBST for five minutes each, the membrane was incubated with the primary antibody solution at 4° C. rotating overnight. For the antibodies GAPDH, E1A, E1B55K, E2A and E4orf6 this step was performed for one hour at room temperature. The antibodies were thereby diluted with different factors in 5% BSA in TBST with 0.02% sodium azide. After additional five washing steps, the membrane was incubated rotating for 30 Minutes at room temperature in a 1:10.000 dilution of the secondary antibody. The secondary antibody (anti-mouse) for the viral antibodies were diluted in 5% BSA-TBST, all others in 5% milk powder in TBST. Those secondary antibodies are conjugated with a horse-radish peroxidase. After five final washing steps, the membrane was incubated five minutes in Enhanced-Chemi-Luminescence (ECL) solution to visualizing the signal of the peroxidase. For the membranes, incubated with the primary antibodies DP-1 and E2F1 the Amersham ECL Prime Western Blotting Detection Reagent by GE-Healthcare was used to achieve brighter signals, for all others, ECL solutions produced in the lab were used. The composition of ECL A and ECL B, that are mixed shortly before usage 1:1 are listed in section Buffers and solutions. Finally, the proteins could be detected by means of developing the signal on a film.

Antibodies:

Checkpoint kinase 1 (sc-377231, Santa Cruz Biotechnology)

total RB (554136, BD Biosciences)

phospho RB Ser 780 (8180, Cell Signaling Technology)

E2F1 (sc-251, Santa Cruz Biotechnology)

E2F2 (ab138515, abcam)

E2F3 (PG37, Thermo FisherScientific)

E2F4 (WUF10, Thermo Fisher Scientific)

E2F5 (sc-999, Santa Cruz Biotechnology)

cyclin D1 (92G2, Cell Signaling Technology)

cyclin E2 (4132, Cell Signaling Technology)

CDK2 (78B2, Cell Signaling Technology)

GAPDH (14C10, Cell Signaling Technology)

actin (A2066, Sigma-Aldrich Chemie GmbH)

E1A (sc-25, Santa Cruz Biotechnology)

E1B55k (kindly provided by M. Dobbelstein)

E4orf6 (kindly provided by M. Dobbelstein

E2A (DBP, kindly provided by M. Dobbelstein)

Hexon (ABIN2686029, Antibodies online)

Small Molecule Inhibitor Treatment

PD-0332991 isethionate (Palbociclib, Sigma-Aldrich Chemie GmbH) and LY-2835219 (Abemaciclib, Selleck Chemicals) were dissolved in sterile water as 10 mM stock solution. LEE011 (Ribociclib, MedChem Express) and Nutlin-3a (Sigma) was dissolved in DMSO as 10 mM and 5 μM stock solution, respectively. Working concentrations were prepared freshly for immediate use.

Virus Infection and Combination Treatment

For determination of virus induced cell killing, cells were seeded in 12-well plates. For combination treatment with PD-033299, LY-2835219, and LEE011, cells were pretreated with the inhibitors for 24 h. Cells were infected with the indicated viruses at indicated MOI in 200-400 μl medium without FBS. At 1 hpi, complete medium with or without small molecule inhibitors was added to the cells.

Cell Viability (SRB Assay)

Cells were fixed with 10% TCA for 1 h at 4° C. and stained with 0.5% sulforhodamine B (SRB, Sigma-Aldrich Chemie GmbH) in 1% acetic acid for 30 min at RT, followed by washing with 1% acetic acid to remove excess of SRB. Dried SRB was dissolved in 10 mM Tris buffer and quantification was performed by photometric measurement at 590 nm.

Titer Test

For determination of infectious viral particle production, infected cells and supernatant were harvested three dpi using cell scrapers. Virus was released from intact cells by multiple cycles of freeze-thaw followed by centrifugation at 1600 rcf. Supernatants of the cell lysates were tested for viral particle production using Hek293 cells as described in AdEasy Viral Titer Kit instruction manual (972500). The following reagents were used: goat-anti-hexon antibody (1056, Chemicon), rabbit-anti-goat antibody (P0449, Dako), DAB solution (Dako).

Example 2: Effect of CDK4/6 Inhibitor PD0332991 on Replication of an E1-Minus Adenovirus It was shown that E1-deleted adenovirus replicates in cancer cells although with very low efficacy. T24 cells were infected with 100 MOI of an E1-minus adenovirus expressing green fluorescent protein (Ad-GFP), and treated with 500 nM PD0332991 one day before infection and during incubation time. Under such conditions, an increase in GFP expression was observed, thus indicating E1A-independent viral replication and gene expression mediated by the activation of the adenovirus E2-early promoter.

EXAMPLE 3: COMBINED USE OF WILD TYPE ADENOVIRUS OR XVIR-N-31 TOGETHER WITH DIFFERENT CDK4/6 INHIBITORS

Based upon results using the E2-early mutated adenovirus Ad-WT/E2M and Ad-GFP in combination with PD0332991, experiments were performed using different CDK4/6 inhibitors in combination with either wild type adenovirus Ad-WT or XVir-N-31. Since these agents arrest cells in phase G1, it was surprising to find that all inhibitors were able to support viral replication.

It was further examined if treatment of cells with the three clinically advanced CDK4/6 inhibitors PD-033299, LY-2835219 and LEE011 could influence the effects upon infection on cell viability, viral replication and viral titer production.

Upon treatment, all three inhibitors display similar effects on the expression and phosphorylation level of RB which has been described in numerous publications before. After an almost complete dephosphorylation and also downregulation of total protein at 24 hours, the phosphorylation level recovers partially over time. CDK2 level were upregulated upon treatment and cyclin D2 as well as cyclin E2 level were downregulated.

EXAMPLE 4: SYNERGISTIC EFFECTS ARISING FROM THE COMBINATION OF CDK4/6 INHIBITORS AND ONCOLYTIC ADENOVIRUSES

CDK4/6 inhibitors PD-033299, LY-2835219 and LEE011 were combined with the infection of cells with adenovirus. Infection of cells has been done 24 hours after treatment because downstream effects on target molecules can only be detected between 8 and 24 hours after treatment.

Figure 1:
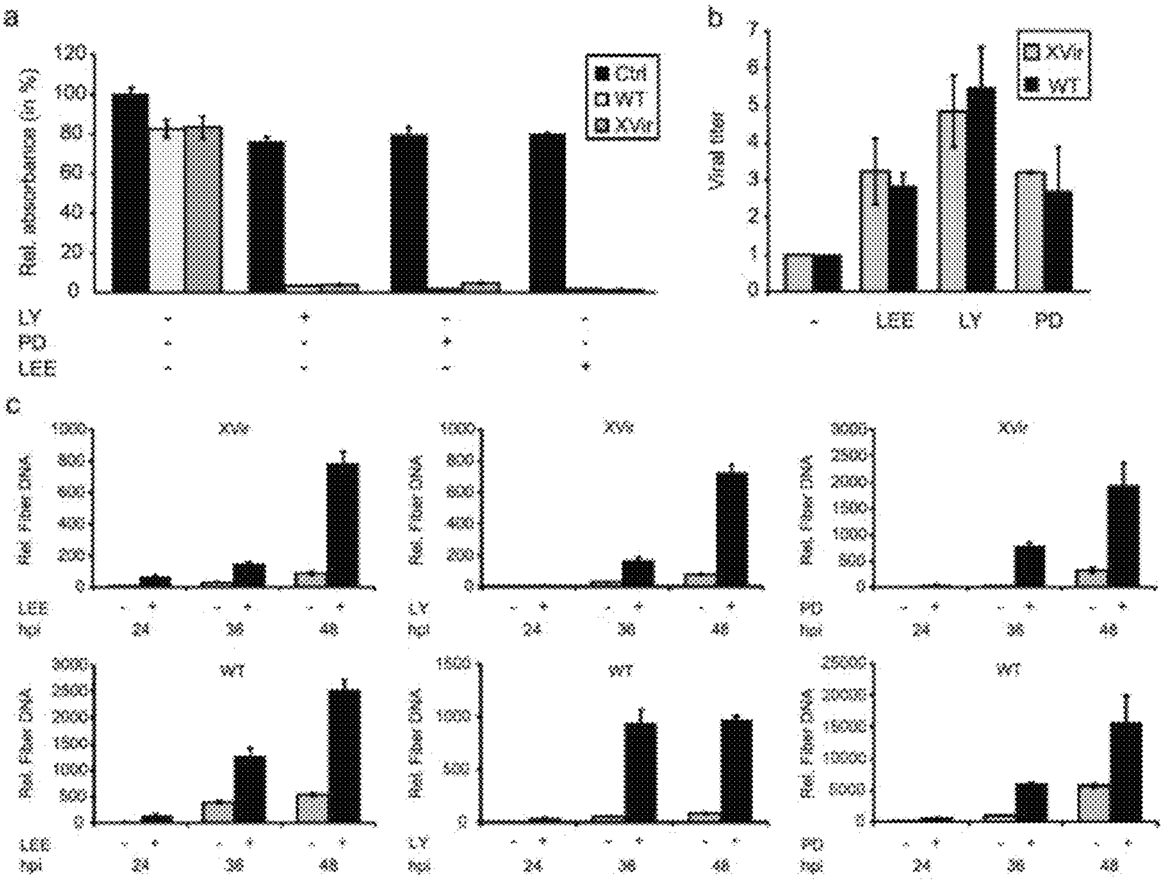

The results are shown in FIG. 1.

CDK4/6 inhibitors induced synergistic effects on cell viability, viral replication and viral titer. (a) Cells were pretreated with the three CDK4/6 inhibitors PD-033299, LY-2835219 and LEE011 for 24 hours and infected with XVir-N-31 (Moi 60) or wild type adenovirus (Moi 80). Four days past infection, cell viability was measured by an SRB assay. Graphs show averages of a minimum of three independent experiments. (b) Three days past infection, lysates were prepared from the cells and a titer test was performed on HEK293 cells. The virus titer is shown as fold change relative to control. (c) DNA was extracted from infected cells at 4, 24, 36 and 48 hpi and analysed for viral replication by using a qPCR for fiber cDNA. Values are normalized to GAPDH at 4 hpi. Graphs show representatives of at least two independent experiments. Error bars represent the standard error.

As evident from FIG. 1, all three CDK4/6 inhibitors dramatically supported cell lysis (FIG. 1*a*), the replication within cells (FIG. 18) and the formation of viral particles (FIG. 1*b*).

EXAMPLE 5: EFFECT OF CDK4/6 INHIBITOR PALBOCICLIB (PD-033299) ON THE EXPRESSION LEVEL OF SELECTED VIRAL PROTEINS

Figure 2:
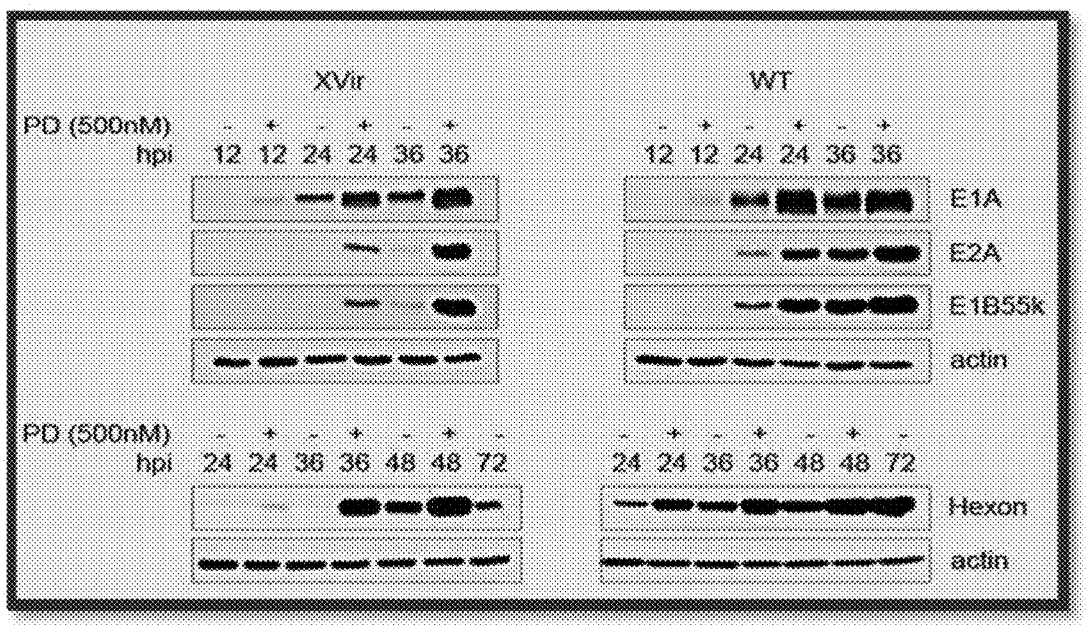

In order to analyze these effects in greater detail, expression level of selected viral proteins was determined in treated or non-treated cells. For this experiment inhibitor palbociclib (PD-033299) was used as a representative CDK4/6 inhibitor. Cells were infected with a MOI of 15. PD treatment with 500 nM took place 24 hours infection and until protein isolation took place. After 12, 24 and 36 hours protein isolation took place using 1% SDS-buffer occurred. Actin was included as a positive control. Since the loading control shows same protein levels of cellular actin in all lines, a proper comparison between the lines is ensured. hpi: hours post infection The results are indicated in FIG. 2 showing results of viral protein expression of Ad-WT and XVir-N-31 infected T24 cells in combination with the CDK4/6 inhibitor PD0332991 (PD). The viral proteins investigated in this experiment (E1A, E1B-55k, DBP (E2A) and Hexon) were all expressed at higher level in cells treated with the CDK4/6 inhibitor PD-0332991 compared to the adenovirus wild type virus. This effect could be observed as early as 12 hpi for E1A and 24 hpi for the other proteins.

EXAMPLE 6: SPECIFICITY OF EFFECTS MEDIATED BY CDK4/6 INHIBITORS

The class of CDK4/6 inhibitors as subject to Example 5 requires expression of RB. Therefor, three RB positive and two RB negative bladder cancer derived cell lines were used and the cells treated with the combination therapy. Cell lines were pretreated for 24 hours with an IC50 concentration of PD-0332991 (T24: 500 nM, RT112: 2000 nM, 253J: 100 nM) and infected with XVir-N-31(T24 MOI50, 253J MOI 25, RT 112 MOI450). Values are the average of at least 2 independent experiments. Error bars show the standard error. Four dpi, cell viability was measured using SRB assays (a, c). (b, d) Lysates of cells were prepared 3 dpi and a titer test was performed on Hek293 cells. Viral titer is shown as fold change relative to control The results are shown in FIG. 3.

Figure 3:
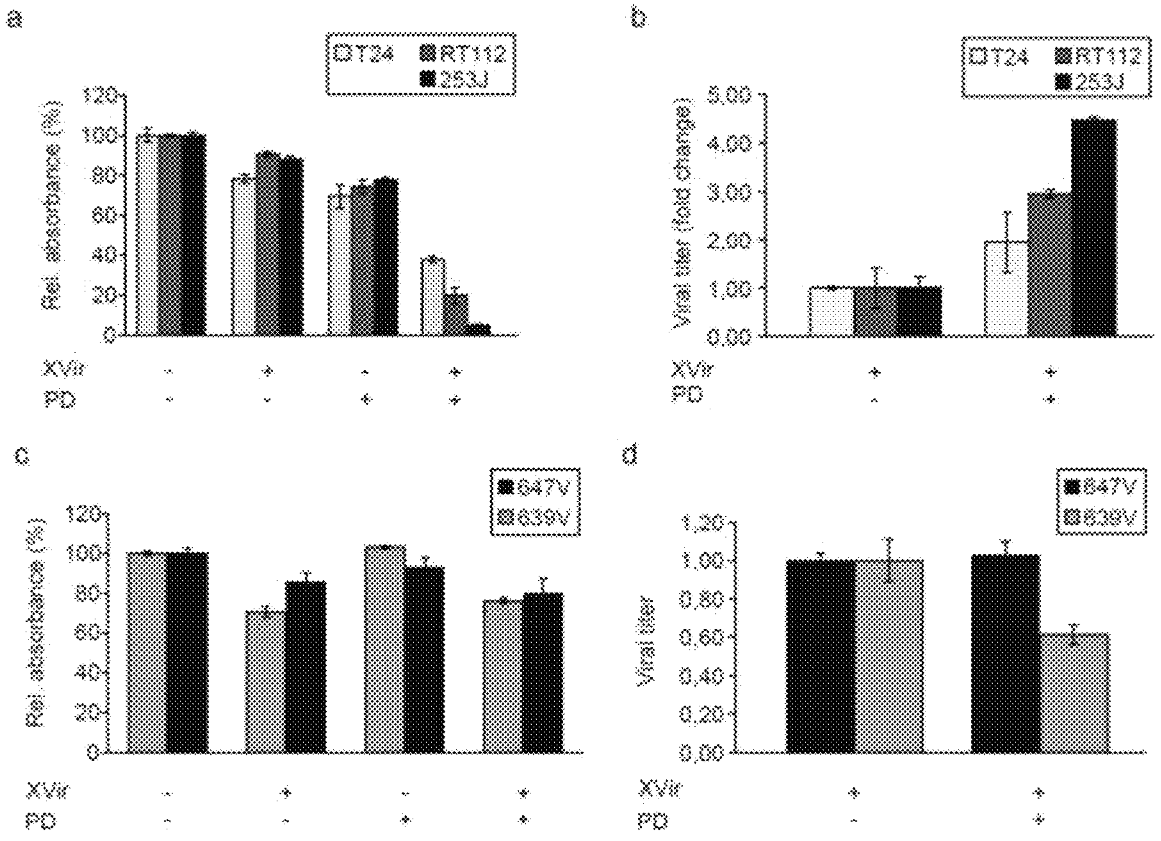

As evident from FIG. 3, only cell lines positive for RB showed a significant decrease in cell growth and cell viability, respectively (FIG. 3 *a, c*). Also, viral particle formation was only increased in RB positive cell lines upon PD-0332991 treatment (FIG. 3 *b, d*).

EXAMPLE 7: EFFECT OF COMBINATION TREATMENT OF CDK4/6 INHIBITOR PD-0332991 WITH XVIR-N-31

In order to investigate the effect of PD-0332991 on viral replication in the RB positive cell lines, a relative quantification of Fiber DNA copies was performed using qPCR. Bladder cancer cell lines were pretreated for 24 hours and infected with XVir-N-31 (T24 MOI 40, UMUC3 and 253J MOI 20, RT112 MOI 400). DNA was extracted 24-48 hpi and analysed for viral fiber using qPCR. Values are normalized to GAPDH. Data are representatives of at least two independent experiments; Error bars S.D.

Figure 4:
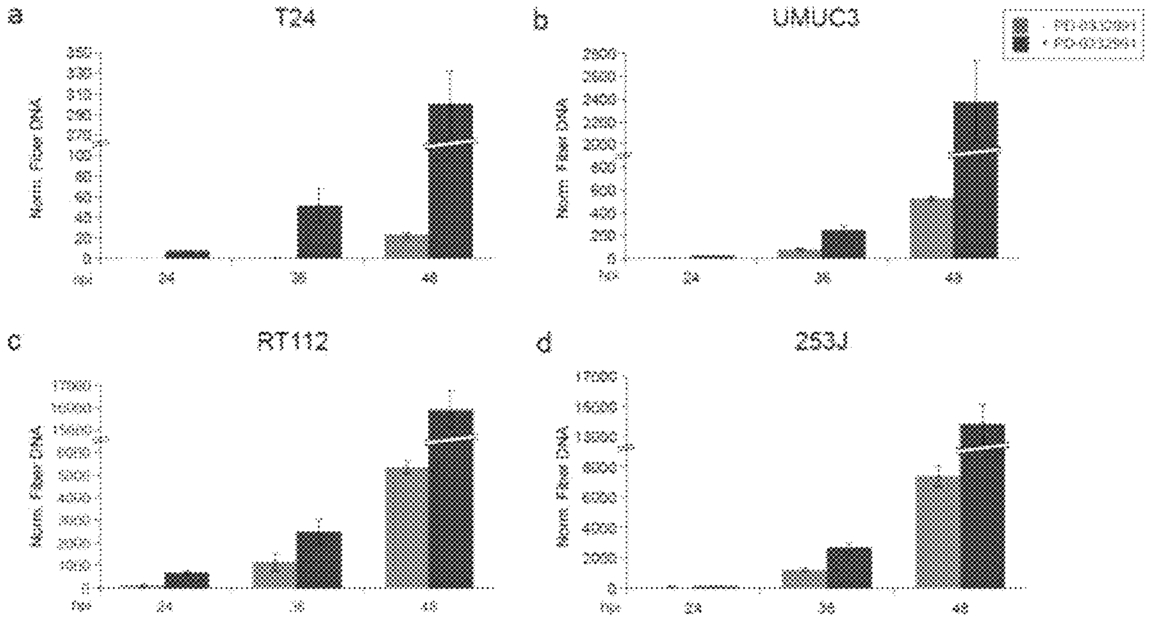

The results are shown in FIG. 4.

As may be taken form FIG. 4, combination treatment of CDK4/6 inhibitor PD-0332991 with XVir-N-31 increases viral replication dramatically.

EXAMPLE 8: TIME KINETICS OF CDK4/6 INHIBITORS

Time kinetics of CDK4/6 inhibitors on the dephosphorylation and degradation of RB are around 10 hours after treatment of cells. Also, the results presented above showed partial recovery of RB downstream targets over time (FIG. 1). This observation implies that time kinetics of the CDK4/6 inhibitor and the effect on viral induced cell death is an important parameter for this combination therapy as exemplified in Example 7. For application of the combination therapy, different time points for pretreatment of cells were tested. In accordance therewith, cells were treated either before (day/hour ante infection, dai/hai) or 1 hour post infection and cell growth was measured using an SRB assay. Error bars represent S.E. and the values are the average of three independent experiments The results are shown in FIG. 5

Figure 5:
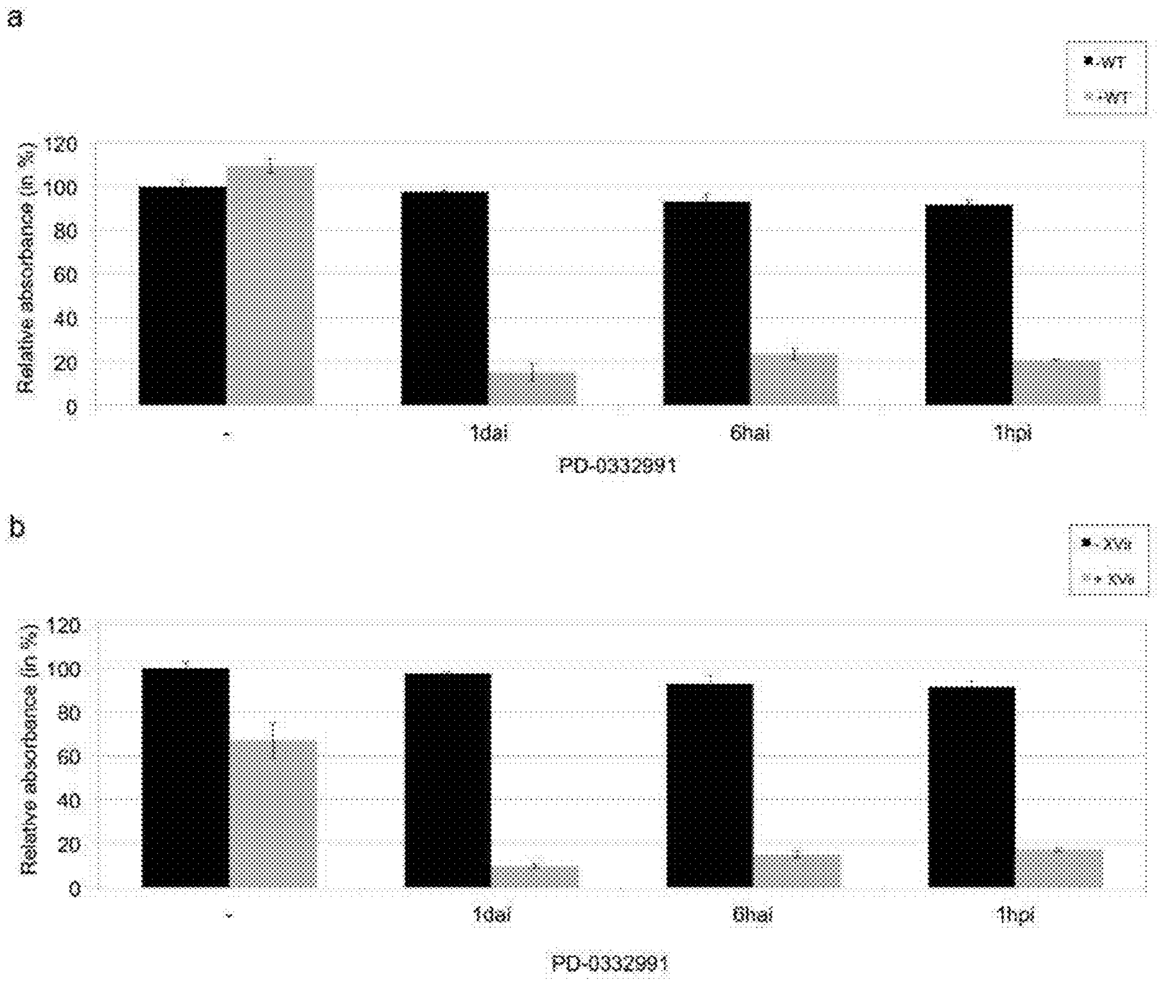
FIG. 5 are bar diagrams.

As evident from FIG. 5, parallel treatment already was sufficient for increase in cell death.

EXAMPLE 9: COMBINATION TREATMENT OF DIFFERENT ADENOVIRUSES WITH CDK4/6 INHIBITOR PD0332991

This example was performed so as to provide experimental evidence that different oncolytic adenoviruses may be used together with CDK4/6 inhibitors such as PD0332991 for cell killing, and that the observed increase in viral replication and cell killing was not restricted to XVir-N-31. In accordance therewith, T24 cancer cells with Ad-Delta24 and Onyx-015 as follows: T24 bladder cancer cells were infected with 20 MOI of the indicated oncolytic adenoviruses. Treatment with 500 nM CDK4/6 inhibitor PD0332991 took place one day before infection and for 4 days post infection. Pictures were taken 4 days post infection. The occurrence of cytopathic effect (CPE) indicates viral replication and cell killing.

Figure 6:
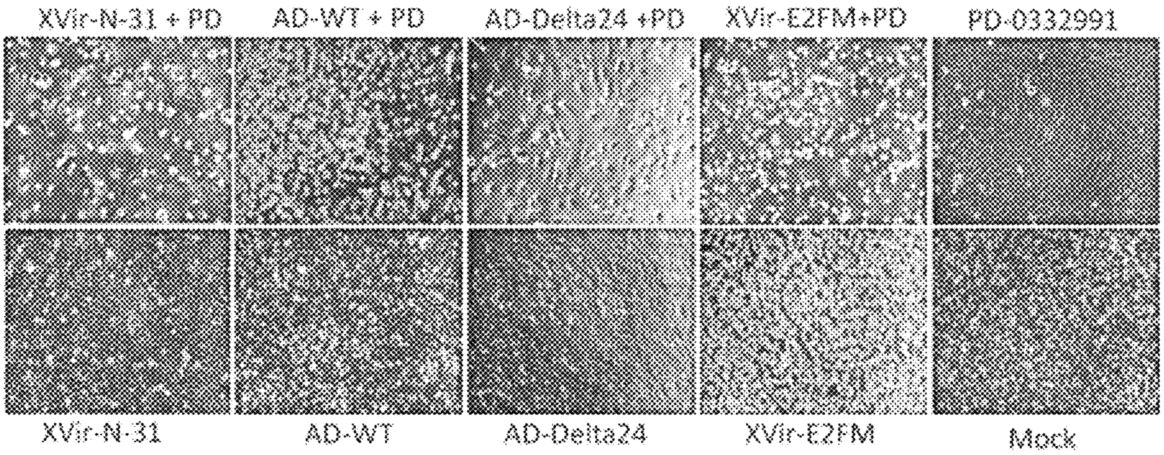
FIG. 6 is a series of microphotographs.

The results are shown in FIG. 6.

As may be taken from FIG. 6, CDK4/6 inhibitor PD0332991 as a representative example of CDK4/6 inhibitors reducing RB phosphorylation, increased cell killing when combined with other oncolytic adenoviruses such as Ad-Delta24 and Onyx-015.

EXAMPLE 10: INFECTION OF T24 CELLS WITH THE RECOMBINANT E1-DELETED ADENOVIRUS EXPRESSING GFP (AD-MINUS/GFP) IN COMBINATION WITH PALBOCICLIB CAUSES INCREASE GFP EXPRESSION 100.000 T24 cells/well were seeded in 6-well plates and grown in RPMI Medium containing 10% FCS at 5% $CO_2$ at 37° C. T24 cells were treated with 500 nM Palbociclib 24 hours before and again 1 hour post infection. Infection of the E1-deleted adenovirus expressing GFP (Ad-minus/GFP) took place in 400 μl Medium without serum. Pictures were taken 48 hours post infection using a fluorescence microscope with 10× magnification.

Figure 7:
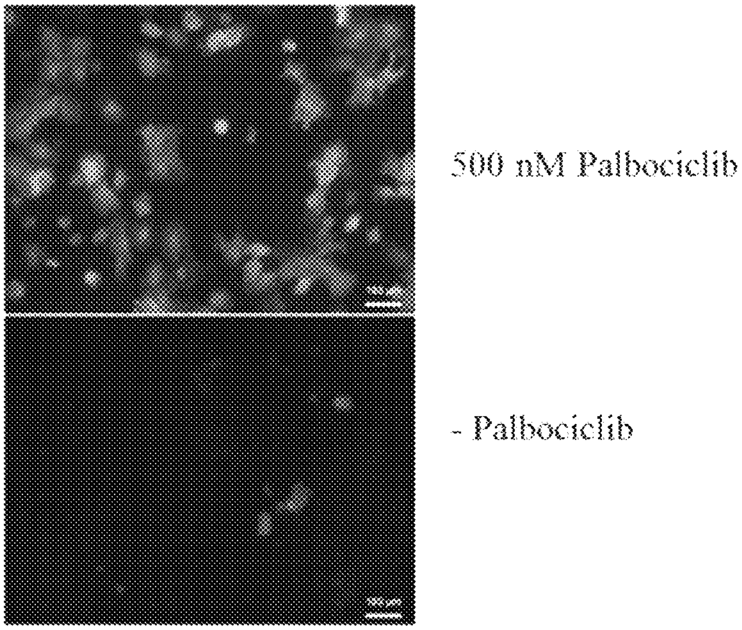
FIG. 7 is a fluorescence microscopic image of T24 cells infected with an E1-deleted Adenovirus expressing GFP with and without Palbociclib treatment.

The result of fluorescence microscopic analysis of GFP expression with and without Palbociclib treatment is shown in FIG. 7.

The result shows that treatment of T24 cells with Palbociclib caused a strong increase of GFP expression which is mediated by viral DNA replication induced by Palbociclib.

EXAMPLE 11: E1A-INDEPENDENT VIRAL REPLICATION IN UMUC CELLS TREATED WITH VARIOUS CELL CYCLE INHIBITORS

To investigate the differences in replication of dl703 (Mantwill et al. 2013, Journal of Translational Medicine, 11, 216) under different treatment conditions, DNA-replication analysis was performed. 100.000 UMUC cells were seeded in 6-well plates and grown in DMEM medium containing 10% FCS in 5% $CO_2$ conditions at 37° C. 24 hours post seeding cells were treated for 24 hours with 10 μM Lee (Ribociclib), 1 μM CI-1040, 10 μM Nutlin-3a and 10 μM Roscovertine and again after infection adding an appropriate amount of inhibitors to the medium. Infection with 50 MOI dl703 (Mastadenovirus, Type C, Serotype 5 with a 3.2 kb sized deletion in E1 region) took place 24 hours post treatment. After 4 and 48 hours post infection DNA were isolated and qPCR was performed using specific primers for the viral fiber gene. Fiber fwd. 5'-AAGCTAGCCCTGCAAACATCA-3' (SEQ ID NO: 17); Fiber rev. 5'-CCCAAGCTACCAGTGGCAGTA-3' (SEQ ID NO: 18).

Figure 8:
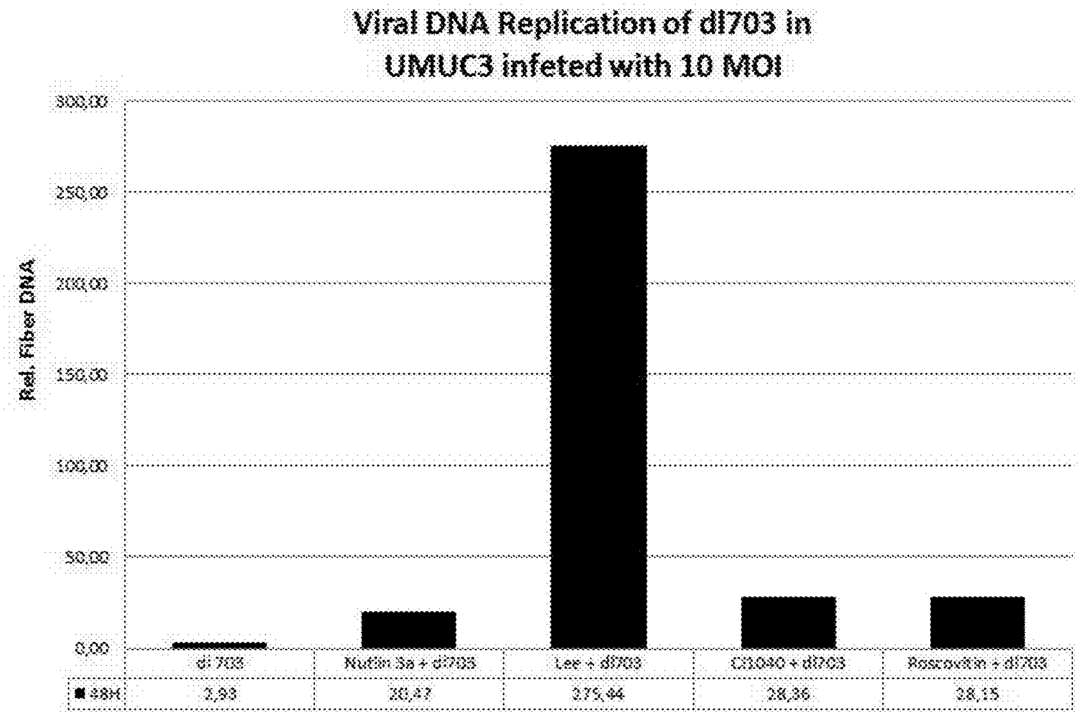
FIG. 8 is a bar diagram showing viral DNA replication of Adenovirus dl703 after 48 h using compounds Nutlin 3a, Lee, Cl1040 and Roscovertine.

The result is shown in FIG. 8.

As evident from FIG. 8, treatment of UMUC cells with the CDK 4/6 inhibitor LEE011 (Ribociclib) caused a dramatic increase of viral DNA replication of the E1-minus adenovirus dl703 (nearly 100-fold). This increase strongly suggests that the specific induced G1-arrest by Ribociclib in conjunction with the inhibition of E2F1 expression facilitates E1-independent adenoviral replication. In consequence, not only viruses with specific deletions in the E1A gene show enhanced adenovirus DNA replication under CDK 4/6 treatment, but even adenoviruses with complete deletion of the E1A gene show an increase in viral DNA replication.

Although the Mek-Inhibitor GI-1040 showed similar properties regarding inhibition of E2F1 expression and G1-arrest, the replication was much lower compared to Ribociclib treated cells. This might be due to the fact that simultaneously other important cell cycle related pathways are inhibited such as MEK/ERK which is necessary for viral replication. In addition, it was shown that inhibition of the MEK/ERK-Pathway reduced particle formation more than 100-fold making it unsuitable, in a clinical setting, for combination therapy with oncolytic adenovirus replication (Schnmann and Doppelstein 2016, Cancer Research, 66, 1282-1288).

EXAMPLE 12: WESTERN BLOT ANALYSIS OF UMUC CELLS TREATED WITH INDICATED CELL CYCLES INHIBITORS

Western Blot analysis of UMUC cells treated with indicated concentrations of CI-1040, Roscovitine, Nutlin-3a and LEE011 (Ribociclib). 1×106 cells were seeded in 10 cm dishes. 24 hours post-treatment proteins were isolated using 1% SDS buffer, to achieve the disruption of the nuclear membrane. All samples were drawn up several times into a syringe to disrupt the DNA and subsequently centrifuged at 30000 rpm at 4° C. for 30 minutes. The supernatant was transferred to a new reaction tube and directly used for further steps or stored at −80° C. To separate the proteins a sodium dodecyl sulfate polyacrylamide gel electrophoresis was performed. By means of electrophoresis for approximately two hours at 100V at 4° C., 40 µg of total proteins were loaded and probed against specific indicated antibodies.

The results are shown in FIGS. 9A, 9B and 9C.

As evident from FIG. 9, whereas Roscovitine and Nutlin-3a had no pronounced effect on Rb, phRB and E2F1 expression, LEE-011 (Ribociclib) at 10 µM and MI-1040 at 1 µM induced inhibition of E2F1 as well as Rb and phRb expression.

EXAMPLE 13: ANALYSIS OF CDK 4/6 INHIBITORS ON VIRAL DNA REPLICATION OF THE E1-DELETED REPLICATION DEFECTIVE ADENOVIRUS dl703

For cell cycle analysis cells were seeded in 6 well plates (2,5×10E4 c/well). 8 hours before infection with dl703, cells were treated with indicated concentration of cell cycle inhibitors. After infection with 10 MOI dl703 cells were again treated for 48 hours. Untreated cells and dl703 infected cells only, served as control. 48 h post infection cells were harvest by trypsinization and fixed with 80% ethanol while vortexing. To investigate the cell cycle status, fixed cells were centrifuged 5 min at RT and 300 g and ethanol was aspirated. Cells were resuspended and washed with 1% BSA-PBS (Bovine Serum Albumin) and again centrifuged. Cells were stained with EDU and cell cycle analysis were performed using the Click-iT™ Plus EdU Flow Cytometry Assay Kits, Catalog nos. C10632 from Thermo Fischer. In addition, after 3× times washing with 1% BSA/PBS cells were stained with PI (Propidium Iodine, 50 µg/ml). Measurement was directly performed after staining with a FACScalibur Flow Cytometry System. Data was analyzed with FlowJo software.

Characteristics of the CDK4/6 Inhibitors

CI1040: The dual specific threonine/tyrosine kinase, map kinase kinase (MEK), is a key component of the RAS/RAF/MEK/ERK signaling pathway that is frequently activated in human tumors. CI-1040 is a benzhydroxamate compound that potently inhibits MEK (Allen et al. 2003, Semin Oncol. (5 Suppl 16):105-16) and causes G1 arrest.

Nutlin-3a: Nutlin-3, a small-molecule antagonist of MDM2, effectively restores p53 function in both normal MDM2 expression and MDM2 overexpression cell lines with wild-type p53, leading to cell cycle arrest and apoptosis (Wang et al 2012, Acta Biochimica et Biophysica *Sinica*, Volume 44, Issue 8, 1 Aug. 2012, Pages 685-691).

Roscovitine (Seliciclib or CYC202) is an experimental drug candidate in the family of pharmacological cyclin-dependent kinase (CDK) inhibitors that preferentially inhibit multiple enzyme targets including CDK2, CDK7 and CDK9, which alter the growth phase or state within the cell cycle of treated cells (Whitaker et al. 2004, Cancer Research 64, 262-272).

LEE011 (Ribociclib; trade name Kisqali]) is an inhibitor of cyclin D1/CDK4 and CDK6, and is used for the treatment of certain kinds of breast cancer. The inhibition of CDK 4/6 causes G1 cell cycle arrest and inhibition of E2F1 expression (Kim S. et al, Oncotarget. 2018 Oct. 16; 9(81):35226-35240; Yang C et al., Oncogene (2017)36, 2255-2264).

The results are shown in FIG. 10.

The CDK 4/6 inhibitors LEE011 (Ribociclib) and CI-1040 induced a clear G1-arrest. Treatment with Roscovitine showed a slight increase of G2/m arrested cells. Nutlin-3a had only little or no effect on the cell cycle in the used concentration. Infection of UMUC cells with the recombinant E1-deleted (having no E1A protein) adenovirus dl703 did not change the cell cycle distribution significantly.

EXAMPLE 14: PALBOCICLIB INCREASED ADENOVIRUS HEXON STAINING IN VITRO POST TREATMENT

Bladder cell lines RT112, T24 and UMUC were seeded in 6-well plates (2×105 cells/well). One day post seeding cells were treated with 500 nM Palbociclib for 24 hours before and again 1 hour post infection. Infection with indicated MOIs of AD-WT took place in 400 µl DMEM-Medium without serum. Hexon staining was performed according manufacturer instructions using Adeasy Viral Titer Kit from Agilent (cat: 972500) two days post infection.

The result is shown in FIG. 11.

As evident from FIG. 11, treatment of Palbociclib (500 nM) as an exemplary CDK4/6 inhibitor increased hexon positive cells significantly in Palbociclib treated cells 48 hours post infection as indicated by the brown/red colour. The conclusion must be reached, that more cells under Palbociclib treatment are capable to produce viral particles and show increase viral DNA replication, since adenovirus hexon expression occurs exclusive onset of viral replication.

From the results subject to Examples 10 to 14, it is evident that only CDK4/6 inhibitors, but no other cell cycle inhibitors were capable of increasing replication and gene expression of replication defective adenovirus (dl703 lacking the E1 genes) and Ad-GFP. Furthermore, a CDK4/6 inhibitor in order to provide such increased viral replication and gene expression must cause G1 arrest of (infected) cells and inhibition of F2F1 expression.

Example 15: Treatment of T24 Cells Using Triple Therapy Comprising XVir-N-31, Palbociclib and a PARP Inhibitor In order to show the efficacy of a triple therapy of T24 cells using triple therapy comprising XVir-N-31, Palbociclib and a PARP inhibitor (BMN673 (Talazolarib)), a potency assay was carried out.

12.500 T24 cells were seeded per well in 12-well plates and grown over-night in RPMI Medium containing 10% FCS at 37° C. Inhibitor-treatment of cells occurred 24 h past cell seeding and again 1 hour after infection by adding indicated concentration to the medium. Infection of cells took place 24 h past inhibitor-treatment in 250 μl medium without serum. Fixation and SRB-staining took place at 4 days post infection. PD, Palbociclib; PARPi: BMN673.

For SRB staining, the medium was removed by aspiration. Cells were fixed with 1 ml (per well) 10% cold TCA at 4° C. for 1 hour. TCA was removed by aspiration and cell layers were washed 4×with tap water. Cells were stained with 1 ml (per well) 0.5% SRB (sulforhodamine B) in 1% acetic acid for 30 min. Unbound SRB was removed in five washing steps with 1 ml 1% acetic acid/well; after each washing step, acetic acid was removed by aspiration. Plates were air-dried for 2 hrs. To solubilize the SRB stained cells, 200 μl of 10 mM Tris base was added to each well. Afterwards 20 μl, respectively, was dispensed into wells of a 96 well plate. The 96 well plate was loaded into an Elisa-plate reader and absorption of the samples was measured at 560 nm. Mock treated cells were set 100% cell survival.

The result is shown in FIG. 12.

The result shown in FIG. 12 clearly demonstrates that the triple therapy consisting of Palbociclib, BMN673 and XVir-N-31 exhibited a superior performance against mono- or combination therapy regarding cell killing. Nearly 90% cell killing could be achieved using 10 MOI of XVir-N-31 in combination with PARP inhibitor PARPi (BMN673) and CDK4/6 inhibitor Palbociclib (PD). The combination of PARPi and Palbociclib without XVir-N-31 killed only 65% of the cells. T24 cells and UMUC cells are sensitive to CDK 4/6-Inhibitors (providing G1 arrest with E2F1 down-regulation).

EXAMPLE 16: KINETICS OF TRIPLE THERAPY COMPRISING XVIR-N-31, PALBOCICLIB AND A PARP INHIBITOR

In order to show the kinetics of a triple therapy of T24 cells using triple therapy comprising XVir-N-31, Palbociclib and a PARP inhibitor (BMN673 (Talazolarib)), a potency assay was carried out and the potency assessed at different points in time.

3000 T24 cells were seeded per well in 12-well plates and grown over-night in RPMI Medium containing 10% FCS at 37° C. Inhibitor-treatment of cells occurred 24 h past cell seeding and again 1 hour after infection by adding indicated concentration to the medium. Infection of cells took place 24 h past inhibitor-treatment in 250 μl Medium without serum. Fixation and SRB-staining took place at 1-5 days post infection (dpi: days post infection). 15 nM PARPi correspond to the IC-80 value in T24 cells.

The results are shown FIG. 13.

As evident from FIG. 13, triple therapy using apart from XVir-N-31 a CDK4/6 inhibitor (Palbociclib (PD) and a PARP inhibitor PARPI (BMN673) is, also from a kinetic point of view, much more effective than a monotherapy using XVir-N-31 only or a combination therapy using XVir-N-31 an either the PARP inhibitor or the CDK4/6 inhibitor. Importantly, the re-growth of tumor cells was significantly reduced at day 4 and 5 in the CDK 4/6 sensitive cell lines UMUC and T24 (dpi: days post infection).

EXAMPLE 17: KINETICS OF TRIPLE THERAPY COMPRISING XVIR-N-31, PALBOCICLIB AND A PARP INHIBITOR

In order to show the kinetics of a triple therapy of UMUC cells using triple therapy comprising XVir-N-31, Palbociclib and a PARP inhibitor (BMN673 (Talazolarib)), a potency assay was carried out and the potency assessed at different points in time.

Seeding of UMUC-3: 3000 cells were seeded per well in 12-well plates and grown over-night in DMEM Medium containing 10% FCS at 37° C. Inhibitor-treatment of cell occurred 24 h past seeding and again 1 hour after infection by adding indicated concentration to the medium. Infection of cells took place 24 h past inhibitor-treatment. Fixation and SRB-staining took place at 1-6 days post infection (dpi: days post infection). 160 nM PARPi correspond to the IC-80 value in UMUC3 cells.

The result is shown in FIG. 14.

The results shown in FIG. 14 clearly demonstrate that the triple therapy consisting of Palbociclib, BMN673 and XVir-N-31 exhibited superior performance against mono- or combination therapy. Importantly, the re-growth of tumor cells was significantly reduced at day 4 and 5 in the CDK 4/6 sensitive cell lines UMUC and T24 (dpi: days post infection).

EXAMPLE 18: TRIPLE THERAPY COMPRISING XVIR-N-31, A CDK4/6 INHIBITOR AND A BROMODOMAIN INHIBITOR

5000 T24 cells were seeded in 12 well plates and grown in 1 ml RPMI-Medium containing 10% FCS. Next day cells were treated with 500 nM Palbociclib and 300 nM JQ-1. 24 hours post treatment cells were infected with indicated MOIs of XVir-N-31 in 200 μl RPMI-Medium containing no FCS. After 1 hour 800 μl RPMI-Medium containing 10% FCS were added into each well. In addition, 500 nM Palbociclib and 300 nM JQ-1 were added to the medium. SRB-Staining took place 5 days post infection. Mock treated cells were set 100% cell survival.

The results are shown in FIG. 15.

As evident from FIG. 15, the bromodomain inhibitor JQ-1 increased the cell killing capacity of XVir-N-31 in combination with the CDK 4/6 inhibitor Palbociclib at low MOIs. Light-microscopic analysis 48 hours post infection reveals already massive cell death in JQ-1/Palbociclib/XVir-N-31 treated cells. The conclusion must be reached that JQ-1 increased viral transcription and thereby viral replication in Palbociclib treated cells, since mono-therapy with 300 nM JQ-1 alone did not increase cell killing of XVir-N-31 at 10 and 20 MOI.

A prerequisite for the observed enhancement of JQ-1 in adenovirus infected cancer cells is the ability of Palbociclib to induce G1-arrest. In cells which are resistant against Palbociclib (see Example 18, identical treatment procedure), no increase of cell killing was observed. This observation was in sharp contrast to Baojie Lv et al 2018, Scientific reports, 8, 11554, where cells where treated with concentrations of JQ-1, causing no G1-arrest and no Palbociclib was used in conjunction.

EXAMPLE 19: TRIPLE THERAPY COMPRISING XVIR-N-31, A CDK4/6 INHIBITOR AND A BROMODOMAIN INHIBITOR 100.000 SK-N-MC cells/well were seeded in 12-well plates and grown in RPMI Medium containing 10% FCS at 5% CO2 at 37° C. Cells were treated with 200 nM Abemaciclib+500 nM JQ-1 24 hours before and again 1 hour post infection by adding appropriate amount to the medium. Infection of XVir-N-31 took place in 500 μl in RPMI Medium without serum. SRB-Staining took place 5 days post infection. Mock treated cells were set 100% cell survival.

The results are shown in FIG. 16.

It is established that SK-N-MC cells are resistant against CDK 4/6 Inhibitors which thus does not cause a G1-arrest. The addition of JQ-1 did not increase cell killing of CDK 4/6 (Abemaciclib) resistant SK-N-MC cells, indicating that the CDK 4/6 mediated G1-arrest is a prerequisite of the JQ-1 mediated effect on cell killing.

Thus, FIG. 16 (as well as FIG. 15) show that bromodomain inhibitors targeting BRD2, BRD3, BRD4 increase the cell killing effect of XVir-N-3 even further under the premise that CDK 4/6 Inhibitors induces a G1-arrest in treated cells.

EXAMPLE 20: WESTERN BLOT ANALYSIS OF SK-N-MC CELLS TREATED WITH CDK 4/6 INHIBITOR LY-2835219 (ABEMACICLIB) AND THE WEE-INHIBITOR MK-1775 (ADAVOSERTIB)

$1\times10^6$ cells were seeded in 10 cm dishes. 24 hours post-treatment proteins were isolated using 1% SDS buffer, to achieve the disruption of the nuclear membrane. All samples were drawn up several times into a syringe to disrupt the DNA and subsequently centrifuged at 30000 rpm at 4° C. for 30 minutes. The supernatant was transferred to a new reaction tube and directly used for further steps or stored at −80° C. To separate the proteins a sodium dodecyl sulfate polyacrylamide gel electrophoresis was performed. By means of electrophoresis for approximately two hours at 100V at 4° C., 40 μg of total proteins were loaded and probed against specific indicated antibodies.

The result is shown in FIG. 17.

It is known that SK-N-MC cells are resistant to Abenaciclib treatment (Dowless M et al., 2018, Clin Cancer Res: 24, 6028-6039). Weel is a critical component of the G2/M cell cycle checkpoint control and mediates cell cycle arrest by regulating the phosphorylation of CDC2. Inhibition of Weel by MK1775 has been reported to enhance the cytotoxic effect of DNA damaging agents in different types of carcinomas. Several studies have demonstrated that pharmacological inhibition of Weel by the small molecule kinase inhibitor MK-1775 leads to removal of CDC2 phosphorylation at Tyr15 in tumor cells (Kreahling et al 2013, PLoS One. 8(3), e 57523). Although a strong G1-arrest is observed in the combination treatment no change in Rb and E2F1 expression is observed.

EXAMPLE 21: TRIPLE THERAPY COMPRISING XVIR-N-31, A CDK4/6 INHIBITOR ABEMACICLIB AND ADAVOSERTIB (WEE-INHIBITOR MK-1775)

100.000 SK-N-MC cells/well were seeded in 12-well plates and grown in RPMI Medium containing 10% FCS at 5% $CO_2$ at 37° C. Cells were treated with 200 nM Abemaciclib 24 hours before and again 1 hour post infection by adding appropriate amount to the medium. Infection of XVir-N-31 took place in 500 μl in RPMI Medium without serum. SRB-Staining took place 5 days post infection. Mock treated cells were set 100% cell survival.

The results are shown in FIG. 18.

FIGS. 17 (and 18) demonstrate that the combination of the CDK 4/6 Inhibitor Abemaciclib and the Wee-Inhibitor MK-1775 induced G1 arrest without inhibition of E2F1. The potency assay in FIG. 18 shows that this combination did not enhance the cell killing effect of the oncolytic adenovirus XVir-N-31. These results clearly demonstrate, that the induced G1-arrest by the combination of the CDK 4/6 Inhibitor Abemaciclib and the Wee-Inhibitor MK-1775 did not facilitate XVir-N-31 cell killing capacity. Thus, the inhibition of E2F1 expression is a further requirement to enhance viral oncolysis.

EXAMPLE 22: G1 ARREST IN COMBINATION WITH E2F1 INHIBITION IS A PREREQUISITE FOR ENHANCED CELL KILLING OF XVIR-N-31 IN COMBINATION WITH CDK 4/6 INHIBITORS 48 hours post treatment cells were washed twice took place with PBS (containing RNase A, 100 U/ml). Cells were trypsinized and centrifuged at 1500 rpm, 4° C. for 5 min. Cells are fixed by adding slowly 1 ml of ice-cold 80% Ethanol drop by drop to the pellet and incubated overnight. Staining was performed by adding 1 ml of staining solution (Propidium Iodine, 50 μg/ml) to the cells and incubating 30-60 min at RT with gentle rocking. MK: MK-1775; LY: LY-2835219.

The result is shown in FIG. 19.

As evident from FIG. 19, treatment of SK-M-NC cells with LY (Abemaciclib) had no effect of the cell cycle. MK-1775 treatment alone caused at 500 nM an increase of cells in G2/M. Combination of both caused a strong G1-arrest.

EXAMPLE 23: ROLE OF E2F1 EXPRESSION ON VIRAL DNA REPLICATION

I.

$2\times10^5$ T24, A549, and HeLa cells were seeded in per well in a 6 well plate and grown in 1.5 ml RPMI 1640 Medium containing (or DMEM-Medium) 10% FBS, penicillin/streptomycin and non-essential amino acids. The following day, 30 pmol siRNA—whether negative control siRNA (Qiagen #1022076) or siE2F1 (Sigma #NM_005225, siRNA ID SASI_Hs01_00162220) was diluted in 150 μL Opti-MEM Medium and 9 μl Lipofectamine RNAiMAX was prepared in 150 μL Opti-MEM. The siRNA-solution and the Lipofectamine RNAiMAX solution were mixed and incubated for 5 minutes. The mixture was dropwise added to the cells. After 48 hours RNA was isolated and RT-qPCR was performed.

The result is shown in FIG. 20. As evident from FIG. 20, E2-early expression is decreased

II.

For each well of a 6 well plate, $2\times10^5$ T24 cells were seeded in 1.5 ml RPMI 1640 Medium containing 10% FBS, penicillin/streptomycin and non-essential amino acids. The following day, 30 pmol siRNA—whether negative control siRNA (Qiagen #1022076) or siE2F1 (Sigma #NM_005225, siRNA ID SASI_Hs01_00162220) was diluted in 150 μL Opti-MEM Medium and 9 μl Lipofectamine RNAiMAX was prepared in 150 μL Opti-MEM. The siRNA-solution and the Lipofectamine RNAiMAX solution were mixed and incubated for 5 minutes. The mixture was dropwise added to the T24 cells. Infection took place 48 h later during incubating the cells with 10 MOI of ADWTRGD in 400 μl of serum free medium and rocking the plate every 10-15 minutes. After 1 h, 1.6 ml full medium was added. RNA isolation was done 24 h after infection.

The result is shown in FIG. 21.

III.

Cells were rinsed with cold PBS and disrupted by adding 500 μl lysis buffer from the MirVana Kit, Thermo Fisher catalog number AM1560, the lysates were collected with a spatula, and pipetted into a 1.5 ml tube. For the organic extraction, 50 μl Homogenate Additive was added and Samples were incubated on ice for 10 min. 500 μl of acid-phenol:chloroform was added and samples were vortexed for 60 s and incubated on ice for 2 minutes. Samples were centrifuged at 14 000×g, at room temperature for 5 min to separate the aqueous and organic phases. The upper phase was carefully transferred to a new tube and an add equal amount of Isopropanol was added. After incubation at room temperature for 10 min, RNA was precipitated (14 000×g, 4° C., 30 min.) and washed twice with 1 mL of 75% ethanol (centrifuge 7500×g, 4° C., 5 min.). RNA was air dried for 5-10 minutes and resuspended in 20-50 μl RNase-free water and resolved by shaking at 500 rpm, 55° C. for 10 min and measured by Nanodrop. After DNA digestion (Deoxyribonuclease I, Invitrogen Cat.No. 18068-015) using 1 μg RNA Sample with 1 μl 10×DNAse I reaction buffer, nuclease-free water to 9 μl volume, 1 μl DNaseI (1 U/μl), incubation 15 min at room temperature, Inactivating the DNAseI by the addition of 1 μl 25 mM EDTA solution, heating for 10 min at 65° C. Reverse transcription was performed using the High-Capacity cDNA Reverse Transcription Kit (Thermo Fisher/Applied Biosystems™ Catalog number: 4368814). Using random hexamere for the transcription for fibre and actin PCR, and using E2 Early Primer for the transcription for the E2Early-PCR.

Used Primers and siRNAs

```
E2 Earlyfw:
                                (SEQ ID NO: 19)
CCGTCATCTCTACAGCCCAT

E2 Earlyrev:
                                (SEQ ID NO: 20)
GGGCTTTGTCAGAGTCTTGC

fiberfw:
                                (SEQ ID NO: 21)
AAGCTAGCCCTGCAAACATCA

fiberrev:
                                (SEQ ID NO: 22)
CCCAAGCTACCAGTGGCAGTA

Actinfw:
```

-continued

```
                                (SEQ ID NO: 23)
TCACCCACACTGTGCCCATCTACG

Actinrev:
                                (SEQ ID NO: 24)
CAGCGGAACCGCTCATTGCCAATGG

E2F1 fw:
                                (SEQ ID NO: 25)
CATCCCAGGAGGTCACTTCTG

E2F1 rev:
                                (SEQ ID NO: 26)
GACAACAGCGGTTCTTGCTC
```

Control siRNA

```
Sense
                                (SEQ ID NO: 27)
UUCUCCGAACGUGUCACGUdTdT

Antisense:
                                (SEQ ID NO: 28)
ACGUGACACGUUCGGAGAAdTdT
```

E2F1 siRNA

```
                                (SEQ ID NO: 29)
CUGAGGAGUUCAUCAGCCU[dT][dT]

                                (SEQ ID NO: 30)
AGGCUGAUGAACUCCUCAG[dT][dT]
```

To proof the role of E2-early expression by RT-qPCR it is absolute necessary to choose the right primer. The primer location should be between the E2-early and the E2-late promoter. Otherwise the E2-late promoter will strongly influence the results. The location of the primers is shown in FIG. 22.

As evident from FIGS. 20 and 21, down-regulation of E2F1 by siRNA causes increase in E2-early expression. This could only be explained by the repressive role of E2F1 in E2-early expression. If E2F1 would be an activator, a decrease of E2-early expression would be the consequence. In addition, siRNA against E2F1 mimic the effect of CDK 4/6 inhibitors, which also inhibits E2F1 expression (Yang C et al., Oncogene 2017, 36, 2255-2264).

EXAMPLE 24: RECOMBINANT ADENOVIRUS WITH MUTATIONS OF THE TWO E2F1-BINDING SITES IN THE ADENOVIRUS E2-EARLY PROMOTER SHOWS INCREASED E2-EARLY EXPRESSION

A mutant adenovirus was generated having mutations at the two E2F1-binding sites of the adenoviral E2 early promoter. The promoter of both the wild type E2 early promoter and the mutant E2 early promoter is shown in FIG. 23 (SEQ ID Nos 44, 45, 46 and 47).

RNA-Expression analysis was carried out in AdWT-RGD and AdE2Fm (contain also the RGD motive) infected T24 cells obtained by RT-qPCR at 24 hours post infection. AD-WT gene expression was set to 100%. The method was identical to the one described in section III of Example 23.

The result is shown in FIG. 24.

As evident from FIG. 24, expression of E2-early gene expression was higher in AdE2Fm infected cells compared to AD-WT infected cells. Therefore, it must be concluded that E2F-1 is playing a repressive role in E2-early promoter activation. This is in sharp contrast to current understanding, where E2F1 is postulated to be an activator (DeCaprio J A, Virology. 2009 Feb. 20; 384(2):274-84.

It is well known, that the structure of the E2-region in all currently known oncolytic adenoviruses is build up as shown in FIG. 22. Thus, the mode of action of E2F1 is identical as described here. In consequence, all of them, i.e. all oncolytic adenoviruses can be used in combination with CDK 4/6 inhibitors, including ColoAd1 and Delta-24-RGD.

ColoAd1 can be characterized as follows:

Enadenotucirev (formerly ColoAd1) is a tumor-selective chimeric adenovirus with demonstrated preclinical activity. The capsid of ColoAd1 is from Ad11p, a serotype with limited seroprevalence in humans. EnAd infects cells by binding to CD46 and/or desmoglein 2,6 both widely expressed on many carcinoma cells. Most of the EnAd genome is derived from Ad11p with a large deletion in E3 and a smaller deletion in E4. In addition, the E2B region consists of a chimera of sequences from Ad11p and Ad3. The E4 deletion in EnAd is in E40RF4, which in Ad5 encodes a protein that inactivates protein phosphatase2A and thereby activates protein translation machinery as well as regulating activity of E1A protein in a feedback inhibitory loop. These deletions, perhaps combined with the chimeric E2B region, probably contribute to the striking cancer-selective replication of EnAd (Deyer et al., Mol Ther Oncolytics. 2017, 16; 5: 62-74)

Delta-24-RGD (DNX-2401) can be characterized as follows:

Delta-24-RGD (DNX-2401) is a conditional replication-competent oncolytic virus engineered to preferentially replicate in and lyse tumor cells with abnormality of p16/RB/E2F1 pathway. Fueyo et al., Oncogene. 2000 Jan. 6; 19(1): 2-12. A mutant oncolytic adenovirus targeting the Rb pathway produces anti-glioma effect in vivo; Dai B. et al. Mol Cancer Therapy. 2017 April; 16(4):662-670.

EXAMPLE 25: TRIPLE THERAPY COMPRISING XVIR-N-31, CDK4/6 INHIBITOR PALBOCICLIB AND PARP INHIBITOR TALAZOPARIB AND FACS ANALYSIS OF T24 AND UMUC-3 CELLS

Potency-Assay/SRB-Staining

The effect of virus induced cell killing alone and in combination with small molecule inhibitors Palbociclib and Talazoparib was analysed in 12-well plates. Therefor, 12.5×$10^3$ T24 or 6.3×$10^3$ UMUC-3/253J cells were seeded and 24 hours later infected with increasing concentration (multiplicity of infection, MOI) of XVir-N-31. For combination treatments with the indicated small molecule inhibitors, cells were treated with respective concentrations of Talazoparib, Palbociclib or the combination of both drugs 24 hours before infection and 1 hour post infection (hpi). Cells were infected in triplicates with the indicated virus in 200 μl medium without fetal bovine serum (FBS). At 1 hpi, complete medium with or without small molecule inhibitors was added to the cells. Four (T24) or five (UMUC-3/253J) days post infection (dpi), cells were fixed with 10% trichloroacetic acid (TCA) for 1 hour at 4° C. and stained with sulforhodamine B (SRB) for 30 minutes at room temperature, followed by washing with 1% acetic acid to remove excess of SRB. Dried SRB was dissolved in 10 mM tris base and quantification was performed by photometric measurement using a multilabel plate reader (PerkinElmer Victor X3) at 562 nm.

The results are shown in FIGS. 35, 36 and 37.

FACS-Analysis

The influence of the applied small molecule inhibitors at their indicated concentrations on the cell cycle of bladder cancer cell lines T24 and UMUC-3 was analysed via flow cytometry analysis after DNA staining. 5×$10^4$ cells were seeded in 6-well plates and 24 hours later treated with appropriate inhibitors. Two days later, at approximately 80% confluency, cells were washed with PBS, trypsinized, washed again and fixated with icecold 80% ethanol. For cell cycle analysis, samples were incubated with the DNA-intercalating dye 7-aminoactinomycine D (7-AAD) and measured via FACS analysis. Evaluation of measured data was performed via the software FlowJo.

The result is shown in FIG. 38.

The results shown in FIGS. 35, 36 and 37 clearly demonstrates that triple therapy consisting of Palbociclib, Talazoparib and XVir-N-31 exhibited superior performance compared to monotherapy or combination therapy regarding cell killing.

FACS analysis of treated bladder cells T24 and UMUC-3 depicted in FIG. 38 shows that the G1 arrest required for increased viral replication is not influenced by the addition of PARP inhibitor Talazoparib.

EXAMPLE 26: TRIPLE THERAPY COMPRISING XVIR-N-31, CDK4/6 INHIBITOR PALBOCICLIB AND BROMODOMAIN INHIBITOR JQ-1

Potency Assay

The effect of virus induced cell killing using virus alone and in combination with small molecule inhibitors was analysed in 12-well plates. Therefor, 2×$10^4$ cells (Cal-33) were seeded and 24 hours later infected with 5 infectious viral particles per cell (multiplicity of infection, MOI) of XVir-N-31. For combination treatments with the indicated small molecule inhibitors, cells were treated with 100 nM Palbociclib, 100 nM JQ-1 or the combination of both drugs 24 hours before infection and 1 hour post infection (hpi). Cells were infected in triplicates with the indicated virus in 200 μl medium without FBS. At 1 hpi, complete medium with or without small molecule inhibitors was added to the cells. Four days post infection (dpi), cells were fixed with 10% trichloroacetic acid (TCA) for 1 hour at 4° C. and stained with sulforhodamine B (SRB) for 30 minutes at room temperature, followed by washing with 1% acetic acid to remove excess of SRB. Dried SRB was dissolved in 10 mM tris base and quantification was performed by photometric measurement using a multilabel plate reader (PerkinElmer Victor X3) at 562 nm.

Assaying Adenoviral Replication

Fiber qPCR

DNA Isolation

For purification of DNA, medium was aspirated, 200 μl lysis-puffer were added to the wells. After adding proteinase K to the solution incubation took place at 56° C. for 10 minutes. 200 μl phenol-chloroform-isoamylalcohol was added to the virus-cell-lysate. After vortexing and subsequent incubation for 5 minutes on ice, a phase separation was achieved by centrifugation for 3 minutes at 16430 g at 4° C. The upper aqueous phase was transferred to a new snap cap containing 200 μl chloroform and 20 μl cresol red in 10 mM TrisCl for better visualization of the phases. After vortexing and incubation for 5 minutes on ice, centrifugation for 3 minutes at 16430 g at 4° C. took place. Again, the upper aqueous phase was combined with 800 μl ethanol and 50 μl 3M sodium acetate solution. 2 μl glycogen solution was added, to achieve a better precipitation. After short inversion of the tube, the solution was centrifuged for 30 minutes at 16430 g at 4° C. Subsequently, the DNA pellet was covered by 400 μl 70% ethanol and incubated for 10 minutes at room temperature. After centrifugation for 7 minutes at 4760 g at room temperature, the DNA pellets were dried for about 5-10 minutes at 37° C. Subsequently, the pellets were dissolved in 100 μl 0,1×TE-buffer and shaken at 40° C. at 400 rpm for approximately 3 hours. When the DNA was completely dissolved, the DNA concentration was measured by means of a spectrophotometer using 2 μl of DNA solution for the measurement and 0,1×TE-buffer as a blank solution. The DNA was then stored at 4° C.

Real-Time PCR

Viral replication was analysed by an adenovirus specific fiber-quantitative PCR (qPCR). Using the ΔΔCT method, the replication of XVir-N-31 was calculated from viral DNA copies per cell (normalisation to cellular β-actin) in relation to the entry level of the virus to the cells (4 hpi value). Cal-33 cells were seeded in 6-well plates ($1,5\times10^5$ per well) and pretreated with the indicated inhibitors for 24 hours. The next day, cells were infected with 10 MOI of XVir-N-31 in 400 μl medium without FBS. At 1 hpi, complete medium with or without small molecule inhibitors was added to the cells. For DNA extraction, cells were harvested at 4, 24 and 48 hpi.

DNA was then isolated using the phenol chloroform extraction method. The via qPCR determined values of fold-changes of the control samples (10 MOI XVir-N-31 without additional small molecule inhibitor) were set to 1.0 and fold changes of further samples were plotted in relation to them. Quantitative PCR was performed on 96-well plates with SYBR Green Mastermix (Eurogentec) under the following cycling conditions: 95° C. for 2 min and 45 cycles 94° C. for 15 s, 60° C. for 15 s, 72° C. for 15 s. Gene expression was calculated using the ΔΔCT-method.

For detection of viral DNA the following specific primers were used:

```
Actin fwd.
                                  (SEQ ID NO: 31)
5'-TAAGTAGGTGCACAGTAGGTCTG-3'

Actin rev.
                                  (SEQ ID NO: 32)
5'-AAAGTGCAAAGAACACGGCTAAG-3'

Fiber fwd.
                                  (SEQ ID NO: 33)
5'-AAGCTAGCCCTGCAAACATCA-3'

Fiber rev.
                                  (SEQ ID NO: 34)
5'-CCCAAGCTACCAGTGGCAGTA-3'
```

A673 cells (ATCC CRL 1598): Ewing sarcoma cell line established 1973. Martinez-Ramirez et al. 2003. Characterization of the A673 cell line (Ewing tumor) by molecular cytogenetic techniques. Cancer Genet Cytogenet. March; 141(2):138-42.

Cal-33 cells: Is a tongue squamous cell carcinoma. CAL 33 is a widely used head and neck squamous cell cancer (HNSCC) cell line for testing of therapeutic agents.

Results

The result of the potency assay for Ewing sarcoma cell line A673 using Xvir-N-31 alone, in combination with CDK4/6 inhibitor Abemaciclib, in combination with bromodomain inhibitor JQ-1 or in combination with CDK4/6 inhibitor Abemaciclib and bromodomain inhibitor JQ-1 with MOIs of 5, 10 and 20 is shown FIG. 39.

The result of the potency assay for head and neck squamous cell carcinoma (HNSCC) cells Cal-33 is shown in FIGS. 40 and 41.

QPCR was carried out for analyzing viral replication under the following treatment conditions: XVir-N-31 MOI: 10; 100 nM Palbociclib, 100 nM JQ-1; cell line: Cal-33; analysis 24 hours post infection and 48 hours post infection). Infection took place with 10 MOI of XVir-N-31 24 hours post treatment with JQ-1, Palbociclib or both (combination). 4, 24 and 48 hours later DNA was isolated and real-time PCR to determine viral replication was performed. Results obtained were normalized to b-actin and the 4 hours values.

The results are shown in FIG. 42A and FIG. 42B. In all cell lines, triple therapy was superior to monotherapy or any dual therapy, i.e. XVir-N-31+CDK4/6 inhibitor; XVir-N-31+bromodomain inhibitor; and CDK4/6 inhibitor+bromodomain inhibitor.

EXAMPLE 27: TRIPLE THERAPY COMPRISING XVIR-N-31, CDK4/6 INHIBITOR PALBOCICLIB AND NUTLIN AND NUTLIN-DERIVATIVES

Example 27.1 Methods and Materials

Potency-Assay/SRB-Staining

Cell killing using XVir-N-31 alone and in combination with small molecule inhibitors was analysed in 12-well plates. Therefor, 20.000 T24 or 25.000 UMUC-3 cells were seeded and 24 hours later infected with increasing concentration (multiplicity of infection, MOI) of XVir-N-31. For combination treatments with the indicated small molecule inhibitors, cells were treated with respective concentrations of Nutlin-3a or Idasanutlin, Palbociclib and the combination of both drugs 24 hours before infection. Cells were infected in triplicates with the indicated virus in 250 μl medium without FBS. At 1 hpi, complete medium with Palbociclib was added to the cells pretreated with Palbociclib. To the control as well as to the Nutlin treated cell complete medium without inhibitors was added. Four days post infection (dpi), cells were fixed with 10% trichloroacetic acid (TCA) for 1 hour at 4° C. and stained with 0.05% sulforhodamine B (SRB) in 1% acetic acid for at least 30 minutes at room temperature, followed by washing with 1% acetic acid to remove excess of SRB. After taking pictures of the plates the dried SRB was dissolved in 10 mM tris base and quantification was performed by photometric measurement using a multilabel plate reader (PerkinElmer Victor X3) at 562 nm.

FACS-Analysis

The influence of the applied small molecule inhibitors at their indicated concentrations on the cell cycle of bladder cancer cell lines T24, T24shRb, UMUC-3 and RT112 was analysed via flow cytometry analysis after DNA staining. Therefor, $5\times10^4$ cells were seeded in 6-well plates and 24 hours later treated with appropriate inhibitors. Two days later, at approximately 80% confluency, cells were washed with PBS, trypsinized, washed again and fixated with icecold 80% ethanol. For cell cycle analysis, samples were incubated with propodium iodine (PI) and measured via FACS analysis. Evaluation of measured data was performed via the software FlowJo.

Adenoviral Replication

Fiber qPCR

DNA Isolation

For purification of DNA, medium was aspirated, 200 μl lysis-puffer were added to the wells. After adding proteinase K to the solution incubation took place at 56° C. for 10 minutes. 200 μl phenol-chloroform-isoamylalcohol was added to the virus-cell-lysate. After vortexing and subsequent incubation for 5 minutes on ice, a phase separation was achieved by centrifugation for 3 minutes at 16.430 g at 4° C. The upper aqueous phase was transferred to a new snap cap, containing 200 μl chloroform and 20 μl cresol red in 10 mM TrisCl for better visualization of the phases. After vortexing and incubation for 5 minutes on ice, centrifugation for 3 minutes at 16430 g at 4° C. took place. Again, the upper aqueous phase was combined with 800 μl ethanol and 50 μl 3 M sodium acetate solution. 2 μl glycogen solution was added, to achieve a better precipitation. After short inversion of the tube, the solution was centrifuged for 30 minutes at 16430 g at 4° C. Subsequently, the DNA pellet was covered by 400 μl 70% ethanol and incubated for 10 minutes at room temperature. After centrifugation for 7 minutes at 4760 g at room temperature, the DNA pellets were dried for about 5-10 minutes at 37° C. Subsequently, the pellets were dissolved in 100 μl 0,1×TE-buffer and shaken at 40° C. at 400 rpm for approximately 3 hours. When the DNA was completely dissolved, the DNA concentration was measured by means of a spectrophotometer using 2 μl of DNA solution for the measurement and 0,1×TE-buffer as a blank solution. The DNA was then stored at 4° C.

Real-Time PCR

Viral replication was analysed by an adenovirus specific fiber-quantitative PCR (qPCR). Using the ΔΔCT method, the replication of XVir-N-31 was calculated from viral DNA copies per cell (normalisation to cellular β-Actin) in relation to the entry level of the virus to the cells (4 hpi value). T24 and T24shRb cells were seeded in 6-well plates ($5\times10^5$ per well) and pretreated with the indicated inhibitors for 24 hours. The next day, cells were infected with 20 MOI of XVir-N-31 in 400 μl medium without FBS. At 1 hpi, complete medium with Palbociclib was added to the cells already pretreated with Palbociclib. To the controls and cells treated with Nutlin complete medium without inhibitors was added. For DNA extraction, cells were harvested at 4 and 48 hpi. DNA was then isolated using the phenol chloroform extraction method. The via qPCR determined values of fold-changes of the control samples (20 MOI XVir-N-31 without additional small molecule inhibitor) were set to 1.0 and fold changes of further samples were plotted in relation to them. Quantitative PCR was performed on 96-well plates with SYBR Green Mastermix (Eurogentec) under the following cycling conditions: 95° C. for 2 min and 45 cycles 94° C. for 15 s, 60° C. for 15 s, 72° C. for 15 s. Gene expression was calculated using the ΔΔCT-Method.

For detection of viral copies following specific primers were used:

```
Actin fwd.
                              (SEQ ID NO: 35)
5'-TAAGTAGGTGCACAGTAGGTCTG-3'

Actin rev.
                              (SEQ ID NO: 36)
5'-AAAGTGCAAAGAACACGGCTAAG-3'

Fiber fwd.
                              (SEQ ID NO: 37)
5'-AAGCTAGCCCTGCAAACATCA-3'

Fiber rev.
                              (SEQ ID NO: 38)
5'-CCCAAGCTACCAGTGGCAGTA-3'
```

EXAMPLE 27.2 TRIPLE THERAPY COMPRISING XVIR-N-31, NUTLIN-3A AND PALBOCICLIB ON T24 CELLS

A potency assay using T24 cells was carried out for determining the cell killing effect of XVir-N-31 alone, XVir-N-31 with Nutlin-3a, XVir-N-31 with Palbociclib, and XVir-N-31 with both Nutlin-3a and Palbociclib.

The result is shown in FIGS. 44 and 45.

As evident from FIGS. 44 and 45, pretreatment of T24 cells with Palbociclib increased cell killing by XVir-N-31. Combination treatment with Palbociclib and Nutlin-3a enhanced this effect. Also, Nutlin-3a treatment enhanced cell killing observed for a combination of XVir-N-31 and Palbociclib.

EXAMPLE 27.3 TRIPLE THERAPY COMPRISING XVIR-N-31, NUTLIN-3A AND PALBOCICLIB ON T24 SHRB CELLS

The same potency assay as subject to Example 27.2 was carried out using T24shRB cells. T24shRB cells are T24 cells without Rb expression. Such lacking Rb expression was generated by means of lentiviral transfection, wherein the lentivirus coded for shRNA directed to Rb. The lentivirus vector used was pLKO-RB1-shRNA19 (obtained from Addgene, Watertown, MA 02472, USA), the sequence of the shRNA was as follows CAGAGATCGTGTATTGAGAT-TCTCGAGAATCTCAATACACGATCTCTG (SEQ ID NO: 39). The procedure is also described by Michaud K et al. (Cancer Res. 2010 Apr. 15. 70(8):3228-38).

The result is shown in FIGS. 46 and 47.

As evident from FIGS. 46 and 47, treatment with Nutlin-3a or Palbociclib alone was not effective in the killing of Rb-negative cells (T24shRb) by XVir-N-31. Only the combination of Palbociclib and Nutlin-3a showed an increase in XVir-N-31 mediated cell killing. Therefor, Nutlin-3a enhanced the oncolytic effect of a dual combination therapy using XVir-N-31 and Palbociclib treated for Rb-negative cells.

EXAMPLE 27.4 TRIPLE THERAPY COMPRISING XVIR-N-31, IDASANUTLIN AND PALBOCICLIB ON T24 CELLS AND T24SHRB CELLS

A potency assay using T24 cells was carried out for determining the cell killing effect of XVir-N-31, XVir-N-31 with Idasanutlin, XVir-N-31 and Palbociclib, and XVir-N-31, Idasanutlin and Palbociclib.

The result is shown in FIGS. 48 and 49.

A similar potency assay using T24shRb cells was carried out for determining the cell killing effect of XVir-N-31, XVir-N- 31 with Idasanutlin, XVir-N-31 and Palbociclib, and XVir-N-31, Idasanutlin and Palbociclib.

The result is shown in FIGS. 50 and 51.

As evident from FIGS. 48 to 51, Idasanutlin had similar effects as nutlin-3a in triple therapy using XVir-N-31 and a CDK4/6 inhibitor.

EXAMPLE 27.5 ASSESSING REPLICATION OF XVIR-N-31 UNDER THE CONDITIONS SUBJECT TO EXAMPLES 27.2 TO 27.4

Replication of XVir-N-31 in T24shRb cells and T24 cells was assessed by determining viral DNA using the ΔΔCT method.

The experimental set up was as follows: Viral replication was determined after 24 and 48 hours. Infection took place with 20 MOI of XVir-N-31 24 hours post treatment with Nutlin-3a, Palbociclib or both (combination). 4 and 48 hours later DNA was isolated and real-time PCR carried out to determine viral replication. Results obtained were normalized to β-actin and the 4 hours values in accordance with the ΔΔCT method.

The result is shown in FIG. 52.

As evident from FIG. 52, Nutlin-3a showed an increase in viral DNA in combination with Palbociclib. While the relative fibre DNA was already high in Palbociclib treated T24 cells, the combination with Nutlin-3a showed a value almost 10× higher than the untreated control. In Rb-negative T24shRb cells, the effect only occurred when combining Nutlin-3a, Palbociclib and XVir-N-31. Here, Palbociclib alone had a less pronounced effect on viral DNA relative to the control.

A Western Blot analysis was carried out on T24shRb cells treated with Nutlin-3a (5 μM, 10 μM or 30 μM), Palbociclib (500 μM) or both (in combination). The result is shown in FIG. 53.

E2F1 protein levels shown in FIG. 53 after treatment with Palbociclib and/or Nutlin-3a (Nutlin-3a (5 μM 10 μM or 30 μM), Palbociclib (500 μM) or both (in combination)) are shown in FIG. 54. E2F1 protein level of untreated cells was set to "1".

As evident from FIGS. 53 and 54, combination treatment with 30 μM Nutlin-3a and 500 nM Palbociclib decreased the relative amount of E2F1 compared to mono therapies.

EXAMPLE 27.6 FACS ANALYSIS OF CELLS OBTAINED FROM THE TREATMENT OF EXAMPLE 27.5

The cells treated as outlined in Example 27.5 were subjected to FACS analysis. Additionally, UMUC cells and RT112 cells were subjected to the same treatment regimen as described in Example 27.5.

Figure 55B:
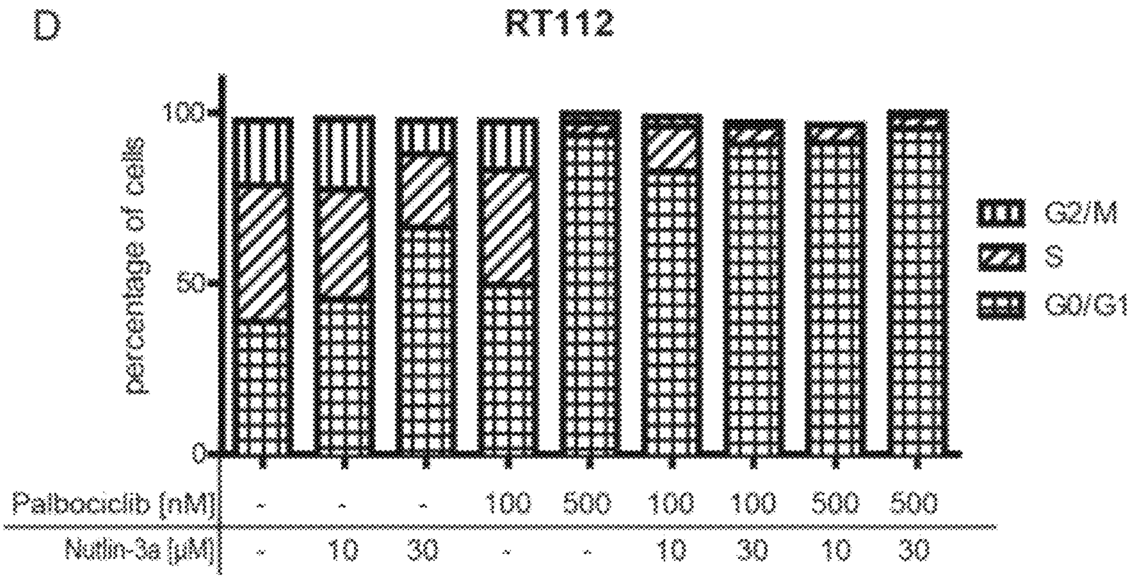

The results are shown in FIG. 55 (A) for T24 cells, FIG. 55 (B) for T24shRb cells, FIG. 55 (C) for UMUC-3 cells and FIG. 55 (D) for RT112 cells.

The result of the further analysis of the results shown in FIGS. 55(A)-(D) focusing on the percentage of cells, in G1 is shown in FIG. 56 (A) for T24 cells, FIG. 56 (B) for T24shRb cells, FIG. 56(C) for UNUC-3 cells and FIG. 56 (D) for RT112 cells.

As evident from said FIGS. 55(A)-(D) and FIGS. 56(A)-(D), the effect on G0/G1 arrest in all cell lines was most pronounced when treated with Nutlin-3a and Palbociclib in combination.

EXAMPLE 28: COMBINATION THERAPY COMPRISING BROMODOMAIN INHIBITOR JQ1 AND XVIR-N-31 IN THE TREATMENT GLIOBLASTOMA $2\times10^4$ cells (U87 cells, LN229 cells or T98G cells) were seeded in 12 well plates in DMEM medium and inhibitor treated at the next day. 48 hours post seeding the cells were infected with XVir-N-31. After 4 days the cells were fixated using 10% TCA. The plates were stained using a 0,1% SRB solution. The surplus was removed and the plates were washed with 1% acetic acid. After removing the acetic acid, the plates were air dried overnight. The SRB was solved in 1 ml of a 10 mM Tris Base solution and a 1:10 dilution was measured using a photometer at 560 nm.

The results are shown in FIGS. 57, 58 and 59.

As evident from FIGS. 57, 58 and 59, combination of JQ1 and XVir-N-31 leads to strongly enhanced cell killing. Using the CDK4/6 inhibitor LEE011 cell killing could be increased even further in all three glioblastoma cell lines.

EXAMPLE 29: REPLICATION OF XVIR-N-31 UPON EXPOSURE TO A COMBINATION OF JQ1 AND RIBOCICLIB $1\times10^5$ cells were seeded in 6 well plates in DMEM medium. The following day the cells were treated with the 500 nM LEE011 and 50 nM JQ1. At the next morning the cells were infected with 20 MOI for U87 and LN229, and 50 MOI for T98G respectively. One hour after infection DMEM Medium containing the inhibitors was added onto the cells. After each time point (4, 24, 48 hours) the cells were washed once with PBS and 200 μl of SDS DNA Lysis Buffer was added. The cells were incubated with Proteinase K for 1 hour before undergoing a phenol-chloroform-isoamylalcohol purification. The DNA was diluted in 1×TE buffer and the concentration of the DNA was determined using a Nanodrop. For each sample a solution of 10 ng/μl was prepared and a RT-qPCR using 50 ng of DNA and a GoTaq Master mix. Specific Fiber forward and reverse primers were used and for the calculation of the Δ ct value specific Actin primers were used as well. For each sample 3 Fiber and 2 Actin values were measured. The calculation was done in excel and each 24 and 48 hours was calculated based on its 4 hours value (initial viral entry, before replication).

The results are shown in FIGS. 60, 61 and 62.

As evident from FIGS. 60, 61 and 62, XVir-N-31 showed a high increase in replication when exposed to JQ1. In two cells lines, this effect was much higher in comparison to the usage of the CDK4/6 Inhibitor LEE011 (LEE). In all three cell lines, the increase of viral replication was highest when a combination of both JQ1 and LEE011 (LEE) was used.

EXAMPLE 30: WESTERN BLOT ANALYSIS OF XVIR-N-31 INFECTED CANCER CELLS $2,5\times10^5$ LN229 cells were seeded in 10 cm plates in DMEM medium. The following day the cells were treated with 500 nM LEE011 and 200 nM JQ1 or a combination of both. At the next morning the cells were infected with XVir-N-31 at 20 MOI. One hour after infection DMEM Medium containing the inhibitors was added on the cells. After each time point (24, 48, 72 hours) the cells were put on ice, washed twice with ice-cold PBS and 300 μl of SDS Protein Lysis Buffer was added. The cells were transferred to reaction tubes and the DNA sheared with a syringe and a needle and the supernatant transferred for further use after centrifugation. The protein concentration was measured with a BCA assay and samples with 4×Lämmli:DTT 6:1 and a concertation of 20 μg were produced and transferred to a 10% SDS gel. The gel electrophoresis started at 90V and was increased to 150V after the ladder started to separate. The proteins on the gel were blotted to a membrane for 2 hours at 100V and blocked in 5% milk in TBS-T for 1 hour at RT. After washing in TBS-T, the first antibody was added according to the manufacturer's information over night at 4° C. The used antibodies were directed to GAPDH, E1A, DBP, E2F1, Rb, pRb for all time points, and caspase 3 and the full length and cleaved version of PARP additionally for the 72 hours samples. The next day, the washing was repeated and the secondary antibody added for 1 hour at RT. Following the washing, ECL was used to image the chemiluminescence by the ChemiDoc™ MP Imaging System.

The results are shown in FIGS. 63, 64, 65, and 66.

As shown in FIG. 63, viral proteins E1A and DBP were increased by a combination treatment of XVir-N-31 with 500 nM LEE011 or/and 200 nM JQ-1. The cellular proteins Rb and pRb remained inhibited in these samples (lane 5, 6 and 7).

As shown in FIG. 64, viral proteins E1A and DBP were increased by a combination treatment of XVir-N-31 with LEE011 or/and JQ-1. The cellular proteins Rb and pRb remained inhibited in these samples and E2F-1 was stabilized in these samples (lane 5, 6 and 7).

As shown in FIG. 65, viral proteins E1A and DBP were increased by a combination treatment of XVir-N-31 with LEE011 or/and JQ-1, while the cellular protein Rb was decreased and E2F1 was enhanced in these samples. Moreover, there were cleavage products of Rb visible at 48 kDa, which indicated apoptosis (Fattman, Cheryl L.; Delach, Scott M.; Dou, Qing Ping; Johnson, Daniel E. (2001): Sequential two-step cleavage of the retinoblastoma protein by caspase-3/-7 during etoposide-induced apoptosis. In: Oncogene 20 (23), S. 2918-2926.).

As shown in FIG. 66, Caspase 3 and PARP were present in all cell lysates, even in the control. The cleaved PARP was detected, not only by the cleaved PARP antibody, but also by the full-length PARP one. Cleaved PARP was only visible in infected cells and its presence increased by the treatment with LEE011 and JQ1. This cleavage was a sign of apoptosis (Chaitanya et al.: PARP-1 cleavage fragments: signatures of cell-death proteases in neurodegeneration. Cell Communication and Signaling 2010 8:31).

EXAMPLE 31: EFFECT OF JQ1 ON DIFFERENT ADENOVIRUSES IN GLIOBLASTOMA

The adenoviral E1A consists of different conserved regions (CR) which bind various cellular proteins and interfere with their function. The CR1 binds p300/CBP, which can also be bound by CR3. Other regions of CR3 can bind different mediator complex subunits, such as MED23, and therefore play a role in the transactivation of the other viral early genes by E1A. The adenovirus region CR1, and also CR2, is able to bind RB. This interaction results in the release of E2F and the following cell cycle progression. Moreover, E2F binds the early promoter of the adenoviral E2 and activate its transcription.

The interacting partners of E1A and location of the conserved region CR1-CR4 are shown in FIG. 67.

In order to find out, which conserved regions of E1A are essential for the effect of JQ1 to enhance viral replication, adenoviruses with different deletions and mutations were used. The wildtype adenovirus, containing RGD motif for better infectivity and a E3 deletion for an unimpaired antiviral response, was used as a control. Other viruses were dl119, which N-Terminus and CR1 and CR2 are deleted and Ad delta24 which is under the control of a CMV promoter and lacks CR2. As a CR3-deleted virus XVir-N-31 was used which also contains the RGD motif and the E3 deletion as well as an E1B-19k deletion to enhance apoptosis. Another utilized virus was ADWT/E2Fm. This virus contains mutations in the E2F binding sites at the E2-early promoter, which blocks the binding of E2F. These characteristics are summarized again in the following:

ADWT: Wild Type E1A

XVir-N-31: ΔCR3 E1A

D1119: ACRI and ΔCR2 E1A

Addelta24: ΔCR2 E1A

ADWT/E2Fm: Wild type E1A

1×10$^5$ LN229 cells were seeded in 6 well plates in DMEM medium. The following day the cells were infected with 20 MOI of the different viruses (AdWt, dl119, Addelta24, XVir-N-31, AdWt/E2Fm). One hour after infection DMEM Medium or DMEM Medium containing 200 nM JQ1 was added on the cells, so that the cells were infected with or without JQ1 treatment. After each timepoint (4, 24, 48 hour) the cells were washed once with PBS and 200 μl of SDS DNA Lysis Buffer was added. The cells were incubated with Proteinase K for 15 min at 56° C. before undergoing a phenol-chloroform-isoamylalcohol purification. The DNA was diluted in AE buffer and the concentration of the DNA was determined using a Nanodrop. For each sample a solution of 10 ng/μl was prepared and a qPCR using 50 ng of DNA and a GoTaq Master mix. Specific Fiber forward and reverse primers were used and for the calculation of the Δ ct value specific Actin primers were used as well. For each sample 3 Fiber and 3 Actin values were measured. The calculation was done in excel and each 24 and 48 hours was calculated based on its 4 hours value (initial viral entry, before replication) and the increase of the replication via JQ1 with regards to the untreated, infected sample.

The nucleotide sequence of the various primers was as follows:

```
b-actinrtfw
                                    (SEQ ID NO: 40)
TAAGTAGGTGCACAGTAGGTCTGA

b-actinrtrev
                                    (SEQ ID NO: 41)
AAAGTGCAAAGAACACGGCTAAG

fiberfw
                                    (SEQ ID NO: 42)
AAGCTAGCCCTGCAAACATCA

fiberrev
                                    (SEQ ID NO: 43)
CCCAAGCTACCAGTGGCAGTA
```

The results are shown in FIGS. 68 and 69.

Among the various viruses, XVir-N-31 showed the highest increase in viral replication under the influence of JQ1 after 48 hours, indicating that a virus with a CR3 deletion benefits strongest from the treatment with JQ1.

EXAMPLE 32: DUAL THERAPY OF XVIR-N-31 AND JQ-1 IN BLADDER CANCER

As a first aspect, replication of XVir-N-31 was assessed. 2.5×10$^4$ UMUC-3 cells were seeded in 12 well plates in DMEM medium. The following day the cells were treated with JQ-1 (priming) or DMEM medium. At the next morning the cells were infected with 10 MOI XVir-N-31. One hour after infection DMEM Medium containing JQ-1 was added on the cells (concurrent treatment). After each 4 and 24 hours, the cells were washed once with PBS and 200 μl of SDS DNA Lysis Buffer was added. The cells were incubated with Proteinase K for at least 1 hour before undergoing a phenol-chloroform-isoamylalcohol purification. The DNA was diluted in 1×TE buffer and the concentration of the DNA was determined using a Nanodrop. For each sample a solution of 15 ng/μl was prepared and a RT-qPCR using 75 ng of DNA and a GoTaq Master mix. Specific fiber forward and reverse primers were used and for the calculation of the Δ ct value specific Actin primers were used as well. For each sample 3 Fiber and 3 Actin values were measured. The calculation was done in excel and each 24 hours value was calculated based on its 4 hours value (initial viral entry, before replication).

The results are shown in FIG. 70.

As evident from FIG. 70, priming per se had no beneficial effect on XVir-N-31 replication. Slight positive effects of priming in the depicted Fig. arose from insufficient wash-out in the experimental setup. Concurrent treatment with JQ-1 was crucial for dual therapy success, whereas prior addition of JQ-1 (priming) resulted in reduced efficiency compared to concurrent treatment.

As a second aspect, particle formation of XVir-N-31 was assessed.

The production of viral particles was analyzed via immunohistochemistry-staining of hexon proteins (Hexon Titer test). Therefor, $2\times10^5$ adherent HEK293 cells per well were seeded in 24-well plates. Cell cultures samples collected after indicated time-points post infection and indicated co-treatment with JQ-1 were pretreated with three cycles thaw-freeze to release viral particles from cells and then serially diluted. The HEK293 cells were infected in volumes of either 50 µl or 10 µl per sample. The plates were then incubated for 40 h at 37° C. and 10% $CO_2$ before checking for detectable cytopathic effects. The medium was aspirated, and the plates were dried for 5-10 min before fixing the cells by adding ice-cold methanol for 10 min at −20° C. The wells were washed twice with PBS+1% BSA. The primary antibody (goat anti-hexon, 1:500) was added and the plates were incubated for 1 h at 37° C. before washing it twice with PBS+1% BSA. Next, the secondary antibody (Rabbit Anti-Goat HRP conjugate, 1:1000) was added and incubated for 1 h at 37° C. Again, the wells were washed twice with PBS containing 1% BSA before the DAB solution was added. After 30 min incubation, 10 different random fields of view (f.o.v.) per well were counted under the 20×objective of a microscope. Counting iterations were averaged and according to this formula, infectious particles per ml were calculated:

$$\text{Titer }(PFU/\text{ml}) = \frac{\text{avg. number of stained cells per } f.o.v. \times \text{total number of } f.o.v. \text{ per Well}}{\text{Vol. added virus sample} \times \text{dilution factor}}$$

The results are shown in FIGS. 71 and 72

As evident from FIG. 71, particle formation of XVir-N-31 was significantly increased in UMUC-3 cells upon addition of 500 nM JQ-1. Furthermore, kinetic of XVir-N-31's particle formation is highly accelerated by concurrent treatment with 500 nM JQ-1.

As a third aspect, a Western blot analysis was carried out.

$1\times10^6$ UMUC-3 cells were seeded in 10 cm plates in DMEM medium and 24 hours post seeding infected with 10 MOI XVir-N-31. 1 hour post infection, culturing media was either refilled by DMEM or DMEM spiked with 500 nM JQ-1. 12, 24, 36 and 48 h.p.i, lysates of total proteins were taken using an SDS-buffer. BCA Assay was applied to adjust equivalent protein concentrations. Then, protein samples were supplemented with Limmli buffer and separated via SDS-PA gelelectrophoresis on 10% PA-Gels. Samples were blotted onto PVDF membranes using a BioRAD Wet Tank System. These membranes were blocked with TBS-Tween buffer containing 5% Skim milk powder for 1 hour at room temperature. Incubation with primary antibodies was conducted over night at 4° C. and with HRP-conjugated secondary antibodies for 1 hour at room temperature. Chemiluminescence was detected using ECL prime (Pierce) with the ChemiDoc Imaging System (BioRad). Figures were designed in Adobe® Illustrator and evaluation was performed with ImageLab.

The results are shown in FIG. 73.

As evident from FIG. 73, absolute viral protein expression and foremost kinetic of XVir-N-31 viral proteins (E1A, E1B55k, DBP and E4Orf6) was highly accelerated by JQ-1 concurrent treatment. Due to JQ-1 treatment, especially later viral proteins like Hexon was expressed in high levels in early time-points after infection with XVir-N-31.

EXAMPLE 33: TRIPLE THERAPY OF BLADDER CANCER USING XVIR-N-31, PALBOCICLIB AND JQ-1

As a first aspect, the influence of the applied small molecule inhibitors at their indicated concentrations on the cell cycle of bladder cancer cell lines UMUC-3 and RT112 was analyzed via flow cytometry analysis after DNA staining.

For such purpose, $5\times10^4$ cells UMUC-3 and RT112, respectively, were seeded in 6-well plates and 24 hours later treated with appropriate inhibitors. 1 day later, at approximately 80% confluency, cells were washed with PBS, trypsinized, washed again and fixated with icecold 80% ethanol. For cell cycle analysis, samples were incubated with the DNA-intercalating dye 7-aminoactinomycine D (7-AAD) and measured via FACS analysis. Evaluation of measured data was performed via the software FlowJo.

The results are shown in FIG. 74.

As evident from FIG. 74, Palbociclib induced a potent arrest in G1-phase of the cell cycle. JQ-1 showed no significant influence on the cell cycle either as monotherapy or in combination with Palbociclib. Notably, JQ-1 was applied in relatively low concentrations which are still sufficient for strongly enhancing the oncolytic potential of XVir-N-31. Inconclusive data for higher doses of JQ-1 inducing either G1- or G2-arrest were found in published scientific literature. However, low doses of JQ-1 did not influence the cell cycle.

As a second aspect, the expression level for specific cellular target proteins after treatment with both JQ-1 and Palbociclib was quantified.

1-$2\times10^6$ UMUC-3 or RT-112 cells were seeded in 10 cm plates in DMEM medium and 24 hours post seeding treated with respective small molecular inhibitors. 24 hours post treatment, lysates of total proteins were taken using an SDS-buffer. BCA Assay was applied to adjust equivalent protein concentrations. Then, protein samples were supplemented with Limmli buffer and separated via SDS-PA gelelectrophoresis on 10% PA-Gels. Samples were blotted onto PVDF membranes using a BioRAD Wet Tank System. These membranes were blocked with TBS-Tween buffer containing 5% Skim milk powder for 1 hour at room temperature. Incubation with primary antibodies was conducted over night at 4° C. and with HRP-conjugated secondary antibodies for 1 hour at room temperature. Chemiluminescence was detected using ECL prime (Pierce) with the ChemiDoc Imaging System (BioRad). Figures were designed in Adobe® Illustrator and evaluation was performed with ImageLab.

The results are shown in FIG. 75.

As evident from FIG. 75, JQ-1 did not show any effects at the indicated concentrations on the cell cycle regulators RB, phospho-RB or E2F-1 protein level neither in monotherapy nor in combination with Palbociclib. The RNA-Polymerase II repressor Hexim1 is downregulated after JQ-1 treatment, but rescued in combination with Palbociclib. Thus, the cell cycle proteins RB and E2F-1 are not responsible for the increase in replication capacity of XVir-N-31 under JQ-1 treatment.

As a third aspect, the cell killing potency of the triple therapy was determined using a potency assay.

1-3x$10^4$ cells were seeded in 12 well plates in DMEM or RPMI medium and inhibitor treated at the next day. 48 hours post seeding the cells were infected with XVir-N-31. After 4 days the cells were fixated using 10% TCA. The plates were stained using a 0.1% SRB solution. The surplus was removed and the plates were washed with 1% acetic acid. After removing the acetic acid, the plates were air dried overnight. The SRB was solved in 1 ml of a 10 mM Tris Base solution and a 1:10 dilution was measured using a photometer at 560 nm.

The results are shown in FIGS. 76, 77 and 78.

As evident from FIGS. 76, 77 and 78, treatment together with low doses of Palbociclib and JQ-1 enables XVir-N-31, even at low MOI, to completely abolish in vitro bladder cancer cell survival as illustrated by the respective effects seen in each and any of bladder cancer cells UMUC-3, RT112 and T24.

As a fourth aspect, the impact of this triple therapy on viral replication was assessed. 2-5x$10^4$ UMUC-3, T24 or RT112 cells were seeded in 12 well plates in DMEM or RPMI medium. The following day the cells were treated with JQ1, Palbociclib (priming) or medium. At the next day, cells were infected with 10, 20 or 50 MOI XVir-N-31. One hour after infection medium containing JQ-1 or Palbociclib was added to the cells. After 4 and 24 hours, cells were washed once with PBS and 200 μl of SDS DNA Lysis Buffer was added. The cells were incubated with Proteinase K for at least 1 hour before undergoing a phenol-chloroform-isoamylalcohol purification. The DNA was diluted in 1×TE buffer and the concentration of the DNA was determined using a Nanodrop. For each sample a solution of 15 ng/μl was prepared and a RT-qPCR using 75 ng of DNA and a GoTaq Master mix. Specific Fiber forward and reverse primers were used and for the calculation of the Δ ct value specific Actin primers were used as well. For each sample 3 Fiber and 3 Actin values were measured. The calculation was done in excel and each 24 hours value was calculated based on its 4 hours value (initial viral entry, before replication).

The results are shown in FIGS. 79, 80 and 81.

As evident from FIGS. 79, 80 and 81, additional treatment with low doses of Palbociclib and JQ-1 highly accelerates XVir-N-31 replication by up to 200-fold.

As a fifth aspect, the impact of this triple therapy on productively infected tumor cells was assessed.

The number of productively infected tumor cells was analyzed via direct immunohistochemistry-staining of hexon proteins of infected UMUC-3 cells (Pseudo-Hexon Titer test). Therefor, 5x$10^5$ UMUC-3 cells per well were seeded in 12-well plates. The next day, cells were primed low doses of JQ-1 and Palbociclib. 48 hours post seeding, cells were then infected with XVir-N-31 (9 MOI) and after one hour concurrently treated with respective inhibitors. The plates were then incubated for 40 h at 37° C. and 10% $CO_2$ before checking for detectable cytopathic effects. The medium was aspirated, and the plates were dried for 5-10 min before fixing the cells by adding ice-cold methanol for 10 min at −20° C. The wells were washed twice with PBS+1% BSA. The primary antibody (Goat Anti-hexon, 1:500) was added and the plates were incubated for 1 h at 37° C. before washing it twice with PBS+1% BSA. Next, the secondary antibody (Rabbit Anti-Goat HRP conjugate, 1:1000) was added and incubated for 1 h at 37° C. Again, the wells were washed twice with PBS containing 1% BSA before the DAB solution was added. After 30 min incubation, 10 different random fields of view (f.o.v.) per well were counted under the 20× objective of a microscope.

The results are shown in FIGS. 82 and 83.

As evident from FIGS. 82 and 83, additional treatment with low doses of Palbociclib and JQ-1 highly accelerates the number of tumor cells passing through XVir-N-31 productive infection.

EXAMPLE 34: EFFECT OF DIFFERENT BET INHIBITORS AND BET-DEGRADER IN COMBINATION WITH XVIR-N-31 IN UMUC3- AND RT112 CELL LINES

The aim of the study was to determine the efficacy of XVir-N-31 in combination with different BET (bromodomain and extra-terminal motive) inhibitors including degraders. BET inhibitor (BETi): OTX015 (monovalent), AZD5153 (bivalent) competitively inhibit BET; BET degrader (BETd): dBet6, ARV55 lead to BET degradation. (See, e.g., Rhyasen G W, et al. AZD5153: A Novel Bivalent BET Bromodomain Inhibitor Highly Active against Hematologic Malignancies. Mol Cancer Ther. 2016 November; 15(11):2563-2574; J. Kay Noel, et al. Abstract C244: Development of the BET bromodomain inhibitor OTX015. Mol Cancer Ther. November 2013 12; C244; Winter G E, et al.: BET Bromodomain Proteins Function as Master Transcription Elongation Factors Independent of CDK9 Recruitment. Mol Cell. 2017 Jul. 6; 67(1):5-18.e19). Raina K, et al.: PROTAC-induced BET protein degradation as a therapy for castration-resistant prostate cancer. Proc Natl Acad Sci USA. 2016 Jun. 28; 113(26):7124-9; the disclosure of which is incorporated herein by reference.)

In a first aspect, cell survival of UMUC3 and RT112 cells after XVir-N-31 infection in combination with BETi and BETd treatment was analyzed by potency assay.

1.3x$10^4$ UMUC-3 cells and 3x$10^4$ RT112 cells were seeded in 12 well plates in DMEM and RT112 medium. At the next day the cells were pretreated with indicated concentration of BETi and BETd. 48 hours' post seeding the cells were infected with the oncolytic adenovirus XVir-N-31, and treated with BETi and BETd. After 5 days the cells were fixated using 10% TCA. The plates were stained using a 0.05% SRB solution. The surplus was removed and the plates were washed with 1% acetic acid. After removing the acetic acid, the plates were air dried overnight. The SRB was solved in 500 μl of a 10 mM Tris Base solution and a 1:10 dilution was measured using a photometer at 562 nm.

The results are shown in FIGS. 84 and 85.

As evident from FIGS. 84 and 85, the combination of BETi and BETd with XVir-N-31 virus was synergistic in both cell lines and lead to strongly reduced cell survival.

In a second aspect, the effect of BETi and BETd on viral replication of fiber DNA in UMUC-3 and RT112 cell lines was analyzed by qPCR.

3x$10^4$ UMUC-3 cells and 4x$10^4$ RT112 cells were seeded in 12 well plates in DMEM and RPMI medium. The following day the cells were pretreated with BETi and BETd. 48 hours post seeding the cells were infected with 10 MOI for UMUC-3 and 50 MOI for RT112 and treated with the indicated concentration of BETi and BETd. After each timepoint (4, 24 hour) the cells were washed once with PBS and 200 μl of SDS DNA Lysis Buffer was added. The cells were incubated with Proteinase K before undergoing a Phenol-Chloroform-Isoamylalcohol purification. The DNA was diluted in DNase free water and the concentration of the DNA was determined using a Nanodrop. For each sample a solution of 15 ng/μl was prepared and a RT-qPCR using 75 ng of DNA and a GoTaq Master mix. Specific Fiber forward and reverse primers were used and for the calculation of the Δ ct value specific Actin primers were used as well. For each sample 3 Fiber and 3 Actin values were measured. The calculation was done in excel and each 24 hours was calculated based on its 4 hours value (initial viral entry, before replication).

The results are shown in FIGS. 86 and 87.

As evident from FIGS. 86 and 87, treatment with BETi and BETd highly increased the replication of XVir-N-31 24 hours post infection. In both cell lines, the increase in viral replication was highest at a combination with the bivalent BETi AZD5153, indicating that bivalent inhibitors in general are more suitable in combination with XVir-N-31.

EXAMPLE 35: COMBINATION OF THE CDK 4/6 INHIBITOR RIBOCICLIB WITH XVIR-N-31 IN A SARCOMA XENOGRAFT NUDE MICE MODEL

Methods

Animal Studies

For the human sarcoma xenograft model, 10-20-week old mice were injected subcutaneously (s.c.) in the right flank with $3\times10^6$ A673 tumors cells in PBS. Tumor size was measured every 2-3 days and tumor volume was calculated with the formula volume=$0.5\times$length$\times$width$^2$. After tumor volume exceeded 100-150 mm$^3$, mice were randomized into indicated treatment/control groups: PBS (i.e. 0.5% methylcellulose without LEE011 and PBS intratumorally [i.t.]), LEE (i.e. 0.5% methylcellulose containing LEE011 and PBS i.t.), XVir only (i.e. 0.5% methylcellulose without LEE011 and XVir-N-31 i.t.) and combo (i.e. 0.5% methylcellulose containing LEE011 and XVir-N-31 i.t.). Then, respective animals received ribociclib succinate (LEE011) 200 mg/kg body weight (dissolved in 0.5% methylcellulose) on day X (DX) until day X+4 (DX+4) or mock control (0.5% methylcellulose without LEE011) via oral gavage. $1\times10^{11}$ VP of XVir-N-31 or PBS (in 50 μL respectively) were injected i.t. on day X+1 (DX+1) and day X+3 (DX+3). On day X+5, 3 representative animals from treatment groups XVir only and combo were sacrificed for histopathological assessment and quantification of viral replication in explanted tumors. Tumor size of remaining mice was measured until tumor volume exceeded 1000 mm$^3$ and mice were sacrificed.

The experimental design of the animal studies is illustrated in FIG. 88

Statistical Analysis

Tumor growth in vivo was analyzed with the open access web tool TumGrowth (https://kroemerlab.shinyapps.io/TumGrowth). Briefly, measured data of tumor volumes were subjected to a linear mixed-effect modelling, allowing longitudinal tumor growth slope comparison as well as treatment response evaluation at desired points in time (cross-sectional analysis). P values were calculated by the software, using type II ANOVA and selected pairwise comparison for longitudinal and cross-sectional analyses (with holm adjustment, when indicated). Tumor growth curves was generated with Prism 5 (GraphPad Software, San Diego, CA, USA). Tumor growth curves were drawn using the mean tumor volume and the standard error of the mean (sem). P values<0.05 were considered statistically significant (* p<0.05; * p<0.005; ** p<0.0005).

Results—Effect of Combination Therapy and Monotherapies in a Xenografted Nude Mouse Model To examine whether biologically relevant advantages of proposed combination strategy might also translate into possible therapeutic benefits, tumor control of xenografted A673 sarcoma cells was assessed in immune-compromised nude mice. Applying the open access web tool TumGrowth, tumor growth control was significantly increased in animals receiving the combination treatment (combo), compared to animals treated with monotherapies (LEE or XVir only) or control (PBS). Maximum differences in treatment response in-between groups were observed at day 12-21 after start of therapy. (Of note, viral replication was significantly increased in explanted tumors of representative animals receiving combo compared to XVir-N-31.)

The results are shown in FIGS. 89, 90 and 91. Selected pairwise comparison for longitudinal analysis is shown in the following table:

Selected pairwise comparisons
P-value adjustement (Adj): Holm

| Group 1 | Group 2 | Difference | P-value | P-value Adj | Wilcox P-value | Wilcox P-value Adj |
|---|---|---|---|---|---|---|
| LEE | PBS | −257.110 [−452.801; −61.420] | 0.0007 | 0.0015 | 0.0173 | 0.042 |
| XVir only | PBS | −518.429 [−707.660; −329.199] | <0.0001 | <0.0001 | 0.0025 | 0.0126 |
| combo | PBS | −684.618 [−873.848; −495.387] | <0.0001 | <0.0001 | 0.0025 | 0.0126 |
| XVir only | LEE | −261.319 [−441.115; −81.522] | 0.0002 | 0.0006 | 0.014 | 0.042 |
| combo | LEE | −427.507 [−607.304; −247.711] | <0.0001 | <0.0001 | 0.0012 | 0.007 |
| combo | XVir only | −166.189 [−338.932; 6.554] | 0.0134 | 0.0134 | 0.0262 | 0.042 |

The results displayed in the FIGS. 29, 30 and 31 clearly demonstrate that the combination therapy comprising XVir-N-31 and Ribociclib is more effective than XVir-N-31 or Ribociclib alone.

The features of the invention disclosed in the preceding specification, the claims as well as the figures can both individually as well as in any combination be important to the realisation of the invention in its various embodiments.

The invention claimed is:

1. A combination comprising an oncolytic adenovirus, a cyclin dependent kinase 4 and 6 (CDK4/6) inhibitor and nutlin or a derivative of nutlin, wherein the adenovirus replicates in a YB-1 dependent manner and wherein the adenovirus is lacking expression of E1A13S protein.

2. The combination of claim 1, wherein the combination further comprises a bromodomain inhibitor.

3. The combination of any one of claim 1, wherein the combination further comprises a Poly (ADP ribose) polymerase (PARP) inhibitor.

4. The combination of claim 1, wherein the adenovirus is selected from the group consisting of XVir-N-31, dl520, AdΔ24, Ad Δ24-RGD, dl922-947, E1Ad/01/07, dl1119/1131, CB 016, VCN-01, E1Ad11107, E1Ad11101, ORCA-010, Enadenotucirev and viruses lacking an expressed viral oncogene which is capable of binding a functional Rb tumor suppressor gene product.

5. The combination of claim 4, wherein the adenovirus is XVir-N-31.

6. The combination of claim 1, wherein the CDK4/6 inhibitor is selected from the group consisting of palbociclib which is also referred to as PD-0332991, abemaciclib which is also referred to as LY-2835219, ribociclib which is also referred to as LEE011, Trilaciclib which is also referred to as G1T28, and Dinaciclib.

7. The combination of claim 1, wherein the adenovirus is replication-deficient in cells which lack YB-1 in the nucleus, but is replicating in cells which have YB-1 in the nucleus.

8. The combination of claim 1, wherein the adenovirus lacks expression of E1B 19 kDa protein.

9. The combination of claim 1, wherein the adenovirus expresses an RGD motif at a fiber.

10. The combination of claim 1, wherein the adenovirus is lacking a functionally active adenoviral E3 region.

* * * * *

SEQUENCE LISTING

```
<160> NUMBER OF SEQ ID NOS: 54

<210> SEQ ID NO 1
<211> LENGTH: 42
<212> TYPE: DNA
<213> ORGANISM: Artificial Sequence
<220> FEATURE:
<223> OTHER INFORMATION: Synthetic

<400> SEQUENCE: 1

aagctagccc tgcaaacatc acccaagcta ccagtggcag ta                        42


<210> SEQ ID NO 2
<211> LENGTH: 40
<212> TYPE: DNA
<213> ORGANISM: Artificial Sequence
<220> FEATURE:
<223> OTHER INFORMATION: Synthetic

<400> SEQUENCE: 2

ccgtcatctc tacagcccat gggctttgtc agagtcttgc                          40


<210> SEQ ID NO 3
<211> LENGTH: 40
<212> TYPE: DNA
<213> ORGANISM: Artificial Sequence
<220> FEATURE:
<223> OTHER INFORMATION: Synthetic

<400> SEQUENCE: 3

cttcctagcg actttgtgcc gtcagagtgg taggcaaggt                          40


<210> SEQ ID NO 4
<211> LENGTH: 45
<212> TYPE: DNA
<213> ORGANISM: Artificial Sequence
<220> FEATURE:
<223> OTHER INFORMATION: Synthetic

<400> SEQUENCE: 4

cgacgaggat gaagtcctgt gtctgctcag gatagcaggc gccat                    45


<210> SEQ ID NO 5
<211> LENGTH: 38
<212> TYPE: DNA
<213> ORGANISM: Artificial Sequence
<220> FEATURE:
<223> OTHER INFORMATION: Synthetic

<400> SEQUENCE: 5

gaggatgaag tcctgtgtct caggatagca ggcgccat                            38


<210> SEQ ID NO 6
<211> LENGTH: 44
<212> TYPE: DNA
<213> ORGANISM: Artificial Sequence
<220> FEATURE:
<223> OTHER INFORMATION: Synthetic

<400> SEQUENCE: 6

tgtttgtcta cagtcctgtg tctgctcagg atagcaggcg ccat                     44
```

<210> SEQ ID NO 7
<211> LENGTH: 38
<212> TYPE: DNA
<213> ORGANISM: Artificial Sequence
<220> FEATURE:
<223> OTHER INFORMATION: Synthetic

<400> SEQUENCE: 7
ttgtctacag tcctgtgtct caggatagca ggcgccat 38

<210> SEQ ID NO 8
<211> LENGTH: 40
<212> TYPE: DNA
<213> ORGANISM: Artificial Sequence
<220> FEATURE:
<223> OTHER INFORMATION: Synthetic

<400> SEQUENCE: 8
tccctcccaa cacacagagt gacaggaaac cgtgtggaat 40

<210> SEQ ID NO 9
<211> LENGTH: 43
<212> TYPE: DNA
<213> ORGANISM: Artificial Sequence
<220> FEATURE:
<223> OTHER INFORMATION: Synthetic

<400> SEQUENCE: 9
agcaaccctc ctaaaccact tgtttgaggt atccatgcta tca 43

<210> SEQ ID NO 10
<211> LENGTH: 41
<212> TYPE: DNA
<213> ORGANISM: Artificial Sequence
<220> FEATURE:
<223> OTHER INFORMATION: Synthetic

<400> SEQUENCE: 10
acgctatgag acctcactga atcctgggtc aacccctcaa g 41

<210> SEQ ID NO 11
<211> LENGTH: 41
<212> TYPE: DNA
<213> ORGANISM: Artificial Sequence
<220> FEATURE:
<223> OTHER INFORMATION: Synthetic

<400> SEQUENCE: 11
cgtccctgag ttcccaaccg cgaagtgtca taccgagtct t 41

<210> SEQ ID NO 12
<211> LENGTH: 44
<212> TYPE: DNA
<213> ORGANISM: Artificial Sequence
<220> FEATURE:
<223> OTHER INFORMATION: Synthetic

<400> SEQUENCE: 12
tggcatggac tgtggtcatg agactggcgt cttcaccacc atgg 44

<210> SEQ ID NO 13
<211> LENGTH: 47
<212> TYPE: DNA
<213> ORGANISM: Artificial Sequence
<220> FEATURE:

<223> OTHER INFORMATION: Synthetic

<400> SEQUENCE: 13
taagtaggtg cacagtaggt ctgaaaagtg caaagaacac ggctaag 47

<210> SEQ ID NO 14
<211> LENGTH: 41
<212> TYPE: DNA
<213> ORGANISM: Artificial Sequence
<220> FEATURE:
<223> OTHER INFORMATION: Synthetic

<400> SEQUENCE: 14
gaaccagggc cgcccatact ggggctttgt cagagtcttg c 41

<210> SEQ ID NO 15
<211> LENGTH: 39
<212> TYPE: DNA
<213> ORGANISM: Artificial Sequence
<220> FEATURE:
<223> OTHER INFORMATION: Synthetic

<400> SEQUENCE: 15
ccgttagccc aagagcaacc ggccgtgatg gtagagaag 39

<210> SEQ ID NO 16
<211> LENGTH: 40
<212> TYPE: DNA
<213> ORGANISM: Artificial Sequence
<220> FEATURE:
<223> OTHER INFORMATION: Synthetic

<400> SEQUENCE: 16
ctgtggtact tcccagagac caggtgagtt ataccctgcc 40

<210> SEQ ID NO 17
<211> LENGTH: 21
<212> TYPE: DNA
<213> ORGANISM: Artificial Sequence
<220> FEATURE:
<223> OTHER INFORMATION: Synthetic

<400> SEQUENCE: 17
aagctagccc tgcaaacatc a 21

<210> SEQ ID NO 18
<211> LENGTH: 21
<212> TYPE: DNA
<213> ORGANISM: Artificial Sequence
<220> FEATURE:
<223> OTHER INFORMATION: Synthetic

<400> SEQUENCE: 18
cccaagctac cagtggcagt a 21

<210> SEQ ID NO 19
<211> LENGTH: 20
<212> TYPE: DNA
<213> ORGANISM: Artificial Sequence
<220> FEATURE:
<223> OTHER INFORMATION: Synthetic

<400> SEQUENCE: 19
ccgtcatctc tacagcccat 20

-continued

<210> SEQ ID NO 20
<211> LENGTH: 20
<212> TYPE: DNA
<213> ORGANISM: Artificial Sequence
<220> FEATURE:
<223> OTHER INFORMATION: Synthetic

<400> SEQUENCE: 20
gggctttgtc agagtcttgc 20

<210> SEQ ID NO 21
<211> LENGTH: 21
<212> TYPE: DNA
<213> ORGANISM: Artificial Sequence
<220> FEATURE:
<223> OTHER INFORMATION: Synthetic

<400> SEQUENCE: 21
aagctagccc tgcaaacatc a 21

<210> SEQ ID NO 22
<211> LENGTH: 21
<212> TYPE: DNA
<213> ORGANISM: Artificial Sequence
<220> FEATURE:
<223> OTHER INFORMATION: Synthetic

<400> SEQUENCE: 22
cccaagctac cagtggcagt a 21

<210> SEQ ID NO 23
<211> LENGTH: 24
<212> TYPE: DNA
<213> ORGANISM: Artificial Sequence
<220> FEATURE:
<223> OTHER INFORMATION: Synthetic

<400> SEQUENCE: 23
tcacccacac tgtgcccatc tacg 24

<210> SEQ ID NO 24
<211> LENGTH: 25
<212> TYPE: DNA
<213> ORGANISM: Artificial Sequence
<220> FEATURE:
<223> OTHER INFORMATION: Synthetic

<400> SEQUENCE: 24
cagcggaacc gctcattgcc aatgg 25

<210> SEQ ID NO 25
<211> LENGTH: 21
<212> TYPE: DNA
<213> ORGANISM: Artificial Sequence
<220> FEATURE:
<223> OTHER INFORMATION: Synthetic

<400> SEQUENCE: 25
catcccagga ggtcacttct g 21

<210> SEQ ID NO 26
<211> LENGTH: 20
<212> TYPE: DNA
<213> ORGANISM: Artificial Sequence
<220> FEATURE:
<223> OTHER INFORMATION: Synthetic

<400> SEQUENCE: 26
gacaacagcg gttcttgctc 20

<210> SEQ ID NO 27
<211> LENGTH: 21
<212> TYPE: DNA
<213> ORGANISM: Artificial Sequence
<220> FEATURE:
<223> OTHER INFORMATION: Synthetic

<400> SEQUENCE: 27
uucuccgaac gugucacgut t 21

<210> SEQ ID NO 28
<211> LENGTH: 21
<212> TYPE: DNA
<213> ORGANISM: Artificial Sequence
<220> FEATURE:
<223> OTHER INFORMATION: Synthetic

<400> SEQUENCE: 28
acgugacacg uucggagaat t 21

<210> SEQ ID NO 29
<211> LENGTH: 21
<212> TYPE: DNA
<213> ORGANISM: Artificial Sequence
<220> FEATURE:
<223> OTHER INFORMATION: Synthetic

<400> SEQUENCE: 29
cugaggaguu caucagccut t 21

<210> SEQ ID NO 30
<211> LENGTH: 21
<212> TYPE: DNA
<213> ORGANISM: Artificial Sequence
<220> FEATURE:
<223> OTHER INFORMATION: Synthetic

<400> SEQUENCE: 30
aggcugauga acuccucagt t 21

<210> SEQ ID NO 31
<211> LENGTH: 23
<212> TYPE: DNA
<213> ORGANISM: Artificial Sequence
<220> FEATURE:
<223> OTHER INFORMATION: Synthetic

<400> SEQUENCE: 31
taagtaggtg cacagtaggt ctg 23

<210> SEQ ID NO 32
<211> LENGTH: 23
<212> TYPE: DNA
<213> ORGANISM: Artificial Sequence
<220> FEATURE:
<223> OTHER INFORMATION: Synthetic

<400> SEQUENCE: 32
aaagtgcaaa gaacacggct aag 23

<210> SEQ ID NO 33
<211> LENGTH: 21

<212> TYPE: DNA
<213> ORGANISM: Artificial Sequence
<220> FEATURE:
<223> OTHER INFORMATION: Synthetic

<400> SEQUENCE: 33
aagctagccc tgcaaacatc a 21

<210> SEQ ID NO 34
<211> LENGTH: 21
<212> TYPE: DNA
<213> ORGANISM: Artificial Sequence
<220> FEATURE:
<223> OTHER INFORMATION: Synthetic

<400> SEQUENCE: 34
cccaagctac cagtggcagt a 21

<210> SEQ ID NO 35
<211> LENGTH: 23
<212> TYPE: DNA
<213> ORGANISM: Artificial Sequence
<220> FEATURE:
<223> OTHER INFORMATION: Synthetic

<400> SEQUENCE: 35
taagtaggtg cacagtaggt ctg 23

<210> SEQ ID NO 36
<211> LENGTH: 23
<212> TYPE: DNA
<213> ORGANISM: Artificial Sequence
<220> FEATURE:
<223> OTHER INFORMATION: Synthetic

<400> SEQUENCE: 36
aaagtgcaaa gaacacggct aag 23

<210> SEQ ID NO 37
<211> LENGTH: 21
<212> TYPE: DNA
<213> ORGANISM: Artificial Sequence
<220> FEATURE:
<223> OTHER INFORMATION: Synthetic

<400> SEQUENCE: 37
aagctagccc tgcaaacatc a 21

<210> SEQ ID NO 38
<211> LENGTH: 21
<212> TYPE: DNA
<213> ORGANISM: Artificial Sequence
<220> FEATURE:
<223> OTHER INFORMATION: Synthetic

<400> SEQUENCE: 38
cccaagctac cagtggcagt a 21

<210> SEQ ID NO 39
<211> LENGTH: 48
<212> TYPE: DNA
<213> ORGANISM: Artificial Sequence
<220> FEATURE:
<223> OTHER INFORMATION: Synthetic

<400> SEQUENCE: 39
cagagatcgt gtattgagat tctcgagaat ctcaatacac gatctctg 48

<210> SEQ ID NO 40
<211> LENGTH: 24
<212> TYPE: DNA
<213> ORGANISM: Artificial Sequence
<220> FEATURE:
<223> OTHER INFORMATION: Synthetic

<400> SEQUENCE: 40
taagtaggtg cacagtaggt ctga 24

<210> SEQ ID NO 41
<211> LENGTH: 23
<212> TYPE: DNA
<213> ORGANISM: Artificial Sequence
<220> FEATURE:
<223> OTHER INFORMATION: Synthetic

<400> SEQUENCE: 41
aaagtgcaaa gaacacggct aag 23

<210> SEQ ID NO 42
<211> LENGTH: 21
<212> TYPE: DNA
<213> ORGANISM: Artificial Sequence
<220> FEATURE:
<223> OTHER INFORMATION: Synthetic

<400> SEQUENCE: 42
aagctagccc tgcaaacatc a 21

<210> SEQ ID NO 43
<211> LENGTH: 21
<212> TYPE: DNA
<213> ORGANISM: Artificial Sequence
<220> FEATURE:
<223> OTHER INFORMATION: Synthetic

<400> SEQUENCE: 43
cccaagctac cagtggcagt a 21

<210> SEQ ID NO 44
<211> LENGTH: 44
<212> TYPE: DNA
<213> ORGANISM: Artificial Sequence
<220> FEATURE:
<223> OTHER INFORMATION: Synthetic

<400> SEQUENCE: 44
agttttcgcg cttaaatttg agaaagggcg cgaaactagt cctt 44

<210> SEQ ID NO 45
<211> LENGTH: 44
<212> TYPE: DNA
<213> ORGANISM: Artificial Sequence
<220> FEATURE:
<223> OTHER INFORMATION: Synthetic

<400> SEQUENCE: 45
aaggactagt ttcgcgccct ttctcaaatt taagcgcgaa aact 44

<210> SEQ ID NO 46
<211> LENGTH: 44
<212> TYPE: DNA
<213> ORGANISM: Artificial Sequence
<220> FEATURE:
<223> OTHER INFORMATION: Synthetic

<400> SEQUENCE: 46
aggagtcgga tttaaatttg agaaagtaat aggtactagt cctt 44

<210> SEQ ID NO 47
<211> LENGTH: 44
<212> TYPE: DNA
<213> ORGANISM: Artificial Sequence
<220> FEATURE:
<223> OTHER INFORMATION: Synthetic

<400> SEQUENCE: 47
aaggactagt acctattact ttctcaaatt taaatccgac tcct 44

<210> SEQ ID NO 48
<211> LENGTH: 30
<212> TYPE: DNA
<213> ORGANISM: Artificial Sequence
<220> FEATURE:
<223> OTHER INFORMATION: Synthetic

<400> SEQUENCE: 48
atcgatctta cctgccacga ggcttttcca 30

<210> SEQ ID NO 49
<211> LENGTH: 11
<212> TYPE: DNA
<213> ORGANISM: Artificial Sequence
<220> FEATURE:
<223> OTHER INFORMATION: Synthetic

<400> SEQUENCE: 49
tacaaaagca g 11

<210> SEQ ID NO 50
<211> LENGTH: 12
<212> TYPE: DNA
<213> ORGANISM: Artificial Sequence
<220> FEATURE:
<223> OTHER INFORMATION: Synthetic

<400> SEQUENCE: 50
acaactccat ct 12

<210> SEQ ID NO 51
<211> LENGTH: 12
<212> TYPE: DNA
<213> ORGANISM: Artificial Sequence
<220> FEATURE:
<223> OTHER INFORMATION: Synthetic

<400> SEQUENCE: 51
atcgattttc ca 12

<210> SEQ ID NO 52
<211> LENGTH: 11
<212> TYPE: DNA
<213> ORGANISM: Artificial Sequence
<220> FEATURE:
<223> OTHER INFORMATION: Synthetic

<400> SEQUENCE: 52
tacaaaaagc a 11

-continued

```
<210> SEQ ID NO 53
<211> LENGTH: 39
<212> TYPE: DNA
<213> ORGANISM: Artificial Sequence
<220> FEATURE:
<223> OTHER INFORMATION: Synthetic

<400> SEQUENCE: 53

acaacttgtg actgccgcgg agactgtttc tgcccatct                          39


<210> SEQ ID NO 54
<211> LENGTH: 12
<212> TYPE: PRT
<213> ORGANISM: Artificial Sequence
<220> FEATURE:
<223> OTHER INFORMATION: Synthetic

<400> SEQUENCE: 54

Thr Thr Cys Asp Cys Arg Gly Asp Cys Phe Cys Ser
1               5                   10
```